US009359633B2

(12) United States Patent
Karsdal et al.

(10) Patent No.: US 9,359,633 B2
(45) Date of Patent: Jun. 7, 2016

(54) BIOCHEMICAL MARKERS FOR CVD RISK ASSESSMENT

(75) Inventors: Morten Karsdal, Copenhagen (DK); Per Qvist, Klampenborg (DK); Natasha Barascuk, Copenhagen (DK)

(73) Assignee: NORDIC BIOSCIENCE A/S, Herlev (DK)

(*) Notice: Subject to any disclaimer, the term of this patent is extended or adjusted under 35 U.S.C. 154(b) by 741 days.

(21) Appl. No.: 12/740,648

(22) PCT Filed: Nov. 4, 2008

(86) PCT No.: PCT/EP2008/064946
§ 371 (c)(1),
(2), (4) Date: Apr. 29, 2010

(87) PCT Pub. No.: WO2009/059972
PCT Pub. Date: May 14, 2009

(65) Prior Publication Data
US 2010/0323377 A1  Dec. 23, 2010

(30) Foreign Application Priority Data

Nov. 5, 2007 (GB) .................................. 0721713.6
Nov. 20, 2007 (GB) .................................. 0722748.1
Feb. 15, 2008 (GB) .................................. 0802814.4

(51) Int. Cl.
| | |
|---|---|
| G01N 31/00 | (2006.01) |
| G01N 33/53 | (2006.01) |
| C12Q 1/37 | (2006.01) |
| C07K 14/775 | (2006.01) |
| G01N 33/542 | (2006.01) |

(52) U.S. Cl.
CPC .............. C12Q 1/37 (2013.01); C07K 14/775 (2013.01); G01N 33/542 (2013.01); G01N 2800/32 (2013.01)

(58) Field of Classification Search
CPC ..... A61K 38/00; A61K 39/00; G01N 33/582; G01N 22/6893; C07K 14/705; C07K 16/18
See application file for complete search history.

(56) References Cited

U.S. PATENT DOCUMENTS

| | | | |
|---|---|---|---|
| 6,010,862 | A | 1/2000 | Eyre |
| 6,703,219 | B1 | 3/2004 | Potempa et al. |
| 2004/0048321 | A1 | 3/2004 | Eyre |
| 2007/0099242 | A1 | 5/2007 | Heinecke et al. |
| 2010/0209940 | A1 | 8/2010 | Veidal et al. |

FOREIGN PATENT DOCUMENTS

| | | |
|---|---|---|
| EP | 1182213 A1 | 2/2002 |
| WO | 9508115 A | 3/1995 |
| WO | 99/24835 A2 | 5/1999 |
| WO | 99/61477 A2 | 12/1999 |
| WO | 02/088750 A2 | 11/2002 |
| WO | 2005/050224 A2 | 6/2005 |
| WO | 2005/124341 A2 | 12/2005 |
| WO | 2007/050661 A2 | 5/2007 |
| WO | WO-2009059972 A2 | 5/2009 |

OTHER PUBLICATIONS

Tascilar et al. (Annals of Oncology 10,Suppl. 4:S107-S110, 1999).*
Tockman et al. (Cancer Research 52:2711s-2718s, 1992).*
Bigg et al., (The FEBS Journal, Mar. 2007; 274(5) pp. 1246-1255).*
Ying S-C et al: "Localization of sequence-determined neoepitopes and neutrophil digestion fragments of C-reactive protein utilizing monoclonal antibodies and synthetic peptides" Molecular Immunology, Pergamon, GB, vol. 29, No. 5, May 1, 1992, pp. 677-687.
Bisoendial et al: "C-reative protein and atherogenesis: From fatty streak to clinical event", Atherosclerosis, Elsevier Ireland Ltd, IE, vol. 195, No. 2, Jul. 21, 2007, pp. e10-e18.
Molloy K J et al: "Unstable carotid plaques exhibit raised matrix metalloproteinase-8 activity" Circulation, vol. 110, No. 3, Jul. 20, 2004, pp. 337-343.
Satta et al: "Incerased turnover of collagen in abdominal aortic aneurysms, demonstrated by measuring the concentration of the aminoterminal propeptide of type III procollagen in peripheral and aortal blood samples" Journal of Vascular Surgery, C.V. Mosby Co., St. Louis, MO, US, vol. 22, No. 2.
Zannad F et al: "Limitationo f excessive extracellular matrix turnover my contribute to survival benefit of spironolactone therapy in patients with congestive heart failure: insights from the rtandomized aldactone evaluation study (RALES). Rales Investigators." Circulation Nov. 28, 2000, vol. 102, No. 22, Nov. 28, 2000, pp. 2700-2706.
Lin Y H et al: "The relation of amino-terminal propeptide of type III procollagen and severity of coronary artery disease in patients without myocardial infarction or hibernation" Clinical Biochemistry, Elsevier Inc, US, CA, vol. 39, No. 9, Sep. 1, 2006, pp. 861-866.
Becker, U et al. "Production and specificity of antibodies against the aminoterminal region in type III collagen", Immunology, 1976;vol. 31:57-65.
U.S. Appl. No. 13/1857,205, Veidal et al.
Acharya PS, Zukas A, Chandan V, Katzenstein AL, Pure E. Fibroblast activation protein: a serine protease expressed at the remodeling interface in idiopathic pulmonary fibrosis. Hum Pathol 2006;37:352-360.
Adams LA, Bulsara M, Rossi E, DeBoer B, Speers D, George J, Kench J, Farrell G, McCaughan GW, Jeffrey GP. Hepascore: an accurate validated predictor of liver fibrosis in chronic hepatitis C infection. Clin Chem 2005;51:1867-1873.

(Continued)

*Primary Examiner* — Lisa Cook
(74) *Attorney, Agent, or Firm* — Benjamin Aaron Adler

(57) ABSTRACT

A method of bioassay for the quantification of peptide fragments comprising a neo-epitope formed by cleavage of a protein of an atherosclerotic plaque such as lumican, versican, perlecan, decorin, biglycan, collagen type III, CRP, ApoE, or elastin, by a proteinase, said comprises contacting a sample such as urine or serum with an antibody reactive with the neo-epitope and determining the level of binding of said immunological binding partner to peptide fragments in said sample. The assay is predictive of risk of cardiovascular disease events.

7 Claims, 7 Drawing Sheets

(56) References Cited

OTHER PUBLICATIONS

Attallah AM, Toson EA, Shiha GE, Omran MM, bdel-Aziz MM, El-Dosoky I. Evaluation of serum procollagen aminoterminal propeptide III, laminin, and hydroxyproline as predictors of severe fibrosis in patients with chronic hepatitis C. J Immunoassay Immunochem 2007;28:199-211.

Bartlett AH, Hayashida K, Park PW. Molecular and cellular mechanisms of syndecans in tissue injury and inflammation. Mol Cells 2007;24:153-166.

Bay-Jensen AC, Hoegh-Madsen S, Dam E, Henriksen K, Sondergaard BC, Pastoureau P, et al. Which elements are involved in reversible and irreversible cartilage degradation in osteoarthritis? Rheumatol Int Feb. 2010;30(4):435-442.

Beliveau et al; Genes and Development 24:2800-2811; 2010.

Benyon RC, Arthur MJ. Extracellular matrix degradation and the role of hepatic stellate cells. Semin Liver Dis 2001;21:373-384.

Berendsen AD, Bronckers AL, Smit TH, Walboomers XF, Everts V. Collagen type V enhances matrix contraction by human periodontal ligament fibroblasts seeded in three-dimensional collagen gels. Matrix Biol Oct. 2006;25(8):515-522.

Birk DE, Fitch JM, Babiarz JP, Linsenmayer TF. Collagen type I and type V are present in the same fibril in the avian corneal stroma. J Cell Biol Mar. 1988;106(3):999-1008.

Blochberger TC, Cornuet PK, Hassell JR. Isolation and partial characterization of lumican and decorin from adult chicken corneas. A keratan sulfate-containing isoform of decorin is developmentally regulated. J Biol Chem 1992;267:20613-20619.

Bobryshev YV. Calcification of elastic fibers in human atherosclerotic plaque. Atherosclerosis 2005;180:293-303.

Boeker KH, Haberkorn CI, Michels D, Flemming P, Manns MP, Lichtinghagen R. Diagnostic potential of circulating TIMP-1 and MMP-2 as markers of liver fibrosis in patients with chronic hepatitis C. Clin Chim Acta Feb. 2002;316(1-2):71-81.

Bourliere M, Penaranda G, Renou C, Botta-Fridlund D, Tran A, Portal I, Lecomte L, Castellani P, Rosenthal-Allieri MA, Gerolami R, Ouzan D, Deydier R, Degott C, Halfon P. Validation and comparison of indexes for fibrosis and cirrhosis prediction in chronic hepatitis C patients: proposal for a pragmatic approach classification without liver biopsies. J Viral Hepat 2006;13:659-670.

Braun J, Pincus T. Mortality, course of disease and prognosis of patients with ankylosing spondylitis. Clin Exp Rheumatol Nov. 2002;20(6 Suppl 28):S16-S22.

Brown, D. C. and K. G. Vogel. "Characteristics of the in vitro interaction of a small proteoglycan (PG II) of bovine tendon with type I collagen." Matrix. 9.6 (1989): 468-78.

Cacoub P, Carrat F, Bedossa P, Lambert J, Penaranda G, Perronne C, Pol S, Halfon P. Comparison of non-invasive liver fibrosis biomarkers in HIV/HCV co-infected patients: the fibrovic study—ANRS HC02. J Hepatol 2008;48:765-773.

Cales P, Laine F, Boursier J, Deugnier Y, Moal V, Oberti F, Hunault G, Rousselet MC, Hubert I, Laafi J, Ducluzeaux PH, Lunel F. Comparison of blood tests for liver fibrosis specific or not to NAFLD. J Hepatol 2008.

Camacho VR, Silveira TR, Oliveira JR, Barros SG, Cerski CT. Relationship between serum concetrations of type III procollagen, hyluronic acid and histopathological findings in the liver of HCV-positive blood donors. Arq Gastroenterol 2007;44:118-122.

Carvalho-Filho RJ, Schiavon LL, Narciso-Schiavon JL, Sampaio JP, Lanzoni VP, Ferraz ML, Silva AE. Optimized cutoffs improve performance of the aspartate aminotransferase to platelet ratio index for predicting significant liver fibrosis in human immunodeficiency virus/hepatitis C virus co-infection. Liver Int 2008;28:486-493.

Castera L, Vergniol J, Foucher J, Le BB, Chanteloup E, Haaser M, Darriet M, Couzigou P, de L, V. Prospective comparison of transient elastography, Fibrotest, APRI, and liver biopsy for the assessment of fibrosis in chronic hepatitis C. Gastroenterology 2005;128:343-350.

Cattin L, Fisicaro M, Tonizzo M, Valenti M, Danek GM, Fonda M, Da Col PG, Casagrande S, Pincetri E, Bovenzi M, and Baralle F. Polymorphism of the apolipoprotein E gene and early carotid atherosclerosis defined by ultrasonography in asymptomatic adults. Arterioscler Thromb Vasc Biol. Jan. 1997;17(1):91-4.

Chapman HA, Riese RJ, Shi GP. Emerging roles for cysteine proteases in human biology. Annu.Rev.Physiol 1997;59:63-88.

Clarkson TB, Kaplan JR. Stage of Reproductive Life, Atherosclerosis Progression and Estrogen Effects on Coronary Artery Atherosclerosis, In: Lobo RA, editor. Treatment of the Postmenopausal Woman: Basic and Clinical Aspects, 3 ed. San Diego: Elsevier; 2007. p. 509-528.

Danielson, K. G., et al. "Targeted disruption of decorin leads to abnormal collagen fibril morphology and skin fragility." J.Cell Biol. 136.3 (1997): 729-43.

Dours-Zimmermann, M. T. and D. R. Zimmermann. "A novel glycosaminoglycan attachment domain identified in two alternative splice variants of human versican." J.Biol.Chem. 269.52 (1994): 32992-98.

Eriksen HA, Satta J, Risteli J, Veijola M, Vare P, Soini Y. Type I and type III collagen synthesis and composition in the valve matrix in aortic valve stenosis. Atherosclerosis 2006;189:91-98.

Evanko, S. P., et al. "Proteoglycan distribution in lesions of atherosclerosis depends on lesion severity, structural characteristics, and the proximity of platelet-derived growth factor and transforming growth factor-beta." Am.J.Pathol. 152.2 (1998): 533-46.

Farkkila M, Rautiainen H, Karkkainen P, Karvonen AL, Nurmi H, Niemela O. Serological markers for monitoring disease progression in noncirrhotic primary biliary cirrhosis on ursodeoxycholic acid therapy. Liver Int 2008;28:787-797.

Fisher LW, Termine JD, Young MF. Deduced protein sequence of bone small proteoglycan I (biglycan) shows homology with proteoglycan II (decorin) and several nonconnective tissue proteins in a variety of species. J Biol Chem 1989;264:4571-4576.

Forns X, Ampurdanes S, Llovet JM, Aponte J, Quinto L, Martinez-Bauer E, Bruguera M, Sanchez-Tapias JM, Rodes J. Identification of chronic hepatitis C patients without hepatic fibrosis by a simple predictive model. Hepatology 2002;36:986-992.

Friedman SL. Mechanisms of disease: Mechanisms of hepatic fibrosis and therapeutic implications. Nat Clin Pract Gastroenterol Hepatol 2004;1:98-105.

Funderburgh, J. L. "Keratan sulfate: structure, biosynthesis, and function." Glycobiology 10.10 (2000): 951-58.

Funderburgh, J. L., et al. "Macrophage receptors for lumican. A corneal keratan sulfate proteoglycan." Invest Ophthalmol.Vis.Sci. 38.6 (1997): 1159-67.

Gabay C, Kushner I. Acute-phase proteins and other systemic responses to inflammation. N Engl J Med 1999;340:448-454.

Gagliano N, Arosio B, Grizzi F, Masson S, Tagliabue J, Dioguardi N, Vergani C, Annoni G. Reduced collagenolytic activity of matrix metalloproteinases and development of liver fibrosis in the aging rat. Mech Ageing Dev 2002;123:413-425.

Gardner CD, Fortmann SP, Krauss RM. Association of small low-density lipoprotein particles with the incidence of coronary artery disease in men and women. JAMA 1996;276:875-81.

Garrone R, Lethias C, Le Guellec D. Distribution of minor collagens during skin development. Microsc Res Tech 1997;38:407-412.

Gefter ML, Margulies DH, Scharff MD. A simple method for poly-ethylene glycol-promoted hybridization of mouse myeloma cells. Somatic Cell Genet Mar. 1977;3(2):231-236.

Gelse K, Poschl E, Aigner T. Collagens—structure, function, and biosynthesis. Adv Drug Deliv Rev 2003;55:1531-1546.

Gilliam AC. Scleroderma. Curr Dir Autoimmun 2008;10:258-279.

Graham I, Atar D, Borch-Johnsen K, Boysen G, Burell G, Cifkova R et al. European guidelines on cardiovascular disease prevention in clinical practice: executive summary. Atherosclerosis 2007;194:1-45.

Gressner AM, Weiskirchen R. Modern pathogenetic concepts of liver fibrosis suggest stellate cells and TGF-beta as major players and therapeutic targets. J Cell Mol Med 2006;10:76-99.

Gressner OA, Weiskirchen R, Gressner AM. Biomarkers of hepatic fibrosis, fibrogenesis and genetic pre-disposition pending between fiction and reality. J Cell Mol Med 2007;11:1031-1051.

(56) References Cited

OTHER PUBLICATIONS

Gressner OA, Weiskirchen R, Gressner AM. Biomarkers of liver fibrosis: clinical translation of molecular pathogenesis or based on liver-dependent malfunction tests. Clin Chim Acta 2007;381:107-113.

Grigorescu M, Rusu M, Neculoiu D, Radu C, Serban A, Catanas M, Grigorescu MD. The FibroTest value in discriminating between insignificant and significant fibrosis in chronic hepatitis C patients. The Romanian experience. J Gastrointestin Liver Dis 2007;16:31-37.

Guanabens N, Pares A, Alvarez L, Martinez de Osaba MJ, Monegal A, Peris P, Ballesta AM, Rodes J. Collagen-related markers of bone turnover reflect the severity of liver fibrosis in patients with primary biliary cirrhosis. J Bone Miner Res 1998;13:731-738.

Guechot J, Poupon RE, Giral P, Balkau B, Giboudeau J, Poupon R. Relationship between procollagen III aminoterminal propeptide and hyaluronan serum levels and histological fibrosis in primary biliary cirrhosis and chronic viral hepatitis C. J Hepatol 1994;20:388-393.

Guo J, Friedman SL. Hepatic fibrogenesis. Semin Liver Dis 2007;27:413-426.

Halfon P, Bacq Y, De MA, Penaranda G, Bourliere M, Ouzan D, Tran A, Botta D, Renou C, Brechot C, Degott C, Paradis V. Comparison of test performance profile for blood tests of liver fibrosis in chronic hepatitis C. J Hepatol 2007;46:395-402.

Halfon P, Bourliere M, Deydier R, Botta-Fridlund D, Renou C, Tran A, Portal I, Allemand I, Bertrand JJ, Rosenthal-Allieri A, Rotily M, Sattonet C, Benderitter T, Saint Paul MC, Bonnot HP, Penaranda G, Degott C, Masseyeff MF, Ouzan D. Independent prospective multicenter validation of biochemical markers (fibrotest-actitest) for the prediction of liver fibrosis and activity in patients with chronic hepatitis C: the fibropaca study. Am J Gastroenterol 2006;101:547-555.

Haraki T, Takegoshi T, Kitoh C, Wakasugi T, Saga T, Hirai JI, Aoyama T, Inazu A and Mabuchi H, Carotid artery intima-media thickness and brachial artery flow-mediated vasodilation in asymptomatic Japanese male subjects amongst apolipoprotein E phenotypes. J Intern Med. Aug. 2002;252(2):114-20.

Hatanaka K, Li XA, Masuda K, Yutani C and Yamamoto A, Immunohistochemical localization of C-reactive protein-binding sites in human atherosclerotic aortic lesions by a modified streptavidin-biotin-staining method. Pathol Int. Sep. 1995;45(9):635-41.

Heegaard AM, Corsi A, Danielsen CC, Nielsen KL, Jorgensen HL, Riminucci M, Young MF and Bianco P, Biglycan deficiency causes spontaneous aortic dissection and rupture in mice. Circulation. May 29, 2007;115(21):2731-8. Epub May 14, 2007.

Heinegard D, Oldberg A. Structure and biology of cartilage and bone matrix noncollagenous macromolecules. FASEB J 1989;3:2042-2051.

Hemmann S, Graf J, Roderfeld M, Roeb E. Expression of MMPs and TIMPs in liver fibrosis—a systematic review with special emphasis on anti-fibrotic strategies. J Hepatol May 2007;46(5):955-975.

Herman MP, Sukhova GK, Libby P, Gerdes N, Tang N, Horton DB et al. Expression of neutrophil collagenase (matrix metalloproteinase-8) in human atheroma: a novel collagenolytic pathway suggested by transcriptional profiling. Circulation 2001;104:1899-904.

Hongbo L, Xiaohui L, Hong K, Wei W, Yong Z. Assessing routine and serum markers of liver fibrosis in CHB patients using parallel and serial interpretation. Clin Biochem 2007;40:562-566.

Hummers LK. Microvascular damage in systemic sclerosis: detection and monitoring with biomarkers. Curr Rheumatol Rep 2006;8:131-137.

Imbert-Bismut F, Ratziu V, Pieroni L, Charlotte F, Benhamou Y, Poynard T. Biochemical markers of liver fibrosis in patients with hepatitis C virus infection: a prospective study. Lancet 2001;357:1069-1075.

Iredale JP, Benyon RC, Arthur MJ, Ferris WF, Alcolado R, Winwood PJ, Clark N, Murphy G. Tissue inhibitor of metalloproteinase-1 messenger RNA expression is enhanced relative to interstitial collagenase messenger RNA in experimental liver injury and fibrosis. Hepatology 1996;24:176-184.

Jacqueminet S, Lebray P, Morra R, Munteanu M, Devers L, Messous D, Bernard M, Hartemann-Heurtier A, Imbert-Bismut F, Ratziu V, Grimaldi A, Poynard T. Screening for liver fibrosis by using a noninvasive biomarker in patients with diabetes. Clin Gastroenterol Hepatol 2008;6:828-831.

Jeppesen J, Hein HO, Suadicani P, Gyntelberg F. High triglycerides/low high-density lipoprotein cholesterol, ischemic electrocardiogram changes, and risk of ischemic heart disease. Am Heart J 2003;145:103-08.

Karsdal MA, Henriksen K, Leeming DJ, Mitchell P, Duffin K, Barascuk N, et al. Biochemical markers and the FDA Critical Path: how biomarkers may contribute to the understanding of pathophysiology and provide unique and necessary tools for drug development. Biomarkers May 2009;14(3):181-202.

Karsdal MA, Madsen SH, Christiansen C, Henriksen K, Fosang AJ, Sondergaard BC. Cartilage degradation is fully reversible in the presence of aggrecanase but not matrix metalloproteinase activity. Arthritis Res Ther 2008;10(3):R63.

Katsuda S, Okada Y, Minamoto T, Oda Y, Matsui Y, Nakanishi I. Collagens in human atherosclerosis. Immunohistochemical analysis using collagen type-specific antibodies. Arterioscler.Thromb. 1992;12:494-502.

Kiani C, Chen L, Wu YJ, Yee AJ, Yang BB. Structure and function of aggrecan. Cell Res 2002;12:19-32.

Kirimlioglu H, Kirimlioglu V, Yilmaz S. Expression of matrix metalloproteinases 2 and 9 in donor liver, cirrhotic liver, and acute rejection after human liver transplantation. Transplant Proc Dec. 2008;40(10):3574-3577.

Klappacher G, Franzen P, Haab D, Mehrabi M, Binder M, Plesch K, Pacher R, Grimm M, Pribill I, Eichler HG, . Measuring extracellular matrix turnover in the serum of patients with idiopathic or ischemic dilated cardiomyopathy and impact on diagnosis and prognosis. Am J Cardiol 1995;75:913-918.

Knox, S. M. and J. M. Whitelock. "Perlecan: how does one molecule do so many things?" Cell Mol.Life Sci. 63.21 (2006): 2435-45.

Koda M, Matunaga Y, Kawakami M, Kishimoto Y, Suou T, Murawaki Y. FibroIndex, a practical index for predicting significant fibrosis in patients with chronic hepatitis C. Hepatology 2007;45:297-306.

Krusius T, Gehlsen KR, Ruoslahti E. A fibroblast chondroitin sulfate proteoglycan core protein contains lectin-like and growth factor-like sequences. J Biol Chem 1987;262:13120-13125.

Kuller LH, Tracy RP, Shaten J and Meilahn EN, Relation of C-reactive protein and coronary heart disease in the MRFIT nested case-control study. Multiple Risk Factor Intervention Trial. Am J Epidemiol. Sep. 15, 1996;144(6):537-47.

Kumar Vaakfn. Tissue renewal and repair: regeneration, healing, and fibrosis. Pathologic basis of disease.Philadelphia, Pennsylvania, USA: Elsevier Saunders, 2005. 87-118.

Kunz J. Matrix metalloproteinases and atherogenesis in dependence of age. Gerontology. 2007;53:63-73.

Kuzuya M, Nakamura K, Sasaki T, Cheng XW, Itohara S, Iguchi A. Effect of MMP-2 deficiency on atherosclerotic lesion formation in apoE-deficient mice. Arterioscler.Thromb.Vasc.Biol 2006;26:1120-25.

Laurent GJ. Dynamic state of collagen: pathways of collagen degradation in vivo and their possible role in regulation of collagen mass. Am J Physiol 1987;252:C1-C9.

Lawrie TD, Mcalpine SG, Rifkind BM, Robinson JF. Serum fatty-acid patterns in coronary-artery disease. Lancet 1961;1:421-24.

Lebensztejn DM, Sobaniec-Lotowska ME, Bauer M, Kaczmarski M, Voelker M, Schuppan D. Serum fibrosis markers as predictors of an antifibrotic effect of interferon alfa in children with chronic hepatitis B. Eur J Gastroenterol Hepatol 2005;17:843-848.

Lebensztejn DM, Sobaniec-Lotowska ME, Kaczmarski M, Voelker M, Schuppan D. Matrix-derived serum markers in monitoring liver fibrosis in children with chronic hepatitis B treated with interferon alpha. World J Gastroenterol 2006;12:3338-3343.

Lee KN, Jackson KW, Christiansen VJ, Lee CS, Chun JG, McKee PA. Antiplasmin-cleaving enzyme is a soluble form of fibroblast activation protein. Blood 2006;107:1397-1404.

Lein M, Wirth M, Miller K, Eickenberg HU, Weissbach L, Schmidt K, Haus U, Stephan C, Meissner S, Loening SA, Jung K. Serial

(56) References Cited

OTHER PUBLICATIONS

Markers of Bone Turnover in Men with Metastatic Prostate Cancer Treated with Zoledronic Acid for Detection of Bone Metastases Progression. Eur Urol 2007.
Leinonen M and Saikku P, Evidence for infectious agents in cardiovascular disease and atherosclerosis. Lancet Infect Dis. Jan. 2002;2(1):11-7.
Leroy V, Halfon P, Bacq Y, Boursier J, Rousselet MC, Bourliere M, De MA, Sturm N, Hunault G, Penaranda G, Brechot MC, Trocme C, Cales P. Diagnostic accuracy, reproducibility and robustness of fibrosis blood tests in chronic hepatitis C: a meta-analysis with individual data. Clin Biochem 2008;41:1368-1376.
Leroy V, Hilleret MN, Sturm N, Trocme C, Renversez JC, Faure P, Morel F, Zarski JP. Prospective comparison of six non-invasive scores for the diagnosis of liver fibrosis in chronic hepatitis C. J Hepatol 2007;46:775-782.
Levy MT, McCaughan GW, Marinos G, Gorrell MD. Intrahepatic expression of the hepatic stellate cell marker fibroblast activation protein correlates with the degree of fibrosis in hepatitis C virus infection. Liver 2002;22:93-101.
Lieber CS, Weiss DG, Paronetto F. Value of fibrosis markers for staging liver fibrosis in patients with precirrhotic alcoholic liver disease. Alcohol Clin Exp Res 2008;32:1031-1039.
Lijnen,H.R. 2001. Plasmin and matrix metalloproteinases in vascular remodeling. Thromb. Haemost. 86:324-333.
Liu J, Sukhova GK, Sun JS, Xu WH, Libby P, Shi GP. Lysosomal cysteine proteases in atherosclerosis. Arterioscler.Thromb.Vasc.Biol 2004;24:1359-66.
Lochter A, Bissell MJ. An odyssey from breast to bone: multi-step control of mammary metastases and osteolysis by matrix metalloproteinases. APMIS Jan. 1999;107(1):128-136.
Lopez-Casillas F, Wrana JL, Massague J. Betaglycan presents ligand to the TGF beta signaling receptor. Cell 1993;73:1435-1444.
Lorenzo-Zuniga V, Bartoli R, Masnou H, Montoliu S, Morillas RM, Planes R. Serum concentrations of insulin-like growth factor-I (igf-I) as a marker of liver fibrosis in patients with chronic hepatitis C. Dig Dis Sci 2007;52:3245-3250.
Lutgens, S. P., et al. "Cathepsin cysteine proteases in cardiovascular disease." FASEB J. 21.12 (2007): 3029-41.
Manolakopoulos S, Bethanis S, Liapi C, Stripeli F, Sklavos P, Margeli A, Christidou A, Katsanika A, Vogiatzakis E, Tzourmakliotis D, Theocharis S. An assessment of serum leptin levels in patients with chronic viral hepatitis: a prospective study. BMC Gastroenterol 2007;7:17.
Marcellin P, Asselah T, Boyer N. Fibrosis and disease progression in hepatitis C. Hepatology 2002;36:S47-S56.
Mariat C. [Diagnosis and follow-up of chronic kidney graft dysfunction: from DFG to new biomarkers]. Nephrol Ther 2008;4 Suppl 3:S204-S207.
Martinez-Hernandez A, Amenta PS. The hepatic extracellular matrix. II. Ontogenesis, regeneration and cirrhosis. Virchows Arch A Pathol Anat Histopathol 1993;423:77-84.
Mayne R. Collagenous proteins of blood vessels. Arteriosclerosis. 1986;6:585-93.
Mays PK, McAnulty RJ, Campa JS, Laurent GJ. Age-related changes in collagen synthesis and degradation in rat tissues. Importance of degradation of newly synthesized collagen in regulating collagen production. Biochem J 1991;276 ( Pt 2):307-313.
McCullagh KG, Duance VC, Bishop KA. The distribution of collagen types I, III and V (AB) in normal and atherosclerotic human aorta. J Pathol 1980;130:45-55.
McHugh NJ, Distler O, Giacomelli R, Riemekasten G. Non organ based laboratory markers in systemic sclerosis. Clin Exp Rheumatol 2003;21:S32-S38.
McHutchison JG, Blatt LM, de Medina M, Craig JR, Conrad A, Schiff ER, Tong MJ. Measurement of serum hyaluronic acid in patients with chronic hepatitis C and its relationship to liver histology. Consensus Interferon Study Group. J Gastroenterol Hepatol 2000;15:945-951.
Mendell MA, Patel P, Ballam L, Strachan D and Northfield TC. C reactive protein and its relation to cardiovascular risk factors: a population based cross sectional study.,BMJ. Apr. 27, 1996;312(7038):1061-5.
Metwally MA, Zein CO, Zein NN. Predictors and noninvasive identification of severe liver fibrosis in patients with chronic hepatitis C. Dig Dis Sci 2007;52:582-588.
Meyer O. Prognostic markers for systemic sclerosis. Joint Bone Spine 2006;73:490-494.
Michalickova K, Susic M, Willing MC, Wenstrup RJ, Cole WG. Mutations of the alpha2(V) chain of type V collagen impair matrix assembly and produce ehlers-danlos syndrome type I. Hum Mol Genet Feb. 1998;7(2):249-255.
Mohamadnejad M, Montazeri G, Fazlollahi A, Zamani F, Nasiri J, Nobakht H, Forouzanfar MH, Abedian S, Tavangar SM, Mohamadkhani A, Ghoujeghi F, Estakhri A, Nouri N, Farzadi Z, Najjari A, Malekzadeh R. Noninvasive markers of liver fibrosis and inflammation in chronic hepatitis B-virus related liver disease. Am J Gastroenterol 2006;101:2537-2545.
Moller S, Hansen M, Hillingso J, Jensen JE, Henriksen JH. Elevated carboxy terminal cross linked telopeptide of type I collagen in alcoholic cirrhosis: relation to liver and kidney function and bone metabolism. Gut 1999;44:417-423.
Monfort J, Nacher M, Montell E, Vila J, Verges J and Benito P, Chondroitin sulfate and hyaluronic acid (500-730 kda) inhibit stromelysin-1 synthesis in human osteoarthritic chondrocytes. Drugs Exp Clin Res. 2005;31(2):71-6.
Muller-Quernheim J. Serum markers for the staging of disease activity of sarcoidosis and other interstitial lung diseases of unknown etiology. Sarcoidosis Vasc Diffuse Lung Dis 1998;15:22-37.
Murasawa Y, Hayashi T, Wang PC. The role of type V collagen fibril as an ECM that induces the motility of glomerular endothelial cells. Exp Cell Res Dec. 10, 2008;314(20):3638-3653.
Myers RP, Tainturier MH, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003;39:222-230.
Naveau S, Raynard B, Ratziu V, Abella A, Imbert-Bismut F, Messous D, Beuzen F, Capron F, Thabut D, Munteanu M, Chaput JC, Poynard T. Biomarkers for the prediction of liver fibrosis in patients with chronic alcoholic liver disease. Clin Gastroenterol Hepatol 2005;3:167-174.
Ngo Y, Munteanu M, Messous D, Charlotte F, Imbert-Bismut F, Thabut D, Lebray P, Thibault V, Benhamou Y, Moussalli J, Ratziu V, Poynard T. A prospective analysis of the prognostic value of biomarkers (FibroTest) in patients with chronic hepatitis C. Clin Chem 2006;52:1887-1896.
Nunes D, Fleming C, Offner G, O'Brien M, Tumilty S, Fix O, Heeren T, Koziel M, Graham C, Craven DE, Stuver S, Horsburgh CR, Jr. HIV infection does not affect the performance of noninvasive markers of fibrosis for the diagnosis of hepatitis C virus-related liver disease. J Acquir Immune Defic Syndr 2005;40:538-544.
Olsen BR. Life without perlecan has its problems. J Cell Biol 1999;147:909-912.
Paggi S, Colli A, Fraquelli M, Vigano M, Del PP, Facciotto C, Colombo M, Ronchi G, Conte D. A non-invasive algorithm accurately predicts advanced fibrosis in hepatitis C: a comparison using histology with internal-external validation. J Hepatol 2008;49:564-571.
Parise ER, Oliveira AC, Figueiredo-Mendes C, Lanzoni V, Martins J, Nader H, Ferraz ML. Noninvasive serum markers in the diagnosis of structural liver damage in chronic hepatitis C virus infection. Liver Int 2006;26:1095-1099.
Pasceri V, Willerson JT and Yeh ET, Direct proinflammatory effect of C-reactive protein on human endothelial cells.Circulation. Oct. 31, 2000;102(18):2165-8.
Patel K, Gordon SC, Jacobson I, Hezode C, Oh E, Smith KM, Pawlotsky JM, McHutchison JG. Evaluation of a panel of non-invasive serum markers to differentiate mild from moderate-to-advanced liver fibrosis in chronic hepatitis C patients. J Hepatol 2004;41:935-942.
Patel K, Nelson DR, Rockey DC, Afdhal NH, Smith KM, Oh E, Hettinger K, Vallee M, Dev A, Smith-Riggs M, McHutchison JG.

(56) References Cited

OTHER PUBLICATIONS

Correlation of FIBROSpect II with histologic and morphometric evaluation of liver fibrosis in chronic hepatitis C. Clin Gastroenterol Hepatol 2008;6:242-247.
Phan SH, Thrall RS. Pulmonary Fibrosis. Lung Biology in Health and Disease. 80 ed. New York: Marcel Dekker, Inc., 1995.
Poynard T, Imbert-Bismut F, Ratziu V, Chevret S, Jardel C, Moussalli J, Messous D, Degos F. Biochemical markers of liver fibrosis in patients infected by hepatitis C virus: longitudinal validation in a randomized trial. J Viral Hepat 2002;9:128-133.
Poynard T, Morra R, Halfon P, Castera L, Ratziu V, Imbert-Bismut F, Naveau S, Thabut D, Lebrec D, Zoulim F, Bourliere M, Cacoub P, Messous D, Munteanu M, de L, V. Meta-analyses of FibroTest diagnostic value in chronic liver disease. BMC Gastroenterol 2007;7:40.
Poynard T, Munteanu M, Imbert-Bismut F, Charlotte F, Thabut D, Le CS, Messous D, Thibault V, Benhamou Y, Moussalli J, Ratziu V. Prospective analysis of discordant results between biochemical markers and biopsy in patients with chronic hepatitis C. Clin Chem 2004;50:1344-1355.
Poynard T, Zoulim F, Ratziu V, Degos F, Imbert-Bismut F, Deny P, Landais P, El HA, Slama A, Blin P, Thibault V, Parvaz P, Munteanu M, Trepo C. Longitudinal assessment of histology surrogate markers (FibroTest-ActiTest) during lamivudine therapy in patients with chronic hepatitis B infection. Am J Gastroenterol 2005;100:1970-1980.
Ratziu V, Massard J, Charlotte F, Messous D, Imbert-Bismut F, Bonyhay L, Tahiri M, Munteanu M, Thabut D, Cadranel JF, Le BB, de L, V, Poynard T. Diagnostic value of biochemical markers (FibroTest-FibroSURE) for the prediction of liver fibrosis in patients with non-alcoholic fatty liver disease. BMC Gastroenterol 2006;6:6.
Rauch U, Karthikeyan L, Maurel P, Margolis RU, Margolis RK. Cloning and primary structure of neurocan, a developmentally regulated, aggregating chondroitin sulfate proteoglycan of brain. J Biol Chem 1992;267:19536-19547.
Register TC, Cann JA, Kaplan JR, Williams JK, Adams MR, Morgan TM et al. Effects of soy isoflavones and conjugated equine estrogens on inflammatory markers in atherosclerotic, ovariectomized monkeys. J Clin Endocrinol Metab 2005;90:1734-40.
Reynolds GD and Vance RP. C-reactive protein immunohistochemical localization in normal and atherosclerotic human aortas. Arch Pathol Lab Med. Mar. 1987;111(3):265-9.
Ridker PM, Hennekens CH, Buring JE and Rifai N. C-reactive protein and other markers of inflammation in the prediction of cardiovascular disease in women. N Engl J Med. Mar. 23, 2000;342(12):836-43.
Ridker PM, Intrinsic fibrinolytic capacity and systemic inflammation: novel risk factors for arterial thrombotic disease. Haemostasis. 1997;27 Suppl 1:2-11.
Rodriguez-Lee M, Bondjers G and Camejo G, Fatty acid-induced atherogenic changes in extracellular matrix proteoglycans. Curr Opin Lipidol. Oct. 2007;18(5):546-53.
Rosen HN, Parker RA, Greenspan SL, Iloputaife ID, Bookman L, Chapin D, Perlmutter I, Kessel B, Qvist P, Rosenblatt M. Evaluation of ability of biochemical markers of bone turnover to predict a response to increased doses of HRT. Calcif Tissue Int 2004;74:415-423.
Rouis M. Matrix metalloproteinases: a potential therapeutic target in atherosclerosis. Curr Drug Targets.Cardiovasc Haematol Disord. 2005;5:541-48.
Rudel LL, Haines J, Sawyer JK, Shah R, Wilson MS, Carr TP. Hepatic origin of cholesteryl oleate in coronary artery atherosclerosis in African green monkeys. Enrichment by dietary monounsaturated fat. J Clin Invest 1997;100:74-83.
Salisbury BG and Wagner, W DJ Biol Chem. Aug. 10, 1981;256(15):8050-7,'Isolation and preliminary characterization of proteoglycans dissociatively extracted from human aorta'.
Satta J, Juvonen T, Haukipuro K, Juvonen M, Kairaluoma MI. Increased turnover of collagen in abdominal aortic aneurysms, demonstrated by measuring the concentration of the aminoterminal propeptide of type III procollagen in peripheral and aortal blood samples. J Vasc.Surg. 1995;22:155-60.
Schaar JA, Mastik F, Regar E, den Uil CA, Gijsen FJ, Wentzel JJ et al. Current diagnostic modalities for vulnerable plaque detection. Curr Pharm Des. 2007;13:995-1001.
Schaller S, Henriksen K, Hoegh-Andersen P, Sondergaard BC, Sumer EU, Tanko LB, et al. In vitro, ex vivo, and in vivo methodological approaches for studying therapeutic targets of osteoporosis and degenerative joint diseases: how biomarkers can assist? Assay Drug Dev Technol Oct. 2005;3(5):553-580.
Schuppan D, Ruehl M, Somasundaram R, Hahn EG. Matrix as a modulator of hepatic fibrogenesis. Semin Liver Dis Aug. 2001;21(3):351-372.
Schwarze U, Atkinson M, Hoffman GG, Greenspan DS, Byers PH. Null alleles of the COL5A1 gene of type V collagen are a cause of the classical forms of Ehlers-Danlos syndrome (types I and II). Am J Hum Genet Jun. 2000;66(6):1757-1765.
Sebastiani G, Vario A, Guido M, Noventa F, Plebani M, Pistis R, Ferrari A, Alberti A. Stepwise combination algorithms of non-invasive markers to diagnose significant fibrosis in chronic hepatitis C. J Hepatol 2006;44:686-693.
Shekhonin BV, Domogatsky SP, Muzykantov VR, Idelson GL, Rukosuev VS. Distribution of type I, III, IV and V collagen in normal and atherosclerotic human arterial wall: immunomorphological characteristics. Coll.Relat Res 1985;5:355-68.
Shin, J., J. E. Edelberg, and M. K. Hong. "Vulnerable atherosclerotic plaque: clinical implications." Curr.Vasc.Pharmacol. 1.2 (2003): 183-204.
Siest G, Pillot T, Regis-Bailly A, Leininger-Muller B, Steinmetz J, Galteau MM and Visvikis S, Apolipoprotein E: an important gene and protein to follow in laboratory medicine. Clin Chem. Aug. 1995;41(8 Pt 1):1068-86.
Snyder N, Gajula L, Xiao SY, Grady J, Luxon B, Lau DT, Soloway R, Petersen J. APRI: an easy and validated predictor of hepatic fibrosis in chronic hepatitis C. J Clin Gastroenterol 2006;40:535-542.
Snyder N, Nguyen A, Gajula L, Soloway R, Xiao SY, Lau DT, Petersen J. The APRI may be enhanced by the use of the FIBROSpect II in the estimation of fibrosis in chronic hepatitis C. Clin Chim Acta 2007;381:119-123.
Stary HC. Composition and classification of human atherosclerotic lesions. Virchows Arch A.Pathol Anat.Histopathol. 1992;421:277-90.
Sundstrom J, Vasan RS. Circulating biomarkers of extracellular matrix remodeling and risk of atherosclerotic events. Curr Opin Lipidol. 2006;17:45-53.
Suzuki,K., Enghild,J.J., Morodomi,T., Salvesen,G., and Nagase,H. 1990. Mechanisms of activation of tissue procollagenase by matrix metalloproteinase 3 (stromelysin). Biochemistry 29:10261-10270.
Svensson L, Oldberg A, Heinegard D. Collagen binding proteins. Osteoarthritis and Cartilage 2001;9:S23-S28.
Symoens S, Renard M, Bonod-Bidaud C, Syx D, Vaganay E, Malfait F, et al. Identification of binding partners interacting with the alpha1-N-propeptide of type V collagen. Biochem J Dec. 22, 2010;433(2):371-381.
Talusan, P., et al. "Analysis of intimal proteoglycans in atherosclerosis-prone and atherosclerosis-resistant human arteries by mass spectrometry." Mol.Cell Proteomics. 4.9 (2005): 1350-57.
Tam LS, Gu J, Yu D. Pathogenesis of ankylosing spondylitis. Nat Rev Rheumatol Jul. 2010;6(7):399-405.
Terry JG, Howard G, Mercuri M, Bond MG and Crouse JR 3rd. Apolipoprotein E polymorphism is associated with segment-specific extracranial carotid artery intima-media thickening., Stroke. Oct. 1996;27(10):1755-9.
Tomasek JJ, Gabbiani G, Hinz B, Chaponnier C, Brown RA. Myofibroblasts and mechano-regulation of connective tissue remodelling. Nat Rev Mol Cell Biol 2002;3:349-363.
Toyama-Sorimachi N, Sorimachi H, Tobita Y, Kitamura F, Yagita H, Suzuki K, Miyasaka M. A novel ligand for CD44 is serglycin, a hematopoietic cell lineage-specific proteoglycan. Possible involvement in lymphoid cell adherence and activation. J Biol Chem 1995;270:7437-7444.
Tracy RP, Lemaitre RN, Psaty BM,Ives DG, Evans RW, Cushman M, Meilahn EN and Kuller LH, Relationship of C-reactive protein to risk

(56) References Cited

OTHER PUBLICATIONS of cardiovascular disease in the elderly. Results from the Cardiovascular Health Study and the Rural Health Promotion Project. Arterioscler Thromb Vasc Biol. Jun. 1997;17(6):1121-7.

Trang T, Petersen JR, Snyder N. Non-invasive markers of hepatic fibrosis in patients co-infected with HCV and HIV: comparison of the APRI and FIB-4 index. Clin Chim Acta 2008;397:51-54.

Trocme C, Leroy V, Sturm N, Hilleret MN, Bottari S, Morel F, Zarski JP. Longitudinal evaluation of a fibrosis index combining MMP-1 and PIINP compared with MMP-9, TIMP-1 and hyaluronic acid in patients with chronic hepatitis C treated by interferon-alpha and ribavirin. J Viral Hepat 2006;13:643-651.

Tsochatzis E, Papatheodoridis GV, Hadziyannis E, Georgiou A, Kafiri G, Tiniakos DG, Manesis EK, Archimandritis AJ. Serum adipokine levels in chronic liver diseases: association of resistin levels with fibrosis severity. Scand J Gastroenterol 2008;43:1128-1136.

Turu MM, Krupinski J, Catena E, Rosell A, Montaner J, Rubio F et al. Intraplaque MMP-8 levels are increased in asymptomatic patients with carotid plaque progression on ultrasound. Atherosclerosis 2006;187:161-69.

Ulrich D, Noah EM, von HD, Pallua N. TIMP-1, MMP-2, MMP-9, and PIIINP as serum markers for skin fibrosis in patients following severe burn trauma. Plast Reconstr Surg 2003;111:1423-1431.

Vassiliadis E, Veidal SS, Simonsen H, Larsen DV, Vainer B, Chen X, et al. Immunological detection of the type V collagen propeptide fragment, PVCP-1230, in connective tissue remodeling associated with liver fibrosis. Biomarkers May 25, 2011.

Venugopal SK, Devaraj S, Yuhanna I, Shaul P and Jialal I. Demonstration that C-reactive protein decreases eNOS expression and bioactivity in human aortic endothelial cells., Circulation. Sep. 17, 2002;106(12):1439-41.

Wang TJ, Gona P, Larson MG, Tofler GH, Levy D, Newton-Cheh C et al. Multiple biomarkers for the prediction of first major cardiovascular events and death. N Engl J Med 2006;355:2631-39.

Wenstrup RJ, Florer JB, Brunskill EW, Bell SM, Chervoneva I, Birk DE. Type V collagen controls the initiation of collagen fibril assembly. J Biol Chem Dec. 17, 2004;279(51):53331-53337.

Wenstrup RJ, Florer JB, Willing MC, Giunta C, Steinmann B, Young F, et al. COL5A1 haploinsufficiency is a common molecular mechanism underlying the classical form of EDS. Am J Hum Genet Jun. 2000;66(6):1766-1776.

Whitelock, J. M. and R. V. Iozzo. "Heparan sulfate: a complex polymer charged with biological activity." Chem. Rev. 105.7 (2005): 2745-64.

Wight TN and Merrilees MJ, Proteoglycans in atherosclerosis and restenosis: key roles for versican. Circ Res. May 14, 2004;94(9):1158-67.

Wight TN, Versican: a versatile extracellular matrix proteoglycan in cell biology.Curr Opin Cell Biol. Oct. 2002;14(5):617-23.

Wight, T. N. "The extracellular matrix and atherosclerosis." Curr. Opin.Lipidol. 6.5 (1995): 326-34.

Wight, T. N., et al. "Vascular cell proteoglycans: evidence for metabolic modulation." Ciba Found.Symp. 124 (1986): 241-59.

Wilson PW, Schaefer EJ, Larson MG and Ordovas JM. Apolipoprotein E alleles and risk of coronary disease. A meta-analysis. Arterioscler Thromb Vasc Biol. Oct. 1996;16(10):1250-5.

Wong VS, Hughes V, Trull A, Wight DG, Petrik J, Alexander GJ. Serum hyaluronic acid is a useful marker of liver fibrosis in chronic hepatitis C virus infection. J Viral Hepat 1998;5:187-192.

World Health Organization. Reducing Risks, Promoting Healthy Life. Peducing Risks, Promoting Healthy Life, Geneva: WHO, 2002:1-230.

Wynn TA. Cellular and molecular mechanisms of fibrosis. J Pathol 2008;214:199-210.

Wynn TA. Common and unique mechanisms regulate fibrosis in various fibroproliferative diseases. J Clin Invest 2007;117:524-529.

Yamada H, Watanabe K, Shimonaka M, Yamaguchi Y. Molecular cloning of brevican, a novel brain proteoglycan of the aggrecan/versican family. J Biol Chem 1994;269:10119-10126.

Yamada Y, Izawa H, Ichihara S, Takatsu F, Ishihara H, Hirayama H et al. Prediction of the risk of myocardial infarction from polymorphisms in candidate genes. N Engl J Med 2002;347:1916-23.

Yang BL, Zhang Y, Cao L, Yang BB. Cell adhesion and proliferation mediated through the G1 domain of versican. J Cell Biochem 1999;72:210-220.

Yoneda M, Mawatari H, Fujita K, Iida H, Yonemitsu K, Kato S, Takahashi H, Kirikoshi H, Inamori M, Nozaki Y, Abe Y, Kubota K, Saito S, Iwasaki T, Terauchi Y, Togo S, Maeyama S, Nakajima A. High-sensitivity C-reactive protein is an independent clinical feature of nonalcoholic steatohepatitis (NASH) and also of the severity of fibrosis in NASH. J Gastroenterol 2007;42:573-582.

Zaman A, Rosen HR, Ingram K, Corless CL, Oh E, Smith K. Assessment of FIBROSpect II to detect hepatic fibrosis in chronic hepatitis C patients. Am J Med 2007;120:280-14.

Zhen EY, Brittain IJ, Laska DA, Mitchell PG, Sumer EU, Karsdal MA, et al. Characterization of metalloprotease cleavage products of human articular cartilage. Arthritis Rheum Aug. 2008;58(8):2420-2431.

Zheng M, Cai WM, Weng HL, Liu RH. ROC curves in evaluation of serum fibrosis indices for hepatic fibrosis. World J Gastroenterol 2002;8:1073-1076.

Zwaka TP, Hombach V and Torzewski J. C-reactive protein-mediated low density lipoprotein uptake by macrophages: implications for atherosclerosis., Circulation. Mar. 6, 2001;103(9):1194-7.

Banks Re, et al., The acute phase protein response in patients receiving subcutaneous UL-6; Clin Exp Immunol 1995; 102:217-223.

Shinohara, T., et al.; Soluble Elastin Fragments in Serum are Elevated in Acute Aortic Dissection; Arterioscler Thromb Vasc. Biol., Oct. 2003, pp. 1839-1844.

Zimmerli, L.U. et al.; Urinary Proteomic Biomarkers in Coronary Artery Disease, Molecular & Cellular Proteomics 7.2, Oct. 18, 2007, pp. 290-298.

\* cited by examiner

BIOCHEMICAL MARKERS FOR CVD RISK ASSESSMENT

RELATED APPLICATION

This application is the U.S. national phase, pursuant to 35 U.S.C. §371, of PCT international application Ser. No. PCT/EP2008/064946, filed Nov. 4, 2008, designating the United States and published in English on May 14, 2009 as publication WO 2009/059972 A2, which claims priority to GB 0721713.6, filed Nov. 5, 2007, GB 0722748.1, filed Nov. 20, 2007 and GB 0802814.4, filed Feb. 15, 2008. The entire contents of the aforementioned patent applications are incorporated herein by this reference.

SEQUENCE LISTING

This application contains a Sequence Listing which has been submitted via EFS-Web and is hereby incorporated by reference in its entirety. Said ASCII copy, created on Aug. 18, 2010, is named 85891US.txt, and is 246,287 bytes in size.

The present invention relates to assays for detection of biochemical markers valuable for diagnostic purposes in cardiovascular disease and prognosis of disease development, including biochemical markers indicative of the risk of cardiovascular events resulting from atherosclerotic development and plaque instability.

Worldwide, cardiovascular disease (CVD) is the leading cause of morbidity and mortality. At present, there are no effective and non-invasive diagnostic methods that allow for diagnosis and classification of patients into different risk-groups and for the diagnosis of low risk patients. Diagnostic and prognostic tools are composed mainly of multivariate analysis of simple markers, such as age, smoking and various lipid and lipoprotein concentrations.

CVD covers several clinical syndromes, primarily, angina pectoris, myocardial infarction (coronary thrombosis) and stroke. All of these syndromes are usually the sequelae of complicated atherosclerosis.

Atherosclerosis begins with intimal thickening in childhood and progresses to fatty streaks in the intima of arteries—these lesions are characterized as type I and II, respectively. Fatty streaks are the earliest macroscopically visible lesions in the development of atherosclerosis and occur among almost all human beings of all races and societies. In the non pathogenic state, endothelial cells (EC) resist adhesive interactions with leukocytes. However, the actions of proinflammatory cytokines and accumulated oxidized lipoprotein in the arterial wall during atherogenesis, initiate expression of adhesion molecules, such as intercellular adhesion molecules (ICAM)-1 and vascular cell adhesion molecules (VCAM)-1, on the surface of aortic ECs. This allows for capturing and transmigration of leukocytes through the endothelial surface, into the intimal part of the vessel wall. The development of plaques involves an increasing number of smooth muscle cells (SMC) that undergo displacement and apoptosis, which results in increased matrix turnover. The impaired collagen synthesis can result in a weakened fibrous cap and an atherosclerotic plaque that is more prone to rupture; however, most investigators believe that the actions of a proteolytic enzymes such as matrix metallo-proteases (MMPs) and other proteases importantly contribute to the risk of plaque rupture (Clarkson and Kaplan 509-28).

Plaques are divisible into two different types: 'vulnerable' and 'stabilized' plaques. However, for detailed histological analyses and molecular understanding, a more detailed classification is often used. There are three major stages in development of plaque: initiation, fatty streaks and the complex/advanced plaque (Stary H. C.).

Atherosclerotic plaques develop within the intima of arteries, and may be classified depending on their composition and structure. This classification divides lesions into eight types (Stary H. C.):

I. Macrophages loaded with and enlarged by lipid droplets (macrophage foam cells) are increased in the intima.

II. Macrophage foam cells accumulate in the deep part of the proteoglycan layer along with lipid droplets within the intimal SMC. The layers of foam cells are visible as fatty streaks. In type II lesions monocytes penetrate the endothelial lining by monocyte chemo attractant proteins (mainly MCP-1), which are over expressed in human atheroma. The early types of lesion (type I and II) can start in infancy and do not necessarily lead to plaque rupture. Furthermore, the development of atherosclerosis may end after the formation of type III lesion, and the formation of plaque is not predictable (Stary H. C.).

III. The type III lesion is determined as the intermediate lesion between the fatty streaks (type II) and the atheroma (type IV). These lesions contain pools of extracellular lipid and thereby expand the spaces between the normally closely adjoining SMCs of the deep musculo-elastic layer of the intima. The pools of material may replace proteoglycans and collagen fibres that normally reside here, but this occurs with little impact at this stage of atherogenesis.

IV. The atheroma is the first clinical sign of atherosclerosis. Displacement of SMCs in the intima of arteries by accumulating extracellular pools of lipids and disruption of the intimal architecture is a hallmark of a type IV lesion. The formation of the lipid cores is the end result of this SMC displacement. Formation of a lipid core accounts for the increased wall thickening. The lipid core is a large and well delineated region of the deep intima where the normal structural elements of this part of the arterial wall have been replaced by densely packed foam cell remnants, free lipids droplets, cholesterol crystals and calcium particles. SMCs normally resident in this area are decreased or completely absent at this stage of atherosclerosis progression. Any remnant SMCs become widely dispersed and have developed elongated cell bodies and very often unusually thick basement membranes. At this stage, the development of a layer overlying the lipid core begins. This layer consists of collagen and proteoglycan-rich intercellular matrix, SMCs with and without lipid droplets, macrophages, and foam cells.

V. The response to type IV lesion is the formation of a reparative fibrous tissue matrix, forming a fibrous "cap". Typically, these lesions will consist of layers of lipid cores and reparative tissue irregularly stacked on top of each other. Events such as hematoma and thrombus formation may additionally complicate these types of lesions. If not fatal, these lesion complications are integrated into the lesion and overgrown by a thin layer of reparative matrix tissue, consisting of collagens and proteoglycans. The content of extracellular matrix proteins collagen and proteoglycans increases in the atherosclerotic plaque during formation of the cap.

VI. The defects of the endothelium such as fissures, erosions, ulcerations, hematoma, thrombus, haemorrhage can if combined lead to more complicated lesion type designated type VI lesion.

VII. The lesion is often referred to as calcified lesion, where more than 50% of the lesion consists of mineral. In addition to calcifications, these lesions contain abundance of reparative fibrous connective tissue. When the SMCs trapped in this undergo apoptosis and disintegrate; their mineralized organelles become a part of the calcification.

VIII. The fibrotic lesion follows the calcific lesion. The fibrotic lesion may consist entirely of collagen and no lipid. (Stary H. C.)

Cardiovascular events are often the result of plaque rupture, in which inflammation and the release of proteases weaken the shoulder regions of the fibrous cap and allow the fatty materials in the plaque to come into contact with the blood precipitating a mural thrombus (Clarkson and Kaplan). Thinning of the fibrous cap by increased protease activity in the combination with decreased matrix production, is considered a hallmark of plaque instability increasing the risk of rupture. Vulnerability of plaques and their risk of rupture is an area of clinical interest. Definition of a vulnerable plaque (VP) is not standardized, but there is a general agreement stating existence of three histological hallmarks compared to stable plaque:

1) A larger lipid core (>40 percent of total lesion).
2) A thinner fibrous cap (65-150 micrometers).
3) Large amount of acute inflammatory cells.

Major criteria for defining VP include: active inflammation (presence of monocytes, macrophages and T cells), thin cap with large lipid core, endothelial denudation with superficial platelet aggregation, fissured plaque, and >90% stenosis of the artery. Other minor criteria include: superficial calcified nodule, intraplaque haemorrhage, endothelial dysfunction, and outward remodelling (Shin, Edelberg, and Hong).

Plaque complications, instability and rupture may be inhibited by medical treatment and/or lifestyle modification. In some cases, however, more invasive methods may be needed, i.e. angioplasty or bypass surgery.

Presently, diagnostic tools are based on either static image analyses still under development or low-technology methods such as systolic and diastolic blood pressure levels related to the risk of CVD. The field has devoted much attention to the development of multivariate analysis that may better identify patients at high risk. One such model is the SCORE-model (Systematic Coronary Risk Evaluation model). In 1994, with a revision in 2003, The European Atherosclerosis Society, The European Society of Cardiology and The European Society of Hypertension issued a set of recommendations regarding prevention of coronary heart diseases. This guideline is based on several assessment techniques, which have been developed to assess the risk of CVD in asymptomatic subjects, i.e. identification of asymptomatic high-risk patients. The SCORE-model integrates gender, age, smoking, systolic blood pressure and either total cholesterol or the cholesterol/HDL ratio as risk factors (Graham et al.).

In order to make a more detailed diagnosis, the SCORE model is not sufficient and imaging techniques are used. Imaging methods are therefore used mostly on patients in the high-risk group or during research.

Imaging Techniques

Coronary angiography (CAG) is currently the gold standard imaging technique for defining the degree of stenosis. CAG images the lumen of the vessel in two dimensions, but is restricted only to the lumen and not the vessel wall thereby CAG can not distinguish between an artery with a stable plaque and an artery with a vulnerable plaque. CAG is often used to determine whether a patient needs surgery; angioplasty or bypass. In order to determine if a point of luminal narrowing is an advanced plaque, other techniques are needed i.e. intravascular coronary ultrasound (IVUS) or angioscopy. IVUS provides two-dimensional cross-sectional images of the plaque and vessel wall, and is considered as a method good for characterization of vessel wall and morphology and the degree of calcification, but poor for assessing the lipids in the lesion. However, IVUS is invasive and requires expertise and expense: therefore, its use is not wide spread. Angioscopy is another useful method in understanding and identifying atherosclerosis. Angioscopy is a direct visualization of plaque surface and has the capability of detecting colour of plaque and thrombosis. Angioscopy is, however, invasive and technically difficult, and so far it is has not been able to detect the degree of plaque extension. Another imaging technique that currently is receiving much attention is Magnetic Resonance imaging (MRI). MRI is non-invasive and able to identify carotid plaque at high risk of stroke. On the other hand, MRI is not the best technique to image coronary arteries, because of small plaque sizes and location of the coronary arteries. Other imaging techniques are under development, i.e. elastography, thermography and optical coherence tomography (Schaar et al.).

The imaging techniques mentioned are all under development and alone, none can identify a vulnerable plaque, but they are useful tools in understanding both the molecular events and plaque turnover prior to rupture. Presently, the only opportunity to diagnose CVD at an early stage is to utilize a range of risk factors for established coronary heart disease, peripheral artery disease and cerebrovascular atherosclerotic disease of the patient in question, as well as close relatives of the patient.

Present Biochemical Markers

At present, several biochemical markers are known as risk factors for atherosclerosis. Recently much attention has been directed to the measurement of biochemical marker concentrations in serum; both lipids such as total cholesterol, low-density lipoprotein cholesterol (LDL-C) and the high-density lipoprotein cholesterol (HDL-C) and inflammatory markers such as C-Reactive Protein (CRP), Interleukin-6 (IL-6), Interleukin-18 (IL-18), Tumor Necrosis Factor-alpha (TNFα), CD40, CD40 ligand (CD40L) and others.

Among lipoprotein markers, there have been at least two noteworthy advances. The size of LDL particles seems to predict the degree of atherosclerosis progression. Increased concentrations of small LDL particles are more related to CVD risk than increased concentrations of large particles (Gardner, Fortmann, and Krauss).

The level of HDL-C is strongly related to triglyceride, and high triglyceride level is correlated to a higher risk of CHD. A cohort study by Jeppesen et al. (2003) found high TG/low HDL-C as the strongest risk factors of IHD (ischemic heart disease) (Jeppesen et al.).

Lipid profiles are important for evaluation of risk factors, but do not allow understanding and measurement of the molecular events associated with plaque turnover. A number of biochemical markers have been suggested as risk factors for CVD, although not specific product of the disease. These include CRP and Bone natriuretic peptide (BNP) (see Table 1). Table 1 summarizes some of the known markers of CVD.

TABLE 1

A selection of present biochemical markers in CVD.

| Marker | Type | Description |
| --- | --- | --- |
| C-reactive protein (CRP) | Inflammatory | Produced in the liver, increases during inflammatory states. |
| Pregnancy-associated plasma protein (PAPP-A) | Inflammatory | Zinc-binding protein that acts as an enzyme, specifically a metallopeptidase. |

TABLE 1-continued

A selection of present biochemical markers in CVD.

| Marker | Type | Description |
|---|---|---|
| Interleukin-6 (IL-6) | Inflammatory cytokine | Elevated level in heart failure and myocardial infarction. |
| Inteleukin-8 (IL-8) | Inflammatory cytokine | Elevated in myocardial infarctions. |
| Interleukin-18 | Inflammatory cytokine | Elevated in myocardial infarction. |
| TNF-α (Tumor Necrosis Factor) | Cytokine | Conc. Elevated in the settings of heart failure. |
| MCP-1 | Chemokine | Recruits monocytes from the blood into early atherosclerotic lesion. |
| Intercellular adhesion molecule-1 (ICAM-1) | Adhesion molecule | Elevated in myocardial infarctions and stroke. |
| Vascular cellular adhesion molecule-1 (VCAM-1) | Adhesion molecule | Elevated in myocardial infarctions and stroke. |
| Brain natriuretic peptide (BNP) | Neurohormonal activity | Produced in atria and ventricles of normal healthy heart. |
| Lipoprotein-associated phospholipase A2 (Lp-PLA$_2$) | Phospholipase | LDL-associated Lp-PLA$_2$ has proatherogenic effects. |
| Creatine phospokinase (CK-MB) | Enzyme | Useful as early detection of myocardial infarction. |
| Myeloperoxidase (MPO) | Heme enzyme | Activates metallo-proteases and promotes destabilization of plaque. |
| Myoglobulin | Heme protein | Released upon tissue necrosis. |
| CD40L | Protein | Released in the early stages of atherogenesis through to plaque rupture. Elevated in stroke. |
| Troponin T (TnT) | Protein | Tool for risk stratification. |
| Heart-Type Fatty Acid-binding protein (H-FABP) | Protein | H-FARB is released from the heart immediately after infarction. |
| Microalbuminurea | Protein | Marker of vascular endothelial dysfunction. |
| Low density lipoprotein cholesterol (LDL-C) | Lipoprotein | Transport cholesterol in the blood. |
| High Density lipoprotein cholersterol (HDL-C) | Lipoprotein | Holds antioxidant and antiinflammatory properties. |
| Triglyceride | Lipid | |
| PIIINP | Procollagen | Marker of type III collagen turnover. |

Thus, a range of different biochemical markers have been suggested as markers of cardiovascular events. Wang et al (2006) have measured 10 different biochemical markers in 3200 patients participating in the Framingham study, described in Table 1. The conclusion was that the measurement of 10 biochemical markers only contributes moderately to diagnosis over and above standard risk factors. Of the 10 biochemical markers, B-type natriuretic peptide level, C-reactive protein level and the urinary albumin-to-creatinine ratio showed the best correlation between marker and death/cardiovascular events (Wang et al.).

C-Reactive Protein

C-reactive protein (CRP) is an acute phase serum protein produced by the liver in response to different clinical conditions such as, inflammation, infection, or trauma (Gabay & Kushner 1999). The production of CRP is induced by cytokines such as IL-6, released from the affected or damaged tissues. The physiological role of CRP is yet unknown and discussions on its pro- or anti-inflammatory actions are ongoing.

There is accumulating evidence that the CRP is a risk factor for CVD in humans. In a study by Ridker et al. 2002, CRP was shown to be a better predictor of future cardiovascular events than LDL cholesterol, in a large population consisting of 28,000 healthy women followed for eight years for the occurrences of acute myocardial infarction, stroke, coronary revascularization, or death from CVD. Many other studies have also reported that baseline CRP levels constitute an independent risk factor for cardiovascular events (Thompson et al. 1995, Mendall et al. 1996, Kuller et al. 1996, Ridker et al. 1997, Tracy et al. 1997, Ridker et al. 2000).

It has been speculated that circulating CRP only reflects the general inflammation occurring in the atherosclerotic process and is not an active component in the pathogenesis of the disease. However, several lines of evidence also support the view that CRP has a role in atherogenesis. First, chronic infections giving rise to CRP are also associated with increased risk for CVD (Leinonen & Saikku 2002). Secondly, we and others have identified CRP is in different levels of atherosclerotic lesions (Reynolds & Vance 1987, Hatanaka et al. 1995). Finally, CRP has been shown to have proatherogenic properties in vitro: CRP may activate endothelial cells to produce adhesion molecules (Pasceri et al. 2000). It may also decrease the production of eNOS in endothelial cells (Venugopal et al. 2002) and enhance the uptake of LDL by macrophages (Zwaka et al. 2001).

Brain Natriuretic Peptide

Brain (B-type) natriuretic peptide (BNP) is a peptide hormone secreted by the ventricles of the heart in response to excessive stretching of cardiac myocytes in the ventricles. T-proBNP (the inactive N-terminal fragment) is, along with the active hormone (BNP), released to the blood stream upon cleavage of proBNP. Both BNP and NT-proBNP have been suggested as potential biochemical markers of cardiovascular events (Wang et al.).

Chemokines

Chemokines are also potential markers of CVD; chemokines are low molecular weight cytokines produced in inflammation. One major chemokine in relation to CVD is monocyte chemo attractant protein 1 (MCP-1). MCP-1 appears to play an early and important role in the recruitment of monocytes to atherosclerotic lesions. In a study using a monkey model of atherosclerosis, plasma concentrations of MCP-1 were highly associated with plaque size and plaque complications (Register et al.).

Lipids Including Cholesterol

Recently much attention has been directed to the measurement of cholesterol concentrations in serum; both total cholesterol, as well as the concentrations of low-density lipoprotein cholesterol (LDL-C) and the high-density lipoprotein cholesterol (HDL-C). Among lipoprotein markers, there have been at least two noteworthy advances. First, LDL particle size seems to predict the degree of atherosclerosis progression. Increased concentrations of small LDL particles are more related to CVD risk than increased concentrations of large particles (Gardner et al). Secondly, the cholesteryl oleate content of LDL particles may become a particularly important marker of CVD risk. In monkeys, enrichment of lipoprotein particle cores with cholesteryl oleate was strongly and positively associated with more severe coronary artery atherosclerosis (Rudel et al) and was additive to the contributions of LDL and HDL cholesterol concentrations. These findings in experimental animals are further supported by earlier human studies (Lawrie et al) that showed plasma lipoproteins with lower proportions of cholesteryl linoleate (and conversely higher proportions of cholesteryl oleate) are typical of patients with complications of CHD (coronary heart disease) compared to normal controls.

The level of HDL-C is strongly related to triglyceride, and high triglyceride level is correlated to a higher risk of CHD. A cohort study by Jeppesen et al) found high TG/low HDL-C as the strongest risk factors of IHD (ischemic heart disease).

These lipid profiles are important for evaluation of risk factors, but do not allow understanding and measurement of the molecular events associated with plaque turnover. A number of biochemical markers have been suggested as risk factors for CVD, although these are not the specific products of the disease. These include CRP and ApoE.

Lipoproteins

The biomarker most commonly used to predict CVD is cholesterol concentration (both total and the cholesterol/HDL ratio). These are used along with other risk factors, such as blood pressure and level of LDL. Both factors are used in the previously mentioned SCORE-model. The level of LDL is important as LDL transports cholesterol in the blood and accumulation of oxidized LDL can promote atherosclerosis (Graham et al). In addition, a significant association between CHD and triglyceride (TG) levels are found, in which an increased risk of CHD was associated with increasing TG levels, independent of both LDL-C and HDL-C levels, although the level of cholesterol is viewed as one of the major risk factors of CVD (Jeppeson et al).

APO-E

Apolipoprotein E is found in chylomicrons, VLDL, and HDL. It is mainly synthesised in the liver, but also in many other organs such as brain, spleen, kidney (Siest et al. 1995). ApoE plays an essential role in lipoprotein metabolism by acting as a ligand for two receptors: the LDL receptor and Apo E specific chylomicron remnant receptor. The interaction between ApoE with these receptors gives a basis for the metabolic regulation of cholesterol. Polymorphism at the apoE gene locus results in three alleles found in most populations: ε2, ε3 and ε4 that determine six apoE phenotypes. Isoforms differ from each other by one aminoacid at positions 112 and 158. Apo E2 has cysteine on both residues and E4 has arginine at both positions. Apo E3 contains cysteine at position 112 and arginine at 158. Allele frequencies differ in different populations. Some studies have assessed the possible relationship between apoE polymorphism and atherosclerosis. A meta-analysis of 14 observation studies demonstrated ε4 allele as associated with coronary disease among both men and women (Wilson et al. 1996). Furthermore, ε4 allele has been associated with carotid artery atherosclerosis (Terry et al. 1996, Cattin et al. 1997, Haraki et al. 2002).

ApoE is 299 amino acids long and transports lipoprotein, fat soluble vitamins, and cholesterol into the lymph system and further into the blood circulation. ApoE is primarily synthesized in the liver. Currently, there are seven mammalian receptors for ApoE which belong to conserved low density lipoprotein receptor gene family.

Additional Biochemical Markers

Microalbuminurea (albumin to creatinine level) is also a potential and independent marker. The urinary albumin excretion rate is a marker of changes in the kidney and, when compared with a small creatinine elevation, it may indicate atherosclerosis (Wang et al.).

Of the procollagen markers, the marker for type III collagen turnover rate (PIIINP) has been investigated as a prognostic marker for hypertension and has been associated with myocardial infarction. Satta et al. examined the correlation between abdominal aortic aneurysm (AAA) and the concentration of the procollagen (PIIINP) in blood. They showed that the turnover of collagen type III is increased in patients with AAA and may be due to enhanced synthesis, enhanced degradation or a combination of both. In the same experiment, the carboxyterminal propeptide of type I procollagen (PICP) was measured, and there was no accelerated synthesis of type I collagen in the aneurysm sac.

Protein Profile of Plaque

Human arteries can be divided into larger or elastic arteries, medium or muscular arteries, and small arteries. The walls of arteries are composed of intima, media and adventitia, separated by the internal elastic lamina and external elastic lamina. The intima consists of connective tissue, smooth muscle cells and a few isolated macrophages. The boundaries of the intima can be defined as a layer between the luminal surface of the endothelium and the internal elastic lamina.

The arterial intima can further be divided into two layers. The inner layer, called a proteoglycan layer, composed of abundant proteoglycans, smooth muscle cells and macrophages. The lower layer, musculoelastic layer, is composed of abundant smooth muscle cells and elastic fibers. In the normal conditions, the two layers of the intima are barely visible by light microscopy, but are distinct and prominent when intimal thickening occurs. The media is the muscular part of the arterial wall, composed of smooth muscle cells, elastin, collagen fibrils.

The adventitia, outer layer, is highly microvascular and contains collagens, elastic fibrils, smooth muscle cells, and lymphatic channels.

Human atherosclerotic plaques are characterized by a lipid-rich core covered by a fibrous cap composed of fibrillar collagens, elastin, proteoglycans and SMC. Proteoglycans hyaluronan are major nonfibrillar components of the extracellular matrix that have the potential to affect lesion development by regulating events such as lipid accumulation, thrombosis, and cell proliferation and migration and by affecting the material properties of the tissue (Wight 1995). Infiltrating ApoE and CRP are also present and we have demonstrated localisation of both in atherosclerotic plaques of coronary arteries at different stages of the atherosclerotic disease.

ApoE and CRP Distribution in Human Beings

Table 2 below shows the distribution of ApoE and CRP in the human body.

TABLE 2

| Protein | Sites of expression |
| --- | --- |
| APOE | Blood, Serum, Plasma, Liver, Saliva, Monocyte, Cerebellum, Cerebrospinal Fluid, Frontal Cortex, Hippocampus, Temporal Cortex |
| CRP | Blood, Kidney, Liver, Peritoneal Fluid, Plasma, Serum |

Table 3 below illustrates known interactions of ApoE and CRP with proteins demonstrated in vivo and/or in vitro.

TABLE 3

| Protein | Interactions with proteins |
| --- | --- |
| ApoE | Albumin, Amyloid beta A4 protein, Macroglobulin, Microtubule associated protein tau, LDL receptor, Cathepsin B, Neurofilament 3, Phospholipid transfer protein, Prion protein, VLDL receptors, Scavenger receptors class B, |

TABLE 3-continued

| Protein | Interactions with proteins |
|---|---|
| CRP | Serum amyloid P, Complement factor H, Fibronectin 1, Histone 1, FC gamma RI, FC gamma RIIb, CD32, Platelet glycoprotein VI, Leptin.<br>Non protein interaction: Calcium, Cholesterol |

Collagen Distribution in Human Beings

Collagen is widely distributed in the human body, i.e. ~30% of the protein mass in the human body is composed of collagen. In Table 4, the major collagen types are listed with their major tissue distribution.

TABLE 4

| Collagen type | Tissue distribution |
|---|---|
| I | Skin, bone, tendon, ligament, cornea |
| II | Cartilage, vitreous |
| III | Skin, vessel, intestine, uterus |
| IV | Basement membranes |
| V | Bone, skin, cornea, placenta |
| VI | Bone, cartilage, cornea, skin, vessel |
| VII | Skin, bladder, oral mucosa, umbilical cord, amnion |
| VIII | Descemet's membrane, vessel, bone, brain, heart, kidney, skin, cartilage |
| XIII | Endothelial cells, skin, eye, heart, skeletal muscle |
| XIV | Vessel, bone, skin, cartilage, eye, nerve, tendon, uterus |
| XXI | Vessel, heart, stomach, kidney, skeletal muscle, placenta |

Type I collagen is the most abundant collagen and is found in most connective tissue. It is especially important for the structure of bone and skin. The major content of collagen in the human body is distributed in the skin and bone, where the major collagenous components are type I and III collagens. Collagen type III is a major component of large arteries, and is also found in smaller amounts in tissues rich type I collagen. In addition, collagen type IV is found in the basement membrane and around blood vessels and nerves. The most common localization of type V collagen is within the characteristic collagen fibrils, in association with the collagen type I and III (Garrone et al).

Some collagens have a restricted tissue distribution: for example, type II, which are found almost exclusively in cartilage (Mayne R.).

Collagen fibrils often consist of more than one collagen type. For example, the type I collagen fibrils often contain small amounts of types III, V and XII, whereas the type II collagen fibrils of cartilage also contain types IX and XI.

Collagens in Arteries

In arteries, six types of collagen are found (types I, III, IV, V, VI and VIII), where type I and III are the most abundant, 80-90% of collagen content. Type I and III are also predominant in the vessel wall. They appear to be co-distributed in different amounts within all three layers of the artery wall, synthesis of collagen type I and III tends to be located in the intima (Mayne R).

Collagens and Other Structural Proteins in Plaque—Turnover

During development of atherosclerotic plaques collagen is accumulated in the fibrous cap (Stary H. C.). In a study by Katsuda et al (1992) collagen types I, III and IV were found in the thickening intima at all stages of the lesion in aortic human tissues. Collagen type VI was distributed in the basement membrane in the region of intimal cells and in advanced lesions also detected around the elongated SMC. Earlier studies of type I and III have provided evidence of an equal distribution in atherosclerotic arterial wall (Shekhonin et al). According to McCullagh et al (1980) type III is the predominant collagen in normal human aortic media (appr. 70% of the extractable collagen). A recent study by Eriksen et al (2006) found a decrease of total collagen content in human aortic valve depending on the degree of stenosis. The molecular mechanism of stenosis is thought to be similar to atherosclerosis. In healthy aortic valves, the collagen content is mainly type I and III. During stenosis, the total content of collagen decreases, which is presumably caused by an increased turnover of collagen type I. Type I collagen accounted for approximately 60-70% of total collagen; whereas the proportion of type III collagen was 30-40% both in healthy valves and in calcified valves.

Type V collagen also increases in advanced atherosclerotic lesions and is distributed throughout the extracellular matrix in both aortic media and in the subendothelial region of the plaques (McCullagh et al).

There seems to be a consensus that the main collagen types to be found in atherosclerotic plaque are type I and III, whether they are equally distributed in healthy and atherosclerotic vessel remains to be further investigated.

In the study by Katsuda et al (1992) no collagen was detected in the center of the atheroma of more advanced lesions.

Elastin

Elastin is one of the most stable proteins in the body and is found in most connective tissue caused by its elasticity and resilience. Elastin dominates the protein content of the arterial wall, where it is the major extracellular matrix protein.

Elastin is the main component in elastic fibers and is related to calcification. Vascular calcification occurs at two distinct sites within the vessel wall: the intima and the media. Intimal calcification is related to atherosclerosis, mainly within the necrotic core. Calcified elastic fiber constitutes the plaque shoulder where the plaques are most prone to rupture; suggesting that calcification of elastic fiber may affect plaque stability (Bobryshev Y. V.). In atherosclerosis, the content of elastic fibers decreases along with lipid deposition, this generates an enhanced susceptibility to elastin degrading enzymes. Thereby the content of elastin in contrast to collagen decreases as the lesion develops.

Distribution of Elastin in Human Beings

Table 5 shows the distribution of Elastin in the human body.

TABLE 5

| Protein | Sites of expression |
|---|---|
| Elastin | Aorta and other Blood vessels, Lung, Skin Fibroblasts |

Table 6 illustrates known interactions of Elastin with proteins demonstrated in vivo and/or in vitro.

TABLE 6

| Protein | Interactions with proteins |
|---|---|
| Elastin | Decorin, Elastase, Fibrillin, Fibulin, Lysozyme, Lysyl Oxidase, Galectin, Biglycan, Nidogen, Ficolin, Proteinase3. |

Proteoglycans as Matrix Components

Proteoglycans (PG) are polysaccharide-protein macromolecules localized predominately in the intercellular matrix of vessel wall (Salisbury and Wagner 1981). PGs are macromolecules characterized by the presence of one, or more, long un-branched and highly polyanionic sugar side chains called GAGs, covalently attached to a core protein through a link region. The repeating unit of the GAG consists of an amino sugar, either N-acetyl-glucosamine (GlcNAc) or N-acetyl-galactosamine (GaINAc), and a hexuronic acid, either glucuronic acid (GlcA) or iduronic acid (IdoA). One or both of the sugars in the repeating unit contain one or more sulfate groups (Rodríguez-Lee 2007). In addition to the GAG chains, most core proteins carry N- and/or O-linked oligosaccharides.

Classification and Nomenclature of PGs

PGs are a very heterogeneous group of macromolecules. A single type of core protein can vary in the number and type of attached GAG chains. The length of the chains and the arrangement of the sulfated residues along the chains vary also.

Four main classes of GAGs are distinguished according to the structure of the repeating disaccharide unit: chondroitin sulfate (CS) and dermatan sulfate (DS), heparin sulfate (HS) and heparin, hyaluronan, and keratin sulfate (KS).

Hyaluronan is the simplest of GAGs. In contrast to all of the others, it does not contain any sulfated sugars. All of its disaccharide units are identical, its chain length is enormous and it is not linked to any core protein.

KS is a sulfated polylactosamine chain. KS-I has originally been described in cornea, and is N-linked to aspargine residues in the core protein, whereas KS-II or cartilage KS, is O-linked to serine or threonine residues (Funderburgh 2000). PGs can be classified according to several parameters:

Attached GAG chain (CS/DS- or HS containing PGs)
Topographic distribution in relation to the cell (extracellular and basement membrane PGs, cell-associated PGs or intracellular PGs)
Core protein homology (hyalectans, small leucine-rich PGs (SLRPs)

Chondroitin/dermatan sulfate PGs (Versican, aggrecan, neurocan, and brevican) belong to the family of hyaluronan-binding proteoglycans. This gene family is collectively termed hyalectans. Each family member has a characteristic distribution, with aggrecan prominent in cartilage, neurocan and brevican prominent in the central nervous system, and versican present in a variety of soft tissues, including arterial walls. The gene and protein structure of versican follows a domain template. The amino-terminal globular end (G1) binds to GAG hyaluronan, and the carboxy-terminal globular domain (G3) resembles the selectin family of proteins, consisting of a C-type lectin adjacent to two epidermal growth factor (EGF) domains and a complement regulatory region. The middle region of versican core protein is encoded by two large exons that specify the CS attachment regions of versican. The region encoded by exon 7 is called αGAG, whereas the region encoded by exon 8 is called βGAG. Four mRNA transcripts arise from alternative splicing of versican, giving rise to V0, V1, V2, and V3 which differ in the length of the core protein and the number of attached GAGs (Dours-Zimmermann and Zimmermann). The number of potential GAG attachment sites in human versican is: 17-23 for V0, 12-15 for V1, 5-8 for V2, and none for V3 (Wight 617-23).

Decorin and biglycan are members of SLRP-family that comprises at least nine members grouped into three classes (I, II, and III) and different subfamilies. They are all characterized by the presence of a central domain containing leucine-rich repeats to achieve strong presence of a central domain containing leucine-rich repeats to achieve strong protein-protein interactions. Decorin and biglycan are members of class I, and show highest amino-acid homology of the family (~57%) and are the only SLRPs with a propeptide. The propeptide is highly conserved across species and may function as a recognition sequence for xylosyltransferase, the first enzyme involved in synthesis of the GAG chain.

Versican, decorin, and biglycan are the major CS/DS PGs in the matrix of the mammalian arterial wall (Wight et al. 1986). The size of Versican V0 core protein is 370 kDa, which makes it roughly 10 times larger than decorin 36 kDa and biglycan 38 kDa. Side-chains show a wide range of sizes, but generally average around 40-90 kDa each.

Heparan sulfate proteoglycans: HSPGs are divided into five distinct classes of cell-associated and pericellular PGs and they account for at least 95% of the HS of mammalian cell surfaces, basement membranes and ECMs. The cell-associated HSPGs include integral membrane syndecans and anchored glypicans. Pericellular HSPGs include mainly perlecan, agrin. These PGs are termed pericellular because of their close association with the plasmamembrane via integrins (Whitelock and Iozzo).

Perlecan is a modular HSPG that is expressed in nearly all basement membranes as well as mesenchymal organs and connective tissues and is one of the largest single-chain polypeptides found in vertebrate and invertebrate animals. The five modules of perlecan and its HS side-chains take part in a large number of molecular interactions such as with fibroblast growth factor-2, vascular endothelial growth factor (VEGF), platelet-derived growth factor (PDGF), and other matrix proteins. The core protein of human perlecan is ~470 kDa and, together with numerous O-linked oligosaccharides and four HS side chains, it can reach a molecular weight of over 800 kDa (Knox and Whitelock).

Proteoglycan Distribution

Proteoglycans (PGs) are macromolecules distributed almost everywhere in the human body. The structure and size of PGs vary extremely. The basic structure of all PGs includes a core protein and at least one, but often many carbohydrate chains glycosaminoglycans (GAGs). PGs can be found intracellularly, on the surface of cells, and in the extracellular matrix. The structural diversity of PGs suggests numerous biological functions, see Table 7.

TABLE 7

| Proteoglycan family | Proteoglycan | Distribution | Function |
|---|---|---|---|
| Keratan sulphate - Small leucine rich PG | Lumican | Cornea | Collagen fibril organization and growth. Corneal transparency. Epithelial cell migration and tissue repair. |
| Chondroitin sulphate | Versican | Smooth muscle cells of blood vessels. Epithelial cells of skin. Cells of central and peripheral nervous system. | Cell adhesion, migration and proliferation. |
| Dermatan Sulphate (Small leucine rich PGs) | Decorin | Connective tissue. Artery wall. | Plays a role in matrix assembly. |
| | Biglycan | Extracellular matrix tissue: bone, cartilage, tendon, arteries. | Role in mineralization of the bone. |

TABLE 7-continued

| Proteoglycan family | Proteoglycan | Distribution | Function |
|---|---|---|---|
| Heparan sulphate | Perlecan | Extracellular matrix of blood vessels. | Binds to and cross-links many extracellular matrix components and cell-surface molecules. |
| Chondroitin sulphate - Large aggregating PG | Aggrecan | Cartilage. Extracellular matrix. | Gives tissues ability to resist compressive loads. |

Table 7 above gives an overview of PG distribution and function.

Proteoglycans in Arteries

At least five types of PGs are present in the extracellular matrix of the artery wall; versican—which interacts with hyaluronan to form large aggregates; small-leucine rich decorin and biglycan, which interact with fibrillar matrix components like collagen and elastin; heparan sulphate—perlecan, which is a component of basal lamina and keratin sulphate—lumican (Talusan et al.).

Versican is one of several ECM molecules that accumulate in lesions of atherosclerosis. Although a number of studies indicate that versican is clearly capable of binding to LDL, versican is generally not detected in the lipid-rich center of the necrotic core (Evanko et al.).

Lumican has been shown to directly bind to macrophages and to enhance macrophage migration. Lumican may therefore directly influence macrophage behavior in the vascular intima as well as stimulate the formation of the necrotic core, characteristic of advanced atherosclerotic lesions (Funderburgh et al. 1997).

Biglycan is found in the fibrous cap. Versican and biglycan have affinity for LDL and form insoluble complexes, which accelerates oxidation of LDL. Biglycan may contribute to the pathogenesis of atherosclerosis by trapping lipoproteins in the artery wall. Changes in the proteoglycan metabolism of the intima of arteries constitute the initial lesions of atherosclerosis and the accumulation of proteoglycans play a fundamental role in the progression of atherosclerosis (Kunz J.).

Perlecan was reported in human intimal hyperplasia as one of the central components of intimal extracellular matrix, by mass spectrometry-based analysis and by immunohistochemistry.

Table 8 illustrates distribution of some PGs in immunohistochemical stainings of PGs in normal and atherosclerotic arteries (Evanko et al).

TABLE 8

| PG or GAG | Normal Vessel | | Fibrous Core | | | | |
|---|---|---|---|---|---|---|---|
| | Endothelial cells | SMCs | Endothelial cells | SMC's | Macrophages | Fibrous Cap | Plaque core |
| Perlecan | +++ | ++ | +++ | +++ | ++ | + | +++ |
| Decorin | + | ++ | + | + | +++ | + | +++ |
| Biglycan | −/+ | ++ | ++ | +++ | + | +++ | −/+ |
| Versican | − | ++ | −/+ | +++ | − | +++ | − |
| Hyaluronan | ++ | + | ++ | +++ | +++ | +++ | +++ |

Staining results:
− undetectable;
−/+ variably detectable;
+ detectable;
++ moderate;
+++ strong Proteoglycan Involvement in Matrix Remodelling A study of atherosclerosis progression in nonhuman primates has demonstrated that accumulation of specific PGs varies with lesion severity and with the distribution of cells and growth factors, suggesting that different PGs play distinct roles during progression of atherosclerosis. Different levels of specific PGs may directly affect material properties of the tissue via their contribution to altering structural arrangements of fibrous matrix components such as elastin and collagen.

Versican and hyaluronan show similar localization in the matrix, suggesting aggregate formation between the two in the atherogenesis. The marked increase in versican and hyaluronan in early lesions could suggest that they play a role in early atherosclerotic lesions, such as proliferation and migration of SMCs and leukocytes. Furthermore, versican and hyaluronan are principal matrix components of human restenotic lesions and have been shown to contribute to neo-intimal thickening after vascular injury in vitro. An abundance of versican early in atherogenesis could also predispose the extracellular matrix to increase lipid entrapment due to the binding of lipoproteins to chondroitin sulphate chains of versican. This idea is supported by co-localization of versican with apoprotein (a) and apolipoprotein E in transplant arteriopathy (Evanko et al). Loss of versican from the plaque may result in matrix instability.

This is further evidenced by upregulation of versican gene observed after vascular injury. Versican was also here identified in all stages of atherogenesis; in the intima of early developing plaques, but also throughout advanced lesions and at the borders of lipid-filled necrotic cores as well as at the plaque-thrombus interface (Wight and Merrilees 2005). These observations implicate versican in lipid accumulation, inflammation, and thrombosis. Furthermore, versican plays an important role in the assembly of ECM and in control of elastic fiber fibrillogenesis, which is of fundamental importance in ECM remodelling during vascular disease (Wight and Merrilees 2005).

The role of biglycan in arterial cell biology is unclear. Some immunohistochemical studies have shown biglycan association with collagen I and III staining in human restenotic lesions (Evanko et al.).

The importance of biglycan as matrix protein was further stated by the generation of BALB/cA mice homozygous for a null mutation of the biglycan gene, where 50% of biglycan-deficient male mice died suddenly within the first 3 months of life as a result of from aortic rupture. This observation suggests biglycan to be essential for the structural and functional integrity of the aortic wall, as well as a potential role of biglycan gene defects in the pathogenesis of aortic dissection and rupture in humans. (Heegaard et al. 2007)

Other studies indicate that biglycan is a major PG associated with elastin in primate arteries; these observations are similar to those of in human coronary arteriopathy (Evanko et al).

Decorin has been shown to bind to collagen and regulate collagen fibril formation (Brown and Vogel) (Danielson et al.).

Protease Profiles

Proteases hydrolyse peptide bonds and are responsible for the degradation of extracellular matrix proteins such as collagen, proteoglycans and elastin in atheroma, see Table 9. In atherosclerotic plaques three main types are found: metalloproteinases (i.e. MMPs), serine proteases and cysteine proteases (i.e. cathepsins). Cathepsins and MMPs are responsible for degradation of all extracellular matrix proteins. As matrix is essential for plaque stability, its removal from the fibrous cap by proteases may invoke plaque rupture (Stary H. C.).

In Table 9 a variety of proteases found in atherosclerotic plaque are listed.

TABLE 9

Proteases detected in atherosclerotic plaques.

| Protease | Degradation substrates |
| --- | --- |
| Cathepsin K | Proteoglycans, elastin, collagen |
| Cathepsin S | Proteoglycans, elastin, collagen |
| Cathepsin L | Proteoglycans, Collagen type I |
| Cathepsin B | Proteoglycans |
| MMP-1 | Collagen type I, II and III |
| MMP-2 | Proteoglycans, elastin |
| MMP-3 | Proteoglycans, collagen type III, elastin |
| MMP-8 | Proteoglycans, collagen type I, II and III |
| MMP-9 | Elastin, collagen type I and III |
| MMP-13 | Proteoglycans, collagen type I, II and III |
| MMP-18 | Collagen type I |

The main source of MMP expression in the plaque is suspected to be related to macrophage and SMC activity. Macrophages in plaques contain abundant MMP-1, -8, -9, and -13 and co-localize with sites of collagen and proteoglycan degradation in situ (Kunz J.). Furthermore, own data suggest localization of MMP-8 and Cathepsin K in atherosclerotic plaques.

Matrix Metalloproteinases (MMP)

MMP is a large group of endopeptidases, capable of degrading most components of the ECM. Presently, more than 25 MMPs have been identified. Metallo-proteinases are characterized by an active site containing a metal atom, typically zinc, and are secreted as zymogens. Specific tissue inhibitors, TIMPs, regulate the activity of MMPs. A great variety of MMPs are found in the atherosclerotic plaques. They are most often located in macrophages bordering the fibrous cap, within plaque shoulders in SMC and macrophages and are rarely identified within the fibrous cap (Kunz J.).]

MMPs are classified in different groups according to their substrate specificity: Collagenases, which degrade fibrillar collagen, like collagen type I, II, III and V but also proteoglycans; Gelatinases, which degrade proteoglycans, collagen type IV, V, VII and elastin; Stromelysin that is active against proteoglycans and elastin (Rouis M). These three subgroups are of particular interest with regards to matrix remodelling in atherosclerotic plaques.

Gelatinases

Insoluble elastin is digested by MMP-2 and -9, both belonging to the gelatinase-family of MMPs. MMP-9 has an important role affecting the size and composition of atherosclerotic plaque. In unstable human atherosclerotic plaques and in vulnerable regions of plaques, greater expression and concentration of MMP-9 have been observed. Moreover, MMP-9 is found intracellularly (indicating active synthesis) in coronary plaques more often in patients with unstable angina compared with those with stable angina. Blood MMP-9 level increases in association with coronary atherosclerosis and predicts adverse cardiovascular events (Sundstrom and Vasan). A recent study by Kuzuya et al (2006) indicates that MMP-2 is responsible for accumulation of SMC in the fibrous cap and thereby inducing plaque instability.

Stromelysin

MMP-3 belongs to the stromelysin proteases and is capable of degrading both elastin and proteoglycans. A study by Yamada et al (2002) indicates that MMP-3 may prove to be a reliable mean of predicting the genetic risk of myocardial infarction in women.

Collagenases

MMP-1, -8 and -13 have all been identified in atherosclerotic plaques where they degrade proteoglycans and collagen types I and III.

MMP-1, -8 and -13 are collagenases, which cleave collagen into two fragments that are further degraded by MMP-2, -3 or -9.

MMP-8 is expressed by neutrophils, not commonly found in human atheroma but has been identified in atherosclerotic plaques. MMP-8 may be partly responsible for degradation of the fibrous cap as MMP-8 has a preference for collagen type I (Herman et al), having a three fold greater activity in degradation of collagen I than MMP-1 and 13. This is supported by Turu et al (2006), in this study the content of MMP-8 in the plasma are significantly higher for patients with vulnerable plaques, than patients with stable plaques.

MMP-13 has been reported to cleave SLRPS, with high specificity for biglycan. Degradation of biglycan by MMP-13 at a specific cleavage site ( . . . $G_{177}/V_{178}$) has previously been demonstrated by Monfort et al. (2005) and proposed to play a important role in early detection of cartilage degradation in osteoarthritis.)

Cathepsins

Human cysteine cathepsins consist of 11 members, including cathepsins B, K, L, and S, and are predominantly expressed within the endosomal/lysosomal compartments of cells. Cathepsins are capable of catalysing the hydrolytic breakdown of proteoglycans, collagen and elastin.

In abdominal aortic aneurysm (AAA) high levels of cathepsins S, K, and L were found compared to normal aorta. Normal human vascular SMC contain no detectable cathepsin K by immunostaining, but cells within atherosclerotic plaques are clearly positive. Cathepsin K is localized in rupture-prone areas such as the fibrous cap, plaque shoulders and at the actual site of plaque ruptures (Chapman et al). Cathepsin S is found to co-localize with regions of increased elastin breakdown in atherosclerotic plaques, and reduced atherosclerosis is observed in cathepsin S- and K-deficient mice (Liu et al).

Figure 1:
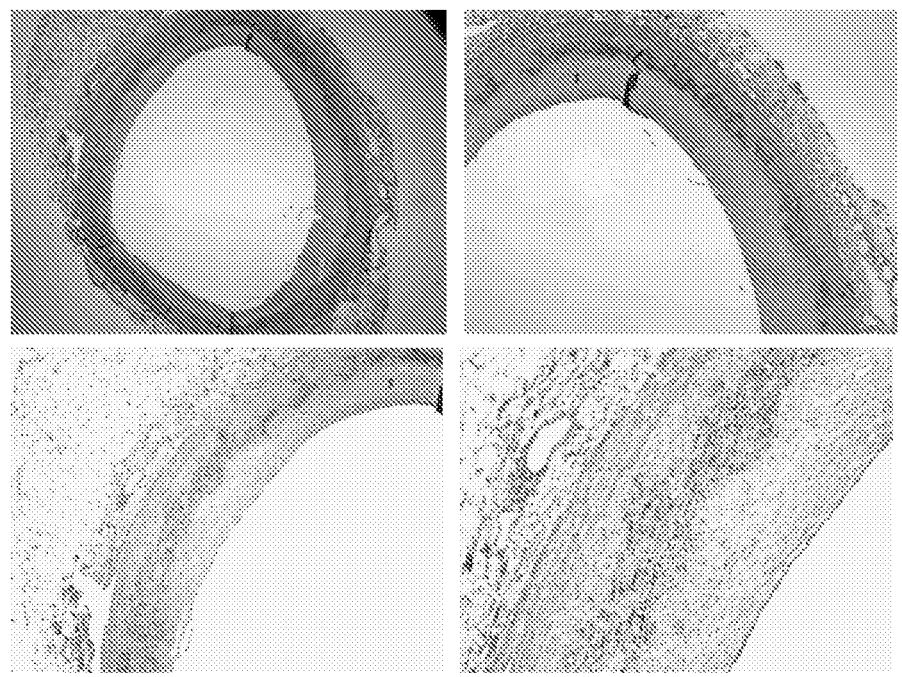
FIG. 1 shows Biglycan staining (magnifications 2, 4, 4 and 10× respectively) using a monoclonal mouse antibody on an aortic sample with type III lesion.

Both cathepsin L and K degrade several proteoglycans and collagen type I and II, cathepsin K degrades within covalently cross-linked triple helices, while cathepsin L cleaves only in the nonhelical telopeptide regions. Cathepsin K is localized in the fibrous cap and plaque shoulder. Cathepsin K expression in normal arteries is very low. Early human atherosclerotic lesions showed cathepsin K expression in the intimal and medial SMCs. In advanced atherosclerotic plaques, cathepsin K was localized mainly in macrophages and SMCs of the fibrous cap (Lutgens et al). Cathepsin K protein levels were increased in atherosclerotic lesions when compared with normal arteries, whereas cathepsin K mRNA levels were similar in both atherosclerotic and normal arteries. Furthermore, it was shown that cathepsin K mRNA and protein levels were highest in advanced but stable human atherosclerotic plaques compared with early atherosclerotic lesions and lesions containing thrombus (Chapman et al).

Cathepsin S is only sparsely expressed in intimal and medial SMCs in early human atherosclerotic lesion and fatty streaks. In advanced human atherosclerotic plaques cathepsin S was localized in macrophages and SMCs of the fibrous cap. EC lining the lumen of the vessel itself and the plaque microvessels also expressed cathepsin S. Furthermore, cathepsin S mRNA and protein levels were increased in human atheroma compared with normal arteries (Lutgens et al). Cathepsin S can degrade proteoglycans, elastin and collagen (Liu et al).

Presently, the determination of CVD risk is occurring at a late stage in atherosclerosis progression; a point in which there is a significant risk of fibrous plaque rupture. There is a need for diagnostic or prognostic assays that will provide information regarding atherosclerosis or CVD risk at both earlier stage and late stages. The findings of Katsuda et al (1992) suggest that there are enzymatic mechanisms for removal of collagens from advanced lesions, suggesting indeed a major role of neo-epitopes in arteriosclerosis.

The present invention provides a method of bioassay for the quantification of peptide fragments comprising a neo-epitope formed by cleavage of a protein of an atherosclerotic plaque by a proteinase, said method comprising contacting a sample comprising said peptide fragments with an immunological binding partner having specific binding affinity for a said neo-epitope and determining the level of binding of said immunological binding partner to peptide fragments in said sample.

The result of said assay may produce an index indicative of the degree of risk in a particular patient of rupture of an atherosclerotic plaque or of the vulnerable status of the atherosclerotic plaques of a patient.

Patients having a value for said index above a threshold level may be recommended for further investigation by plaque imaging methods (including those discussed above) or for the prescribing of medication for treatment of atherosclerosis or for surgical treatment of atherosclerosis, and such follow up investigations or treatment may form part of the method of the invention.

Proteins of the atherosclerotic plaque include lumican, versican, perlecan, decorin, biglycan, collagen type III, CRP, ApoE and elastin. Collagen type I is not considered to be proteins of the atherosclerotic plaque. Proteins present in the atherosclerotic plaque which are exposed there to proteases to a higher degree than elsewhere in the body are of particular interest.

Said immunological binding partner may have specific binding affinity for peptide fragments comprising a C-terminal neo-epitope or an N-terminal neo-epitope.

Proteoglycan Assays

Said peptide fragments may be fragments of proteoglycans versican (SEQ ID NO 1), lumican (SEQ ID NO 2), perlecan (SEQ ID NO 3), biglycan (SEQ ID NO 4) and decorin (SEQ ID NO 5), which are all identified in normal and atherosclerotic arteries. Proteoglycans are some of the main proteins constituting atherosclerotic plaques and plaque cap together with elastin and collagens. The content of proteoglycans varies during the progression of atherosclerosis, which makes the potential neo-epitopes of proteoglycans a good marker of disease staging and disease progression. Since especially versican and lumican are not abundant in many other organs, this makes them more specific biochemical marker candidates.

Several candidate proteases may be responsible for the digestion of proteoglycans in the plaque, as the literature reports many different proteases in the atherosclerotic plaques. Most likely, this is the result of a large range of complicated processes eventually leading to plaque rupture. However, in our assessment, early phases may consist of a range of MMPs, whereas later stages may rely more on cathepsin degradation of the matrix, resulting in different neo-epitope profiles dependent on the stages of the disease. We have determined that the enzymes listed in table 4 generate lumican, versican, biglycan, perlecan and decorin resulting in at least following cleavage products:

TABLE 4

Protease generated peptides

| Protease | | SEQ ID NO |
|---|---|---|
| Biglycan | | |
| MMP-3 | K*SVPKEISPDTTLLDLQNNDISE*L | 6 |
| MMP-3 | L*KSVPKEISPDTTLLDLQNNDISE*L | 7 |
| MMP-9 | E*NSGFEPGAFDGLKLNYLRISEAK*L | 8 |

TABLE 4-continued

Protease generated peptides

| Protease | | SEQ ID NO |
|---|---|---|
| MMP-9 | G*LKSVPKEISPDTTLLDLQNNDISE*L | 9 |
| MMP-12 | Y*LRISEAKLTGIPKDLPET*L | 10 |
| MMP-13 | G*LKSVPKEISPDTTLLDLQNNDISE*L | 11 |
| MMP-13 | *LTGIPKDLPETLNELHLDHNKIQAIE* | 12 |
| ADAMTS4 | K*RISEAKLTGIPKDLPETLNE*L | 13 |
| ADAMTS4 | Q*AIELEDLLRYSK*L | 14 |
| ADAMTS4 | Q*AIELEDLLRY*S | 15 |
| ADAMTS4 | S*EAKLTGIPKDLPETLNE*L | 16 |
| ADAMTS4 | -*LKAVPKEISPDTILLDLQNNDISE*L | 17 |
| MMP-8 | T*LLDLQNNDISELRKDD*F | 18 |
| MMP-8 | A*IELEDLLRYS*K | 19 |
| CathepsinS | E*NSGFEPGAFDGLK*L | 20 |
| Decorin | | |
| MMP-12 | M*IVIELGTNPLK*S | 21 |
| MMP-3 | E*DEASGIGPEVPDDR*D | 22 |
| MMP-3 | E*LHLDGNKISRVDAAS*L | 23 |
| MMP-3 | L*VNNKISKVSPGAFTPL*V | 24 |
| MMP-3 | A*LILVNNKISKVSPGAFTPLVKLER*L | 25 |
| MMP-9 | F*SNPVQYWEIQPSTFR*C | 26 |
| CathepsinK | K*SSGIENGAFQGMK*K | 27 |
| CathepsinK | K*SSGIENGAFQGMKKLS*Y | 28 |
| ADAMTS1 | N*KITEIKDGDFK*N | 29 |
| ADAMTS1 | Q*GLPPSLTELHLDGNK*I | 30 |
| Versican | | |
| Unknown | K*LLASDAGLYR*C | 31 |
| Unknown | *LATVGELQAAWR*N | 32 |
| Unknown | K*ETTVLVAQNGNIK*I | 33 |
| Lumican | | |
| Unknown | -*SLEDLQLTHNK*I | 34 |
| Unknown | R*LKEDAVSAAFK*G | 35 |
| Perlecan | | |
| Unknown | R*SIEYSPQLEDAGSR*E | 36 |
| Unknown | R*LEGDTLIIPR*V | 37 |
| ADAMTS4 | E*VSEAVVEKLEPEYR*- | 38 |
| ADAMTS4 | R*EVSEAVVEKLEPEYR*- | 39 |
| ADAMTS4 | R*SIEYSPQLED*A | 40 |

-cleavage products of proteoglycans.
*indicates a site of cleavage.

Accordingly, in a method of the invention, said peptide fragments preferably comprise a neo-epitope formed by cleavage of versican, lumican, perlecan, decorin or biglycan by a protease at a site marked by the sign * in any one of the above partial sequences thereof.

Also, in a method of the invention, said peptide fragments preferably comprise a neo-epitope formed by cleavage of following proteoglycans: versican, lumican, perlecan, decorin and biglycan; by a (or more) protease(s) at a site in any one of the following partial sequences of versican, lumican, decorin, perlecan, and biglycan, or the immunological binding partner is specifically reactive with one of the following sequences:

TABLE 10

Peptide fragments of proteoglycan cleavage.

| Sequence | SEQ ID NO |
|---|---|
| SVPKEISPDTTLLDLQNNDISE | 41 |
| KSVPKEISPDTTLLDLQNNDISE | 42 |
| NSGFEPGAFDGLKLNYLRISEAK | 43 |
| LKSVPKEISPDTTLLDLQNNDISE | 44 |
| LRISEAKLTGIPKDLPET | 45 |
| LKSVPKEISPDTTLLDLQNNDISE | 46 |
| LTGIPKDLPETLNELHLDHNKIQAIE | 47 |
| IVIELGTNPLK | 48 |
| LLASDAGLYR | 49 |
| LATVGELQAAWR | 50 |
| ETTVLVAQNGNIK | 51 |
| SLEDLQLTHNK | 52 |
| LKEDAVSAAFK | 53 |
| SIEYSPQLEDAGSR | 54 |
| LEGDTLIIPR | 55 |
| RISEAKLTGIPKDLPETLNE | 56 |
| AIELEDLLRYSK | 57 |
| AIELEDLLRY | 58 |
| EAKLTGIPKDLPETLNE | 59 |
| LKAVPKEISPDTTLLDLQNNDISE | 60 |
| LLDLQNNDISELRKDD | 61 |
| IELEDLLRYS | 62 |
| NSGFEPGAFDGLK | 63 |
| DEASGIGPEVPDDR | 64 |
| LHLDGNKISRVDAAS | 65 |
| VNNKISKVSPGAFTPL | 66 |
| LILVNNKISKVSPGAFTPLVKLER | 67 |
| SNPVQYWEIQPSTFR | 68 |

TABLE 10-continued

Peptide fragments of proteoglycan cleavage.

| Sequence | SEQ ID NO |
|---|---|
| SSGIENGAFQGMK | 69 |
| SSGIENGAFQGMKKLS | 70 |
| KITEIKDGDFK | 71 |
| GLPPSLTELHLDGNK | 72 |
| VSEAVVEKLEPEYR | 73 |
| EVSEAVVEKLEPEYR | 74 |
| SIEYSPQLEDASAKEFR | 75 |

Preferably, said immunological binding partner is not reactive with intact versican, lumican, decorin, perlecan, and biglycan. Preferably, said immunological binding partner is not reactive with a said sequence listed above if prolonged past the respective c-terminal and N-terminal ends of generated fragments.

The immunological binding partner may be one specifically reactive with a C-terminal or N-terminal neo-epitope formed by cleavage of type versican, lumican, decorin, perlecan, and biglycan.

Suitable immunological binding partners may therefore be specifically reactive with any of the following sequences in Table 11 at the N terminal of a peptide:

TABLE 11

N-terminal sequences of protease generated peptide fragments of proteoglycans.

| | | SEQ ID NO |
|---|---|---|
| Biglycan | SVPKEI | 76 |
| | NSGFEP | 77 |
| | LKSVPK | 78 |
| | LRISEA | 79 |
| | GLKLNY | 80 |
| | LKSVPK | 81 |
| | QCSDLG | 82 |
| | LTGIPK | 83 |
| | RISEAK | 84 |
| | AIELED | 85 |
| | EAKLTG | 86 |
| | LKAVPK | 87 |
| | LLDLQN | 88 |
| | IELEDL | 89 |
| | NSGFEP | 90 |

TABLE 11-continued

N-terminal sequences of protease generated peptide fragments of proteoglycans.

| | | SEQ ID NO |
|---|---|---|
| Decorin | IVIELG | 91 |
| | NGLNQM | 92 |
| | DEASGI | 93 |
| | LHLDGN | 94 |
| | VNNKIS | 95 |
| | LILVNN | 96 |
| | SNPVQY | 97 |
| | SSGIEN | 98 |
| | KITEIK | 99 |
| | GLPPSL | 100 |
| Versican | LLASDA | 101 |
| | LATVGE | 102 |
| | ETTVLV | 103 |
| | SLTVVK | 104 |
| | ENQDAR | 105 |
| | NGFDQC | 106 |
| Lumican | SLEDLQ | 107 |
| | LKEDAV | 108 |
| | HLQHNR | 109 |
| | LQHNRL | 110 |
| Perlecan | SIEYSP | 111 |
| | LVNFTR | 112 |
| | VSEAVV | 113 |
| | EVSEAV | 114 |
| | SIEYSP | 115 | or with any of the following sequences in Table 12, at the C-terminal of a peptide:

TABLE 12

C-terminal fragments of protease generated peptide fragments of proteoglycans.

| | | SEQ ID NO |
|---|---|---|
| Biglycan | NNDISE | 116 |
| | RISEAK | 117 |
| | LRKDDF | 118 |

TABLE 12-continued

C-terminal fragments of protease generated peptide fragments of proteoglycans.

|  |  | SEQ ID NO |
|---|---|---|
|  | KDLPET | 119 |
|  | LNELHL | 120 |
|  | YWEVQP | 121 |
|  | KIQAIE | 122 |
|  | PETLNE | 123 |
|  | LLRYSK | 124 |
|  | EDLLRY | 125 |
|  | NNDISE | 126 |
|  | ELRKDD | 127 |
|  | DLLRYS | 128 |
|  | AFDGLK | 129 |
| Decorin | GTNPLK | 130 |
|  | SSGIEN | 131 |
|  | EVPDDR | 132 |
|  | RVDAAS | 133 |
|  | GAFTPL | 134 |
|  | LVKLER | 135 |
|  | QPSTFR | 136 |
|  | AFQGMK | 137 |
|  | GMKKLS | 138 |
|  | KDGDFK | 139 |
|  | HLDGNK | 140 |
| Versican | CDVMYG | 141 |
|  | NGFDQC | 142 |
|  | QNGNIK | 143 |
|  | IGQDYK | 144 |

TABLE 12-continued

C-terminal fragments of protease generated peptide fragments of proteoglycans.

|  |  | SEQ ID NO |
|---|---|---|
| Lumican | QLTHNK | 145 |
|  | VSAAFK | 146 |
|  | GLKSLE | 147 |
| Perlecan | EDAGSR | 148 |
|  | EFREVS | 149 |
|  | VAQQDS | 150 |
|  | LEPEYR | 151 |
|  | SAKEFR | 152 |

Further cleavage sites defining neo-epitopes that may be assayed in a similar manner can be identified by exposing proteoglycans or other atherosclerotic plaque proteins to any of the enzymes described herein and isolating and sequencing peptides thereby produced.

Collagen Assays

Said peptide fragments may be fragments of Type III collagen (SEQ ID NO 153), preferably of mature Type III collagen, i.e. not of collagen type III propeptide. The main proteins in the atherosclerotic plaques are collagen type I and III as well as elastin, whereas proteoglycan contributes only to a minor extent to the matrix of the plaque. Of the three major proteins found in atherosclerotic plaques collagen type I and III are dominant, whereas elastin dominates the protein profile in arteries, but not the main protein component in the plaque. Collagen type I is abundant throughout the human body, whereas type III has a more restricted tissue location, and thereby in our view constitutes a more specific candidate as biochemical marker.

Several candidate proteases may be responsible for the digestion of collagen in the plaque as the literature reports many different proteases in the atherosclerotic plaque. Most likely, this is the result of the large range of complicated processes eventually leading to plaque rupture. However, in our assessment, early phases may consist of a range of MMPs, whereas later stages may rely more on cathepsin K degradation of the matrix, resulting in different neo-epitope profiles dependent on the levels of disease. We have determined that the enzymes listed in the following table cleave type III collagen at at least the following cleavage sites (marked *):

| Protease | Neo-Epitope | SEQ ID NO |
|---|---|---|
| MMP-1 | A*GIPGAPGLMGARGPPGPA*G | 154 |
| MMP-1 | K*GDPGPPGIPGRNGDPGI*P | 155 |
| MMP-1 | G*LAGPPGMPGPRGSPGPQG*V | 156 |
| MMP-1 | G*ERGLPGPPGIKGPAGIPGF*P | 157 |
| MMP-1 | G*IAGITGARGLAGPPGMPGPR*G | 158 |
| MMP-1 | G*IKGHRGFPGNPGAPGSPGPAG*Q | 159 |
| MMP-1 | A*RGLAGPPGMPGPRGSPGPQGV*K | 160 |

-continued

| Protease | Neo-Epitope | SEQ ID NO |
|---|---|---|
| MMP-1 | I*TGARGLAGPPGMPGPRGSPGPQG*V | 161 |
| MMP-1 | I*TGARGLAGPPGMPGPRGSPGPQGV*K | 162 |
| MMP-1 | G*ITGARGLAGPPGMPGPRGSPGPQG*V | 163 |
| MMP-1 | G*VKGESGKPGANGLSGERGPPGPQG*L | 164 |
| MMP-1 | G*SRGAPGPQGPRGDKGETGERGAAG*I | 165 |
| MMP-1 | P*KGDAGQPGEKGSPGAQGPPGAPGPLG*I | 166 |
| MMP-1 | G*ITGARGLAGPPGMPGPRGSPGPQGV*K | 167 |
| MMP-1 | G*LRGGAGPPGPEGGKGAAGPPGPPGAAGTPG*L | 168 |
| MMP-1 | G*HAGAQGPPGPPGINGSPGGKGEMGPAGIPGAPG*L | 169 |
| MMP-1 | A*GKSGDRGESGPAGPAGAPGPAGSRGAPGPQGPRGDKGETGERGAAG*I | 170 |
| MMP-1 | G*LQGLPGTGGPPGENGKPGEPGPKGDAGAPGAPGGKGDAGAPGERGPPG*L | 171 |
| MMP-3 | G*ERGLPGPPGIKGPAGIPGF*P | 172 |
| MMP-3 | A*VGGLAGYPGPAGPPGPPGPPGT*S | 173 |
| MMP-3 | K*DGTSGHPGPIGPPGPRGNRGER*G | 174 |
| MMP-3 | A*VGGLAGYPGPAGPPGPPGPPGTSGHPG*S | 175 |
| MMP-3 | G*IAGITGARGLAGPPGMPGPRGSPGPQG*V | 176 |
| MMP-3 | A*PGAPGGKGDAGAPGERGPPGLAGAPGLRG*G | 177 |
| MMP-3 | A*VGGLAGYPGPAGPPGPPGPPGTSGHPGSPG*S | 178 |
| MMP-2 | A*IGSPGPAGPRGPVGPSGPPG*K | 179 |
| MMP-3 and -8 | G*AIGSPGPAGPRGPVGPSGPPG*K | 180 |
| MMP-8 | P*AGQQGAIGSPGPA*G | 181 |
| MMP-8 | G*PPGVAGPPGGSGPAGPP*G | 182 |
| MMP-8 | L*AGPPGMPGPRGSPGPQG*V | 183 |
| MMP-8 | G*LSGERGPPGPQGLPGLA*G | 184 |
| MMP-8 | R*GLAGPPGMPGPRGSPGPQG*V | 185 |
| MMP-8 | G*LAGPPGMPGPRGSPGPQGV*K | 186 |
| MMP-8 | R*GLAGPPGMPGPRGSPGPQGV*K | 187 |
| MMP-8 | G*PQGPPGKNGETGPQGPPGP*T | 188 |
| MMP-8 | G*VKGERGSPGGPGAAGFPGAR*G | 189 |
| MMP-8 | A*RGLAGPPGMPGPRGSPGPQG*V | 190 |
| MMP-8 | N*GLSGERGPPGPQGLPGLAGTA*G | 191 |
| MMP-8 | A*VGGLAGYPGPAGPPGPPGPPGT*S | 192 |
| MMP-8 | G*SPGGKGEMGPAGIPGAPGLMGA*R | 193 |
| MMP-8 | T*GARGLAGPPGMPGPRGSPGPQG*V | 194 |
| MMP-8 | V*KGESGKPGANGLSGERGPPGPQG*L | 195 |
| MMP-8 | G*VKGERGSPGGPGAAGFPGARGLPGPPGSNGNPGPPGPSGSPGKDGPPGPAG*N | 196 |

| Protease | Neo-Epitope | SEQ ID NO |
|---|---|---|
| MMP-8 | G*SPGAQGPPGAPGPLGIAGITGARGLAGPPG*M | 197 |
| MMP-8 | R*GAPGEKGEGGPPGVAGPPGGSGPAGPPGPQ*G | 198 |
| MMP-8 | R*GAPGEKGEGGPPGVAGPPGGSGPAGPPGPQ*G | 199 |
| MMP-8 | G*IAGITGARGLAGPPGMPGPRGSPGPQG*V | 200 |
| MMP-9 | G*IKGPAGIPGFPG*M | 201 |
| MMP-9 | G*QPGVMGFPGPKG*N | 202 |
| MMP-9 | G*IKGPAGIPGFPGMK*G | 203 |
| MMP-9 | G*IKGPAGIPGFPGMKG*H | 204 |
| MMP-9 | I*PGAPGLMGARGPPGPAG*A | 205 |
| MMP-9 | G*ERGLPGPPGIKGPAGIP*G | 206 |
| MMP-9 | G*IPGAPGLMGARGPPGPAG*A | 207 |
| MMP-9 | G*FRGPAGPNGIPGEKGPAG*E | 208 |
| MMP-9 | P*GIPGQPGSPGSPGPPGIC*E | 209 |
| MMP-9 | G*ERGLPGPPGIKGPAGIPGF*P | 210 |
| MMP-9 | A*VGGLAGYPGPAGPPGPPGPPG*T | 211 |
| MMP-9 | G*VKGERGSPGGPGAAGFPGARG*L | 212 |
| MMP-9 | G*DAGAPGAPGGKGDAGAPGERGPPG*L | 213 |
| MMP-9 | Q*GPPGPTGPGGDKGDTGPPGPQGL*Q | 214 |
| MMP-9 | G*INGSPGGKGEMGPAGIPGAPGLM*G | 215 |
| MMP-9 | Q*GPPGEPGQAGPSGPPGPPGAIGPS*G | 216 |
| MMP-9 | P*GPPGINGSPGGKGEMGPAGIPGAP*G | 217 |
| MMP-9 | R*GLPGPPGSNGNPGPPGPSGSPGKDGPPGPAG*N | 218 |
| MMP-9 | G*KNGETGPQGPPGPTGPGGDKGDTGPPGPQG*L | 219 |
| MMP-9 | G*LPGIAGPRGSPGERGETGPPGPAGFPGAPG*Q | 220 |
| MMP-9 | G*INGSPGGKGEMGPAGIPGAPGLMGARGPPGPAG*A | 221 |
| MMP-9 | P*GINGSPGGKGEMGPAGIPGAPGLMGARGPPGPAG*A | 222 |
| MMP-9 | P*PGENGKPGEPGPKGDAGAPGAPGGKGDAGAPGERGPPG*L | 223 |
| MMP-9 | G*LKGENGLPGENGAPGPMGPRGAPGERGRPGLPGAAG*A | 224 |
| MMP-9 | G*NTGAPGSPGVSGPKGDAGQPGEKGSPGAQGPPGAPGPLG*I | 225 |
| MMP-9 | G*LMGARGPPGPAGANGAPGLRGGAGEPGKNGAKGEPGPRG*E | 226 |
| MMP-9 | G*LRGGAGPPGPEGGKGAAGPPGPPGAAGTPGLQGMPGERGGLGSPGPKG*D | 227 |
| MMP-8 and -9 | G*QQGAIGSPGPAGPRGPVGPSGPPG*K | 228 |
| MMP-9 | K*GDPGPPGIPGRNGDPGIPGQPG*S | 229 |
| MMP-9 | G*LRGGAGPPGPEGGKGAAGPPGPPG*A | 230 |
| MMP-9 | G*KNGETGPQGPPGPTGPGGDKGDTGPPGPQG*L | 231 |
| MMP-9 | G*YQGPPGEPGQAGPSGPPGPPG*A | 232 |

| Protease | Neo-Epitope | SEQ ID NO |
|---|---|---|
| MMP-9 | G*VAGPPGGSGPAGPPGPQG*V | 233 |
| MMP-8, -9 and -13 | G*DKGEPGGPGADGVPGKDGPRGPTGPIGPPGPAG*Q | 234 |
| ADAMTS-5 | Q*GHAGAQGPPGPPGIN*G | 235 |
| CathepsinK | A*GERGAPGPA*G | 236 |
| CathepsinK | A*GIPGFPGMK*G | 237 |
| CathepsinK | F*PGMKGHRGFD*G | 238 |
| CathepsinK | G*FPGARGLPGPPG*S | 239 |
| CathepsinK | A*GFPGARGLPGPPG*S | 240 |
| CathepsinK | P*PGPPGPPGTSGHP*G | 241 |
| CathepsinK | G*FPGMKGHRGFD*G | 242 |
| CathepsinK | Q*PGDKGEGGAPGLPGI*A | 243 |
| CathepsinK | R*GDKGETGERGAAGIK*G | 244 |
| CathepsinK | D*GRNGEKGETGAPGLK*G | 245 |
| CathepsinK | A*GQPGDKGEGGAPGLPGIA*G | 246 |
| CathepsinK | G*GPPGENGKPGEPGPKGD*A | 247 |
| CathepsinK | A*GIPGFPGMKGHRGFD*G | 248 |
| CathepsinK | R*GGAGEPGKNGAKGEPGPR*G | 249 |
| CathepsinK | K*GERGSPGGPGAAGFPGARGLPGPP*G | 250 |
| CathepsinK | I*PGVPGAKGEDGKDGSPGEPGANGLP*G | 251 |
| CathepsinK | G*AAGFPGARGLPGPPGSNGNPGPPGPS*G | 252 |
| CathepsinK | R*PGPPGPSGPRGQPGVMGFPGPKGN*D | 253 |
| CathepsinK | Q*GPPGPPGINGSPGGKGEMGPAGIPGAP*G | 254 |
| CathepsinK | A*GKDGESGRPGRPGERGLPGPPGIK*G | 255 |
| CathepsinK | A*GARGNDGARGSDGQPGPPGPPGTAGFPG*S | 256 |
| CathepsinK | S*PGVSGPKGDAGQPGEKGSPGAQGPPGAPG*P | 257 |
| CathepsinK | R*GSDGQPGPPGPPGTAGFPGSPGAKGEVGPA*G | 258 |
| CathepsinK | Q*GPPGPPGINGSPGGKGEMGPAGIPGAPGLM*G | 259 |
| CathepsinK | A*GPPGPPGPPGTSGHPGSPGSPGYQGPPGEPG*Q | 260 |
| CathepsinK | F*PGAPGQNGEPGGKGERGAPGEKGEGGPPGVA*G | 261 |
| CathepsinK | A*GFPGAPGQNGEPGGKGERGAPGEKGEGGPPG*V | 262 |
| CathepsinK | A*GARGNDGARGSDGQPGPPGPPGTAGFPGSPGAKGEVGPA*G | 263 |
| CathepsinK | R*GAAGEPGRDGVPGGPGMRGMPGSPGGPGSDGKPGPPGSQGESGRPGPPGPS*G | 264 |
| CathepsinS | G*IAGITGARGL*A | 265 |
| CathepsinS | AGPPGPPGAAGTPGLQGM | 266 |
| CathepsinS | N*GLSGERGPPGPQGLPG*L | 267 |
| CathepsinS | M*GARGPPGPAGANGAPGLR*G | 268 |

-continued

| Protease | Neo-Epitope | SEQ ID NO |
|---|---|---|
| CathepsinS | N*GLSGERGPPGPQGLPGLA*G | 269 |
| CathepsinS | G*IAGITGARGLAGPPGMPGPRG*S | 270 |
| CathepsinS | G*IAGITGARGLAGPPGMPGPRGSPGPQG*V | 271 |
| CathepsinS | R*GGAGPPGPEGGKGAAGPPGPPGAAGTPGLQ*G | 272 |
| CathepsinS | S*GPKGDAGQPGEKGSPGAQGPPGAPGPLG*I | 273 |
| CathepsinS | G*IAGITGARGLAGPPGMPGPRGSPGPQGVK*G | 274 |
| CathepsinS | A*VGGLAGYPGPAGPPGPPGPPGTSGHPGSPGSPGYQ*G | 275 |
| CathepsinS | E*PGPQGHAGAQGPPGPPGINGSPGGKGEMGPAGIPGAPG*L | 276 |
| ADAMTS1 | I*PGFPGMKGHR*G | 277 |
| ADAMTS1 | R*GSPGGPGAAGFPGAR*G | 278 |
| ADAMTS1 | K*GPAGIPGFPGMKGHR*G | 279 |
| ADAMTS1 | R*GLAGPPGMPGPRGSPGPQ*G | 280 |
| ADAMTS1 | A*GITGARGLAGPPGMPGPR*G | 281 |
| ADAMTS1 | L*GIAGITGARGLAGPPGMPGPR*G | 282 |
| ADAMTS1 | T*GARGLAGPPGMPGPRGSPGPQ*G | 283 |
| ADAMTS1 | Q*GPPGPPGINGSPGGKGEMGPAG*I | 284 |
| ADAMTS1 | L*PGPPGIKGPAGIPGFPGMKGHR*G | 285 |
| ADAMTS1 | A*GITGARGLAGPPGMPGPRGSPGPQ*G | 286 |
| ADAMTS1 | T*GARGLAGPPGMPGPRGSPGPQGVK*G | 287 |
| ADAMTS1 | R*GLPGPPGIKGPAGIPGFPGMKGHR*G | 288 |
| ADAMTS1 | G*RPGLPGAAGARGNDGARGSDGQPGPPG*P | 289 |
| ADAMTS1 | N*GAPGPMGPRGAPGERGRPGLPGAAGAR*G | 290 |
| ADAMTS1 | A*GSRGAPGPQGPRGDKGETGERGAAGIK*G | 291 |
| ADAMTS1 | R*GLAGPPGMPGPRGSPGPQGVKGESGKPGAN*G | 292 |
| ADAMTS1 | R*GLAGPPGMPGPRGSPGPQGVKGESGKPGANGL*S | 293 |
| ADAMTS1 | P*GPPGSNGNPGPPGPSGSPGKDGPPGPAGNTGAPGS*P | 294 |
| ADAMTS1 | T*GARGLAGPPGMPGPRGSPGPQGVKGESGKPGAN*G | 295 |
| ADAMTS1 | R*GAPGEKGEGGPPGVAGPPGGSGPAGPPGPQGVKGER*G | 296 |
| ADAMTS1 | G*GPPGVAGPPGGSGPAGPPGPQGVKGERGSPGGPAAGF*P | 297 |
| ADAMTS1 | K*SGDRGESGPAGPAGAPGPAGSRGAPGPQGPRGDKGETGERGAAGIK*G | 298 |
| ADAMTS4 | I*PGFPGMKGHR*G | 299 |
| ADAMTS4 | R*GLAGPPGMPGPR*G | 300 |
| ADAMTS4 | G*PQGLQGLPGTGGPP*G | 301 |
| ADAMTS4 | K*GPAGIPGFPGMKGHR*G | 302 |
| ADAMTS4 | R*GLAGPPGMPGPRGSPGPQG*V | 303 |
| ADAMTS4 | G*GPPGENGKPGEPGPKGDAGAP*G | 304 |
| ADAMTS4 | A*PGFRGPAGPNGIPGEKGPAGER*G | 305 |
| ADAMTS4 | E*KGSPGAQGPPGAPGPLGIAGITGAR*G | 306 |

-continued

| Protease | Neo-Epitope | SEQ ID NO |
|---|---|---|
| ADAMTS4 | L*PGPPGIKGPAGIPGFPGMKGHR*G | 307 |
| ADAMTS4 | R*GAPGFRGPAGPNGIPGEKGPAGER*G | 308 |
| ADAMTS4 | R*GLPGPPGIKGPAGIPGFPGMKGHR*G | 309 |
| ADAMTS4 | R*GPVGPSGPPGKDGTSGHPGPIGPPGPR*G | 310 |
| ADAMTS4 | A*PGPQGPRGDKGETGERGAAGIKGHR*G | 311 |
| ADAMTS4 | R*GAPGPQGPRGDKGETGERGAAGIKGHR*G | 312 |
| ADAMTS4 | R*GFPGNPGAPGSPGPAGQQGAIGSPGPAGPR*G | 313 |
| ADAMTS4 | L*PGPPGIKGPAGIPGFPGMKGHRGFDGR*N | 314 |
| ADAMTS4 | D*AGQPGEKGSPGAQGPPGAPGPLGIAGITGAR*G | 315 |
| ADAMTS4 | R*GPTGPIGPPGPAGQPGDKGEGGAPGLPGIAGPR*G | 316 |
| ADAMTS4 | K*GDAGQPGEKGSPGAQGPPGAPGPLGIAGITGAR*G | 317 |
| ADAMTS4 | R*NGEKGETGAPGLKGENGLPGENGAPGPMGPR*G | 318 |
| ADAMTS4 | A*PGFRGPAGPNGIPGEKGPAGERGAPGPAGPRGA*A | 319 |
| ADAMTS4 | R*GAPGFRGPAGPNGIPGEKGPAGERGAPGPAGPR*G | 320 |
| ADAMTS4 | R*GSPGERGETGPPGPAGFPGAPGQNGEPGGKGER*G | 321 |
| ADAMTS4 | G*HAGAQGPPGPPGINGSPGGKGEMGPAGIPGAPGLMG*A | 322 |
| ADAMTS4 | R*GLAGPPGMPGPRGSPGPQGVKGESGKPGANGLSGER*G | 323 |
| ADAMTS8 | L*GIAGITGARGL*A | 324 |
| ADAMTS8 | I*PGFPGMKGHR*G | 325 |
| ADAMTS8 | R*GLAGPPGMPGPR*G | 326 |
| ADAMTS8 | Q*GPPGAPGPLGIAGITGAR*G | 327 |
| ADAMTS8 | A*GITGARGLAGPPGMPGPR*G | 328 |
| ADAMTS8 | A*GIPGAPGLMGARGPPGPAGAN*G | 329 |
| ADAMTS8 | R*GLAGPPGMPGPRGSPGPQGVKG*E | 330 |
| ADAMTS8 | K*GSPGAQGPPGAPGPLGIAGITGAR*G | 331 |
| ADAMTS8 | L*PGPPGIKGPAGIPGFPGMKGHR*G | 332 |
| ADAMTS8 | K*DGTSGHPGPIGPPGPRGNRGER*G | 333 |
| ADAMTS8 | A*GITGARGLAGPPGMPGPRGSPGPQ*G | 334 |
| ADAMTS8 | R*GLAGPPGMPGPRGSPGPQGVKGESG*K | 335 |
| ADAMTS8 | R*GLAGPPGMPGPRGSPGPQGVKGESGKPGAN*G | 336 |
| ADAMTS8 | R*GLAGPPGMPGPRGSPGPQGVKGESGKPGANGL*S | 337 |
| ADAMTS8 | P*GPPGSNGNPGPPGPSGSPGKDGPPGPAGNTGAPGS*P | 338 |
| ADAMTS8 | R*GAPGEKGEGGPPGVAGPPGGSGPAGPPGPQGVKGER*G | 339 |
| ADAMTS8 | K*SGDRGESGPAGPAGAPGPAGSRGAPGPQGPRGDKGETERGA*A | 340 |
| ADAMTS8 | R*GAPGEKGEGGPPGVAGPPGGSGPAGPPGPQGVKGERGSPGGPGAAGFPGAR*G | 341 |

-continued

| Protease | Neo-Epitope | SEQ ID NO |
|---|---|---|
| MMP9 | _*AIGPSG_____*_ | 342 |
| unknown | -AGGFAP* | 781 |

Accordingly, in a method of the invention, said peptide fragments preferably comprise a neo-epitope formed by cleavage of Type III collagen by a protease at a site marked by the sign * in any one of the above partial sequences of Type III collagen.

Also, in a method of the invention, said peptide fragments preferably comprise a neo-epitope formed by cleavage of collagen type III by a (or more) protease(s) at a site in any one of the above partial sequences of collagen type III between the *s, or the immunological binding partner is specifically reactive with a sequence extending between the *s in any entry in the above table.

Preferably, said immunological binding partner is not reactive with intact type III collagen. Preferably, said immunological binding partner is not reactive with a said sequence listed above if prolonged past the respective cleavage site.

The immunological binding partner may be one specifically reactive with a C-terminal or N-terminal neoepitope formed by cleavage of type III collagen.

Suitable immunological binding partners may therefore be specifically reactive with any of the following sequences at the N terminal of a peptide: (Sequence ID Nos follow each sequence)

| | | | | |
|---|---|---|---|---|
| GIPGAP 343 | GDPGPP 408 | LAGPPG 470 | ERGLPG 534 | IAGITG 598 |
| IKGHRG 344 | RGLAGP 409 | TGARGL 471 | | ITGARG 599 |
| VKGESG 345 | SRGAPG 410 | KGDAGQ 472 | ITGARG 535 | LRGGAG 600 |
| HAGAQG 346 | GKSGDR 411 | LQGLPG 473 | ERGLPG 536 | KDGTSG 763 |
| DGTSGH 347 | VGGLAG 412 | IAGITG 474 | PGAPGG 537 | VGGLAG 601 |
| IGSPGP 348 | AIGSPG 413 | AGQQGA 475 | GPPGVA 538 | AGPPGM 602 |
| LSGERG 349 | GLAGPP 414 | LAGPPG 476 | GLAGPP 539 | PQGPPG 603 |
| VKGERG 350 | RGLAGP 415 | GLSGER 477 | VGGLAG 540 | SPGGKG 604 |
| GARGLA 351 | KGESGK 416 | VKGERG 478 | SPGAQG 541 | GAPGEK 605 |
| GAPGEK 352 | IAGITG 417 | IKGPAG 479 | QPGVMG 542 | IKGPAG 606 |
| IKGPAG 353 | PGAPGL 418 | ERGLPG 480 | IPGAPG 543 | FRGPAG 607 |
| GIPGQP 354 | ERGLPG 419 | VGGLAG 481 | VKGERG 544 | DAGAPG 608 |
| GPPGPT 355 | INGSPG 420 | GPPGEP 482 | GPPGIN 545 | GLPGPP 609 |
| KNGETG 356 | LPGIAG 421 | INGSPG 483 | GINGSP 546 | PGENGK 610 |
| LKGENG 357 | NTGAPG 422 | LMGARG 484 | LRGGAG 547 | QQGAIG 611 |
| GDPGPP 358 | LRGGAG 423 | KNGETG 485 | YQGPPG 548 | VAGPPG 612 |
| DKGEPG 359 | GHAGAQ 424 | GERGAP 486 | GIPGFP 549 | PGMKGH 613 |
| FPGARG 360 | GFPGAR 425 | PGPPGP 487 | FPGMKG 550 | PGDKGE 614 |
| GDKGET 361 | GRNGEK 426 | GQPGDK 488 | GPPGEN 551 | |
| GGAGEP 362 | GERGSP 427 | PGVPGA 489 | AAGFPG 552 | |
| GPPGPP 363 | GKDGES 428 | GARGND 490 | PGVSGP 553 | GSDGQP 615 |
| | | PGAPGQ 491 | GFPGAP 554 | GARGND 616 |
| GAAGEP 365 | IAGITG 429 | GPPGPP 492 | GLSGER 555 | GARGPP 617 |
| GLSGER 366 | | IAGITG 493 | GGAGPP 556 | GPKGDA 618 |
| IAGITG 367 | GPKGDA 430 | | VGGLAG 557 | PGPQGH 619 |
| PGFPGM 368 | GSPGGP 431 | GPAGIP 494 | GLAGPP 558 | |
| GIAGIT 369 | | GPPGPP 495 | PGPPGI 559 | GITGAR 620 |

| | | | | |
|---|---|---|---|---|
| GARGLA 370 | GLPGPP 432 | RPGLPG 496 | GAPGPM 560 | GSRGAP 621 |
| GLAGPP 371 | | GPPGSN 497 | GARGLA 561 | GAPGEK 622 |
| GPPGVA 372 | SGDRGE 433 | PGFPGM 498 | GLAGPP 562 | PQGLQG 623 |
| GPAGIP 373 | GLAGPP 434 | GPPGEN 499 | PGFRGP 563 | KGSPGA 624 |
| PGPPGI 374 | GAPGFR 435 | GLPGPP 500 | GPVGPS 564 | PGPQGP 625 |
| GAPGPQ 375 | GFPGNP 436 | PGPPGI 501 | AGQPGE 565 | GPTGPI 626 |
| GDAGQP 376 | NGEKGE 437 | PGFRGP 502 | GAPGFR 566 | GSPGER 627 |
| HAGAQG 377 | GLAGPP 438 | GIAGIT 503 | PGFPGM 567 | |
| GPPGAP 378 | GITGAR 439 | GIPGAP 504 | GLAGPP 568 | GSPGAQ 628 |
| | DGTSGH 440 | GITGAR 505 | | GLAGPP 629 |
| GLAGPP 379 | GPPGSN 441 | GAPGEK 506 | SGDRGE 569 | GAPGEK 630 |
| AIGPSG 380 | | | | | or with any of the following sequences at the C-terminal of a peptide:

| | | | | |
|---|---|---|---|---|
| GPPGPA 381 | NGDPGI 442 | SPGPQG 507 | AGIPGF 570 | GMPGPR 631 |
| SPGPAG 382 | PGPQGV 443 | PPGPQG 508 | ERGAAG 571 | PGPLGI 632 |
| AAGTPG 383 | IPGAPG 444 | ERGPPG 509 | PGPPGT 572 | GNRGER 633 |
| TSGHPG 384 | SPGPQG 445 | APGLRG 510 | HPGSPG 573 | PSGPPG 634 |
| PSGPPG 385 | GSPGPA 446 | GPAGPP 511 | SPGPQG 574 | GLPGLA 635 |
| | QGPPGP 447 | SPGPQG 512 | GLAGTA 575 | PGPPGT 636 |
| PGLMGA 386 | | LAGPPG 513 | GPPGPQ 576 | GPPGPQ 637 |
| SPGPQG 387 | IPGFPG 448 | FPGPKG 514 | GFPGMK 577 | FPGMKG 638 |
| | GPAGIP 449 | PPGPAG 515 | EKGPAG 578 | GPPGIC 640 |
| PPGPPG 388 | FPGARG 450 | | PGPQGL 579 | GAPGLM 641 |
| GAIGPS 389 | GIPGAP 451 | | FPGAPG 580 | |
| PPGPAG 390 | ERGPPG 452 | LPGAAG 516 | APGPLG 581 | EPGPRG 642 |
| SPGPKG 391 | PSGPPG 453 | IPGQPG 517 | | |
| PPGPAG 392 | GPPGIN 454 | GAPGPA 518 | GFPGMK 582 | GHRGFD 643 |
| LPGPPG 393 | GTSGHP 455 | GHRGFD 519 | PGLPGI 583 | GAAGIK 644 |
| GAPGLK 394 | GLPGIA 456 | PGPKGD 520 | GHRGFD 584 | GEPGPR 645 |
| GLPGPP 395 | GANGLP 457 | GPPGPS 521 | PGPKGN 585 | GIPGAP 646 |
| GPPGIK 396 | TAGFPG 458 | PPGAPG 522 | GEVGPA 586 | GAPGLM 647 |
| GPPGVA 397 | EGGPPG 459 | GEVGPA 523 | GPPGPS 587 | TGARGL 648 |
| TPGLQG 398 | PQGLPG 460 | GAPGLR 524 | GLPGLA 588 | MPGPRG 649 |
| GTPGLQ 399 | APGPLG 461 | GPQGVK 525 | GSPGYQ 589 | GMKGHR 650 |
| GFPGAR 400 | GSPGPQ 462 | GMPGPR 526 | EMGPAG 590 | GPQGVK 651 |
| QPGPPG 401 | GAAGAR 463 | GAAGIK 527 | GKPGAN 591 | PGANGL 652 |
| TGAPGS 402 | GVKGER 464 | PGAAGF 528 | GMPGPR 592 | GTGGPP 653 |
| SPGPQG 403 | GDAGAP 465 | GPAGER 529 | GITGAR 593 | GPPGPR 654 |

```
GPAGPR 404    RGFDGR 466    GIAGPR 530    AGPRGA 594    GGKGER 655

APGLMG 405    GLSGER 467    TGARGL 531    GPAGAN 595    PQGVKG 656

GNRGER 406    GSPGPQ 468    VKGESG 532    GKPGAN 596    PGANGL 657

TGAPGS 407    GVKGER 469    TGERGA 533    GFPGAR 597
```

Further cleavage sites defining neoepitopes that may be assayed in a similar manner can be identified by exposing collagen type III or another atherosclerotic plaque protein to any of the enzymes described herein and isolating and sequencing peptides thereby produced.

CRP AND ApoE Assays

Said peptide fragments may be fragments of CRP (SEQ ID NO 658) or ApoE (SEQ ID NO 659). For ApoE, preferably the chosen fragments occur in all of the identified isotypes of ApoE, ε2, ε3 and ε4.

Even though both CRP and ApoE are abundant throughout the human body, their localization in the atherosclerotic tissue exposes them to the action of local proteases. These molecules are thereby good and specific candidates as biochemical markers.

Several candidate proteases may be responsible for the digestion of CRP and ApoE in the plaque as the literature reports many different proteases in the atherosclerotic plaque. Most likely, this is the result of the large range of complicated processes eventually leading to plaque rupture. However, early phases may consist of a range of MMPs, whereas later stages may rely more on cathepsin K degradation of the matrix, resulting in different neo-epitope profiles dependent on the levels of disease.

We have through a range of in vitro cleavages of pure native proteins determined that the enzymes listed in the following table cleave CRP and ApoE at least following cleavage sites (marked *):

TABLE 13

CRP and APOE fragments generated by specific proteases.

| Protease/Protein | Neo-epitope | SEQ ID NO |
|---|---|---|
| APOE + MMP3 | A*KVEQAVETEPEPELR*Q | 660 |
| APOE + MMP9 | A*KVEQAVETEPEPELR*Q | 661 |
| APOE + MMP1 | V*AEVRAKLEEQAQQI*R | 662 |
| APOE + MMP3 | A*KVEQAVETEPEPELR*Q | 663 |
| APOE + MMP3 | A*MLGQSTEELRV*R (M-oxidized) | 664 |
| APOE + ADAMTS1 | E*QAVETEPEPELR*Q | 665 |
| APOE + ADAMTS1 | R*QQTEWQSGQRWE*L | 666 |
| APOE + ADAMTS1 | L*AVYQAGAREGAERGLS*A | 667 |
| APOE + ADAMTS1 | R*AKLEEQAQQIR*L | 668 |
| APOE + ADAMTS1 | A*KLEEQAQQIRLQ*A | 669 |
| APOE + CathepsinK | A*KVEQAVETEPEPELR*Q | 670 |
| APOE + CathepsinK | K*VEQAVETEPEPELR*Q | 671 |
| APOE + CathepsinK | E*QAVETEPEPELR*Q | 672 |

TABLE 13-continued

CRP and APOE fragments generated by specific proteases.

| Protease/Protein | Neo-epitope | SEQ ID NO |
|---|---|---|
| APOE + CathepsinK | D*EVKEQVAEVRAKLE*E | 673 |
| CRP + CatK | K*ESDTSYVSLKAPLT*K | 674 |
| CRP + CatK | G*GNFEGSQSLVGDIG*N | 675 |
| CRP + MMP9 | A*LKYEVQGEVFTKPQ*L | 676 |
| CRP + MMP9 | G*IVEFWVDGKPRV*R | 677 |
| CRP + MMP1/MMP3 | R*KAFVFPKE*S | 678 |
| CRP + MMP3 | K*YEVQGEVFTKPQLWP*- | 679 |
| CRP + MMP3 | D*SFGGNFEGSQS*L | 680 |
| CRP + MMP3 | D*FVLSPDEINT*I | 681 |
| CRP + MMP3 | S*LKKGYTVGAEA*S | 682 |
| CRP + MMP3 | A*FGQTDMSRKA*F | 683 |
| CRP + MMP3 | S*LKKGYTVGAEAS*I | 684 |
| CRP + MMP3 | G*EVFTKPQLWP*- | 685 |
| CRP + MMP3 | S*IILGQEQDSFGGN*F | 686 |
| CRP + MMP3 | K*YEVQGEVFTKPQ*L | 687 |

Accordingly, in a method of the invention, said peptide fragments preferably comprise a neo-epitope formed by cleavage of CRP and ApoE by a protease at a site marked by the sign * in any one of the following partial sequences of CRP and APOE, or the immunological binding partner is specifically reactive with a sequence defined between the *s in one of the following sequences:

TABLE 14

Cleavage fragments of CRP and APOE.

| ApoE fragments | SEQ ID NO |
|---|---|
| V*AEVRAKLEEQAQQI*R | 660 |
| A*KVEQAVETEPEPELR*Q | 662 |
| A*MLGQSTEELRV*R (M-oxidized) | 664 |
| E*QAVETEPEPELR*Q | 665 |
| R*QQTEWQSGQRWE*L | 666 |
| L*AVYQAGAREGAERGLS*A | 667 |
| R*AKLEEQAQQIR*L | 668 |
| A*KLEEQAQQIRLQ*A | 669 |
| K*VEQAVETEPEPELR*Q | 671 |
| D*EVKEQVAEVRAKLE*E | 673 |

TABLE 14-continued

Cleavage fragments of CRP and APOE.

| ApoE fragments | SEQ ID NO |
|---|---|
| CRP fragments | |
| K*ESDTSYVSLKAPLT*K | 674 |
| G*GNFEGSQSLVGDIG*N | 675 |
| A*LKYEVQGEVFTKPQ*L | 676 |
| G*IVEFWVDGKPRV*R | 677 |
| R*KAFVFPKE*S | 678 |
| K*YEVQGEVFTKPQLWP*- | 679 |
| D*SFGGNFEGSQS*L | 680 |
| D*FVLSPDEINT*I | 681 |
| S*LKKGYTVGAEA*S | 682 |
| A*FGQTDMSRKA*F | 683 |
| S*LKKGYTVGAEAS*I | 684 |
| G*EVFTKPQLWP*- | 685 |
| S*IILGQEQDSFGGN*F | 686 |
| K*YEVQGEVFTKPQ*L | 687 |

Suitable immunological binding partners may therefore be specifically reactive with any of the following sequences at the N terminal of a peptide:

| APOE | SEQ ID NO | CRP | SEQ ID NO |
|---|---|---|---|
| KVEQAV | 688 | AFVFPK | 699 |
| AEVRAK | 689 | YEVQGE | 700 |
| MLGQST | 690 | KAFVFP | 701 |
| QAVETE | 691 | SFGGNF | 702 |
| QQTEWQ | 692 | FVLSPD | 703 |
| AVYQAG | 693 | LKKGYT | 704 |
| AKLEEQ | 694 | FGQTDM | 705 |
| KLEEQA | 695 | LKKGYT | 706 |
| VEQAVE | 696 | IILGQE | 707 |
| QAVETE | 697 | YEVQGE | 708 |
| EVKEQV | 698 | LKYEVQ | 709 |
| | | IVEFWV | 710 |
| | | ESDTSY | 711 |
| | | GNFEGS | 712 | or with any of the following sequences at the C-terminal of a peptide:

| APOE | | CRP | |
|---|---|---|---|
| TEPEPE | 714 | KAFVFPK | 725 |
| EQAQQI | 715 | AFVFPK | 726 |
| TEELRV | 716 | KPQLWP | 727 |
| PEPELR | 717 | FVFPKE | 728 |
| SGQRWE | 718 | PDEINT | 729 |
| EGAERG | 719 | DMSRKA | 730 |
| QAQQIR | 720 | VGAEAS | 731 |
| QQIRLQ | 721 | KPQLWP | 732 |
| EPEPEL | 722 | DSFGGN | 733 |
| PEPELR | 723 | VFTKPQ | 734 |
| EVRAKL | 724 | | |

Further cleavage sites defining neo-epitopes that may be assayed in a similar manner can be identified by exposing CRP and AppoE or another atherosclerotic plaque protein to any of the enzymes described herein and isolating and sequencing peptides thereby produced.

Elastin Assays

Said peptide fragments may be fragments of elastin (SEQ ID NO 735). Even though elastin is abundant throughout the human body, its localization in the atherosclerotic tissue exposes it to the action of local proteases, which is why these molecules are good and specific candidates as biochemical markers of atherosclerotic plaque turnover.

Several candidate proteases may be responsible for the digestion of elastin in the plaque as the literature reports many different proteases in the atherosclerotic plaque. Most likely, this is the result of the large range of complicated processes eventually leading to plaque rupture. However, early phases may consist of a range of MMPs, whereas later stages may rely more on cathepsin K degradation of the matrix, resulting in different neo-epitope profiles dependent on the levels of disease. We have through a range of in vitro cleavages of pure native proteins determined that the enzymes listed in the following table cleave elastin at at least following cleavage sites (marked *):

TABLE 15

Elastin fragments generated by specific proteases.

| Protease/Protein | Neo-epitope | SEQ ID NO |
|---|---|---|
| ADAMTS4 | A*RPGVGVGGIPTYGVGAGG*F | 736 |
| Cat K | G*LPYTTGKLPYGYGPG*G | 737 |
| Cat S | G*VAPGVGVAPGVGVAPGIGPGGVA*A | 738 |
| Cat S | G*GAGVPGVPGAIPGIGGIAGVG*T | 739 |
| ADAMTS4 | G*GAGVPGVPGAIPGIGGIAGVG*T | 740 |
| Cat K | G*VGISPEAQAAAAAK*A | 741 |
| ADAMTS1 | G*VGISPEAQAAAAAK*A | 742 |

Accordingly, in a method of the invention, said peptide fragments preferably comprise a neo-epitope formed by cleavage of elastin by a protease at a site marked by the sign * in any one of the following partial sequences of Elastin, or the immunological binding partner is specifically reactive with a sequence defined between the *s in one of the following sequences:

TABLE 16

Cleavage fragments of Elastin.

| Elastin fragments | SEQ ID NO |
|---|---|
| A*RPGVGVGGIPTYGVGAGG*F | 736 |
| G*LPYTTGKLPYGYGPG*G | 737 |
| G*VAPGVGVAPGVGVAPGIGPGGVA*A | 738 |
| G*GAGVPGVPGAIPGIGGIAGVG*T | 739 |
| G*VGISPEAQAAAAAK*A | 741 |

Suitable immunological binding partners may therefore be specifically reactive with any of the following sequences at the N terminal of a peptide:

| Elastin | SEQ ID NO |
|---|---|
| RPGVGV | 743 |
| LPYTTG | 744 |
| VAPGVG | 745 |
| GAGVPG | 746 |
| VGISPE | 747 |
| RPGVGV | 748 |
| LPYTTG | 749 | or with any of the following sequences at the C-terminal of a peptide:

| Elastin | SEQ ID NO |
|---|---|
| GVGAGG | 750 |
| YGYGPG | 751 |
| GPGGVA | 752 |
| GIAGVG | 753 |

Further cleavage sites defining neo-epitopes that may be assayed in a similar manner can be identified by exposing elastin or another atherosclerotic plaque protein to any of the enzymes described herein and isolating and sequencing peptides thereby produced.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

The term 'protein' used herein includes lipoproteins and proteoglycans and other protein-(non-protein) naturally occurring conjugates.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be a synthetic peptide or a purified native peptide formed by cleavage of the protein to which the neo-epitope belongs to reveal said neo-epitope. Thus, the peptide may be derived from any of versican, lumican, perlecan, decorin, biglycan, collagen type III, ApoE, CRP or elastin.

One suitable method could be a competition immunoassay using monoclonal antibodies or antibody binding fragments binding to neo-epitopes of fragments of any of these proteins or neo-epitopes on peptide fragments from other proteins derived from atherosclerotic plaques. Appropriately selected synthetic peptides coated onto the solid surface of a microtitre plate could compete with the sample for binding to the monoclonal antibodies or binding fragments. Alternatively, purified, native fragments from one or more of these proteins carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin. The sample may be a sample of urine, serum, blood, plasma or other, e.g. atherosclerotic plaque biopsy.

In certain preferred methods, the sample is a patient derived sample, and the method further comprises comparing the determined level of said binding of said peptide fragments with values characteristic of (a) comparable healthy individuals and/or (b) a pathological atherosclerotic condition and optionally associating a higher level of the measured peptide (normally indicated by a higher level of binding) with a more severe degree of a said condition.

An aspect of the present invention relates to the development of monoclonal antibodies recognising neo-epitopes as described above. This can be achieved by immunising mice with synthetic peptides originating from the amino acid sequence of the protein molecule concerned (including the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-prolongated form of the immunising peptide (for a C-terminal neo-epitope) or an N-terminal prolongated form of the immunising peptide (for an N-terminal neo-epitope). Antibodies for neo-epitopes may also be evaluated to establish a lack of binding capacity to native protein. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of a said protein by a protease at an end-site in any one of the partial sequences set out above, and may be for instance a monoclonal antibody or a binding fragment thereof.

The invention includes a cell line producing a monoclonal antibody against a C-terminal or N-terminal neo-epitope formed by cleavage of an atherosclerotic plaque protein at the end-sites of sequences in any one of the partial sequences o set out above.

The invention further provides a peptide comprising a C-terminal or N-terminal neo-epitope formed by cleavage of a said protein in any one of the partial sequences of these proteins set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of a said protein in any one of the partial sequences set out above.

The invention further comprises a vector comprising a nucleic acid sequence comprising an expression signal and a coding sequence which codes for the expression of a peptide comprising a C-terminal or N-terminal neo-epitope formed by cleavage of a said protein in any one of the partial sequences set out above and further includes a host cell transformed with such a vector and expressing a said peptide.

Yet another aspect of the invention relates to kits, which can be used conveniently for carrying out the methods described above. Such kits may include (1) a microtitre plate coated with synthetic peptide; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native protein fragments; (2) a monoclonal antibody recognising a neo-epitope on fragments of any one of said proteins, and reactive with said purified fragments; and (3) a labelled anti-mouse IgG immunoglobulin. Alternatively, such kits may include (1) a microtitre plate coated with streptavidin; (2) a synthetic peptide linked to biotin; (3) a monoclonal antibody recognising a neo-epitope on said protein fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin; (3) a monoclonal antibody recognising a neo-epitope on said protein fragments (and reactive with said synthetic peptide) and conjugated to horseradish peroxidase.

Thus, the invention includes an immunoassay kit comprising an immunological binding partner as described herein, and a competition agent which binds said immunological binding partner, and optionally one or more of a wash reagent, a buffer, a stopping reagent, an enzyme label, an enzyme label substrate, calibration standards, an anti-mouse antibody and instructions for conducting a said immunoassay.

The assays described herein are useful in the diagnosis of atherosclerotic disease in patients. In addition, the tests are useful for the assessment of disease progression, and the monitoring of response to therapy. The immunological binding partners of the invention may also be used in immunostaining to show the presence or location of cleavage products of any atherosclerotic plaque protein described herein.

Example 1

For analysis of localization of proteoglycans and proteases we performed immunohistochemical stainings of human arterial samples derived from left coronary descending arteries (LAD).
In the following, co-localization of Cathepsin K protease and biglycan is demonstrated.

Figure 2:
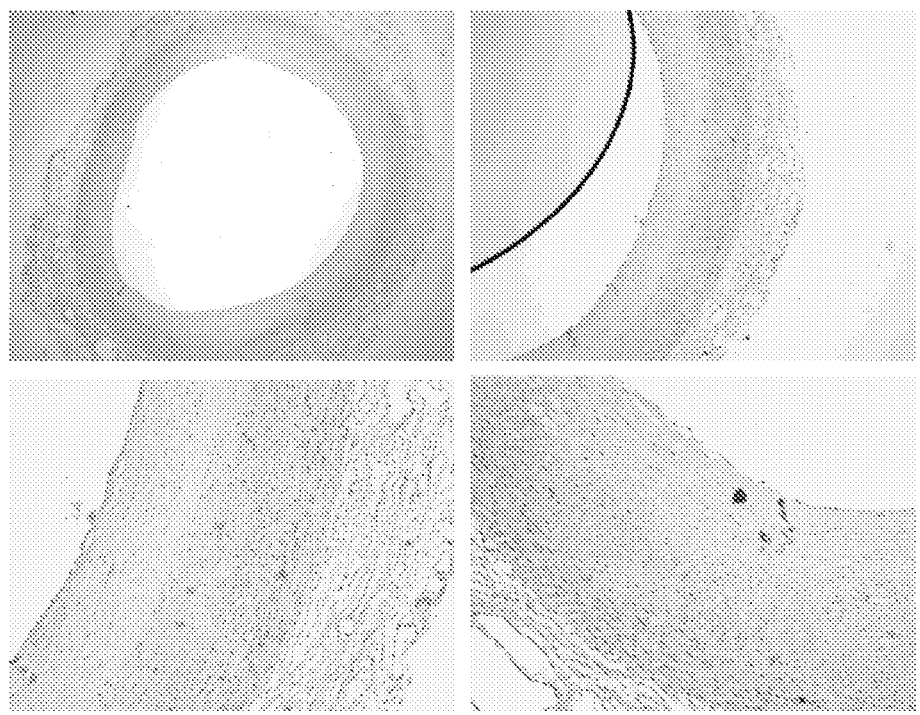
FIG. 2 shows Cathepsin K staining (magnifications 2, 4, 10 and 10× respectively) using a monoclonal mouse antibody on an aortic sample with type III lesion.
Figure 3:
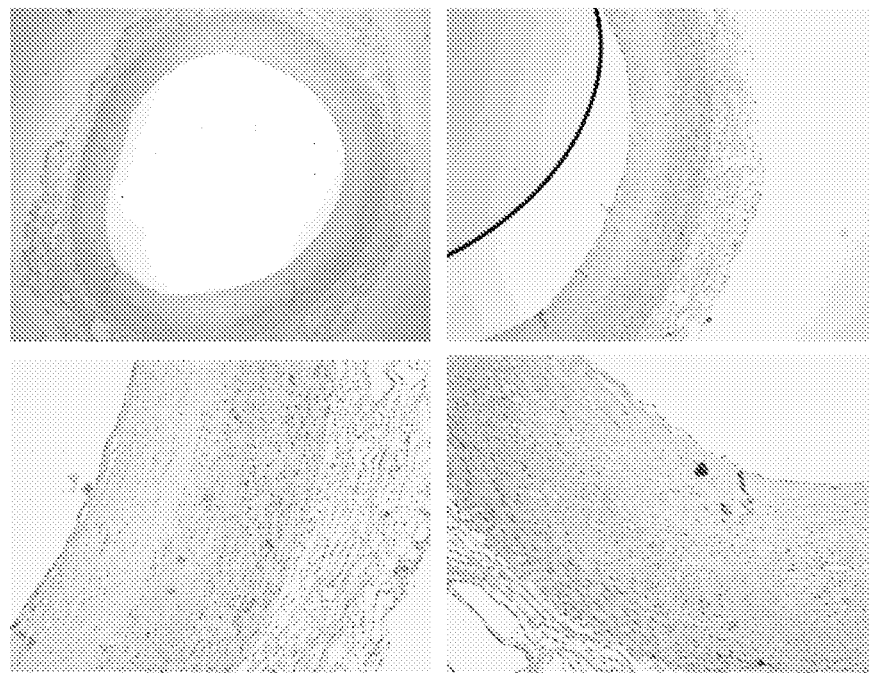
FIG. 3 shows Biglycan staining (magnifications 2, 4, 10 and 10× respectively) using a monoclonal mouse antibody on an aortic sample with type V lesion.
Figure 4:
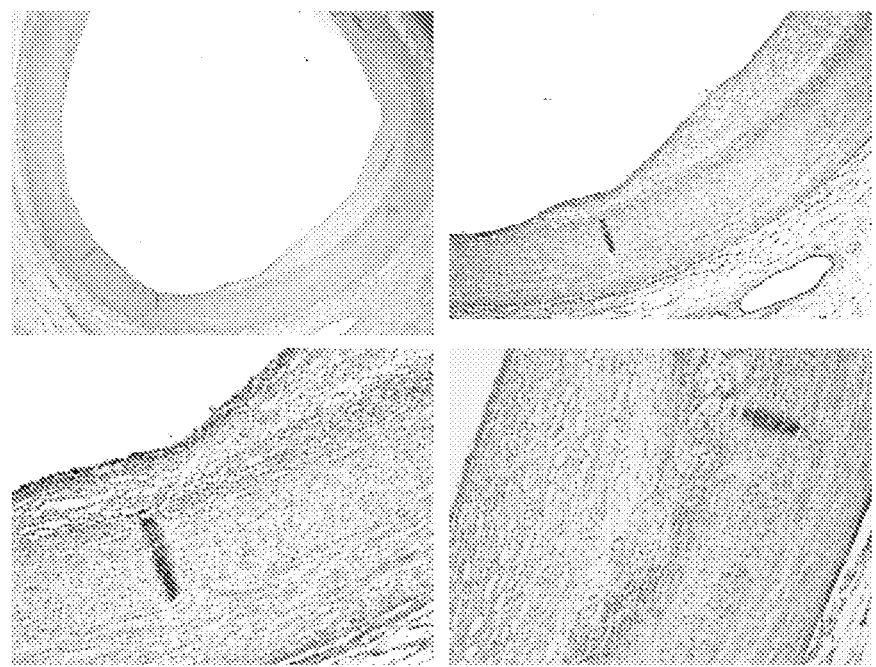
FIG. 4 shows Cathepsin K staining (magnifications 2, 4, 10 and 10× respectively) using a monoclonal mouse antibody on an aortic sample containing type V lesion.

Immunohistochemical staining as seen in FIGS. 1 and 2 revealed a co-localization of biglycan and cathepsin K. This may suggest that biglycan is a preferred substrate of cathepsin K. The same immunohistochemical staining was performed on the aortic samples, where the atherosclerotic plaque was formed and as a result of this normal aortic architecture was replaced by macrophage foam cell infiltrates and calcifications. The results of these immunostainings are collected in FIGS. 3 and 4.

Immunohistochemical staining of biglycan and cathepsin K were shown to co-localize in a progressed atherosclerotic lesion. These results together generate hypothesis of specific cathepsin K cleavage sites in biglycan, resulting in increased neo-epitope generation in atherosclerotic lesions. To test this hypothesis, we cleaved biglycan with different proteases.

Example 2

Figure 5:
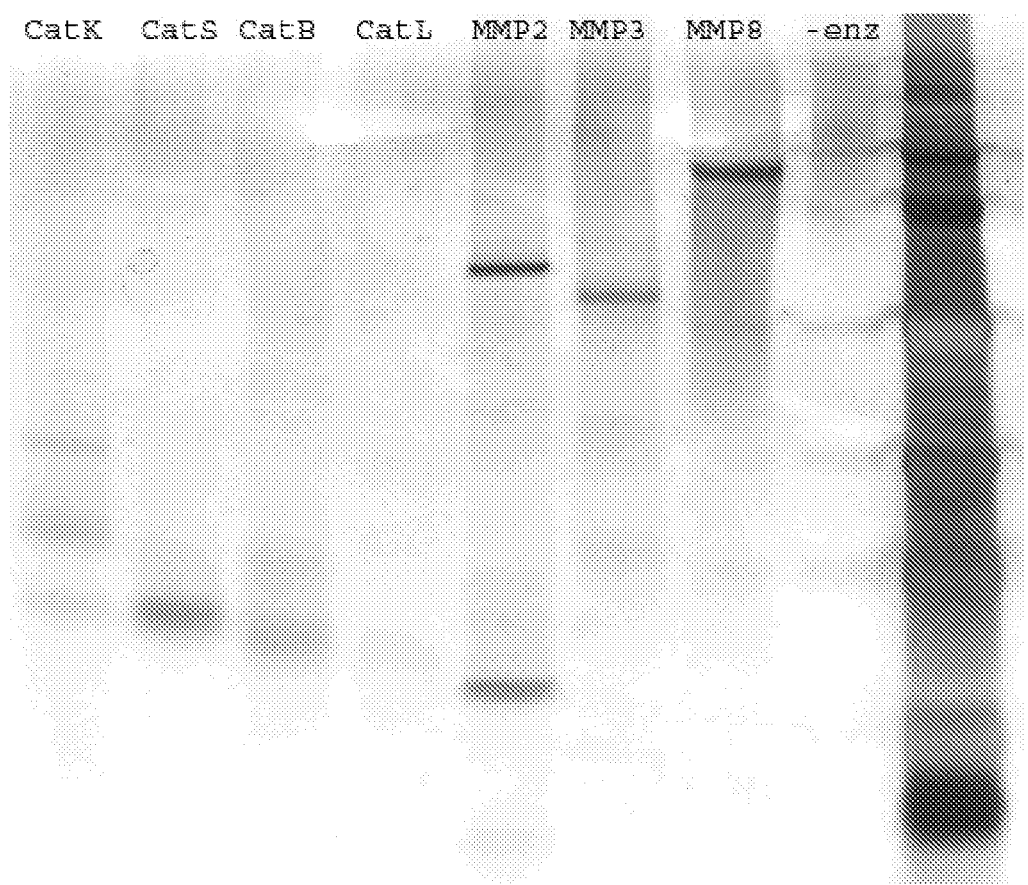
FIG. 5 shows cleavage products of biglycan generated by proteases: MMP2, MMP3, MMP8, cathepsin K, cathepsin S, cathepsin B, and cathepsin L. M=Rainbow marker. −enz=no enzyme digestion, run on a gel in Example 2.

Degradation of biglycan for assessment of degradation fragments. Biglycan from bovine articular cartilage (B8041-Sigma-Aldrich) was cleaved by following proteases: MMP2, MMP3, MMP8, Cathepsin K, Cathepsin S, Cathepsin B, and Cathepsin L. Fragments of proteoglycans generated by enzymatic cleavage of above mentioned proteases were separated on 10% NuPage® Bis-Tris gels and afterwards silver-stained by "Silver Express"—silver staining kit (Invitrogen cat.nr. LC6100, lot.nr.341099). Results of separation of proteolytically derived and biglycan and silver-stainings are represented by FIG. 5.

Example 3

Mice were immunised with collagen type III derived peptides conjugated with ovalbumin. Sera were screened for reactivity with screening peptide sequences conjugated to biotin. Monoclonal antibody secreting clones were produced and screened using the screening sequences. Clones were checked for lack of reactivity with elongated versions of the target peptide which are continued with the adjacent sequences from collagen type III (deselection peptide) and for lack of reactivity with a nonsense peptide. None of the clones positive for the target sequences reacted with either the elongated or the nonsense sequences.

The target sequences, immunogens, screening sequences and deselection sequences were as follows:

| No: | Target sequence (SEQ ID NO) | Immunogen (SEQ ID NO) | Screening Sequence (SEQ ID NO) | De-selection sequence (SEQ ID NO) | Mouse No. |
|---|---|---|---|---|---|
| NB51 | KNGETG (356) | KNGETGPQGPGGC-OVA (801) | KNGETGPQGP-PG-K-Biotin (802) | KDGETGAAGPPGK-Biotin | 278; 279; |
|  |  |  |  |  | 289; 345; |
|  |  |  |  | KDGEAGAQGPPGK-Biotin | 346; 347 |
|  |  |  |  | PGKNGETPGPQ-GP-K-Biotin (805) |  |

-continued

| No: | Target sequence (SEQ ID NO) | Immunogen (SEQ ID NO) | Screening Sequence (SEQ ID NO) | De-selection sequence (SEQ ID NO) | Mouse No. |
|---|---|---|---|---|---|
| NB26 | IAGITG (429) | IAGITGARGLGGC-KLH (806) | IAGITGARGL-AG-K-Biotin IAGLTGARGL-AG-K-Biotin) (808) | LGIAGITGARGL-AG-K-Biotin (809) | 146; 147; 148; 149; 156; 157; |
| NB52 | IAGITG (429) | IAGITGARGLGGC-OVA (806) | IAGITGARGL-AG-K-Biotin IAGLTGARGL-AG-K-Biotin (808) | LGIAGITGARGL-AG-K-Biotin (809) | 348; 349; 357; 358; 359; |
| NB27 | KDGTSG (763) | KDGTSGHPGPGGC-OVA (810) | KDGTSGHPGP-IG-K-Biotin KDGSSGHPGP-IG-K-Biotin (812) | PGKDGTSGHP-GP-K-Biotin (813) | 158; 159; 167; 168; 169; 178; |
| NB67 | APGPLG (581) | OVA-CGG-GPPGAPGPLG (814) | Biotin-AQ-GPPGAPGPLG Biotin-AQ-GPPGSPGPLG (816) | Biotin-DD-GPSGAEGPPG Biotin-GP-PGAPGPLGIA (818) | 167; 168; 169; 178; 179; 189; |
| NB68 | NTGAPG (422) | NTGAPGSPGV-CGG-OVA (819) | NTGAPGSPGVSG-K-Biotin NSGSPGNPGVAG-K-Biotin (821) | AGNTGAPGSP-GV-Biotin (822) | 234; 235; 236; 237; 238; 239; |
| NB69 | AIGPSG (380) | AIGPSGPAGK-GGC-OVA (808680) (823) | AIGPAGPAGKDG-K-Biotin AIGPAGPAGKDG-K-Biotin (825) | PGAIGPSGPAG-KD-Biotin (826) | 245; 246; 247; 248; 249; 256; |
| NB57 | AGGFAP (781) | KLH-CGG-EKAGGFAP (827) | Biotin-CG-EKAGGFAP Biotin-CG-EKSGGFSP (829) | Biotin-GG-EKAGGFAPYY (830) | 1; 2; 3; 4; 5; 6; |

Example 4

Reactivity of Collagen Type III Neo-Epitope Monoclonal Antibodies with Human Urine The reactivity of selected monoclonal antibody clones from example 3 with human urine was determined in a competition assay format using the immunising peptides as competition agent. In a typical procedure, 96 well streptavidin coated plates were coated for 30 min with 10 ng/mL Biotin-peptide in PBS-BTE at 20° C. with shaking and washed 5× in washing buffer. 20 μl of diluted sample was added (either urine or peptide solution). 100 μL of unpurified antibody solution (supernatant from cell culture) diluted as detailed below was added. The plates were incubated for 1 hr at 20° C. with shaking at 300 rpm and were then washed 5× in washing buffer. 100 μL secondary antibody-POD (1:5000) was added and incubated for 1 hr at 20° C. with shaking at 300 rpm before washing 5× in washing buffer. 100 μL TMB was added and incubated for 15 min in darkness shaking at 300 rpm before adding 100 μL stopping solution. The plates were read at 450 nm on an ELISA reader with 650 nm as reference. Competition therefore occurred between the peptide on the plate and peptide in solution for the antibody and the amount of plate bound antibody was determined by the peroxidase colour forming reaction.

Figure 6:
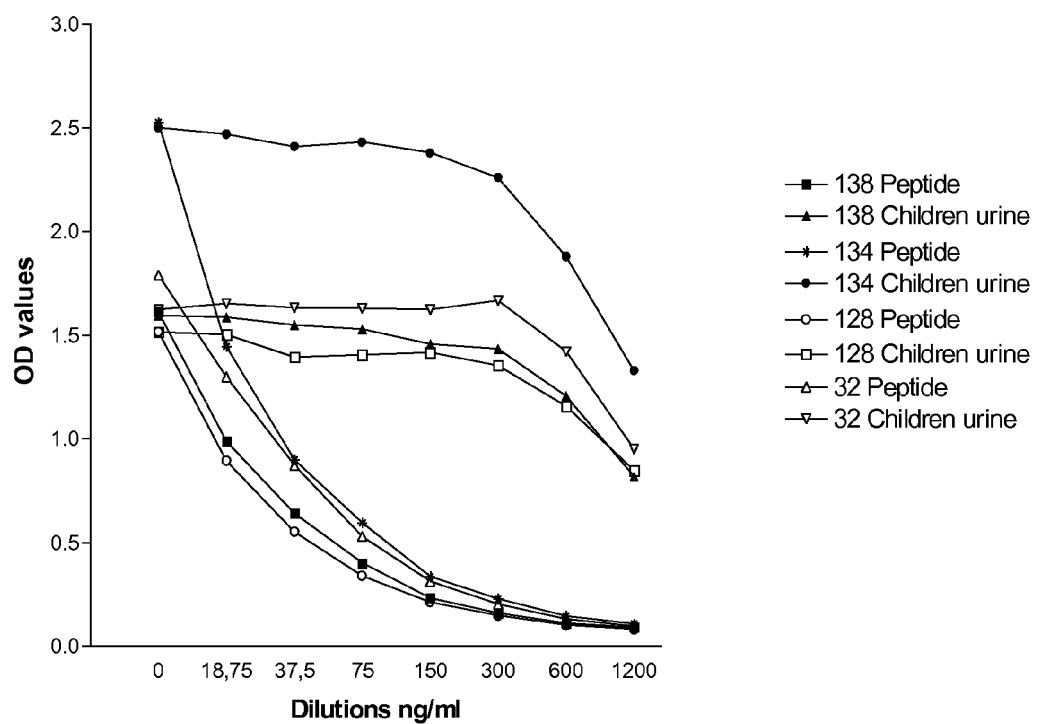
FIGS. 6 to 8 show competition study results obtained in Example 4.

Results are seen in FIG. 6 for four different clones. It can be seen that the antibodies each detect relevant sequences in urine.

Figure 7:
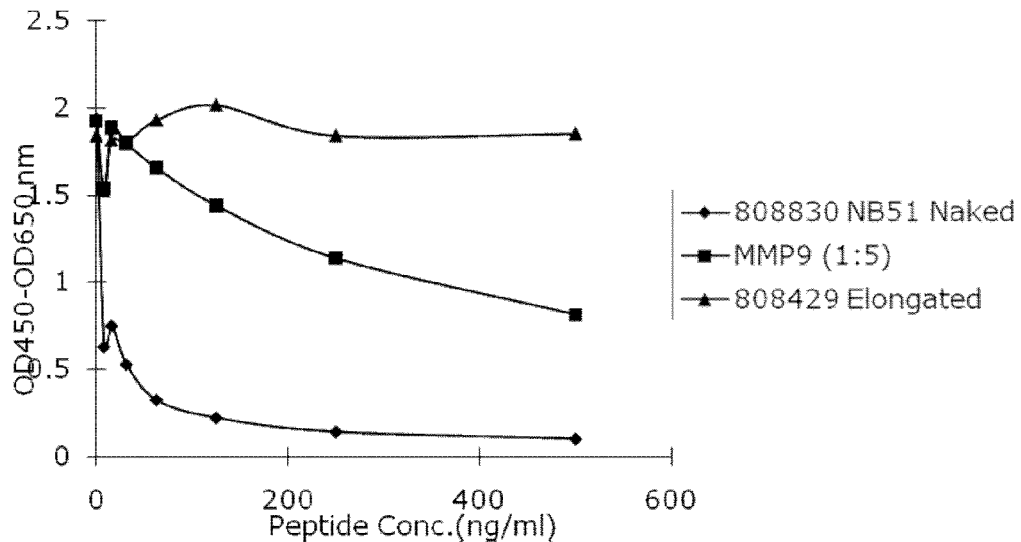

Further competition studies were performed on one selected clone to test competition for antibody binding between the immunising peptide and native collagen type III cleaved in vitro by MMP9. Results are shown in FIG. 7 for the cleaved collagen, the peptide KNGETG and an elongated version of that sequence. It can be seen that the antibody binds the immunising peptide sequence and the enzyme cleaved collagen, but not the extended sequence.

Figure 8:
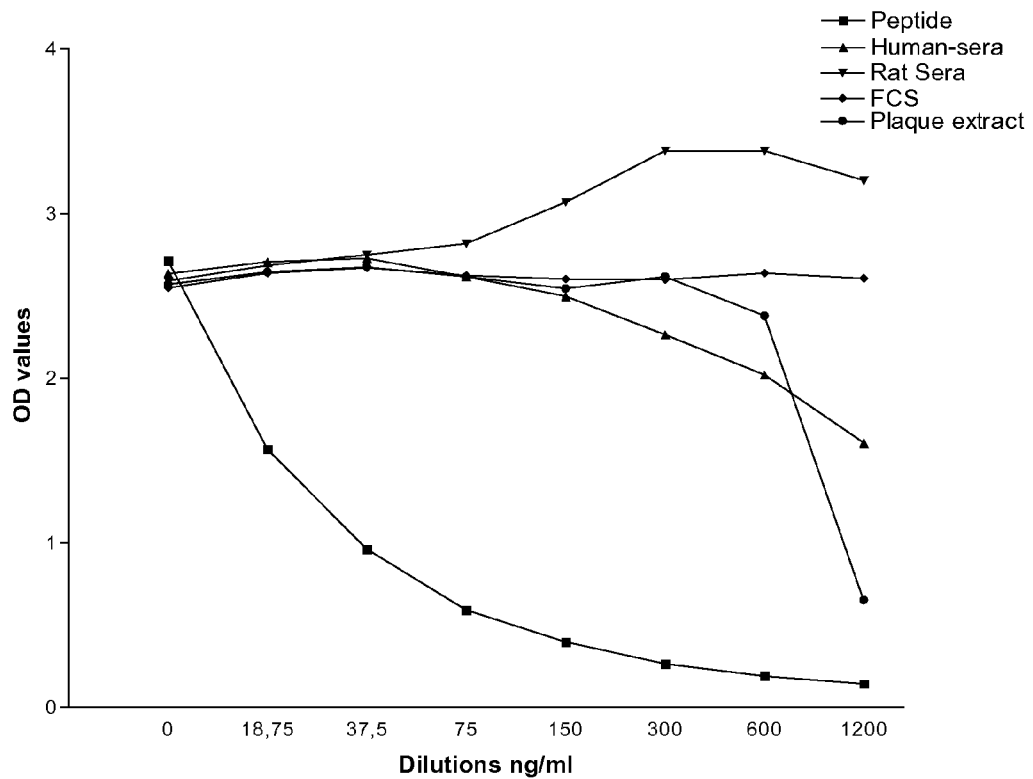

Further competition studies on the same clone are seen in FIG. 8 where the competition agents were the peptide KNGETG, human serum, rat serum, FCS (fetal calf serum), and atherosclerotic plaque extracts respectively. It is seen that the antibody is reactive with the peptide, the plaque extract and human serum, but not the rat serum or FCS.

Example 5

Raising of Anti-Sera to Decorin, Biglycan and Versican Sequences

Anti-sera were raised and monoclonal antibodies were obtained as in Example 3, but using the following immunogens, screening sequences and deselection sequences:

| No | Epitope | Target sequence (SEQ ID NO) | Immunogen (SEQ ID NO) | Screening Sequence (SEQ ID NO) | De-selection sequence (SEQ ID NO) | Mouse No. |
|---|---|---|---|---|---|---|
| NB62 | Decorin-176N | IVIELG (91) | IVIELGTNPL-GGC-KLH (831) | IVIELGTNPL-KS-K-Biotin (832) LVIELGGNPL-KN-K-Biotin (833) IVVELGGNPL-TN-K-Biotin (834) | QMIVIELGTNPLK-K-Biotin (835) NVLVIELGGNPL-K-Biotin (836) | 7; 8; 9; 10; 12; 13 |
| NB63 | Biglycan-108C | NNDISE (116) | OVA-CGG-LDLQNNDISE (837) | Biotin-TL-LDLQNNDISE (838) | Biotin-LDLQNNDISELR (839) | 14; 15; 16; 17; 18; 19 |
| NB64 | Versican-87N | QNGNIK (143) | QNGNIKIGQD-GGC-KLH (840) | QNGNIKIGQD-YK-Biotin (841) QDGNIKIGQD-YK-Biotin (842) | VAQNGNIKIGQD-K-Biotin (843) VAQDGNIKIGQD-K-Biotin (844) | 23; 24 25; 26; 27; 28; |

Example 6

Reactivity of Decorin Neo-Epitope Monoclonal Antibody with Human Urine

A competition ELISA was carried out generally as in Example 5 using one anti-decorin unpurified monoclonal antibody (NB62)

Figure 9:
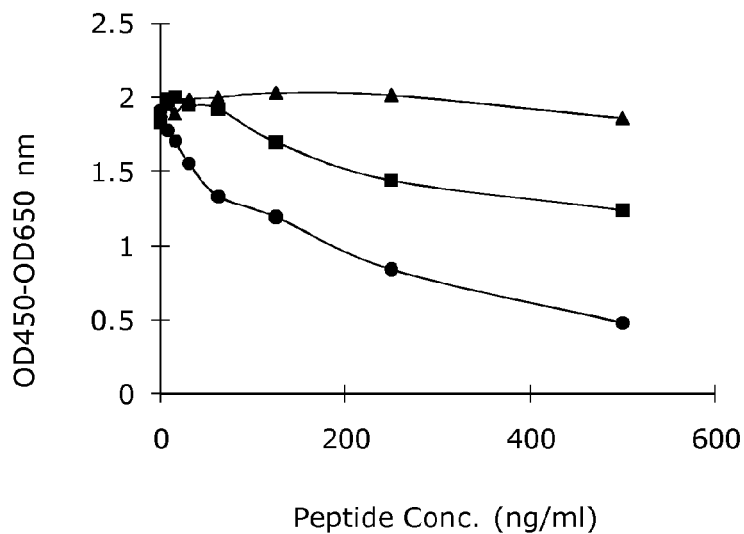
FIG. 9 shows competition study results obtained in Example 6.

Results are shown in FIG. 9. Reactivity is seen against the peptide sequence against which the antibody was raised and selected and against urine, but not against the irrelevant peptide sequence NB18.

Example 7

Reactivity of versican neo-epitope monoclonal antibody with human urine

A competition ELISA was carried out generally as in Example 5 using two anti-versican unpurified monoclonal antibody clones raised against sequence (NB64).

Figure 10:
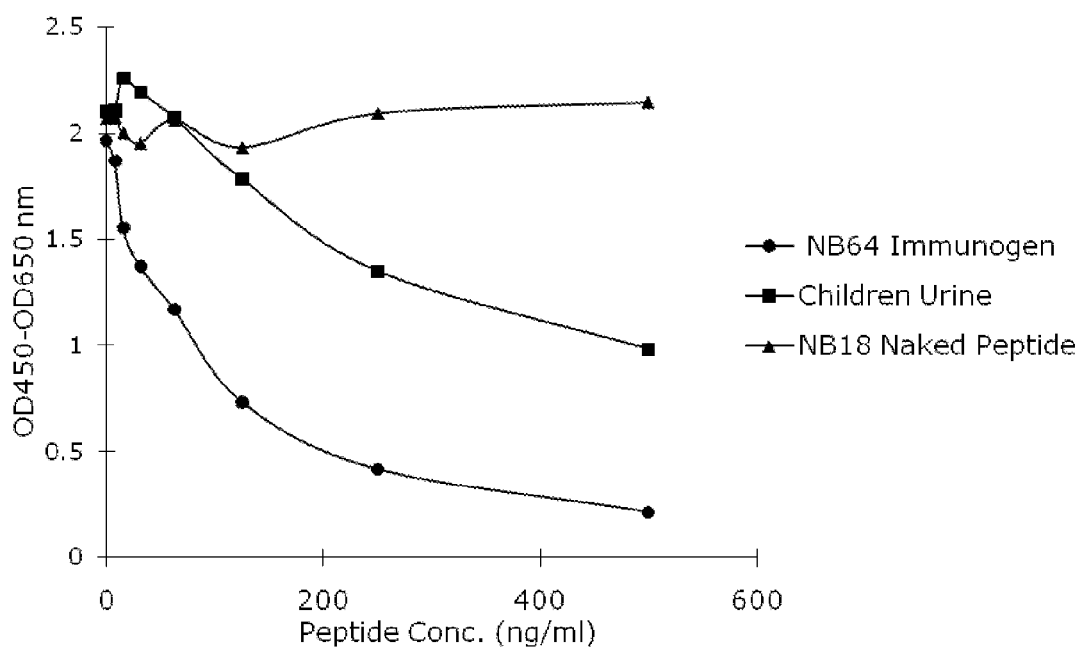
FIGS. 10 and 11 show competition study results obtained in Example
Figure 11:
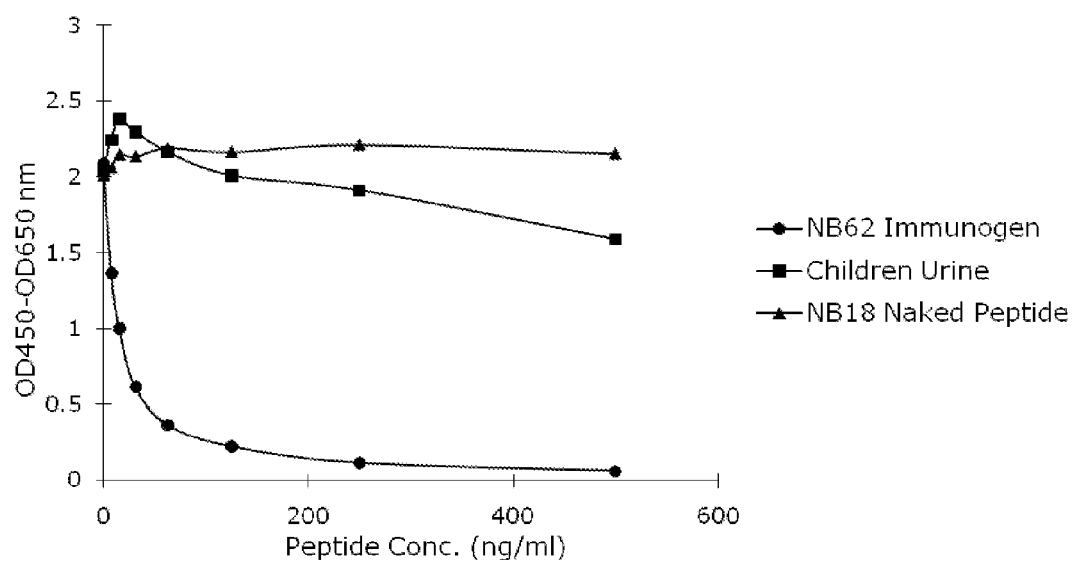

Results are shown in FIGS. 10 and 11 for the respective clones. In each case reactivity is seen against the peptide sequence against which the antibody was raised and selected and against urine, but not against the irrelevant peptide sequence NB18.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

REFERENCE LIST

Bobryshev Y V. Calcification of elastic fibers in human atherosclerotic plaque. Atherosclerosis 2005; 180:293-303.

Brown, D. C. and K. G. Vogel. "Characteristics of the in vitro interaction of a small proteoglycan (PG II) of bovine tendon with type I collagen." Matrix. 9.6 (1989): 468-78.

Cattin L, Fisicaro M, Tonizzo M, Valenti M, Danek G M, Fonda M, Da Col P G, Casagrande S, Pincetri E, Bovenzi M, and Baralle F. Polymorphism of the apolipoprotein E gene and early carotid atherosclerosis defined by ultrasonography in asymptomatic adults. Arterioscler Thromb Vasc Biol. 1997 January; 17(1):91-4.

Chapman H A, Riese R J, Shi G P. Emerging roles for cysteine proteases in human biology. Annu. Rev. Physiol 1997; 59:63-88.

Clarkson T B, Kaplan J R. Stage of Reproductive Life, Atherosclerosis Progression and Estrogen Effects on Coronary Artery Atherosclerosis, In: Lobo R A, editor. Treatment of the Postmenopausal Woman: Basic and Clinical Aspects, 3 ed. San Diego: Elsevier; 2007. p. 509-28.

Danielson, K. G., et al. "Targeted disruption of decorin leads to abnormal collagen fibril morphology and skin fragility." J. Cell Biol. 136.3 (1997): 729-43.

Dours-Zimmermann, M. T. and D. R. Zimmermann. "A novel glycosaminoglycan attachment domain identified in two alternative splice variants of human versican." J. Biol. Chem. 269.52 (1994): 32992-98.

Eriksen H A, Satta J, Risteli J, Veijola M, Vare P, Soini Y. Type I and type III collagen synthesis and composition in the valve matrix in aortic valve stenosis. Atherosclerosis 2006; 189:91-98.

Evanko, S. P., et al. "Proteoglycan distribution in lesions of atherosclerosis depends on lesion severity, structural characteristics, and the proximity of platelet-derived growth factor and transforming growth factor-beta." Am. J. Pathol. 152.2 (1998): 533-46.

Funderburgh, J. L. "Keratan sulfate: structure, biosynthesis, and function." Glycobiology 10.10 (2000): 951-58.

Funderburgh, J. L., et al. "Macrophage receptors for lumican. A corneal keratan sulfate proteoglycan." Invest Ophthalmol. Vis. Sci. 38.6 (1997): 1159-67.

Gabay C and Kushner I. Acute-phase proteins and other systemic responses to inflammation. N Engl J Med. 1999 Feb. 11; 340(6):448-54.

Gardner C D, Fortmann S P, Krauss R M. Association of small low-density lipoprotein particles with the incidence of coronary artery disease in men and women. JAMA 1996; 276:875-81.

Garrone R, Lethias C, Le Guellec D. Distribution of minor collagens during skin development. Microsc. Res Tech. 1997; 38:407-12.

Graham I, Atar D, Borch-Johnsen K, Boysen G, Burell G, Cifkova R et al. European guidelines on cardiovascular disease prevention in clinical practice: executive summary. Atherosclerosis 2007; 194:1-45.

Haraki T, Takegoshi T, Kitoh C, Wakasugi T, Saga T, Hirai J I, Aoyama T, Inazu A and Mabuchi H, Carotid artery intima-media thickness and brachial artery flow-mediated vasodilation in asymptomatic Japanese male subjects amongst apolipoprotein E phenotypes. J Intern Med. 2002 August; 252(2):114-20.

Hatanaka K, Li X A, Masuda K, Yutani C and Yamamoto A, Immunohistochemical localization of C-reactive protein-binding sites in human atherosclerotic aortic lesions by a modified streptavidin-biotin-staining method. Pathol Int. 1995 September; 45(9):635-41.

Heegaard A M, Corsi A, Danielsen C C, Nielsen K L, Jorgensen H L, Riminucci M, Young M F and Bianco P, Biglycan deficiency causes spontaneous aortic dissection and rupture in mice. Circulation. 2007 May 29; 115(21): 2731-8. Epub 2007 May 14.

Herman M P, Sukhova G K, Libby P, Gerdes N, Tang N, Horton D B et al. Expression of neutrophil collagenase (matrix metalloproteinase-8) in human atheroma: a novel collagenolytic pathway suggested by transcriptional profiling. Circulation 2001; 104:1899-904.

Jeppesen J, Hein H O, Suadicani P, Gyntelberg F. High triglycerides/low high-density lipoprotein cholesterol, ischemic electrocardiogram changes, and risk of ischemic heart disease. Am Heart J 2003; 145:103-08.

Lawrie T D, Mcalpine S G, Rifkind B M, Robinson J F. Serum fatty-acid patterns in coronary-artery disease. Lancet 1961; 1:421-24.

Katsuda S, Okada Y, Minamoto T, Oda Y, Matsui Y, Nakanishi I. Collagens in human atherosclerosis. Immunohistochemical analysis using collagen type-specific antibodies. Arterioscler. Thromb. 1992; 12:494-502.

Knox, S. M. and J. M. Whitelock. "Perlecan: how does one molecule do so Many things?" Cell Mol. Life Sci. 63.21 (2006): 2435-45.

Kuller L H, Tracy R P, Shaten J and Meilahn E N, Relation of C-reactive protein and coronary heart disease in the MRFIT nested case-control study. Multiple Risk Factor Intervention Trial. Am J Epidemiol. 1996 Sep 15; 144(6): 537-47.

Kunz J. Matrix metalloproteinases and atherogenesis in dependence of age. Gerontology. 2007; 53:63-73.

Kuzuya M, Nakamura K, Sasaki T, Cheng X W, Itohara S, Iguchi A. Effect of MMP-2 deficiency on atherosclerotic lesion formation in apoE-deficient mice. Arterioscler. Thromb. Vasc. Biol 2006; 26:1120-25.

Leinonen M and Saikku P, Evidence for infectious agents in cardiovascular disease and atherosclerosis. Lancet Infect Dis. 2002 January; 2(1):11-7.

Liu J, Sukhova G K, Sun J S, Xu W H, Libby P, Shi G P. Lysosomal cysteine proteases in atherosclerosis. Arterioscler. Thromb. Vasc. Biol 2004; 24:1359-66.

Lutgens, S. P., et al. "Cathepsin cysteine proteases in cardiovascular disease." FASEB J. 21.12 (2007): 3029-41.

Mayne R. Collagenous proteins of blood vessels. Arteriosclerosis. 1986; 6:585-93.

McCullagh K G, Duance V C, Bishop K A. The distribution of collagen types I, III and V (AB) in normal and atherosclerotic human aorta. J Pathol 1980; 130:45-55.

Mendall M A, Patel P, Ballam L, Strachan D and Northfield T C. C reactive protein and its relation to cardiovascular risk factors: a population based cross sectional study, BMJ. 1996 Apr. 27; 312(7038):1061-5.

Monfort J, Nacher M, Montell E, Vila J, Verges J and Benito P, Chondroitin sulfate and hyaluronic acid (500-730 kda) inhibit stromelysin-1 synthesis in human osteoarthritic chondrocytes. Drugs Exp Clin Res. 2005; 31(2):71-6.

Pasceri V, Willerson J T and Yeh E T, Direct proinflammatory effect of C-reactive protein on human endothelial cells. Circulation. 2000 Oct. 31; 102(18):2165-8.

Register T C, Cann J A, Kaplan J R, Williams J K, Adams M R, Morgan T M et al. Effects of soy isoflavones and conjugated equine estrogens on inflammatory markers in atherosclerotic, ovariectomized monkeys. J Clin Endocrinol Metab 2005; 90:1734-40.

Reynolds G D and Vance R P. C-reactive protein immunohistochemical localization in normal and atherosclerotic human aortas. Arch Pathol Lab Med. 1987 March; 111(3): 265-9.

Ridker P M, Intrinsic fibrinolytic capacity and systemic inflammation: novel risk factors for arterial thrombotic disease. Haemostasis. 1997; 27 Suppl 1:2-11.

Ridker P M, Hennekens C H, Buring J E and Rifai N. C-reactive protein and other markers of inflammation in the prediction of cardiovascular disease in women. N Engl J Med. 2000 Mar. 23; 342(12):836-43.

Rodriguez-Lee M, Bondjers G and Camejo G, Fatty acid-induced atherogenic changes in extracellular matrix proteoglycans. Curr Opin Lipidol. 2007 October; 18(5):546-53

Rouis M. Matrix metalloproteinases: a potential therapeutic target in atherosclerosis. Curr Drug Targets. Cardiovasc Haematol Disord. 2005; 5:541-48.

Rudel L L, Haines J, Sawyer J K, Shah R, Wilson M S, Carr T P. Hepatic origin of cholesteryl oleate in coronary artery atherosclerosis in African green monkeys. Enrichment by dietary monounsaturated fat. J Clin Invest 1997; 100:74-83.

Salisbury B G and Wagner, W D J Biot Chem. 1981 Aug. 10; 256(15):8050-7, 'Isolation and preliminary characterization of proteoglycans dissociatively extracted from human aorta'.

Satta J, Juvonen T, Haukipuro K, Juvonen M, Kairaluoma M I. Increased turnover of collagen in abdominal aortic aneurysms, demonstrated by measuring the concentration of the aminoterminal propeptide of type III procollagen in peripheral and aortal blood samples. J Vasc. Surg. 1995; 22:155-60.

Schaar J A, Mastik F, Regar E, den Uil C A, Gijsen F J, Wentzel J J et al. Current diagnostic modalities for vulnerable plaque detection. Curr Pharm Des. 2007; 13:995-1001.

Siest G, Pilot T, Regis-Baily A, Leininger-Muller B, Steinmetz J, Galteau M M and Visvikis S, Apolipoprotein E: an important gene and protein to follow in laboratory medicine. Clin Chem. 1995 August; 41(8 Pt 1):1068-86.

Shin, J., J. E. Edelberg, and M. K. Hong. "Vulnerable atherosclerotic plaque: clinical implications." Curr. Vasc. Pharmacol. 1.2 (2003): 183-204.

Shekhonin B V, Domogatsky S P, Muzykantov V R, Idelson G L, Rukosuev V S. Distribution of type I, III, IV and V collagen in normal and atherosclerotic human arterial wall: immunomorphological characteristics. Coll. Relat Res 1985; 5:355-68.

Stary H C. Composition and classification of human atherosclerotic lesions. Virchows Arch A. Pathol Anat. Histopathol. 1992; 421:277-90.

Sundstrom J, Vasan R S. Circulating biomarkers of extracellular matrix remodeling and risk of atherosclerotic events. Curr Opin Lipidol. 2006; 17:45-53.

Talusan, P., et al. "Analysis of intimal proteoglycans in atherosclerosis-prone and atherosclerosis-resistant human arteries by mass spectrometry." Mol. Cell Proteomics. 4.9 (2005): 1350-57.

Thompson D, Banks R E, Forbes M A, Storr M, Higginson J, Raynes J, Illingworth J M, Perren T J, Selby P J and Whicher J T, The acute phase protein response in patients receiving subcutaneous IL-6. Clin Exp Immunol. 1995 October; 102(1):217-23.

Terry J G, Howard G, Mercuri M, Bond M G and Crouse J R 3rd. Apolipoprotein E polymorphism is associated with segment-specific extracranial carotid artery intima-media thickening, Stroke. 1996 October; 27(10):1755-9.

Tracy R P, Lemaitre R N, Psaty B M, Ives D G, Evans R W, Cushman M, Meilahn E N and Kuller L H, Relationship of C-reactive protein to risk of cardiovascular disease in the elderly. Results from the Cardiovascular Health Study and the Rural Health Promotion Project. Arterioscler Thromb Vasc Biol. 1997 June; 17(6):1121-7.

Turu M M, Krupinski J, Catena E, Rosell A, Montaner J, Rubio F et al. Intraplaque MMP-8 levels are increased in asymptomatic patients with carotid plaque progression on ultrasound. Atherosclerosis 2006; 187:161-69.

Venugopal S K, Devaraj S, Yuhanna I, Shaul P and Jialal I. Demonstration that C-reactive protein decreases eNOS expression and bioactivity in human aortic endothelial cells, Circulation. 2002 Sep. 17; 106(12):1439-41.

Wang T J, Gona P, Larson M G, Tofler G H, Levy D, Newton-Cheh C et al. Multiple biomarkers for the prediction of first major cardiovascular events and death. N Engl J Med 2006; 355:2631-39.

Whitelock, J. M. and R. V. Iozzo. "Heparan sulfate: a complex polymer charged with biological activity." Chem. Rev. 105.7 (2005): 2745-64.

Wight, T. N. The extracellular matrix and atherosclerosis." Curr. Opin. Lipidol. 6.5 (1995): 326-34.

Wight, T. N., et al. "Vascular cell proteoglycans: evidence for metabolic modulation." Ciba Found. Symp. 124 (1986): 241-59.

Wight T N, Versican: a versatile extracellular matrix proteoglycan in cell biology. Curr Opin Cell Biol. 2002 October; 14(5):617-23.

Wight T N and Merrilees M J, Proteoglycans in atherosclerosis and restenosis: key roles for versican. Circ Res. 2004 May 14; 94(9):1158-67.

Wilson P W, Schaefer E J, Larson M G and Ordovas J M. Apolipoprotein E alleles and risk of coronary disease. A meta-analysis. Arterioscler Thromb Vasc Biol. 1996 October; 16(10):1250-5.

Yamada Y, Izawa H, Ichihara S, Takatsu F, Ishihara H, Hirayama H et al. Prediction of the risk of myocardial infarction from polymorphisms in candidate genes. N Engl J Med 2002; 347:1916-23.

Zwaka T P, Hombach V and Torzewski J. C-reactive protein-mediated low density lipoprotein uptake by macrophages: implications for atherosclerosis, Circulation. 2001 Mar. 6; 103(9):1194-7.

---

The invention claimed is:

1. A method of diagnosis or of quantitation of cardiovascular disease comprising;
obtaining a patient biofluid sample,
conducting an immunoassay to measure fragments of collagen type III comprising an N- or C-terminal neo-epitope formed by cleavage of collagen type III by MMP-1, MMP-2, MMP-3, MMP-8, MMP-9, MMP-13, ADAMTS-5, CathepsinK, CathepsinS, ADAMTS1, ADAMTS4 or ADAMTS8, said fragments being naturally present in a said biofluid sample, and
associating an elevation of said measure in said patient above a normal level with the presence or extent of cardiovascular disease, wherein said bioassay immunoassay is conducted by a method comprising:
contacting the fragments of collagen type III having said N- or C-terminal neo-epitope that are naturally present in said sample with an immunological binding partner specifically reactive with the N-terminal or C-terminal neo-epitope, but not reactive with intact collagen type III, and,
measuring the extent of binding of the N- or C-terminal neo-epitope to said immunological binding partner to measure therein fragments comprising said neo-epitope;
wherein said immunological binding partner is raised against a synthetic peptide corresponding to an N- or C-terminal neo epitope amino acid sequence formed by cleavage of the collagen type III by MMP-1, MMP-2, MMP-3, MMP-8, MMP-9, MMP-13, ADAMTS5, CathepsinK, CathepsinS, ADAMTS1, ADAMTS4 or ADAMTS8 and specifically binds a neo-epitope constituted by said N- or C-terminal amino acid sequence, said N-terminal amino acid sequence selected from the group consisting of any sequence directly following the sign * in any one the following sequences or said C-terminal amino acid sequence selected from the group consisting of any sequence directly preceding the sign * in any one of the following sequences:

| Protease | | SEQ ID NO |
|---|---|---|
| MMP-1 | A*GIPGAPGLMGARGPPGPA*G | 154 |
| MMP-1 | K*GDPGPPGIPGRNGDPGI*P | 155 |
| MMP-1 | G*LAGPPGMPGPRGSPGPQG*V | 156 |
| MMP-1 | G*ERGLPGPPGIKGPAGIPGF*P | 157 |
| MMP-1 | G*IAGITGARGLAGPPGMPGPR*G | 158 |
| MMP-1 | G*IKGHRGFPGNPGAPGSPGPAG*Q | 159 |
| MMP-1 | A*RGLAGPPGMPGPRGSPGPQGV*K | 160 |
| MMP-1 | I*TGARGLAGPPGMPGPRGSPGPQG*V | 161 |
| MMP-1 | I*TGARGLAGPPGMPGPRGSPGPQGV*K | 162 |
| MMP-1 | G*ITGARGLAGPPGMPGPRGSPGPQG*V | 163 |
| MMP-1 | G*VKGESGKPGANGLSGERGPPGPQG*L | 164 |
| MMP-1 | G*SRGAPGPQGPRGDKGETGERGAAG*I | 165 |
| MMP-1 | P*KGDAGQPGEKGSPGAQGPPGAPGPLG*I | 166 |
| MMP-1 | G*ITGARGLAGPPGMPGPRGSPGPQGV*K | 167 |
| MMP-1 | G*LRGGAGPPGPEGGKGAAGPPGPPGAAGTPG*L | 168 |
| MMP-1 | G*HAGAQGPPGPPGINGSPGGKGEMGP AGIPGAPG*L | 169 |
| MMP-1 | A*GKSGDRGESGPAGPAGAPGPAGSRGAPGPQG PRGDKGETGERGAAG*I | 170 |
| MMP-1 | G*LQGLPGTGGPPGENGKPGEPGPKGDAGAPGA PGGKGDAGAPGERGPPG*L | 171 |
| MMP-3 | G*ERGLPGPPGIKGPAGIPGF*P | 172 |
| MMP-3 | A*VGGLAGYPGPAGPPGPPGPPGT*S | 173 |
| MMP-3 | K*DGTSGHPGPIGPPGPPGRGNRGER*G | 174 |
| MMP-3 | A*VGGLAGYPGPAGPPGPPGPPGTSGHPG*S | 175 |
| MMP-3 | G*IAGITGARGLAGPPGMPGPRGSPGPQG*V | 176 |
| MMP-3 | A*PGAPGGKGDAGAPGERGPPGLAGAPGLRG*G | 177 |
| MMP-3 | A*VGGLAGYPGPAGPPGPPGPPGTSGHPGSPG*S | 178 |
| MMP-2 | A*IGSPGPAGPRGPVGPSGPPG*K | 179 |
| MMP-3 and -8 | G*AIGSPGPAGPRGPVGPSGPPG*K | 180 |
| MMP-8 | P*AGQQGAIGSPGPA*G | 181 |
| MMP-8 | G*GPPGVAGPPGGSGPAGPP*G | 182 |
| MMP-8 | L*AGPPGMPGPRGSPGPQG*V | 183 |
| MMP-8 | G*LSGERGPPGPQGLPGLA*G | 184 |
| MMP-8 | R*GLAGPPGMPGPRGSPGPQG*V | 185 |
| MMP-8 | G*LAGPPGMPGPRGSPGPQGV*K | 186 |
| MMP-8 | R*GLAGPPGMPGPRGSPGPQGV*K | 187 |
| MMP-8 | G*PQGPPGKNGETGPQGPPGP*T | 188 |
| MMP-8 | G*VKGERGSPGGPGAAGFPGAR*G | 189 |
| MMP-8 | A*RGLAGPPGMPGPRGSPGPQG*V | 190 |
| MMP-8 | N*GLSGERGPPGPQGLPGLAGTA*G | 191 |
| MMP-8 | A*VGGLAGYPGPAGPPGPPGPPGT*S | 192 |
| MMP-8 | G*SPGGKGEMGPAGIPGAPGLMGA*R | 193 |
| MMP-8 | T*GARGLAGPPGMPGPRGSPGPQG*V | 194 |
| MMP-8 | V*KGESGKPGANGLSGERGPPGPQG*L | 195 |

| Protease | Sequence | SEQ ID NO |
|---|---|---|
| MMP-8 | G*VKGERGSPGGPGAAGFPGARGLPGPPGSNGNPGPPGPSGSPGKDGPPGPAG*N | 196 |
| MMP-8 | G*SPGAQGPPGAPGPLGIAGITGARGLAGPPG*M | 197 |
| MMP-8 | R*GAPGEKGEGGGPPGVAGPPGGSGPAGPPGPQ*G | 198 |
| MMP-8 | R*GAPGEKGEGGGPPGVAGPPGGSGPAGPPGPQ*G | 199 |
| MMP-8 | G*IAGITGARGLAGPPGMPGPRGSPGPQG*V | 200 |
| MMP-9 | G*IKGPAGIPGFPGPPG*M | 201 |
| MMP-9 | G*QPGVMGFPGPKG*N | 202 |
| MMP-9 | G*IKGPAGIPGFPGPMK*G | 203 |
| MMP-9 | G*IKGPAGIPGFPGMKG*H | 204 |
| MMP-9 | I*PGAPGLMGARGPPGPAG*A | 205 |
| MMP-9 | G*ERGLPGPPGIKGPAGIP*G | 206 |
| MMP-9 | G*IPGAPGLMGARGPPGPAG*A | 207 |
| MMP-9 | G*FRGPAGPNGIPGEKGPAG*E | 208 |
| MMP-9 | P*GIPGQPGSPGSPGPPGIC*E | 209 |
| MMP-9 | G*ERGLPGPPGIKGPAGIPGF*P | 210 |
| MMP-9 | A*VGGLAGYPGPAGPPGPPGPPG*T | 211 |
| MMP-9 | G*VKGERGSPGGPGAAGFPGARG*L | 212 |
| MMP-9 | G*DAGAPGAPGGKGDAGAPGERGPPG*L | 213 |
| MMP-9 | Q*GPPGPTGPGGDKGDTGPPGPQGL*Q | 214 |
| MMP-9 | G*INGSPGGKGEMGPAGIPGAPGLM*G | 215 |
| MMP-9 | Q*GPPGEPGQAGPSGPPGPPGAIGPS*A | 216 |
| MMP-9 | P*GPPGINGSPGGKGEMGPAGIPGAP*G | 217 |
| MMP-9 | R*GLPGPPGPSNGNPGPPGPSGSPGKDGPPGPAG*N | 218 |
| MMP-9 | G*KNGETGPQGPPGPTGPGGDKGDTGPPGPQG*L | 219 |
| MMP-9 | G*LPGIAGPRGSPGERGETGPPGPAGFPGAPG*Q | 220 |
| MMP-9 | G*INGSPGGKGEMGPAGIPGAPGLMGARGPPGPAG*A | 221 |
| MMP-9 | P*GINGSPGGKGEMGPAGIPGAPGLMGARGPPGPAG*A | 222 |
| MMP-9 | P*PGENGKPGEPGPKGDAGAPGAPGGKGDAGAPGERGPPG*L | 223 |
| MMP-9 | G*LKGENGLPGENGAPGPMGPRGAPGERGRPGLPGAAG*A | 224 |
| MMP-9 | G*NTGAPGSPGVSGPKGDAGQPGEKGSPGAQGPPGAPGPLG*I | 225 |
| MMP-9 | G*LMGARGPPGPAGANGAPGLRGGAGEPGENGKGEPGPRG*E | 226 |
| MMP-9 | G*LRGGAGPPGPEGGKGAAGPPGPPGAAGTPGLQGMPGERGGLGSPGPKG*D | 227 |
| MMP-8 and -9 | G*QQGAIGSPGPAGPRGPVGPSGPPG*K | 228 |
| MMP-9 | K*GDPGPPGIPGRNGDPGIPGQPG*S | 229 |
| MMP-9 | G*LRGGAGPPGPEGGKGAAGPPGPPG*A | 230 |
| MMP-9 | G*KNGETGPQGPPGPTGPGGDKGDTGPPGPQG*L | 231 |
| MMP-9 | G*YQGPPGEPGQAGPSGPPGPPG*A | 232 |
| MMP-9 | G*VAGPPGGSGPAGPPGPQG*V | 233 |
| MMP-8, -9, and -13 | G*DKGEPGGPGADGVPGKDGPRGPTGPIGPPGPAG*Q | 234 |
| ADAMTS-5 | Q*GHAGAQGPPGPPGIN*G | 235 |
| CathepsinK | A*GERGAPGPA*G | 236 |
| CathepsinK | A*GIPGFPGMK*G | 237 |
| CathepsinK | F*PGMKGHRGFD*G | 238 |
| CathepsinK | G*FPGARGLPGPPG*S | 239 |
| CathepsinK | A*GFPGARGLPGPPG*S | 240 |
| CathepsinK | P*PGPPGPPGTSGHP*G | 241 |
| CathepsinK | G*FPGMKGHRGFD*G | 242 |
| CathepsinK | Q*PGDKGEGGAPGLPGI*A | 243 |
| CathepsinK | R*GDKGETGERGAAGIK*G | 244 |
| CathepsinK | D*GRNGEKGETGAPGLK*G | 245 |
| CathepsinK | A*GQPGDKGEGGAPGLPGIA*G | 246 |
| CathepsinK | G*PPGENGKPGEPGPKGD*A | 247 |
| CathepsinK | A*GIPGFPGMKGHRGFD*G | 248 |
| CathepsinK | R*GGAGEPGKNGAGEPGPR*G | 249 |
| CathepsinK | K*GERGSPGGPGAAGFPGARGLPGPP*G | 250 |
| CathepsinK | I*PGVPGAKGEDGKDGSPGEPGANGLP*G | 251 |
| CathepsinK | G*AAGFPGARGLPGPPGSNGNPGPPGPS*G | 252 |
| CathepsinK | R*PGPPGPSGPRGQPGVMGFPGPKGN*D | 253 |
| CathepsinK | Q*GPPGPPGINGSPGGKGEMGPAGIPGAP*G | 254 |
| CathepsinK | A*GKDGESGRPGPERGLPGPPGIK*G | 255 |
| CathepsinK | A*GARGNDGARGSDGQPGPPGPPGTAGFPG*S | 256 |
| CathepsinK | S*PGVSGPKGDAGQPGEKGSPGAQGPPGAPG*P | 257 |
| CathepsinK | R*GSDGQPGPPGPPGTAGFPGSPGAKGEVGPA*G | 258 |
| CathepsinK | Q*GPPGPPGINGSPGGKGEMGPAGIPGAPGLM*G | 259 |
| CathepsinK | A*GPPGPPGPPGPPGTSGHPGSPGSPGPYQGPPGEPG*Q | 260 |
| CathepsinK | F*PGAPGQNGEPGGKGERGAPGEKGEGGPPGVA*G | 261 |
| CathepsinK | A*GFPGAPGQNGEPGGKGERGAPGEKGEGGPPG*V | 262 |
| CathepsinK | A*GARGNDGARGSDGQPGPPGPPGTAGFPGSPGAKGEVGPA*G | 263 |
| CathepsinK | R*GAAGEPGRDGVPGGPGMRGMPGSPGGPGSDGKPGPPGSQGESGRPGPPGPS*G | 264 |
| CathepsinS | G*IAGITGARGL*A | 265 |
| CathepsinS | A*GPPGPPGAAGTPGLQG*M | 266 |
| CathepsinS | N*GLSGERGPPGPQGLPG*L | 267 |
| CathepsinS | M*GARGPPGPAGANGAPGLR*G | 268 |
| CathepsinS | N*GLSGERGPPGPQGLPGLA*G | 269 |
| CathepsinS | G*IAGITGARGLAGPPGMPGPRG*S | 270 |
| CathepsinS | G*IAGITGARGLAGPPGMPGPRGSPGPQG*V | 271 |
| CathepsinS | R*GGAGPPGPEGGKGAAGPPGPPGAAGTPGLQG*V | 272 |
| CathepsinS | S*GPKGDAGQPGEKGSPGAQGPPGAPGPLG*I | 273 |
| CathepsinS | G*IAGITGARGLAGPPGMPGPRGSPGPQGVK*G | 274 |
| CathepsinS | A*VGGLAGYPGPAGPPGPPGPPGTSGHPGSPGSPGYQ*G | 275 |
| CathepsinS | E*PGPQGHAGAQGPPGPPGINGSPGGKGEMGPAGIPGAPG*L | 276 |
| ADAMTS1 | I*PGFPGMKGHR*G | 277 |
| ADAMTS1 | R*GSPGGPGAAGFPGAR*G | 278 |
| ADAMTS1 | K*GPAGIPGFPGMKGHR*G | 279 |
| ADAMTS1 | R*GLAGPPGMPGPRGSPGPQ*G | 280 |
| ADAMTS1 | A*GITGARGLAGPPGMPGPR*G | 281 |
| ADAMTS1 | L*GIAGITGARGLAGPPGMPGPR*G | 282 |
| ADAMTS1 | T*GARGLAGPPGMPGPRGSPGPQ*G | 283 |
| ADAMTS1 | Q*GPPGPPGINGSPGGKGEMGPAG*I | 284 |
| ADAMTS1 | L*PGPPGIKGPAGIPGFPGMKGHR*G | 285 |
| ADAMTS1 | A*GITGARGLAGPPGMPGPRGSPGPQ*G | 286 |
| ADAMTS1 | T*GARGLAGPPGMPGPRGSPGPQGVK*G | 287 |
| ADAMTS1 | R*GLPGPPGIKGPAGIPGFPGMKGHR*G | 288 |
| ADAMTS1 | G*RPGLPGAAGARGNDGARGSDGQPGPPG*P | 289 |
| ADAMTS1 | N*GAPGPMGPRGAPGERGRPGLPGAAGAR*G | 290 |
| ADAMTS1 | A*GSRGAPGPAGPRGDKGETGERGAAGIK*G | 291 |
| ADAMTS1 | R*GLAGPPGMPGPRGSPGPQGVKGESGKPGAN*G | 292 |
| ADAMTS1 | R*GLAGPPGMPGPRGSPGPQGVKGESGKPGANGL*S | 293 |
| ADAMTS1 | P*GPPGSNGNPGPPGPSGSPGKDGPPGPAGNTGAPGS*P | 294 |
| ADAMTS1 | T*GARGLAGPPGMPGPRGSPGPQGVKGESGKPGAN*G | 295 |
| ADAMTS1 | R*GAPGEKGEGGGPPGVAGPPGGSGPAGPPGPQGVKGER*G | 296 |
| ADAMTS1 | G*PPGVAGPPGGSGPAGPPGPQGVKGERGSPGGPGAAGF*P | 297 |
| ADAMTS1 | K*SGDRGESGPAGPAGAPGPAGSRGAPGPQGPRGDKGETGERGAAGIK*G | 298 |
| ADAMTS4 | I*PGFPGMKGHR*G | 299 |
| ADAMTS4 | R*GLAGPPGMPGPR*G | 300 |
| ADAMTS4 | G*PQGLQGLPGTGGPP*G | 301 |
| ADAMTS4 | K*GPAGIPGFPGMKGHR*G | 302 |
| ADAMTS4 | R*GLAGPPGMPGPRGSPGPQG*V | 303 |
| ADAMTS4 | G*PPGENGKPGEPGPKGDAGAP*G | 304 |
| ADAMTS4 | A*PGFRGPAGPNGIPGEKGPAGER*G | 305 |
| ADAMTS4 | E*KGSPGAQGPPGAPGPLGIAGITGAR*G | 306 |
| ADAMTS4 | L*PGPPGIKGPAGIPGFPGMKGHR*G | 307 |
| ADAMTS4 | R*GAPGFRGPAGPNGIPGEKGPAGER*G | 308 |
| ADAMTS4 | R*GLPGPPGIKGPAGIPGFPGMKGHR*G | 309 |
| ADAMTS4 | R*GPVGPSGPPGKDGTSGHPGPIGPPGPR*G | 310 |
| ADAMTS4 | A*PGPQGPRGDKGETGERGAAGIKGHR*G | 311 |
| ADAMTS4 | R*GAPGPQGPRGDKGETGERGAAGIKGHR*G | 312 |
| ADAMTS4 | R*GFPGNPGAPGSPGAPGQQGAIGSPGPAGPR*G | 313 |
| ADAMTS4 | L*PGPPGIKGPAGIPGFPGMKGHRGFDGR*N | 314 |
| ADAMTS4 | D*AGQPGEKGSPGAQGPPGAPGPLGIAGITGAR*G | 315 |
| ADAMTS4 | R*GPTGPIGPPGPAGQPGDKGEGGAPGLPGIAGPR*G | 316 |
| ADAMTS4 | K*GDAGQPGEKGSPGAQGPPGAPGPLGIAGITGAR*G | 317 |
| ADAMTS4 | R*NGEKGETGAPGLKGENGLPGENGAPGPMGPR*G | 318 |
| ADAMTS4 | A*PGFRGPAGPNGIPGEKGPAGERGAPGPAGPRGA*A | 319 |
| ADAMTS4 | R*GAPGFRGPAGPNGIPGEKGPAGERGAPGPAGPR*G | 320 |

-continued

| Pro-tease | | SEQ ID NO |
|---|---|---|
| ADAMTS4 | R*GSPGERGETPPGPAGFPGAPGQNGEPGGKGER*G | 321 |
| ADAMTS4 | G*HAGAQGPPGPPGINGSPGGKGEMGPAGIPGAPGLMG*A | 322 |
| ADAMTS4 | R*GLAGPPGMPGPRGSPGPQGVKGESGKPGANGLSGER*G | 323 |
| ADAMTS8 | L*GIAGITGARGL*A | 324 |
| ADAMTS8 | I*PGFPGMKGHR*G | 325 |
| ADAMTS8 | R*GLAGPPGMPGPR*G | 326 |
| ADAMTS8 | Q*GPPGAPGPLGIAGITGAR*G | 327 |
| ADAMTS8 | A*GITGARGLAGPPGMPGPR*G | 328 |
| ADAMTS8 | A*GIPGAPGLMGARGPPGPAGAN*G | 329 |
| ADAMTS8 | R*GLAGPPGMPGPRGSPGPQGVKG*E | 330 |
| ADAMTS8 | K*GSPGAQGPPGAPGPLGIAGITGAR*G | 331 |
| ADAMTS8 | L*PGPPGIKGPAGIPGFPGMKGHR*G | 332 |
| ADAMTS8 | K*DGTSGHPGPIGPPGPRGNRGER*G | 333 |
| ADAMTS8 | A*GITGARGLAGPPGMPGPRGSPGPQ*G | 334 |
| ADAMTS8 | R*GLAGPPGMPGPRGSPGPQGVKGESG*K | 335 |
| ADAMTS8 | R*GLAGPPGMPGPRGSPGPQGVKGESGKPGAN*G | 336 |
| ADAMTS8 | R*GLAGPPGMPGPRGSPGPQGVKGESGKPGANGL*S | 337 |
| ADAMTS8 | P*GPPGSNGNPGPPGPSGSPGKDGPPGPAGNTGAPGS*P | 338 |
| ADAMTS8 | R*GAPGEKGEGGPPGVAGPPGGSGPAGPPGPQGVKGER*G | 339 |
| ADAMTS8 | K*SGDRGESGPAGPAGAPGPAGSRGAPGPQGPRGDKGETGERGA*A | 340 |
| ADAMTS8 | R*GAPGEKGEGGPPGVAGPPGGSGPAGPPGPQGVKGERGSPGGPGAAGFPGAR*G | 341 |
| MMP9 | _*AIGPSG_____*_ | 342 |
| unknown | AGGFAP* | 781. |

2. A method as claimed in claim 1, wherein said immunological binding partner is raised against a synthetic peptide corresponding to an N-terminal neo epitope amino acid sequence formed by cleavage of collagen type III by MMP-1, MMP-2, MMP-3, MMP-8, MMP-9, MMP-13, ADAMTS5, CathepsinK, CathepsinS, ADAMTS1, ADAMTS4 or ADAMTS8 and specifically binds a neo-epitope constituted by said N-terminal amino acid sequence, said N-terminal amino acid sequence selected from the group consisting of:

| Peptide (SEQ ID NO:) | Peptide (SEQ ID NO:) | Peptide (SEQ ID NO:) | Peptide (SEQ ID NO:) | Peptide (SEQ ID NO:) |
|---|---|---|---|---|
| GIPGAP 343 | GDPGPP 408 | LAGPPG 470 | ERGLPG 534 | IAGITG 598 |
| IKGHRG 344 | RGLAGP 409 | TGARGL 471 | | ITGARG 599 |
| VKGESG 345 | SRGAPG 410 | KGDAGQ 472 | ITGARG 535 | LRGGAG 600 |
| HAGAQG 346 | GKSGDR 411 | LQGLPG 473 | ERGLPG 536 | KDGTSG 763 |
| DGTSGH 347 | VGGLAG 412 | IAGITG 474 | PGAPGG 537 | VGGLAG 601 |
| IGSPGP 348 | AIGSPG 413 | AGQQGA 475 | GPPGVA 538 | AGPPGM 602 |
| LSGERG 349 | GLAGPP 414 | LAGPPG 476 | GLAGPP 539 | PQGPPG 603 |
| VKGERG 350 | RGLAGP 415 | GLSGER 477 | VGGLAG 540 | SPGGKG 604 |
| GARGLA 351 | KGESGK 416 | VKGERG 478 | SPGAQG 541 | GAPGEK 605 |
| GAPGEK 352 | IAGITG 417 | IKGPAG 479 | QPGVMG 542 | IKGPAG 606 |
| IKGPAG 353 | PGAPGL 418 | ERGLPG 480 | IPGAPG 543 | FRGPAG 607 |
| GIPGQP 354 | ERGLPG 419 | VGGLAG 481 | VKGERG 544 | DAGAPG 608 |
| GPPGPT 355 | INGSPG 420 | GPPGEP 482 | GPPGIN 545 | GLPGPP 609 |
| KNGETG 356 | LPGIAG 421 | INGSPG 483 | GINGSP 546 | PGENGK 610 |
| LKGENG 357 | NTGAPG 422 | LMGARG 484 | LRGGAG 547 | QQGAIG 611 |
| GDPGPP 358 | LRGGAG 423 | KNGETG 485 | YQGPPG 548 | VAGPPG 612 |
| DKGEPG 359 | GHAGAQ 424 | GERGAP 486 | GIPGFP 549 | PGMKGH 613 |
| FPGARG 360 | GFPGAR 425 | PGPPGP 487 | FPGMKG 550 | PGDKGE 614 |
| GDKGET 361 | GRNGEK 426 | GQPGDK 488 | GPPGEN 551 | |
| GGAGEP 362 | GERGSP 427 | PGVPGA 489 | AAGFPG 552 | |
| GPPGPP 363 | GKDGES 428 | GARGND 490 | PGVSGP 553 | GSDGQP 615 |
| | | PGAPGQ 491 | GFPGAP 554 | GARGND 616 |
| GAAGEP 365 | IAGITG 429 | GPPGPP 492 | GLSGER 555 | GARGPP 617 |
| GLSGER 366 | | IAGITG 493 | GGAGPP 556 | GPKGDA 618 |

| Peptide (SEQ ID NO:) | Peptide (SEQ ID NO:) | Peptide (SEQ ID NO:) | Peptide (SEQ ID NO:) | Peptide (SEQ ID NO:) |
|---|---|---|---|---|
| IAGITG 367 | GPKGDA 430 | | VGGLAG 557 | PGPQGH 619 |
| PGFPGM 368 | GSPGGP 431 | GPAGIP 494 | GLAGPP 558 | |
| GIAGIT 369 | | GPPGPP 495 | PGPPGI 559 | GITGAR 620 |
| GARGLA 370 | GLPGPP 432 | RPGLPG 496 | GAPGPM 560 | GSRGAP 621 |
| GLAGPP 371 | | GPPGSN 497 | GARGLA 561 | GAPGEK 622 |
| GPPGVA 372 | SGDRGE 433 | PGFPGM 498 | GLAGPP 562 | PQGLQG 623 |
| GPAGIP 373 | GLAGPP 434 | GPPGEN 499 | PGFRGP 563 | KGSPGA 624 |
| PGPPGI 374 | GAPGFR 435 | GLPGPP 500 | GPVGPS 564 | PGPQGP 625 |
| GAPGPQ 375 | GFPGNP 436 | PGPPGI 501 | AGQPGE 565 | GPTGPI 626 |
| GDAGQP 376 | NGEKGE 437 | PGFRGP 502 | GAPGFR 566 | GSPGER 627 |
| HAGAQG 377 | GLAGPP 438 | GIAGIT 503 | PGFPGM 567 | |
| GPPGAP 378 | GITGAR 439 | GIPGAP 504 | GLAGPP 568 | GSPGAQ 628 |
| | DGTSGH 440 | GITGAR 505 | | GLAGPP 629 |
| GLAGPP 379 | GPPGSN 441 | GAPGEK 506 | SGDRGE 569 | GAPGEK 630 |
| AIGPSG 380 | | | | | or wherein said immunological binding partner is raised against a synthetic peptide corresponding to a C-terminal neo epitope amino acid sequence formed by cleavage of collagen type III by MMP-1, MMP-2, MMP-3, MMP-8, MMP-9, MMP-13, ADAMTS5, CathepsinK, CathepsinS, ADAMTS1, ADAMTS4 or ADAMTS8 and specifically binds a neo-epitope constituted by said C-terminal amino acid sequence, said C-terminal amino acid sequence selected from the group consisting of:

| Peptide (SEQ ID NO:) | Peptide (SEQ ID NO:) | Peptide (SEQ ID NO:) | Peptide (SEQ ID NO:) | Peptide (SEQ ID NO:) |
|---|---|---|---|---|
| GPPGPA 381 | NGDPGI 442 | SPGPQG 507 | AGIPGF 570 | GMPGPR 631 |
| SPGPAG 382 | PGPQGV 443 | PPGPQG 508 | ERGAAG 571 | PGPLGI 632 |
| AAGTPG 383 | IPGAPG 444 | ERGPPG 509 | PGPPGT 572 | GNRGER 633 |
| TSGHPG 384 | SPGPQG 445 | APGLRG 510 | HPGSPG 573 | PSGPPG 634 |
| PSGPPG 385 | GSPGPA 446 | GPAGPP 511 | SPGPQG 574 | GLPGLA 635 |
| | QGPPGP 447 | SPGPQG 512 | GLAGTA 575 | PGPPGT 636 |
| PGLMGA 386 | | LAGPPG 513 | GPPGPQ 576 | GPPGPQ 637 |
| SPGPQG 387 | IPGFPG 448 | FPGPKG 514 | GFPGMK 577 | FPGMKG 638 |
| | GPAGIP 449 | PPGPAG 515 | EKGPAG 578 | GPPGIC 640 |
| PPGPPG 388 | FPGARG 450 | | PGPQGL 579 | GAPGLM 641 |
| GAIGPS 389 | GIPGAP 451 | | FPGAPG 580 | |
| PPGPAG 390 | ERGPPG 452 | LPGAAG 516 | APGPLG 581 | EPGPRG 642 |
| SPGPKG 391 | PSGPPG 453 | IPGQPG 517 | | |
| PPGPAG 392 | GPPGIN 454 | GAPGPA 518 | GFPGMK 582 | GHRGFD 643 |
| LPGPPG 393 | GTSGHP 455 | GHRGFD 519 | PGLPGI 583 | GAAGIK 644 |
| GAPGLK 394 | GLPGIA 456 | PGPKGD 520 | GHRGFD 584 | GEPGPR 645 |
| GLPGPP 395 | GANGLP 457 | GPPGPS 521 | PGPKGN 585 | GIPGAP 646 |

-continued

| Peptide (SEQ ID NO:) | Peptide (SEQ ID NO:) | Peptide (SEQ ID NO:) | Peptide (SEQ ID NO:) | Peptide (SEQ ID NO:) |
|---|---|---|---|---|
| GPPGIK 396 | TAGFPG 458 | PPGAPG 522 | GEVGPA 586 | GAPGLM 647 |
| GPPGVA 397 | EGGPPG 459 | GEVGPA 523 | GPPGPS 587 | TGARGL 648 |
| TPGLQG 398 | PQGLPG 460 | GAPGLR 524 | GLPGLA 588 | MPGPRG 649 |
| GTPGLQ 399 | APGPLG 461 | GPQGVK 525 | GSPGYQ 589 | GMKGHR 650 |
| GFPGAR 400 | GSPGPQ 462 | GMPGPR 526 | EMGPAG 590 | GPQGVK 651 |
| QPGPPG 401 | GAAGAR 463 | GAAGIK 527 | GKPGAN 591 | PGANGL 652 |
| TGAPGS 402 | GVKGER 464 | PGAAGF 528 | GMPGPR 592 | GTGGPP 653 |
| SPGPQG 403 | GDAGAP 465 | GPAGER 529 | GITGAR 593 | GPPGPR 654 |
| GPAGPR 404 | RGFDGR 466 | GIAGPR 530 | AGPRGA 594 | GGKGER 655 |
| APGLMG 405 | GLSGER 467 | TGARGL 531 | GPAGAN 595 | PQGVKG 656 |
| GNRGER 406 | GSPGPQ 468 | VKGESG 532 | GKPGAN 596 | PGANGL 657 |
| TGAPGS 407 | GVKGER 469 | TGERGA 533 | GFPGAR 597 | |

3. A method as claimed in claim 1, wherein said immunological binding partner is a monoclonal antibody or a fragment of a monoclonal antibody having specific binding affinity.

4. A method as claimed in claim 1, wherein said method is conducted as a competition immunoassay in which said immunological binding partner and a competition agent are incubated in the presence of said sample and the competition agent competes with the fragments of collagen type III in the sample to bind to the immunological binding partner.

5. A method as claimed in claim 4, wherein said competition agent is a synthetic peptide or is a purified native peptide formed by cleavage of collagen type III by MMP-1, MMP-2, MMP-3, MMP-8, MMP-9, MMP-13, ADAMTS5, CathepsinK, CathepsinS, ADAMTS1, ADAMTS4 or ADAMTS8 from which said epitope comes so as to reveal said neo-epitope.

6. A method as claimed in claim 1, wherein the sample is a sample of urine, serum, blood, or plasma.

7. A method as claimed in claim 1, wherein said immunological binding partner is raised against a synthetic peptide corresponding to an N- or C-terminal neo epitope amino acid sequence formed by cleavage of collagen type III by MMP9 and specifically binds a neo-epitope constituted by said N- or C-terminal neo epitope amino acid sequence, said N-terminal amino acid sequence being any sequence directly following the sign * in the following sequence, or said C-terminal amino being any sequence directly preceding the sign * in the following sequence:

G*KNGETGPQGPPGPTGPGGDKGDTGPPGPQG*L (SEQ ID NO: 231).

* * * * *

SEQUENCE LISTING

```
<160> NUMBER OF SEQ ID NOS: 844

<210> SEQ ID NO 1
<211> LENGTH: 3396
<212> TYPE: PRT
<213> ORGANISM: Homo sapiens

<400> SEQUENCE: 1
```

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

```
Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Pro Lys Glu Ala Thr
            340                 345                 350

Thr Ile Asp Leu Ser Ile Leu Ala Glu Thr Ala Ser Pro Ser Leu Ser
        355                 360                 365

Lys Glu Pro Gln Met Val Ser Asp Arg Thr Thr Pro Ile Ile Pro Leu
370                 375                 380

Val Asp Glu Leu Pro Val Ile Pro Thr Glu Phe Pro Pro Val Gly Asn
385                 390                 395                 400

Ile Val Ser Phe Glu Gln Lys Ala Thr Val Gln Pro Gln Ala Ile Thr
                405                 410                 415

Asp Ser Leu Ala Thr Lys Leu Pro Thr Pro Thr Gly Ser Thr Lys Lys
            420                 425                 430

Pro Trp Asp Met Asp Asp Tyr Ser Pro Ser Ala Ser Gly Pro Leu Gly
        435                 440                 445

Lys Leu Asp Ile Ser Glu Ile Lys Glu Glu Val Leu Gln Ser Thr Thr
450                 455                 460

Gly Val Ser His Tyr Ala Thr Asp Ser Trp Asp Gly Val Val Glu Asp
465                 470                 475                 480

Lys Gln Thr Gln Glu Ser Val Thr Gln Ile Glu Gln Ile Glu Val Gly
                485                 490                 495

Pro Leu Val Thr Ser Met Glu Ile Leu Lys His Ile Pro Ser Lys Glu
            500                 505                 510

Phe Pro Val Thr Glu Thr Pro Leu Val Thr Ala Arg Met Ile Leu Glu
        515                 520                 525

Ser Lys Thr Glu Lys Lys Met Val Ser Thr Val Ser Glu Leu Val Thr
530                 535                 540

Thr Gly His Tyr Gly Phe Thr Leu Gly Glu Glu Asp Glu Asp Arg
545                 550                 555                 560

Thr Leu Thr Val Gly Ser Asp Glu Ser Thr Leu Ile Phe Asp Gln Ile
                565                 570                 575

Pro Glu Val Ile Thr Val Ser Lys Thr Ser Glu Asp Thr Ile His Thr
            580                 585                 590

His Leu Glu Asp Leu Glu Ser Val Ser Ala Ser Thr Thr Val Ser Pro
        595                 600                 605

Leu Ile Met Pro Asp Asn Asn Gly Ser Ser Met Asp Asp Trp Glu Glu
610                 615                 620
```

```
Arg Gln Thr Ser Gly Arg Ile Thr Glu Glu Phe Leu Gly Lys Tyr Leu
625                 630                 635                 640

Ser Thr Thr Pro Phe Pro Ser Gln His Arg Thr Glu Ile Glu Leu Phe
            645                 650                 655

Pro Tyr Ser Gly Asp Lys Ile Leu Val Glu Gly Ile Ser Thr Val Ile
            660                 665                 670

Tyr Pro Ser Leu Gln Thr Glu Met Thr His Arg Arg Glu Arg Thr Glu
        675                 680                 685

Thr Leu Ile Pro Glu Met Arg Thr Asp Thr Tyr Thr Asp Glu Ile Gln
690                 695                 700

Glu Glu Ile Thr Lys Ser Pro Phe Met Gly Lys Thr Glu Glu Glu Val
705                 710                 715                 720

Phe Ser Gly Met Lys Leu Ser Thr Ser Leu Ser Glu Pro Ile His Val
                725                 730                 735

Thr Glu Ser Ser Val Glu Met Thr Lys Ser Phe Asp Phe Pro Thr Leu
            740                 745                 750

Ile Thr Lys Leu Ser Ala Glu Pro Thr Glu Val Arg Asp Met Glu Glu
        755                 760                 765

Asp Phe Thr Ala Thr Pro Gly Thr Thr Lys Tyr Asp Glu Asn Ile Thr
770                 775                 780

Thr Val Leu Leu Ala His Gly Thr Leu Ser Val Glu Ala Ala Thr Val
785                 790                 795                 800

Ser Lys Trp Ser Trp Asp Glu Asp Asn Thr Thr Ser Lys Pro Leu Glu
                805                 810                 815

Ser Thr Glu Pro Ser Ala Ser Ser Lys Leu Pro Pro Ala Leu Leu Thr
            820                 825                 830

Thr Val Gly Met Asn Gly Lys Asp Lys Asp Ile Pro Ser Phe Thr Glu
        835                 840                 845

Asp Gly Ala Asp Glu Phe Thr Leu Ile Pro Asp Ser Thr Gln Lys Gln
850                 855                 860

Leu Glu Glu Val Thr Asp Glu Asp Ile Ala Ala His Gly Lys Phe Thr
865                 870                 875                 880

Ile Arg Phe Gln Pro Thr Thr Ser Thr Gly Ile Ala Glu Lys Ser Thr
                885                 890                 895

Leu Arg Asp Ser Thr Thr Glu Glu Lys Val Pro Pro Ile Thr Ser Thr
            900                 905                 910

Glu Gly Gln Val Tyr Ala Thr Met Glu Gly Ser Ala Leu Gly Glu Val
        915                 920                 925

Glu Asp Val Asp Leu Ser Lys Pro Val Ser Thr Val Pro Gln Phe Ala
930                 935                 940

His Thr Ser Glu Val Glu Gly Leu Ala Phe Val Ser Tyr Ser Ser Thr
945                 950                 955                 960

Gln Glu Pro Thr Thr Tyr Val Asp Ser Ser His Thr Ile Pro Leu Ser
                965                 970                 975

Val Ile Pro Lys Thr Asp Trp Gly Val Leu Val Pro Ser Val Pro Ser
            980                 985                 990

Glu Asp Glu Val Leu Gly Glu Pro Ser Gln Asp Ile Leu Val Ile Asp
        995                 1000                1005

Gln Thr Arg Leu Glu Ala Thr Ile Ser Pro Glu Thr Met Arg Thr
        1010                1015                1020

Thr Lys Ile Thr Glu Gly Thr Gln Glu Glu Phe Pro Trp Lys
        1025                1030                1035

Glu Gln Thr Ala Glu Lys Pro Val Pro Ala Leu Ser Ser Thr Ala
```

-continued

```
               1040                1045                1050

Trp  Thr  Pro  Lys  Glu  Ala  Val  Thr  Pro  Leu  Asp  Glu  Gln  Glu  Gly
               1055                1060                1065

Asp  Gly  Ser  Ala  Tyr  Thr  Val  Ser  Glu  Asp  Glu  Leu  Leu  Thr  Gly
               1070                1075                1080

Ser  Glu  Arg  Val  Pro  Val  Leu  Glu  Thr  Thr  Pro  Val  Gly  Lys  Ile
               1085                1090                1095

Asp  His  Ser  Val  Ser  Tyr  Pro  Pro  Gly  Ala  Val  Thr  Glu  His  Lys
               1100                1105                1110

Val  Lys  Thr  Asp  Glu  Val  Val  Thr  Leu  Thr  Pro  Arg  Ile  Gly  Pro
               1115                1120                1125

Lys  Val  Ser  Leu  Ser  Pro  Gly  Pro  Glu  Gln  Lys  Tyr  Glu  Thr  Glu
               1130                1135                1140

Gly  Ser  Ser  Thr  Thr  Gly  Phe  Thr  Ser  Ser  Leu  Ser  Pro  Phe  Ser
               1145                1150                1155

Thr  His  Ile  Thr  Gln  Leu  Met  Glu  Glu  Thr  Thr  Thr  Glu  Lys  Thr
               1160                1165                1170

Ser  Leu  Glu  Asp  Ile  Asp  Leu  Gly  Ser  Gly  Leu  Phe  Glu  Lys  Pro
               1175                1180                1185

Lys  Ala  Thr  Glu  Leu  Ile  Glu  Phe  Ser  Thr  Ile  Lys  Val  Thr  Val
               1190                1195                1200

Pro  Ser  Asp  Ile  Thr  Thr  Ala  Phe  Ser  Ser  Val  Asp  Arg  Leu  His
               1205                1210                1215

Thr  Thr  Ser  Ala  Phe  Lys  Pro  Ser  Ser  Ala  Ile  Thr  Lys  Lys  Pro
               1220                1225                1230

Pro  Leu  Ile  Asp  Arg  Glu  Pro  Gly  Glu  Glu  Thr  Thr  Ser  Asp  Met
               1235                1240                1245

Val  Ile  Ile  Gly  Glu  Ser  Thr  Ser  His  Val  Pro  Pro  Thr  Thr  Leu
               1250                1255                1260

Glu  Asp  Ile  Val  Ala  Lys  Glu  Thr  Glu  Thr  Asp  Ile  Asp  Arg  Glu
               1265                1270                1275

Tyr  Phe  Thr  Thr  Ser  Ser  Pro  Pro  Ala  Thr  Gln  Pro  Thr  Arg  Pro
               1280                1285                1290

Pro  Thr  Val  Glu  Asp  Lys  Glu  Ala  Phe  Gly  Pro  Gln  Ala  Leu  Ser
               1295                1300                1305

Thr  Pro  Gln  Pro  Pro  Ala  Ser  Thr  Lys  Phe  His  Pro  Asp  Ile  Asn
               1310                1315                1320

Val  Tyr  Ile  Ile  Glu  Val  Arg  Glu  Asn  Lys  Thr  Gly  Arg  Met  Ser
               1325                1330                1335

Asp  Leu  Ser  Val  Ile  Gly  His  Pro  Ile  Asp  Ser  Glu  Ser  Lys  Glu
               1340                1345                1350

Asp  Glu  Pro  Cys  Ser  Glu  Glu  Thr  Asp  Pro  Val  His  Asp  Leu  Met
               1355                1360                1365

Ala  Glu  Ile  Leu  Pro  Glu  Phe  Pro  Asp  Ile  Ile  Glu  Ile  Asp  Leu
               1370                1375                1380

Tyr  His  Ser  Glu  Glu  Asn  Glu  Glu  Glu  Glu  Glu  Cys  Ala  Asn
               1385                1390                1395

Ala  Thr  Asp  Val  Thr  Thr  Thr  Pro  Ser  Val  Gln  Tyr  Ile  Asn  Gly
               1400                1405                1410

Lys  His  Leu  Val  Thr  Thr  Val  Pro  Lys  Asp  Pro  Glu  Ala  Ala  Glu
               1415                1420                1425

Ala  Arg  Arg  Gly  Gln  Phe  Glu  Ser  Val  Ala  Pro  Ser  Gln  Asn  Phe
               1430                1435                1440
```

```
                                        -continued

Ser Asp Ser Ser Glu Ser Asp Thr His Pro Phe Val Ile Ala Lys
    1445            1450            1455

Thr Glu Leu Ser Thr Ala Val Gln Pro Asn Glu Ser Thr Glu Thr
    1460            1465            1470

Thr Glu Ser Leu Glu Val Thr Trp Lys Pro Glu Thr Tyr Pro Glu
    1475            1480            1485

Thr Ser Glu His Phe Ser Gly Gly Glu Pro Asp Val Phe Pro Thr
    1490            1495            1500

Val Pro Phe His Glu Glu Phe Glu Ser Gly Thr Ala Lys Lys Gly
    1505            1510            1515

Ala Glu Ser Val Thr Glu Arg Asp Thr Glu Val Gly His Gln Ala
    1520            1525            1530

His Glu His Thr Glu Pro Val Ser Leu Phe Pro Glu Glu Ser Ser
    1535            1540            1545

Gly Glu Ile Ala Ile Asp Gln Glu Ser Gln Lys Ile Ala Phe Ala
    1550            1555            1560

Arg Ala Thr Glu Val Thr Phe Gly Glu Glu Val Glu Lys Ser Thr
    1565            1570            1575

Ser Val Thr Tyr Thr Pro Thr Ile Val Pro Ser Ser Ala Ser Ala
    1580            1585            1590

Tyr Val Ser Glu Glu Ala Val Thr Leu Ile Gly Asn Pro Trp
    1595            1600            1605

Pro Asp Asp Leu Leu Ser Thr Lys Glu Ser Trp Val Glu Ala Thr
    1610            1615            1620

Pro Arg Gln Val Val Glu Leu Ser Gly Ser Ser Ile Pro Ile
    1625            1630            1635

Thr Glu Gly Ser Gly Glu Ala Glu Glu Asp Glu Asp Thr Met Phe
    1640            1645            1650

Thr Met Val Thr Asp Leu Ser Gln Arg Asn Thr Thr Asp Thr Leu
    1655            1660            1665

Ile Thr Leu Asp Thr Ser Arg Ile Ile Thr Glu Ser Phe Phe Glu
    1670            1675            1680

Val Pro Ala Thr Thr Ile Tyr Pro Val Ser Glu Gln Pro Ser Ala
    1685            1690            1695

Lys Val Val Pro Thr Lys Phe Val Ser Glu Thr Asp Thr Ser Glu
    1700            1705            1710

Trp Ile Ser Ser Thr Thr Val Glu Glu Lys Lys Arg Lys Glu Glu
    1715            1720            1725

Glu Gly Thr Thr Gly Thr Ala Ser Thr Phe Glu Val Tyr Ser Ser
    1730            1735            1740

Thr Gln Arg Ser Asp Gln Leu Ile Leu Pro Phe Glu Leu Glu Ser
    1745            1750            1755

Pro Asn Val Ala Thr Ser Ser Asp Ser Gly Thr Arg Lys Ser Phe
    1760            1765            1770

Met Ser Leu Thr Thr Pro Thr Gln Ser Glu Arg Glu Met Thr Asp
    1775            1780            1785

Ser Thr Pro Val Phe Thr Glu Thr Asn Thr Leu Glu Asn Leu Gly
    1790            1795            1800

Ala Gln Thr Thr Glu His Ser Ser Ile His Gln Pro Gly Val Gln
    1805            1810            1815

Glu Gly Leu Thr Thr Leu Pro Arg Ser Pro Ala Ser Val Phe Met
    1820            1825            1830
```

```
Glu Gln Gly Ser Gly Glu Ala Ala Asp Pro Glu Thr Thr Thr
1835                1840                1845

Val Ser Ser Phe Ser Leu Asn Val Glu Tyr Ala Ile Gln Ala Glu
1850                1855                1860

Lys Glu Val Ala Gly Thr Leu Ser Pro His Val Glu Thr Thr Phe
1865                1870                1875

Ser Thr Glu Pro Thr Gly Leu Val Leu Ser Thr Val Met Asp Arg
1880                1885                1890

Val Val Ala Glu Asn Ile Thr Gln Thr Ser Arg Glu Ile Val Ile
1895                1900                1905

Ser Glu Arg Leu Gly Glu Pro Asn Tyr Gly Ala Glu Ile Arg Gly
1910                1915                1920

Phe Ser Thr Gly Phe Pro Leu Glu Glu Asp Phe Ser Gly Asp Phe
1925                1930                1935

Arg Glu Tyr Ser Thr Val Ser His Pro Ile Ala Lys Glu Glu Thr
1940                1945                1950

Val Met Met Glu Gly Ser Gly Asp Ala Ala Phe Arg Asp Thr Gln
1955                1960                1965

Thr Ser Pro Ser Thr Val Pro Thr Ser Val His Ile Ser His Ile
1970                1975                1980

Ser Asp Ser Glu Gly Pro Ser Ser Thr Met Val Ser Thr Ser Ala
1985                1990                1995

Phe Pro Trp Glu Glu Phe Thr Ser Ser Ala Glu Gly Ser Gly Glu
2000                2005                2010

Gln Leu Val Thr Val Ser Ser Ser Val Val Pro Val Leu Pro Ser
2015                2020                2025

Ala Val Gln Lys Phe Ser Gly Thr Ala Ser Ser Ile Ile Asp Glu
2030                2035                2040

Gly Leu Gly Glu Val Gly Thr Val Asn Glu Ile Asp Arg Arg Ser
2045                2050                2055

Thr Ile Leu Pro Thr Ala Glu Val Glu Gly Thr Lys Ala Pro Val
2060                2065                2070

Glu Lys Glu Glu Val Lys Val Ser Gly Thr Val Ser Thr Asn Phe
2075                2080                2085

Pro Gln Thr Ile Glu Pro Ala Lys Leu Trp Ser Arg Gln Glu Val
2090                2095                2100

Asn Pro Val Arg Gln Glu Ile Glu Ser Glu Thr Thr Ser Glu Glu
2105                2110                2115

Gln Ile Gln Glu Glu Lys Ser Phe Glu Ser Pro Gln Asn Ser Pro
2120                2125                2130

Ala Thr Glu Gln Thr Ile Phe Asp Ser Gln Thr Phe Thr Glu Thr
2135                2140                2145

Glu Leu Lys Thr Thr Asp Tyr Ser Val Leu Thr Thr Lys Lys Thr
2150                2155                2160

Tyr Ser Asp Asp Lys Glu Met Lys Glu Glu Asp Thr Ser Leu Val
2165                2170                2175

Asn Met Ser Thr Pro Asp Pro Asp Ala Asn Gly Leu Glu Ser Tyr
2180                2185                2190

Thr Thr Leu Pro Glu Ala Thr Glu Lys Ser His Phe Phe Leu Ala
2195                2200                2205

Thr Ala Leu Val Thr Glu Ser Ile Pro Ala Glu His Val Val Thr
2210                2215                2220

Asp Ser Pro Ile Lys Lys Glu Glu Ser Thr Lys His Phe Pro Lys
```

-continued

```
                2225                2230                2235
Gly Met Arg Pro Thr Ile Gln Glu Ser Asp Thr Glu Leu Leu Phe
        2240                2245                2250
Ser Gly Leu Gly Ser Gly Glu Glu Val Leu Pro Thr Leu Pro Thr
        2255                2260                2265
Glu Ser Val Asn Phe Thr Glu Val Glu Gln Ile Asn Asn Thr Leu
        2270                2275                2280
Tyr Pro His Thr Ser Gln Val Glu Ser Thr Ser Ser Asp Lys Ile
        2285                2290                2295
Glu Asp Phe Asn Arg Met Glu Asn Val Ala Lys Glu Val Gly Pro
        2300                2305                2310
Leu Val Ser Gln Thr Asp Ile Phe Glu Gly Ser Gly Ser Val Thr
        2315                2320                2325
Ser Thr Thr Leu Ile Glu Ile Leu Ser Asp Thr Gly Ala Glu Gly
        2330                2335                2340
Pro Thr Val Ala Pro Leu Pro Phe Ser Thr Asp Ile Gly His Pro
        2345                2350                2355
Gln Asn Gln Thr Val Arg Trp Ala Glu Glu Ile Gln Thr Ser Arg
        2360                2365                2370
Pro Gln Thr Ile Thr Glu Gln Asp Ser Asn Lys Asn Ser Ser Thr
        2375                2380                2385
Ala Glu Ile Asn Glu Thr Thr Thr Ser Ser Thr Asp Phe Leu Ala
        2390                2395                2400
Arg Ala Tyr Gly Phe Glu Met Ala Lys Glu Phe Val Thr Ser Ala
        2405                2410                2415
Pro Lys Pro Ser Asp Leu Tyr Tyr Glu Pro Ser Gly Glu Gly Ser
        2420                2425                2430
Gly Glu Val Asp Ile Val Asp Ser Phe His Thr Ser Ala Thr Thr
        2435                2440                2445
Gln Ala Thr Arg Gln Glu Ser Ser Thr Thr Phe Val Ser Asp Gly
        2450                2455                2460
Ser Leu Glu Lys His Pro Glu Val Pro Ser Ala Lys Ala Val Thr
        2465                2470                2475
Ala Asp Gly Phe Pro Thr Val Ser Val Met Leu Pro Leu His Ser
        2480                2485                2490
Glu Gln Asn Lys Ser Ser Pro Asp Pro Thr Ser Thr Leu Ser Asn
        2495                2500                2505
Thr Val Ser Tyr Glu Arg Ser Thr Asp Gly Ser Phe Gln Asp Arg
        2510                2515                2520
Phe Arg Glu Phe Glu Asp Ser Thr Leu Lys Pro Asn Arg Lys Lys
        2525                2530                2535
Pro Thr Glu Asn Ile Ile Ile Asp Leu Asp Lys Glu Asp Lys Asp
        2540                2545                2550
Leu Ile Leu Thr Ile Thr Glu Ser Thr Ile Leu Glu Ile Leu Pro
        2555                2560                2565
Glu Leu Thr Ser Asp Lys Asn Thr Ile Ile Asp Ile Asp His Thr
        2570                2575                2580
Lys Pro Val Tyr Glu Asp Ile Leu Gly Met Gln Thr Asp Ile Asp
        2585                2590                2595
Thr Glu Val Pro Ser Glu Pro His Asp Ser Asn Asp Glu Ser Asn
        2600                2605                2610
Asp Asp Ser Thr Gln Val Gln Glu Ile Tyr Glu Ala Ala Val Asn
        2615                2620                2625
```

```
Leu Ser Leu Thr Glu Glu Thr Phe Gly Ser Ala Asp Val Leu
    2630            2635            2640

Ala Ser Tyr Thr Gln Ala Thr His Asp Glu Ser Met Thr Tyr Glu
    2645            2650            2655

Asp Arg Ser Gln Leu Asp His Met Gly Phe His Phe Thr Thr Gly
    2660            2665            2670

Ile Pro Ala Pro Ser Thr Glu Thr Glu Leu Asp Val Leu Leu Pro
    2675            2680            2685

Thr Ala Thr Ser Leu Pro Ile Pro Arg Lys Ser Ala Thr Val Ile
    2690            2695            2700

Pro Glu Ile Glu Gly Ile Lys Ala Glu Ala Lys Ala Leu Asp Asp
    2705            2710            2715

Met Phe Glu Ser Ser Thr Leu Ser Asp Gly Gln Ala Ile Ala Asp
    2720            2725            2730

Gln Ser Glu Ile Ile Pro Thr Leu Gly Gln Phe Glu Arg Thr Gln
    2735            2740            2745

Glu Glu Tyr Glu Asp Lys Lys His Ala Gly Pro Ser Phe Gln Pro
    2750            2755            2760

Glu Phe Ser Ser Gly Ala Glu Glu Ala Leu Val Asp His Thr Pro
    2765            2770            2775

Tyr Leu Ser Ile Ala Thr Thr His Leu Met Asp Gln Ser Val Thr
    2780            2785            2790

Glu Val Pro Asp Val Met Glu Gly Ser Asn Pro Pro Tyr Tyr Thr
    2795            2800            2805

Asp Thr Thr Leu Ala Val Ser Thr Phe Ala Lys Leu Ser Ser Gln
    2810            2815            2820

Thr Pro Ser Ser Pro Leu Thr Ile Tyr Ser Gly Ser Glu Ala Ser
    2825            2830            2835

Gly His Thr Glu Ile Pro Gln Pro Ser Ala Leu Pro Gly Ile Asp
    2840            2845            2850

Val Gly Ser Ser Val Met Ser Pro Gln Asp Ser Phe Lys Glu Ile
    2855            2860            2865

His Val Asn Ile Glu Ala Thr Phe Lys Pro Ser Ser Glu Glu Tyr
    2870            2875            2880

Leu His Ile Thr Glu Pro Pro Ser Leu Ser Pro Asp Thr Lys Leu
    2885            2890            2895

Glu Pro Ser Glu Asp Asp Gly Lys Pro Glu Leu Leu Glu Glu Met
    2900            2905            2910

Glu Ala Ser Pro Thr Glu Leu Ile Ala Val Glu Gly Thr Glu Ile
    2915            2920            2925

Leu Gln Asp Phe Gln Asn Lys Thr Asp Gly Gln Val Ser Gly Glu
    2930            2935            2940

Ala Ile Lys Met Phe Pro Thr Ile Lys Thr Pro Glu Ala Gly Thr
    2945            2950            2955

Val Ile Thr Thr Ala Asp Glu Ile Glu Leu Glu Gly Ala Thr Gln
    2960            2965            2970

Trp Pro His Ser Thr Ser Ala Ser Ala Thr Tyr Gly Val Glu Ala
    2975            2980            2985

Gly Val Val Pro Trp Leu Ser Pro Gln Thr Ser Glu Arg Pro Thr
    2990            2995            3000

Leu Ser Ser Ser Pro Glu Ile Asn Pro Glu Thr Gln Ala Ala Leu
    3005            3010            3015
```

```
Ile Arg Gly Gln Asp Ser Thr Ile Ala Ala Ser Glu Gln Gln Val
    3020            3025            3030

Ala Ala Arg Ile Leu Asp Ser Asn Asp Gln Ala Thr Val Asn Pro
    3035            3040            3045

Val Glu Phe Asn Thr Glu Val Ala Thr Pro Pro Phe Ser Leu Leu
    3050            3055            3060

Glu Thr Ser Asn Glu Thr Asp Phe Leu Ile Gly Ile Asn Glu Glu
    3065            3070            3075

Ser Val Glu Gly Thr Ala Ile Tyr Leu Pro Gly Pro Asp Arg Cys
    3080            3085            3090

Lys Met Asn Pro Cys Leu Asn Gly Gly Thr Cys Tyr Pro Thr Glu
    3095            3100            3105

Thr Ser Tyr Val Cys Thr Cys Val Pro Gly Tyr Ser Gly Asp Gln
    3110            3115            3120

Cys Glu Leu Asp Phe Asp Glu Cys His Ser Asn Pro Cys Arg Asn
    3125            3130            3135

Gly Ala Thr Cys Val Asp Gly Phe Asn Thr Phe Arg Cys Leu Cys
    3140            3145            3150

Leu Pro Ser Tyr Val Gly Ala Leu Cys Glu Gln Asp Thr Glu Thr
    3155            3160            3165

Cys Asp Tyr Gly Trp His Lys Phe Gln Gly Gln Cys Tyr Lys Tyr
    3170            3175            3180

Phe Ala His Arg Arg Thr Trp Asp Ala Ala Glu Arg Glu Cys Arg
    3185            3190            3195

Leu Gln Gly Ala His Leu Thr Ser Ile Leu Ser His Glu Glu Gln
    3200            3205            3210

Met Phe Val Asn Arg Val Gly His Asp Tyr Gln Trp Ile Gly Leu
    3215            3220            3225

Asn Asp Lys Met Phe Glu His Asp Phe Arg Trp Thr Asp Gly Ser
    3230            3235            3240

Thr Leu Gln Tyr Glu Asn Trp Arg Pro Asn Gln Pro Asp Ser Phe
    3245            3250            3255

Phe Ser Ala Gly Glu Asp Cys Val Val Ile Ile Trp His Glu Asn
    3260            3265            3270

Gly Gln Trp Asn Asp Val Pro Cys Asn Tyr His Leu Thr Tyr Thr
    3275            3280            3285

Cys Lys Lys Gly Thr Val Ala Cys Gly Gln Pro Pro Val Val Glu
    3290            3295            3300

Asn Ala Lys Thr Phe Gly Lys Met Lys Pro Arg Tyr Glu Ile Asn
    3305            3310            3315

Ser Leu Ile Arg Tyr His Cys Lys Asp Gly Phe Ile Gln Arg His
    3320            3325            3330

Leu Pro Thr Ile Arg Cys Leu Gly Asn Gly Arg Trp Ala Ile Pro
    3335            3340            3345

Lys Ile Thr Cys Met Asn Pro Ser Ala Tyr Gln Arg Thr Tyr Ser
    3350            3355            3360

Met Lys Tyr Phe Lys Asn Ser Ser Ala Lys Asp Asn Ser Ile
    3365            3370            3375

Asn Thr Ser Lys His Asp His Arg Trp Ser Arg Arg Trp Gln Glu
    3380            3385            3390

Ser Arg Arg
    3395
```

-continued

```
<210> SEQ ID NO 2
<211> LENGTH: 338
<212> TYPE: PRT
<213> ORGANISM: Homo sapiens

<400> SEQUENCE: 2

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser
290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 3
<211> LENGTH: 4391
<212> TYPE: PRT
<213> ORGANISM: Homo sapiens

<400> SEQUENCE: 3
```

-continued

```
Met Gly Trp Arg Ala Pro Gly Ala Leu Leu Ala Leu Leu Leu His
 1               5                  10                  15

Gly Arg Leu Leu Ala Val Thr His Gly Leu Arg Ala Tyr Asp Gly Leu
             20                  25                  30

Ser Leu Pro Glu Asp Ile Glu Thr Val Thr Ala Ser Gln Met Arg Trp
         35                  40                  45

Thr His Ser Tyr Leu Ser Asp Asp Glu Asp Met Leu Ala Asp Ser Ile
     50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                 85                  90                  95

Ser Pro Gln Leu Glu Asp Ala Gly Ser Arg Glu Phe Arg Glu Val Ser
             100                 105                 110

Glu Ala Val Val Asp Thr Leu Glu Ser Glu Tyr Leu Lys Ile Pro Gly
         115                 120                 125

Asp Gln Val Val Ser Val Val Phe Ile Lys Glu Leu Asp Gly Trp Val
     130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                 165                 170                 175

Tyr Val Thr Ser Pro Gln Gly Phe Gln Phe Arg Arg Leu Gly Thr Val
             180                 185                 190

Pro Gln Phe Pro Arg Ala Cys Thr Glu Ala Glu Phe Ala Cys His Ser
         195                 200                 205

Tyr Asn Glu Cys Val Ala Leu Glu Tyr Arg Cys Asp Arg Arg Pro Asp
     210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                 245                 250                 255

Arg Pro Glu Thr Thr Ile Met Arg Gln Pro Pro Val Thr His Ala Pro
             260                 265                 270

Gln Pro Leu Leu Pro Gly Ser Val Arg Pro Leu Pro Cys Gly Pro Gln
         275                 280                 285

Glu Ala Ala Cys Arg Asn Gly His Cys Ile Pro Arg Asp Tyr Leu Cys
     290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                 325                 330                 335

Cys Ala Leu Lys Leu Trp Arg Cys Asp Gly Asp Phe Asp Cys Glu Asp
             340                 345                 350

Arg Thr Asp Glu Ala Asn Cys Pro Thr Lys Arg Pro Glu Glu Val Cys
         355                 360                 365

Gly Pro Thr Gln Phe Arg Cys Val Ser Thr Asn Met Cys Ile Pro Ala
     370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                 405                 410                 415
```

```
Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
        435                 440                 445

Ser His Pro Arg Val Thr Val Thr Ser Glu Gly Arg Gly Thr Leu
    450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
    530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
    610                 615                 620

Gly Met Leu Glu Pro Val Gln Arg Pro Asp Val Val Leu Val Gly Ala
625                 630                 635                 640

Gly Tyr Arg Leu Leu Ser Arg His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Ser Cys Asn Gly
        755                 760                 765

His Ala Ser Ser Cys Asp Pro Val Tyr Gly His Cys Leu Asn Cys Gln
    770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
```

-continued

```
                835                 840                 845
Arg Arg Cys Glu Ser Cys Ala Pro Gly Tyr Glu Gly Asn Pro Ile Gln
    850                 855                 860
Pro Gly Gly Lys Cys Arg Pro Val Asn Gln Glu Ile Val Arg Cys Asp
865                 870                 875                 880
Glu Arg Gly Ser Met Gly Thr Ser Gly Glu Ala Cys Arg Cys Lys Asn
                885                 890                 895
Asn Val Val Gly Arg Leu Cys Asn Glu Cys Ala Asp Gly Ser Phe His
                900                 905                 910
Leu Ser Thr Arg Asn Pro Asp Gly Cys Leu Lys Cys Phe Cys Met Gly
                915                 920                 925
Val Ser Arg His Cys Thr Ser Ser Trp Ser Arg Ala Gln Leu His
    930                 935                 940
Gly Ala Ser Glu Glu Pro Gly His Phe Ser Leu Thr Asn Ala Ala Ser
945                 950                 955                 960
Thr His Thr Thr Asn Glu Gly Ile Phe Ser Pro Thr Pro Gly Glu Leu
                965                 970                 975
Gly Phe Ser Ser Phe His Arg Leu Leu Ser Gly Pro Tyr Phe Trp Ser
                980                 985                 990
Leu Pro Ser Arg Phe Leu Gly Asp Lys Val Thr Ser Tyr Gly Gly Glu
                995                 1000                1005
Leu Arg Phe Thr Val Thr Gln Arg Ser Gln Pro Gly Ser Thr Pro
    1010                1015                1020
Leu His Gly Gln Pro Leu Val Val Leu Gln Gly Asn Asn Ile Ile
    1025                1030                1035
Leu Glu His His Val Ala Gln Glu Pro Ser Pro Gly Gln Pro Ser
    1040                1045                1050
Thr Phe Ile Val Pro Phe Arg Glu Gln Ala Trp Gln Arg Pro Asp
    1055                1060                1065
Gly Gln Pro Ala Thr Arg Glu His Leu Leu Met Ala Leu Ala Gly
    1070                1075                1080
Ile Asp Thr Leu Leu Ile Arg Ala Ser Tyr Ala Gln Gln Pro Ala
    1085                1090                1095
Glu Ser Arg Val Ser Gly Ile Ser Met Asp Val Ala Val Pro Glu
    1100                1105                1110
Glu Thr Gly Gln Asp Pro Ala Leu Glu Val Glu Gln Cys Ser Cys
    1115                1120                1125
Pro Pro Gly Tyr Arg Gly Pro Ser Cys Gln Asp Cys Asp Thr Gly
    1130                1135                1140
Tyr Thr Arg Thr Pro Ser Gly Leu Tyr Leu Gly Thr Cys Glu Arg
    1145                1150                1155
Cys Ser Cys His Gly His Ser Glu Ala Cys Glu Pro Glu Thr Gly
    1160                1165                1170
Ala Cys Gln Gly Cys Gln His His Thr Glu Gly Pro Arg Cys Glu
    1175                1180                1185
Gln Cys Gln Pro Gly Tyr Tyr Gly Asp Ala Gln Arg Gly Thr Pro
    1190                1195                1200
Gln Asp Cys Gln Leu Cys Pro Cys Tyr Gly Asp Pro Ala Ala Gly
    1205                1210                1215
Gln Ala Ala His Thr Cys Phe Leu Asp Thr Asp Gly His Pro Thr
    1220                1225                1230
Cys Asp Ala Cys Ser Pro Gly His Ser Gly Arg His Cys Glu Arg
    1235                1240                1245
```

-continued

```
Cys Ala Pro Gly Tyr Tyr Gly Asn Pro Ser Gln Gly Gln Pro Cys
    1250              1255              1260

Gln Arg Asp Ser Gln Val Pro Gly Pro Ile Gly Cys Asn Cys Asp
    1265              1270              1275

Pro Gln Gly Ser Val Ser Ser Gln Cys Asp Ala Ala Gly Gln Cys
    1280              1285              1290

Gln Cys Lys Ala Gln Val Glu Gly Leu Thr Cys Ser His Cys Arg
    1295              1300              1305

Pro His His Phe His Leu Ser Ala Ser Asn Pro Asp Gly Cys Leu
    1310              1315              1320

Pro Cys Phe Cys Met Gly Ile Thr Gln Gln Cys Ala Ser Ser Ala
    1325              1330              1335

Tyr Thr Arg His Leu Ile Ser Thr His Phe Ala Pro Gly Asp Phe
    1340              1345              1350

Gln Gly Phe Ala Leu Val Asn Pro Gln Arg Asn Ser Arg Leu Thr
    1355              1360              1365

Gly Glu Phe Thr Val Glu Pro Val Pro Glu Gly Ala Gln Leu Ser
    1370              1375              1380

Phe Gly Asn Phe Ala Gln Leu Gly His Glu Ser Phe Tyr Trp Gln
    1385              1390              1395

Leu Pro Glu Thr Tyr Gln Gly Asp Lys Val Ala Ala Tyr Gly Gly
    1400              1405              1410

Lys Leu Arg Tyr Thr Leu Ser Tyr Thr Ala Gly Pro Gln Gly Ser
    1415              1420              1425

Pro Leu Ser Asp Pro Asp Val Gln Ile Thr Gly Asn Asn Ile Met
    1430              1435              1440

Leu Val Ala Ser Gln Pro Ala Leu Gln Gly Pro Glu Arg Arg Ser
    1445              1450              1455

Tyr Glu Ile Met Phe Arg Glu Glu Phe Trp Arg Arg Pro Asp Gly
    1460              1465              1470

Gln Pro Ala Thr Arg Glu His Leu Leu Met Ala Leu Ala Asp Leu
    1475              1480              1485

Asp Glu Leu Leu Ile Arg Ala Thr Phe Ser Ser Val Pro Leu Val
    1490              1495              1500

Ala Ser Ile Ser Ala Val Ser Leu Glu Val Ala Gln Pro Gly Pro
    1505              1510              1515

Ser Asn Arg Pro Arg Ala Leu Glu Val Glu Glu Cys Arg Cys Pro
    1520              1525              1530

Pro Gly Tyr Ile Gly Leu Ser Cys Gln Asp Cys Ala Pro Gly Tyr
    1535              1540              1545

Thr Arg Thr Gly Ser Gly Leu Tyr Leu Gly His Cys Glu Leu Cys
    1550              1555              1560

Glu Cys Asn Gly His Ser Asp Leu Cys His Pro Glu Thr Gly Ala
    1565              1570              1575

Cys Ser Gln Cys Gln His Asn Ala Ala Gly Glu Phe Cys Glu Leu
    1580              1585              1590

Cys Ala Pro Gly Tyr Tyr Gly Asp Ala Thr Ala Gly Thr Pro Glu
    1595              1600              1605

Asp Cys Gln Pro Cys Ala Cys Pro Leu Thr Asn Pro Glu Asn Met
    1610              1615              1620

Phe Ser Arg Thr Cys Glu Ser Leu Gly Ala Gly Gly Tyr Arg Cys
    1625              1630              1635
```

```
Thr Ala Cys Glu Pro Gly Tyr Thr Gly Gln Tyr Cys Glu Gln Cys
    1640            1645                1650

Gly Pro Gly Tyr Val Gly Asn Pro Ser Val Gln Gly Gly Gln Cys
    1655            1660                1665

Leu Pro Glu Thr Asn Gln Ala Pro Leu Val Val Glu Val His Pro
    1670            1675                1680

Ala Arg Ser Ile Val Pro Gln Gly Ser His Ser Leu Arg Cys
    1685            1690                1695

Gln Val Ser Gly Ser Pro Pro His Tyr Phe Tyr Trp Ser Arg Glu
    1700            1705                1710

Asp Gly Arg Pro Val Pro Ser Gly Thr Gln Gln Arg His Gln Gly
    1715            1720                1725

Ser Glu Leu His Phe Pro Ser Val Gln Pro Ser Asp Ala Gly Val
    1730            1735                1740

Tyr Ile Cys Thr Cys Arg Asn Leu His Gln Ser Asn Thr Ser Arg
    1745            1750                1755

Ala Glu Leu Leu Val Thr Glu Ala Pro Ser Lys Pro Ile Thr Val
    1760            1765                1770

Thr Val Glu Glu Gln Arg Ser Gln Ser Val Arg Pro Gly Ala Asp
    1775            1780                1785

Val Thr Phe Ile Cys Thr Ala Lys Ser Lys Ser Pro Ala Tyr Thr
    1790            1795                1800

Leu Val Trp Thr Arg Leu His Asn Gly Lys Leu Pro Thr Arg Ala
    1805            1810                1815

Met Asp Phe Asn Gly Ile Leu Thr Ile Arg Asn Val Gln Leu Ser
    1820            1825                1830

Asp Ala Gly Thr Tyr Val Cys Thr Gly Ser Asn Met Phe Ala Met
    1835            1840                1845

Asp Gln Gly Thr Ala Thr Leu His Val Gln Ala Ser Gly Thr Leu
    1850            1855                1860

Ser Ala Pro Val Val Ser Ile His Pro Pro Gln Leu Thr Val Gln
    1865            1870                1875

Pro Gly Gln Leu Ala Glu Phe Arg Cys Ser Ala Thr Gly Ser Pro
    1880            1885                1890

Thr Pro Thr Leu Glu Trp Thr Gly Gly Pro Gly Gly Gln Leu Pro
    1895            1900                1905

Ala Lys Ala Gln Ile His Gly Gly Ile Leu Arg Leu Pro Ala Val
    1910            1915                1920

Glu Pro Thr Asp Gln Ala Gln Tyr Leu Cys Arg Ala His Ser Ser
    1925            1930                1935

Ala Gly Gln Gln Val Ala Arg Ala Val Leu His Val His Gly Gly
    1940            1945                1950

Gly Gly Pro Arg Val Gln Val Ser Pro Glu Arg Thr Gln Val His
    1955            1960                1965

Ala Gly Arg Thr Val Arg Leu Tyr Cys Arg Ala Ala Gly Val Pro
    1970            1975                1980

Ser Ala Thr Ile Thr Trp Arg Lys Glu Gly Gly Ser Leu Pro Pro
    1985            1990                1995

Gln Ala Arg Ser Glu Arg Thr Asp Ile Ala Thr Leu Leu Ile Pro
    2000            2005                2010

Ala Ile Thr Thr Ala Asp Ala Gly Phe Tyr Leu Cys Val Ala Thr
    2015            2020                2025

Ser Pro Ala Gly Thr Ala Gln Ala Arg Ile Gln Val Val Val Leu
```

2030                2035                2040

Ser Ala Ser Asp Ala Ser Pro Pro Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
    2270                2275                2280

Ser Leu Pro Ala Arg His Gln Val Arg Gly Ser Arg Leu Tyr Ile
    2285                2290                2295

Phe Gln Ala Ser Pro Ala Asp Ala Gly Gln Tyr Val Cys Arg Ala
    2300                2305                2310

Ser Asn Gly Met Glu Ala Ser Ile Thr Val Thr Val Thr Gly Thr
    2315                2320                2325

Gln Gly Ala Asn Leu Ala Tyr Pro Ala Gly Ser Thr Gln Pro Ile
    2330                2335                2340

Arg Ile Glu Pro Ser Ser Ser Gln Val Ala Glu Gly Gln Thr Leu
    2345                2350                2355

Asp Leu Asn Cys Val Val Pro Gly Gln Ser His Ala Gln Val Thr
    2360                2365                2370

Trp His Lys Arg Gly Gly Ser Leu Pro Val Arg His Gln Thr His
    2375                2380                2385

Gly Ser Leu Leu Arg Leu Tyr Gln Ala Ser Pro Ala Asp Ser Gly
    2390                2395                2400

Glu Tyr Val Cys Arg Val Leu Gly Ser Ser Val Pro Leu Glu Ala
    2405                2410                2415

Ser Val Leu Val Thr Ile Glu Pro Ala Gly Ser Val Pro Ala Leu
    2420                2425                2430

-continued

```
Gly Val Thr Pro Thr Val Arg Ile Glu Ser Ser Ser Ser Gln Val
2435                2440                2445

Ala Glu Gly Gln Thr Leu Asp Leu Asn Cys Leu Val Ala Gly Gln
2450                2455                2460

Ala His Ala Gln Val Thr Trp His Lys Arg Gly Gly Ser Leu Pro
2465                2470                2475

Ala Arg His Gln Val His Gly Ser Arg Leu Arg Leu Leu Gln Val
2480                2485                2490

Thr Pro Ala Asp Ser Gly Glu Tyr Val Cys Arg Val Val Gly Ser
2495                2500                2505

Ser Gly Thr Gln Glu Ala Ser Val Leu Val Thr Ile Gln Gln Arg
2510                2515                2520

Leu Ser Gly Ser His Ser Gln Gly Val Ala Tyr Pro Val Arg Ile
2525                2530                2535

Glu Ser Ser Ser Ala Ser Leu Ala Asn Gly His Thr Leu Asp Leu
2540                2545                2550

Asn Cys Leu Val Ala Ser Gln Ala Pro His Thr Ile Thr Trp Tyr
2555                2560                2565

Lys Arg Gly Gly Ser Leu Pro Ser Arg His Gln Ile Val Gly Ser
2570                2575                2580

Arg Leu Arg Ile Pro Gln Val Thr Pro Ala Asp Ser Gly Glu Tyr
2585                2590                2595

Val Cys His Val Ser Asn Gly Ala Gly Ser Arg Glu Thr Ser Leu
2600                2605                2610

Ile Val Thr Ile Gln Gly Ser Gly Ser Ser His Val Pro Ser Val
2615                2620                2625

Ser Pro Pro Ile Arg Ile Glu Ser Ser Ser Pro Thr Val Val Glu
2630                2635                2640

Gly Gln Thr Leu Asp Leu Asn Cys Val Val Ala Arg Gln Pro Gln
2645                2650                2655

Ala Ile Ile Thr Trp Tyr Lys Arg Gly Gly Ser Leu Pro Ser Arg
2660                2665                2670

His Gln Thr His Gly Ser His Leu Arg Leu His Gln Met Ser Val
2675                2680                2685

Ala Asp Ser Gly Glu Tyr Val Cys Arg Ala Asn Asn Asn Ile Asp
2690                2695                2700

Ala Leu Glu Ala Ser Ile Val Ile Ser Val Ser Pro Ser Ala Gly
2705                2710                2715

Ser Pro Ser Ala Pro Gly Ser Ser Met Pro Ile Arg Ile Glu Ser
2720                2725                2730

Ser Ser Ser His Val Ala Glu Gly Glu Thr Leu Asp Leu Asn Cys
2735                2740                2745

Val Val Pro Gly Gln Ala His Ala Gln Val Thr Trp His Lys Arg
2750                2755                2760

Gly Gly Ser Leu Pro Ser His His Gln Thr Arg Gly Ser Arg Leu
2765                2770                2775

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820
```

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
3005                3010                3015

Leu Arg Ser Pro Val Ile Ser Ile Asp Pro Pro Ser Ser Thr Val
3020                3025                3030

Gln Gln Gly Gln Asp Ala Ser Phe Lys Cys Leu Ile His Asp Gly
3035                3040                3045

Ala Ala Pro Ile Ser Leu Glu Trp Lys Thr Arg Asn Gln Glu Leu
3050                3055                3060

Glu Asp Asn Val His Ile Ser Pro Asn Gly Ser Ile Ile Thr Ile
3065                3070                3075

Val Gly Thr Arg Pro Ser Asn His Gly Thr Tyr Arg Cys Val Ala
3080                3085                3090

Ser Asn Ala Tyr Gly Val Ala Gln Ser Val Val Asn Leu Ser Val
3095                3100                3105

His Gly Pro Pro Thr Val Ser Val Leu Pro Glu Gly Pro Val Trp
3110                3115                3120

Val Lys Val Gly Lys Ala Val Thr Leu Glu Cys Val Ser Ala Gly
3125                3130                3135

Glu Pro Arg Ser Ser Ala Arg Trp Thr Arg Ile Ser Ser Thr Pro
3140                3145                3150

Ala Lys Leu Glu Gln Arg Thr Tyr Gly Leu Met Asp Ser His Ala
3155                3160                3165

Val Leu Gln Ile Ser Ser Ala Lys Pro Ser Asp Ala Gly Thr Tyr
3170                3175                3180

Val Cys Leu Ala Gln Asn Ala Leu Gly Thr Ala Gln Lys Gln Val
3185                3190                3195

Glu Val Ile Val Asp Thr Gly Ala Met Ala Pro Gly Ala Pro Gln
3200                3205                3210

Val Gln Ala Glu Glu Ala Glu Leu Thr Val Glu Ala Gly His Thr

```
            3215                3220                3225

Ala Thr Leu Arg Cys Ser Ala Thr Gly Ser Pro Ala Pro Thr Ile
            3230                3235                3240

His Trp Ser Lys Leu Arg Ser Pro Leu Pro Trp Gln His Arg Leu
            3245                3250                3255

Glu Gly Asp Thr Leu Ile Ile Pro Arg Val Ala Gln Gln Asp Ser
            3260                3265                3270

Gly Gln Tyr Ile Cys Asn Ala Thr Ser Pro Ala Gly His Ala Glu
            3275                3280                3285

Ala Thr Ile Ile Leu His Val Glu Ser Pro Pro Tyr Ala Thr Thr
            3290                3295                3300

Val Pro Glu His Ala Ser Val Gln Ala Gly Glu Thr Val Gln Leu
            3305                3310                3315

Gln Cys Leu Ala His Gly Thr Pro Pro Leu Thr Phe Gln Trp Ser
            3320                3325                3330

Arg Val Gly Ser Ser Leu Pro Gly Arg Ala Thr Ala Arg Asn Glu
            3335                3340                3345

Leu Leu His Phe Glu Arg Ala Ala Pro Glu Asp Ser Gly Arg Tyr
            3350                3355                3360

Arg Cys Arg Val Thr Asn Lys Val Gly Ser Ala Glu Ala Phe Ala
            3365                3370                3375

Gln Leu Leu Val Gln Gly Pro Pro Gly Ser Leu Pro Ala Thr Ser
            3380                3385                3390

Ile Pro Ala Gly Ser Thr Pro Thr Val Gln Val Thr Pro Gln Leu
            3395                3400                3405

Glu Thr Lys Ser Ile Gly Ala Ser Val Glu Phe His Cys Ala Val
            3410                3415                3420

Pro Ser Asp Arg Gly Thr Gln Leu Arg Trp Phe Lys Glu Gly Gly
            3425                3430                3435

Gln Leu Pro Pro Gly His Ser Val Gln Asp Gly Val Leu Arg Ile
            3440                3445                3450

Gln Asn Leu Asp Gln Ser Cys Gln Gly Thr Tyr Ile Cys Gln Ala
            3455                3460                3465

His Gly Pro Trp Gly Lys Ala Gln Ala Ser Ala Gln Leu Val Ile
            3470                3475                3480

Gln Ala Leu Pro Ser Val Leu Ile Asn Ile Arg Thr Ser Val Gln
            3485                3490                3495

Thr Val Val Val Gly His Ala Val Glu Phe Glu Cys Leu Ala Leu
            3500                3505                3510

Gly Asp Pro Lys Pro Gln Val Thr Trp Ser Lys Val Gly Gly His
            3515                3520                3525

Leu Arg Pro Gly Ile Val Gln Ser Gly Gly Val Val Arg Ile Ala
            3530                3535                3540

His Val Glu Leu Ala Asp Ala Gly Gln Tyr Arg Cys Thr Ala Thr
            3545                3550                3555

Asn Ala Ala Gly Thr Thr Gln Ser His Val Leu Leu Leu Val Gln
            3560                3565                3570

Ala Leu Pro Gln Ile Ser Met Pro Gln Glu Val Arg Val Pro Ala
            3575                3580                3585

Gly Ser Ala Ala Val Phe Pro Cys Ile Ala Ser Gly Tyr Pro Thr
            3590                3595                3600

Pro Asp Ile Ser Trp Ser Lys Leu Asp Gly Ser Leu Pro Pro Asp
            3605                3610                3615
```

-continued

```
Ser Arg Leu Glu Asn Asn Met Leu Met Leu Pro Ser Val Arg Pro
    3620              3625              3630

Gln Asp Ala Gly Thr Tyr Val Cys Thr Ala Thr Asn Arg Gln Gly
    3635              3640              3645

Lys Val Lys Ala Phe Ala His Leu Gln Val Pro Glu Arg Val Val
    3650              3655              3660

Pro Tyr Phe Thr Gln Thr Pro Tyr Ser Phe Leu Pro Leu Pro Thr
    3665              3670              3675

Ile Lys Asp Ala Tyr Arg Lys Phe Glu Ile Lys Ile Thr Phe Arg
    3680              3685              3690

Pro Asp Ser Ala Asp Gly Met Leu Leu Tyr Asn Gly Gln Lys Arg
    3695              3700              3705

Val Pro Gly Ser Pro Thr Asn Leu Ala Asn Arg Gln Pro Asp Phe
    3710              3715              3720

Ile Ser Phe Gly Leu Val Gly Gly Arg Pro Glu Phe Arg Phe Asp
    3725              3730              3735

Ala Gly Ser Gly Met Ala Thr Ile Arg His Pro Thr Pro Leu Ala
    3740              3745              3750

Leu Gly His Phe His Thr Val Thr Leu Leu Arg Ser Leu Thr Gln
    3755              3760              3765

Gly Ser Leu Ile Val Gly Asp Leu Ala Pro Val Asn Gly Thr Ser
    3770              3775              3780

Gln Gly Lys Phe Gln Gly Leu Asp Leu Asn Glu Glu Leu Tyr Leu
    3785              3790              3795

Gly Gly Tyr Pro Asp Tyr Gly Ala Ile Pro Lys Ala Gly Leu Ser
    3800              3805              3810

Ser Gly Phe Ile Gly Cys Val Arg Glu Leu Arg Ile Gln Gly Glu
    3815              3820              3825

Glu Ile Val Phe His Asp Leu Asn Leu Thr Ala His Gly Ile Ser
    3830              3835              3840

His Cys Pro Thr Cys Arg Asp Arg Pro Cys Gln Asn Gly Gly Gln
    3845              3850              3855

Cys His Asp Ser Glu Ser Ser Tyr Val Cys Val Cys Pro Ala
    3860              3865              3870

Gly Phe Thr Gly Ser Arg Cys Glu His Ser Gln Ala Leu His Cys
    3875              3880              3885

His Pro Glu Ala Cys Gly Pro Asp Ala Thr Cys Val Asn Arg Pro
    3890              3895              3900

Asp Gly Arg Gly Tyr Thr Cys Arg Cys His Leu Gly Arg Ser Gly
    3905              3910              3915

Leu Arg Cys Glu Glu Gly Val Thr Val Thr Thr Pro Ser Leu Ser
    3920              3925              3930

Gly Ala Gly Ser Tyr Leu Ala Leu Pro Ala Leu Thr Asn Thr His
    3935              3940              3945

His Glu Leu Arg Leu Asp Val Glu Phe Lys Pro Leu Ala Pro Asp
    3950              3955              3960

Gly Val Leu Leu Phe Ser Gly Gly Lys Ser Gly Pro Val Glu Asp
    3965              3970              3975

Phe Val Ser Leu Ala Met Val Gly Gly His Leu Glu Phe Arg Tyr
    3980              3985              3990

Glu Leu Gly Ser Gly Leu Ala Val Leu Arg Ser Ala Glu Pro Leu
    3995              4000              4005
```

-continued

Ala Leu Gly Arg Trp His Arg Val Ser Ala Glu Arg Leu Asn Lys
4010                4015                4020

Asp Gly Ser Leu Arg Val Asn Gly Gly Arg Pro Val Leu Arg Ser
4025                4030                4035

Ser Pro Gly Lys Ser Gln Gly Leu Asn Leu His Thr Leu Leu Tyr
4040                4045                4050

Leu Gly Gly Val Glu Pro Ser Val Pro Leu Ser Pro Ala Thr Asn
4055                4060                4065

Met Ser Ala His Phe Arg Gly Cys Val Gly Glu Val Ser Val Asn
4070                4075                4080

Gly Lys Arg Leu Asp Leu Thr Tyr Ser Phe Leu Gly Ser Gln Gly
4085                4090                4095

Ile Gly Gln Cys Tyr Asp Ser Ser Pro Cys Glu Arg Gln Pro Cys
4100                4105                4110

Gln His Gly Ala Thr Cys Met Pro Ala Gly Glu Tyr Glu Phe Gln
4115                4120                4125

Cys Leu Cys Arg Asp Gly Phe Lys Gly Asp Leu Cys Glu His Glu
4130                4135                4140

Glu Asn Pro Cys Gln Leu Arg Glu Pro Cys Leu His Gly Gly Thr
4145                4150                4155

Cys Gln Gly Thr Arg Cys Leu Cys Leu Pro Gly Phe Ser Gly Pro
4160                4165                4170

Arg Cys Gln Gln Gly Ser Gly His Gly Ile Ala Glu Ser Asp Trp
4175                4180                4185

His Leu Glu Gly Ser Gly Gly Asn Asp Ala Pro Gly Gln Tyr Gly
4190                4195                4200

Ala Tyr Phe His Asp Asp Gly Phe Leu Ala Phe Pro Gly His Val
4205                4210                4215

Phe Ser Arg Ser Leu Pro Glu Val Pro Glu Thr Ile Glu Leu Glu
4220                4225                4230

Val Arg Thr Ser Thr Ala Ser Gly Leu Leu Leu Trp Gln Gly Val
4235                4240                4245

Glu Val Gly Glu Ala Gly Gln Gly Lys Asp Phe Ile Ser Leu Gly
4250                4255                4260

Leu Gln Asp Gly His Leu Val Phe Arg Tyr Gln Leu Gly Ser Gly
4265                4270                4275

Glu Ala Arg Leu Val Ser Glu Asp Pro Ile Asn Asp Gly Glu Trp
4280                4285                4290

His Arg Val Thr Ala Leu Arg Glu Gly Arg Arg Gly Ser Ile Gln
4295                4300                4305

Val Asp Gly Glu Glu Leu Val Ser Gly Arg Ser Pro Gly Pro Asn
4310                4315                4320

Val Ala Val Asn Ala Lys Gly Ser Val Tyr Ile Gly Gly Ala Pro
4325                4330                4335

Asp Val Ala Thr Leu Thr Gly Gly Arg Phe Ser Ser Gly Ile Thr
4340                4345                4350

Gly Cys Val Lys Asn Leu Val Leu His Ser Ala Arg Pro Gly Ala
4355                4360                4365

Pro Pro Pro Gln Pro Leu Asp Leu Gln His Arg Ala Gln Ala Gly
4370                4375                4380

Ala Asn Thr Arg Pro Cys Pro Ser
4385                4390

<210> SEQ ID NO 4
<211> LENGTH: 368
<212> TYPE: PRT
<213> ORGANISM: Homo sapiens

<400> SEQUENCE: 4

```
Met Trp Pro Leu Trp Arg Leu Val Ser Leu Ala Leu Ser Gln Ala
 1               5                  10                  15

Leu Pro Phe Glu Gln Arg Gly Phe Trp Asp Phe Thr Leu Asp Asp Gly
                20                  25                  30

Pro Phe Met Met Asn Asp Glu Glu Ala Ser Gly Ala Asp Thr Ser Gly
                35                  40                  45

Val Leu Asp Pro Asp Ser Val Thr Pro Thr Tyr Ser Ala Met Cys Pro
 50                  55                  60

Phe Gly Cys His Cys His Leu Arg Val Val Gln Cys Ser Asp Leu Gly
 65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
                100                 105                 110

Leu Gln His Leu Tyr Ala Leu Val Leu Val Asn Asn Lys Ile Ser Lys
                115                 120                 125

Ile His Glu Lys Ala Phe Ser Pro Leu Arg Lys Leu Gln Lys Leu Tyr
 130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
                180                 185                 190

Asn Pro Leu Glu Asn Ser Gly Phe Glu Pro Gly Ala Phe Asp Gly Leu
                195                 200                 205

Lys Leu Asn Tyr Leu Arg Ile Ser Glu Ala Lys Leu Thr Gly Ile Pro
 210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
                260                 265                 270

Leu Ser Phe Leu Pro Thr Leu Arg Glu Leu His Leu Asp Asn Asn Lys
                275                 280                 285

Leu Ala Arg Val Pro Ser Gly Leu Pro Asp Leu Lys Leu Leu Gln Val
 290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
                340                 345                 350

Arg Cys Val Thr Asp Arg Leu Ala Ile Gln Phe Gly Asn Tyr Lys Lys
                355                 360                 365
```

<210> SEQ ID NO 5
<211> LENGTH: 359

<212> TYPE: PRT
<213> ORGANISM: Homo sapiens

<400> SEQUENCE: 5

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
        195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
        275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 6
<211> LENGTH: 24
<212> TYPE: PRT
<213> ORGANISM: Homo sapiens

```
<400> SEQUENCE: 6

Lys Ser Val Pro Lys Glu Ile Ser Pro Asp Thr Thr Leu Leu Asp Leu
1               5                   10                  15

Gln Asn Asn Asp Ile Ser Glu Leu
            20

<210> SEQ ID NO 7
<211> LENGTH: 25
<212> TYPE: PRT
<213> ORGANISM: Homo sapiens

<400> SEQUENCE: 7

Leu Lys Ser Val Pro Lys Glu Ile Ser Pro Asp Thr Thr Leu Leu Asp
1               5                   10                  15

Leu Gln Asn Asn Asp Ile Ser Glu Leu
            20                  25

<210> SEQ ID NO 8
<211> LENGTH: 25
<212> TYPE: PRT
<213> ORGANISM: Homo sapiens

<400> SEQUENCE: 8

Glu Asn Ser Gly Phe Glu Pro Gly Ala Phe Asp Gly Leu Lys Leu Asn
1               5                   10                  15

Tyr Leu Arg Ile Ser Glu Ala Lys Leu
            20                  25

<210> SEQ ID NO 9
<211> LENGTH: 26
<212> TYPE: PRT
<213> ORGANISM: Homo sapiens

<400> SEQUENCE: 9

Gly Leu Lys Ser Val Pro Lys Glu Ile Ser Pro Asp Thr Thr Leu Leu
1               5                   10                  15

Asp Leu Gln Asn Asn Asp Ile Ser Glu Leu
            20                  25

<210> SEQ ID NO 10
<211> LENGTH: 20
<212> TYPE: PRT
<213> ORGANISM: Homo sapiens

<400> SEQUENCE: 10

Tyr Leu Arg Ile Ser Glu Ala Lys Leu Thr Gly Ile Pro Lys Asp Leu
1               5                   10                  15

Pro Glu Thr Leu
            20

<210> SEQ ID NO 11
<211> LENGTH: 26
<212> TYPE: PRT
<213> ORGANISM: Homo sapiens

<400> SEQUENCE: 11

Gly Leu Lys Ser Val Pro Lys Glu Ile Ser Pro Asp Thr Thr Leu Leu
1               5                   10                  15

Asp Leu Gln Asn Asn Asp Ile Ser Glu Leu
            20                  25
```

```
<210> SEQ ID NO 12
<211> LENGTH: 26
<212> TYPE: PRT
<213> ORGANISM: Homo sapiens

<400> SEQUENCE: 12

Leu Thr Gly Ile Pro Lys Asp Leu Pro Glu Thr Leu Asn Glu Leu His
1               5                   10                  15

Leu Asp His Asn Lys Ile Gln Ala Ile Glu
            20                  25

<210> SEQ ID NO 13
<211> LENGTH: 22
<212> TYPE: PRT
<213> ORGANISM: Homo sapiens

<400> SEQUENCE: 13

Lys Arg Ile Ser Glu Ala Lys Leu Thr Gly Ile Pro Lys Asp Leu Pro
1               5                   10                  15

Glu Thr Leu Asn Glu Leu
            20

<210> SEQ ID NO 14
<211> LENGTH: 14
<212> TYPE: PRT
<213> ORGANISM: Homo sapiens

<400> SEQUENCE: 14

Gln Ala Ile Glu Leu Glu Asp Leu Leu Arg Tyr Ser Lys Leu
1               5                   10

<210> SEQ ID NO 15
<211> LENGTH: 12
<212> TYPE: PRT
<213> ORGANISM: Homo sapiens

<400> SEQUENCE: 15

Gln Ala Ile Glu Leu Glu Asp Leu Leu Arg Tyr Ser
1               5                   10

<210> SEQ ID NO 16
<211> LENGTH: 19
<212> TYPE: PRT
<213> ORGANISM: Homo sapiens

<400> SEQUENCE: 16

Ser Glu Ala Lys Leu Thr Gly Ile Pro Lys Asp Leu Pro Glu Thr Leu
1               5                   10                  15

Asn Glu Leu

<210> SEQ ID NO 17
<211> LENGTH: 25
<212> TYPE: PRT
<213> ORGANISM: Homo sapiens

<400> SEQUENCE: 17

Leu Lys Ala Val Pro Lys Glu Ile Ser Pro Asp Thr Thr Leu Leu Asp
1               5                   10                  15

Leu Gln Asn Asn Asp Ile Ser Glu Leu
            20                  25

<210> SEQ ID NO 18
```

```
<211> LENGTH: 18
<212> TYPE: PRT
<213> ORGANISM: Homo sapiens

<400> SEQUENCE: 18

Thr Leu Leu Asp Leu Gln Asn Asn Asp Ile Ser Glu Leu Arg Lys Asp
1               5                   10                  15

Asp Phe

<210> SEQ ID NO 19
<211> LENGTH: 12
<212> TYPE: PRT
<213> ORGANISM: Homo sapiens

<400> SEQUENCE: 19

Ala Ile Glu Leu Glu Asp Leu Leu Arg Tyr Ser Lys
1               5                   10

<210> SEQ ID NO 20
<211> LENGTH: 15
<212> TYPE: PRT
<213> ORGANISM: Homo sapiens

<400> SEQUENCE: 20

Glu Asn Ser Gly Phe Glu Pro Gly Ala Phe Asp Gly Leu Lys Leu
1               5                   10                  15

<210> SEQ ID NO 21
<211> LENGTH: 13
<212> TYPE: PRT
<213> ORGANISM: Homo sapiens

<400> SEQUENCE: 21

Met Ile Val Ile Glu Leu Gly Thr Asn Pro Leu Lys Ser
1               5                   10

<210> SEQ ID NO 22
<211> LENGTH: 13
<212> TYPE: PRT
<213> ORGANISM: Homo sapiens

<400> SEQUENCE: 22

Met Ile Val Ile Glu Leu Gly Thr Asn Pro Leu Lys Ser
1               5                   10

<210> SEQ ID NO 23
<211> LENGTH: 17
<212> TYPE: PRT
<213> ORGANISM: Homo sapiens

<400> SEQUENCE: 23

Glu Leu His Leu Asp Gly Asn Lys Ile Ser Arg Val Asp Ala Ala Ser
1               5                   10                  15

Leu

<210> SEQ ID NO 24
<211> LENGTH: 18
<212> TYPE: PRT
<213> ORGANISM: Homo sapiens

<400> SEQUENCE: 24

Leu Val Asn Asn Lys Ile Ser Lys Val Ser Pro Gly Ala Phe Thr Pro
1               5                   10                  15
```

Leu Val

<210> SEQ ID NO 25
<211> LENGTH: 26
<212> TYPE: PRT
<213> ORGANISM: Homo sapiens

<400> SEQUENCE: 25

Ala Leu Ile Leu Val Asn Asn Lys Ile Ser Lys Val Ser Pro Gly Ala
1               5                   10                  15

Phe Thr Pro Leu Val Lys Leu Glu Arg Leu
            20                  25

<210> SEQ ID NO 26
<211> LENGTH: 17
<212> TYPE: PRT
<213> ORGANISM: Homo sapiens

<400> SEQUENCE: 26

Phe Ser Asn Pro Val Gln Tyr Trp Glu Ile Gln Pro Ser Thr Phe Arg
1               5                   10                  15

Cys

<210> SEQ ID NO 27
<211> LENGTH: 15
<212> TYPE: PRT
<213> ORGANISM: Homo sapiens

<400> SEQUENCE: 27

Lys Ser Ser Gly Ile Glu Asn Gly Ala Phe Gln Gly Met Lys Lys
1               5                   10                  15

<210> SEQ ID NO 28
<211> LENGTH: 18
<212> TYPE: PRT
<213> ORGANISM: Homo sapiens

<400> SEQUENCE: 28

Lys Ser Ser Gly Ile Glu Asn Gly Ala Phe Gln Gly Met Lys Lys Leu
1               5                   10                  15

Ser Tyr

<210> SEQ ID NO 29
<211> LENGTH: 13
<212> TYPE: PRT
<213> ORGANISM: Homo sapiens

<400> SEQUENCE: 29

Asn Lys Ile Thr Glu Ile Lys Asp Gly Asp Phe Lys Asn
1               5                   10

<210> SEQ ID NO 30
<211> LENGTH: 17
<212> TYPE: PRT
<213> ORGANISM: Homo sapiens

<400> SEQUENCE: 30

Gln Gly Leu Pro Pro Ser Leu Thr Glu Leu His Leu Asp Gly Asn Lys
1               5                   10                  15

Ile

<210> SEQ ID NO 31

```
<211> LENGTH: 12
<212> TYPE: PRT
<213> ORGANISM: Homo sapiens

<400> SEQUENCE: 31

Lys Leu Leu Ala Ser Asp Ala Gly Leu Tyr Arg Cys
1               5                   10

<210> SEQ ID NO 32
<211> LENGTH: 13
<212> TYPE: PRT
<213> ORGANISM: Homo sapiens

<400> SEQUENCE: 32

Leu Ala Thr Val Gly Glu Leu Gln Ala Ala Trp Arg Asn
1               5                   10

<210> SEQ ID NO 33
<211> LENGTH: 15
<212> TYPE: PRT
<213> ORGANISM: Homo sapiens

<400> SEQUENCE: 33

Lys Glu Thr Thr Val Leu Val Ala Gln Asn Gly Asn Ile Lys Ile
1               5                   10                  15

<210> SEQ ID NO 34
<211> LENGTH: 12
<212> TYPE: PRT
<213> ORGANISM: Homo sapiens

<400> SEQUENCE: 34

Ser Leu Glu Asp Leu Gln Leu Thr His Asn Lys Ile
1               5                   10

<210> SEQ ID NO 35
<211> LENGTH: 13
<212> TYPE: PRT
<213> ORGANISM: Homo sapiens

<400> SEQUENCE: 35

Arg Leu Lys Glu Asp Ala Val Ser Ala Ala Phe Lys Gly
1               5                   10

<210> SEQ ID NO 36
<211> LENGTH: 16
<212> TYPE: PRT
<213> ORGANISM: Homo sapiens

<400> SEQUENCE: 36

Arg Ser Ile Glu Tyr Ser Pro Gln Leu Glu Asp Ala Gly Ser Arg Glu
1               5                   10                  15

<210> SEQ ID NO 37
<211> LENGTH: 12
<212> TYPE: PRT
<213> ORGANISM: Homo sapiens

<400> SEQUENCE: 37

Arg Leu Glu Gly Asp Thr Leu Ile Ile Pro Arg Val
1               5                   10

<210> SEQ ID NO 38
<211> LENGTH: 15
<212> TYPE: PRT
```

<213> ORGANISM: Homo sapiens

<400> SEQUENCE: 38

Glu Val Ser Glu Ala Val Val Glu Lys Leu Glu Pro Glu Tyr Arg
1               5                   10                  15

<210> SEQ ID NO 39
<211> LENGTH: 16
<212> TYPE: PRT
<213> ORGANISM: Homo sapiens

<400> SEQUENCE: 39

Arg Glu Val Ser Glu Ala Val Val Glu Lys Leu Glu Pro Glu Tyr Arg
1               5                   10                  15

<210> SEQ ID NO 40
<211> LENGTH: 12
<212> TYPE: PRT
<213> ORGANISM: Homo sapiens

<400> SEQUENCE: 40

Arg Ser Ile Glu Tyr Ser Pro Gln Leu Glu Asp Ala
1               5                   10

<210> SEQ ID NO 41
<211> LENGTH: 22
<212> TYPE: PRT
<213> ORGANISM: Homo sapiens

<400> SEQUENCE: 41

Ser Val Pro Lys Glu Ile Ser Pro Asp Thr Thr Leu Leu Asp Leu Gln
1               5                   10                  15

Asn Asn Asp Ile Ser Glu
            20

<210> SEQ ID NO 42
<211> LENGTH: 23
<212> TYPE: PRT
<213> ORGANISM: Homo sapiens

<400> SEQUENCE: 42

Lys Ser Val Pro Lys Glu Ile Ser Pro Asp Thr Thr Leu Leu Asp Leu
1               5                   10                  15

Gln Asn Asn Asp Ile Ser Glu
            20

<210> SEQ ID NO 43
<211> LENGTH: 23
<212> TYPE: PRT
<213> ORGANISM: Homo sapiens

<400> SEQUENCE: 43

Asn Ser Gly Phe Glu Pro Gly Ala Phe Asp Gly Leu Lys Leu Asn Tyr
1               5                   10                  15

Leu Arg Ile Ser Glu Ala Lys
            20

<210> SEQ ID NO 44
<211> LENGTH: 24
<212> TYPE: PRT
<213> ORGANISM: Homo sapiens

<400> SEQUENCE: 44

-continued

Leu Lys Ser Val Pro Lys Glu Ile Ser Pro Asp Thr Thr Leu Leu Asp
1               5                   10                  15

Leu Gln Asn Asn Asp Ile Ser Glu
            20

<210> SEQ ID NO 45
<211> LENGTH: 18
<212> TYPE: PRT
<213> ORGANISM: Homo sapiens

<400> SEQUENCE: 45

Leu Arg Ile Ser Glu Ala Lys Leu Thr Gly Ile Pro Lys Asp Leu Pro
1               5                   10                  15

Glu Thr

<210> SEQ ID NO 46
<211> LENGTH: 24
<212> TYPE: PRT
<213> ORGANISM: Homo sapiens

<400> SEQUENCE: 46

Leu Lys Ser Val Pro Lys Glu Ile Ser Pro Asp Thr Thr Leu Leu Asp
1               5                   10                  15

Leu Gln Asn Asn Asp Ile Ser Glu
            20

<210> SEQ ID NO 47
<211> LENGTH: 26
<212> TYPE: PRT
<213> ORGANISM: Homo sapiens

<400> SEQUENCE: 47

Leu Thr Gly Ile Pro Lys Asp Leu Pro Glu Thr Leu Asn Glu Leu His
1               5                   10                  15

Leu Asp His Asn Lys Ile Gln Ala Ile Glu
            20                  25

<210> SEQ ID NO 48
<211> LENGTH: 11
<212> TYPE: PRT
<213> ORGANISM: Homo sapiens

<400> SEQUENCE: 48

Ile Val Ile Glu Leu Gly Thr Asn Pro Leu Lys
1               5                   10

<210> SEQ ID NO 49
<211> LENGTH: 10
<212> TYPE: PRT
<213> ORGANISM: Homo sapiens

<400> SEQUENCE: 49

Leu Leu Ala Ser Asp Ala Gly Leu Tyr Arg
1               5                   10

<210> SEQ ID NO 50
<211> LENGTH: 12
<212> TYPE: PRT
<213> ORGANISM: Homo sapiens

<400> SEQUENCE: 50

Leu Ala Thr Val Gly Glu Leu Gln Ala Ala Trp Arg
1               5                   10

```
<210> SEQ ID NO 51
<211> LENGTH: 13
<212> TYPE: PRT
<213> ORGANISM: Homo sapiens

<400> SEQUENCE: 51

Glu Thr Thr Val Leu Val Ala Gln Asn Gly Asn Ile Lys
1               5                   10

<210> SEQ ID NO 52
<211> LENGTH: 11
<212> TYPE: PRT
<213> ORGANISM: Homo sapiens

<400> SEQUENCE: 52

Ser Leu Glu Asp Leu Gln Leu Thr His Asn Lys
1               5                   10

<210> SEQ ID NO 53
<211> LENGTH: 11
<212> TYPE: PRT
<213> ORGANISM: Homo sapiens

<400> SEQUENCE: 53

Leu Lys Glu Asp Ala Val Ser Ala Ala Phe Lys
1               5                   10

<210> SEQ ID NO 54
<211> LENGTH: 14
<212> TYPE: PRT
<213> ORGANISM: Homo sapiens

<400> SEQUENCE: 54

Ser Ile Glu Tyr Ser Pro Gln Leu Glu Asp Ala Gly Ser Arg
1               5                   10

<210> SEQ ID NO 55
<211> LENGTH: 10
<212> TYPE: PRT
<213> ORGANISM: Homo sapiens

<400> SEQUENCE: 55

Leu Glu Gly Asp Thr Leu Ile Ile Pro Arg
1               5                   10

<210> SEQ ID NO 56
<211> LENGTH: 20
<212> TYPE: PRT
<213> ORGANISM: Homo sapiens

<400> SEQUENCE: 56

Arg Ile Ser Glu Ala Lys Leu Thr Gly Ile Pro Lys Asp Leu Pro Glu
1               5                   10                  15

Thr Leu Asn Glu
            20

<210> SEQ ID NO 57
<211> LENGTH: 12
<212> TYPE: PRT
<213> ORGANISM: Homo sapiens

<400> SEQUENCE: 57

Ala Ile Glu Leu Glu Asp Leu Leu Arg Tyr Ser Lys
```

```
1               5                   10
```

<210> SEQ ID NO 58
<211> LENGTH: 10
<212> TYPE: PRT
<213> ORGANISM: Homo sapiens

<400> SEQUENCE: 58

```
Ala Ile Glu Leu Glu Asp Leu Leu Arg Tyr
1               5                   10
```

<210> SEQ ID NO 59
<211> LENGTH: 17
<212> TYPE: PRT
<213> ORGANISM: Homo sapiens

<400> SEQUENCE: 59

```
Glu Ala Lys Leu Thr Gly Ile Pro Lys Asp Leu Pro Glu Thr Leu Asn
1               5                   10                  15

Glu
```

<210> SEQ ID NO 60
<211> LENGTH: 24
<212> TYPE: PRT
<213> ORGANISM: Homo sapiens

<400> SEQUENCE: 60

```
Leu Lys Ala Val Pro Lys Glu Ile Ser Pro Asp Thr Thr Leu Leu Asp
1               5                   10                  15

Leu Gln Asn Asn Asp Ile Ser Glu
            20
```

<210> SEQ ID NO 61
<211> LENGTH: 16
<212> TYPE: PRT
<213> ORGANISM: Homo sapiens

<400> SEQUENCE: 61

```
Leu Leu Asp Leu Gln Asn Asn Asp Ile Ser Glu Leu Arg Lys Asp Asp
1               5                   10                  15
```

<210> SEQ ID NO 62
<211> LENGTH: 10
<212> TYPE: PRT
<213> ORGANISM: Homo sapiens

<400> SEQUENCE: 62

```
Ile Glu Leu Glu Asp Leu Leu Arg Tyr Ser
1               5                   10
```

<210> SEQ ID NO 63
<211> LENGTH: 13
<212> TYPE: PRT
<213> ORGANISM: Homo sapiens

<400> SEQUENCE: 63

```
Asn Ser Gly Phe Glu Pro Gly Ala Phe Asp Gly Leu Lys
1               5                   10
```

<210> SEQ ID NO 64
<211> LENGTH: 14
<212> TYPE: PRT
<213> ORGANISM: Homo sapiens

```
<400> SEQUENCE: 64

Asp Glu Ala Ser Gly Ile Gly Pro Glu Val Pro Asp Asp Arg
1               5                   10

<210> SEQ ID NO 65
<211> LENGTH: 15
<212> TYPE: PRT
<213> ORGANISM: Homo sapiens

<400> SEQUENCE: 65

Leu His Leu Asp Gly Asn Lys Ile Ser Arg Val Asp Ala Ala Ser
1               5                   10                  15

<210> SEQ ID NO 66
<211> LENGTH: 16
<212> TYPE: PRT
<213> ORGANISM: Homo sapiens

<400> SEQUENCE: 66

Val Asn Asn Lys Ile Ser Lys Val Ser Pro Gly Ala Phe Thr Pro Leu
1               5                   10                  15

<210> SEQ ID NO 67
<211> LENGTH: 24
<212> TYPE: PRT
<213> ORGANISM: Homo sapiens

<400> SEQUENCE: 67

Leu Ile Leu Val Asn Asn Lys Ile Ser Lys Val Ser Pro Gly Ala Phe
1               5                   10                  15

Thr Pro Leu Val Lys Leu Glu Arg
            20

<210> SEQ ID NO 68
<211> LENGTH: 15
<212> TYPE: PRT
<213> ORGANISM: Homo sapiens

<400> SEQUENCE: 68

Ser Asn Pro Val Gln Tyr Trp Glu Ile Gln Pro Ser Thr Phe Arg
1               5                   10                  15

<210> SEQ ID NO 69
<211> LENGTH: 13
<212> TYPE: PRT
<213> ORGANISM: Homo sapiens

<400> SEQUENCE: 69

Ser Ser Gly Ile Glu Asn Gly Ala Phe Gln Gly Met Lys
1               5                   10

<210> SEQ ID NO 70
<211> LENGTH: 16
<212> TYPE: PRT
<213> ORGANISM: Homo sapiens

<400> SEQUENCE: 70

Ser Ser Gly Ile Glu Asn Gly Ala Phe Gln Gly Met Lys Lys Leu Ser
1               5                   10                  15

<210> SEQ ID NO 71
<211> LENGTH: 11
<212> TYPE: PRT
<213> ORGANISM: Homo sapiens
```

-continued

<400> SEQUENCE: 71

Lys Ile Thr Glu Ile Lys Asp Gly Asp Phe Lys
1               5                   10

<210> SEQ ID NO 72
<211> LENGTH: 15
<212> TYPE: PRT
<213> ORGANISM: Homo sapiens

<400> SEQUENCE: 72

Gly Leu Pro Pro Ser Leu Thr Glu Leu His Leu Asp Gly Asn Lys
1               5                   10                  15

<210> SEQ ID NO 73
<211> LENGTH: 14
<212> TYPE: PRT
<213> ORGANISM: Homo sapiens

<400> SEQUENCE: 73

Val Ser Glu Ala Val Val Glu Lys Leu Glu Pro Glu Tyr Arg
1               5                   10

<210> SEQ ID NO 74
<211> LENGTH: 15
<212> TYPE: PRT
<213> ORGANISM: Homo sapiens

<400> SEQUENCE: 74

Glu Val Ser Glu Ala Val Val Glu Lys Leu Glu Pro Glu Tyr Arg
1               5                   10                  15

<210> SEQ ID NO 75
<211> LENGTH: 17
<212> TYPE: PRT
<213> ORGANISM: Homo sapiens

<400> SEQUENCE: 75

Ser Ile Glu Tyr Ser Pro Gln Leu Glu Asp Ala Ser Ala Lys Glu Phe
1               5                   10                  15

Arg

<210> SEQ ID NO 76
<211> LENGTH: 6
<212> TYPE: PRT
<213> ORGANISM: Homo sapiens

<400> SEQUENCE: 76

Ser Val Pro Lys Glu Ile
1               5

<210> SEQ ID NO 77
<211> LENGTH: 6
<212> TYPE: PRT
<213> ORGANISM: Homo sapiens

<400> SEQUENCE: 77

Asn Ser Gly Phe Glu Pro
1               5

<210> SEQ ID NO 78
<211> LENGTH: 6
<212> TYPE: PRT
<213> ORGANISM: Homo sapiens

<400> SEQUENCE: 78

Leu Lys Ser Val Pro Lys
1               5

<210> SEQ ID NO 79
<211> LENGTH: 6
<212> TYPE: PRT
<213> ORGANISM: Homo sapiens

<400> SEQUENCE: 79

Leu Arg Ile Ser Glu Ala
1               5

<210> SEQ ID NO 80
<211> LENGTH: 6
<212> TYPE: PRT
<213> ORGANISM: Homo sapiens

<400> SEQUENCE: 80

Gly Leu Lys Leu Asn Tyr
1               5

<210> SEQ ID NO 81
<211> LENGTH: 6
<212> TYPE: PRT
<213> ORGANISM: Homo sapiens

<400> SEQUENCE: 81

Leu Lys Ser Val Pro Lys
1               5

<210> SEQ ID NO 82
<211> LENGTH: 6
<212> TYPE: PRT
<213> ORGANISM: Homo sapiens

<400> SEQUENCE: 82

Gln Cys Ser Asp Leu Gly
1               5

<210> SEQ ID NO 83
<211> LENGTH: 6
<212> TYPE: PRT
<213> ORGANISM: Homo sapiens

<400> SEQUENCE: 83

Leu Thr Gly Ile Pro Lys
1               5

<210> SEQ ID NO 84
<211> LENGTH: 6
<212> TYPE: PRT
<213> ORGANISM: Homo sapiens

<400> SEQUENCE: 84

Arg Ile Ser Glu Ala Lys
1               5

<210> SEQ ID NO 85
<211> LENGTH: 6
<212> TYPE: PRT
<213> ORGANISM: Homo sapiens

<400> SEQUENCE: 85

```
Ala Ile Glu Leu Glu Asp
1               5

<210> SEQ ID NO 86
<211> LENGTH: 6
<212> TYPE: PRT
<213> ORGANISM: Homo sapiens

<400> SEQUENCE: 86

Glu Ala Lys Leu Thr Gly
1               5

<210> SEQ ID NO 87
<211> LENGTH: 6
<212> TYPE: PRT
<213> ORGANISM: Homo sapiens

<400> SEQUENCE: 87

Leu Lys Ala Val Pro Lys
1               5

<210> SEQ ID NO 88
<211> LENGTH: 6
<212> TYPE: PRT
<213> ORGANISM: Homo sapiens

<400> SEQUENCE: 88

Leu Leu Asp Leu Gln Asn
1               5

<210> SEQ ID NO 89
<211> LENGTH: 6
<212> TYPE: PRT
<213> ORGANISM: Homo sapiens

<400> SEQUENCE: 89

Ile Glu Leu Glu Asp Leu
1               5

<210> SEQ ID NO 90
<211> LENGTH: 6
<212> TYPE: PRT
<213> ORGANISM: Homo sapiens

<400> SEQUENCE: 90

Asn Ser Gly Phe Glu Pro
1               5

<210> SEQ ID NO 91
<211> LENGTH: 6
<212> TYPE: PRT
<213> ORGANISM: Homo sapiens

<400> SEQUENCE: 91

Ile Val Ile Glu Leu Gly
1               5

<210> SEQ ID NO 92
<211> LENGTH: 6
<212> TYPE: PRT
<213> ORGANISM: Homo sapiens

<400> SEQUENCE: 92

Asn Gly Leu Asn Gln Met
```

```
<210> SEQ ID NO 93
<211> LENGTH: 6
<212> TYPE: PRT
<213> ORGANISM: Homo sapiens

<400> SEQUENCE: 93

Asp Glu Ala Ser Gly Ile
1               5

<210> SEQ ID NO 94
<211> LENGTH: 6
<212> TYPE: PRT
<213> ORGANISM: Homo sapiens

<400> SEQUENCE: 94

Leu His Leu Asp Gly Asn
1               5

<210> SEQ ID NO 95
<211> LENGTH: 6
<212> TYPE: PRT
<213> ORGANISM: Homo sapiens

<400> SEQUENCE: 95

Val Asn Asn Lys Ile Ser
1               5

<210> SEQ ID NO 96
<211> LENGTH: 6
<212> TYPE: PRT
<213> ORGANISM: Homo sapiens

<400> SEQUENCE: 96

Leu Ile Leu Val Asn Asn
1               5

<210> SEQ ID NO 97
<211> LENGTH: 6
<212> TYPE: PRT
<213> ORGANISM: Homo sapiens

<400> SEQUENCE: 97

Ser Asn Pro Val Gln Tyr
1               5

<210> SEQ ID NO 98
<211> LENGTH: 6
<212> TYPE: PRT
<213> ORGANISM: Homo sapiens

<400> SEQUENCE: 98

Ser Ser Gly Ile Glu Asn
1               5

<210> SEQ ID NO 99
<211> LENGTH: 6
<212> TYPE: PRT
<213> ORGANISM: Homo sapiens

<400> SEQUENCE: 99

Lys Ile Thr Glu Ile Lys
1               5
```

```
<210> SEQ ID NO 100
<211> LENGTH: 6
<212> TYPE: PRT
<213> ORGANISM: Homo sapiens

<400> SEQUENCE: 100

Gly Leu Pro Pro Ser Leu
1               5

<210> SEQ ID NO 101
<211> LENGTH: 6
<212> TYPE: PRT
<213> ORGANISM: Homo sapiens

<400> SEQUENCE: 101

Leu Leu Ala Ser Asp Ala
1               5

<210> SEQ ID NO 102
<211> LENGTH: 6
<212> TYPE: PRT
<213> ORGANISM: Homo sapiens

<400> SEQUENCE: 102

Leu Ala Thr Val Gly Glu
1               5

<210> SEQ ID NO 103
<211> LENGTH: 6
<212> TYPE: PRT
<213> ORGANISM: Homo sapiens

<400> SEQUENCE: 103

Glu Thr Thr Val Leu Val
1               5

<210> SEQ ID NO 104
<211> LENGTH: 6
<212> TYPE: PRT
<213> ORGANISM: Homo sapiens

<400> SEQUENCE: 104

Ser Leu Thr Val Val Lys
1               5

<210> SEQ ID NO 105
<211> LENGTH: 6
<212> TYPE: PRT
<213> ORGANISM: Homo sapiens

<400> SEQUENCE: 105

Glu Asn Gln Asp Ala Arg
1               5

<210> SEQ ID NO 106
<211> LENGTH: 6
<212> TYPE: PRT
<213> ORGANISM: Homo sapiens

<400> SEQUENCE: 106

Asn Gly Phe Asp Gln Cys
1               5

<210> SEQ ID NO 107
```

```
<211> LENGTH: 6
<212> TYPE: PRT
<213> ORGANISM: Homo sapiens

<400> SEQUENCE: 107

Ser Leu Glu Asp Leu Gln
1               5

<210> SEQ ID NO 108
<211> LENGTH: 6
<212> TYPE: PRT
<213> ORGANISM: Homo sapiens

<400> SEQUENCE: 108

Leu Lys Glu Asp Ala Val
1               5

<210> SEQ ID NO 109
<211> LENGTH: 6
<212> TYPE: PRT
<213> ORGANISM: Homo sapiens

<400> SEQUENCE: 109

His Leu Gln His Asn Arg
1               5

<210> SEQ ID NO 110
<211> LENGTH: 6
<212> TYPE: PRT
<213> ORGANISM: Homo sapiens

<400> SEQUENCE: 110

Leu Gln His Asn Arg Leu
1               5

<210> SEQ ID NO 111
<211> LENGTH: 6
<212> TYPE: PRT
<213> ORGANISM: Homo sapiens

<400> SEQUENCE: 111

Ser Ile Glu Tyr Ser Pro
1               5

<210> SEQ ID NO 112
<211> LENGTH: 6
<212> TYPE: PRT
<213> ORGANISM: Homo sapiens

<400> SEQUENCE: 112

Leu Val Asn Phe Thr Arg
1               5

<210> SEQ ID NO 113
<211> LENGTH: 6
<212> TYPE: PRT
<213> ORGANISM: Homo sapiens

<400> SEQUENCE: 113

Val Ser Glu Ala Val Val
1               5

<210> SEQ ID NO 114
<211> LENGTH: 6
<212> TYPE: PRT
```

```
<213> ORGANISM: Homo sapiens

<400> SEQUENCE: 114

Glu Val Ser Glu Ala Val
1               5

<210> SEQ ID NO 115
<211> LENGTH: 6
<212> TYPE: PRT
<213> ORGANISM: Homo sapiens

<400> SEQUENCE: 115

Ser Ile Glu Tyr Ser Pro
1               5

<210> SEQ ID NO 116
<211> LENGTH: 6
<212> TYPE: PRT
<213> ORGANISM: Homo sapiens

<400> SEQUENCE: 116

Asn Asn Asp Ile Ser Glu
1               5

<210> SEQ ID NO 117
<211> LENGTH: 6
<212> TYPE: PRT
<213> ORGANISM: Homo sapiens

<400> SEQUENCE: 117

Arg Ile Ser Glu Ala Lys
1               5

<210> SEQ ID NO 118
<211> LENGTH: 6
<212> TYPE: PRT
<213> ORGANISM: Homo sapiens

<400> SEQUENCE: 118

Leu Arg Lys Asp Asp Phe
1               5

<210> SEQ ID NO 119
<211> LENGTH: 6
<212> TYPE: PRT
<213> ORGANISM: Homo sapiens

<400> SEQUENCE: 119

Lys Asp Leu Pro Glu Thr
1               5

<210> SEQ ID NO 120
<211> LENGTH: 6
<212> TYPE: PRT
<213> ORGANISM: Homo sapiens

<400> SEQUENCE: 120

Leu Asn Glu Leu His Leu
1               5

<210> SEQ ID NO 121
<211> LENGTH: 6
<212> TYPE: PRT
<213> ORGANISM: Homo sapiens
```

```
<400> SEQUENCE: 121

Tyr Trp Glu Val Gln Pro
1               5

<210> SEQ ID NO 122
<211> LENGTH: 6
<212> TYPE: PRT
<213> ORGANISM: Homo sapiens

<400> SEQUENCE: 122

Lys Ile Gln Ala Ile Glu
1               5

<210> SEQ ID NO 123
<211> LENGTH: 6
<212> TYPE: PRT
<213> ORGANISM: Homo sapiens

<400> SEQUENCE: 123

Pro Glu Thr Leu Asn Glu
1               5

<210> SEQ ID NO 124
<211> LENGTH: 6
<212> TYPE: PRT
<213> ORGANISM: Homo sapiens

<400> SEQUENCE: 124

Leu Leu Arg Tyr Ser Lys
1               5

<210> SEQ ID NO 125
<211> LENGTH: 6
<212> TYPE: PRT
<213> ORGANISM: Homo sapiens

<400> SEQUENCE: 125

Glu Asp Leu Leu Arg Tyr
1               5

<210> SEQ ID NO 126
<211> LENGTH: 6
<212> TYPE: PRT
<213> ORGANISM: Homo sapiens

<400> SEQUENCE: 126

Asn Asn Asp Ile Ser Glu
1               5

<210> SEQ ID NO 127
<211> LENGTH: 6
<212> TYPE: PRT
<213> ORGANISM: Homo sapiens

<400> SEQUENCE: 127

Glu Leu Arg Lys Asp Asp
1               5

<210> SEQ ID NO 128
<211> LENGTH: 6
<212> TYPE: PRT
<213> ORGANISM: Homo sapiens

<400> SEQUENCE: 128
```

```
Asp Leu Leu Arg Tyr Ser
1               5

<210> SEQ ID NO 129
<211> LENGTH: 6
<212> TYPE: PRT
<213> ORGANISM: Homo sapiens

<400> SEQUENCE: 129

Ala Phe Asp Gly Leu Lys
1               5

<210> SEQ ID NO 130
<211> LENGTH: 6
<212> TYPE: PRT
<213> ORGANISM: Homo sapiens

<400> SEQUENCE: 130

Gly Thr Asn Pro Leu Lys
1               5

<210> SEQ ID NO 131
<211> LENGTH: 6
<212> TYPE: PRT
<213> ORGANISM: Homo sapiens

<400> SEQUENCE: 131

Ser Ser Gly Ile Glu Asn
1               5

<210> SEQ ID NO 132
<211> LENGTH: 6
<212> TYPE: PRT
<213> ORGANISM: Homo sapiens

<400> SEQUENCE: 132

Glu Val Pro Asp Asp Arg
1               5

<210> SEQ ID NO 133
<211> LENGTH: 6
<212> TYPE: PRT
<213> ORGANISM: Homo sapiens

<400> SEQUENCE: 133

Arg Val Asp Ala Ala Ser
1               5

<210> SEQ ID NO 134
<211> LENGTH: 6
<212> TYPE: PRT
<213> ORGANISM: Homo sapiens

<400> SEQUENCE: 134

Gly Ala Phe Thr Pro Leu
1               5

<210> SEQ ID NO 135
<211> LENGTH: 6
<212> TYPE: PRT
<213> ORGANISM: Homo sapiens

<400> SEQUENCE: 135

Leu Val Lys Leu Glu Arg
1               5
```

<210> SEQ ID NO 136
<211> LENGTH: 6
<212> TYPE: PRT
<213> ORGANISM: Homo sapiens

<400> SEQUENCE: 136

Gln Pro Ser Thr Phe Arg
1               5

<210> SEQ ID NO 137
<211> LENGTH: 6
<212> TYPE: PRT
<213> ORGANISM: Homo sapiens

<400> SEQUENCE: 137

Ala Phe Gln Gly Met Lys
1               5

<210> SEQ ID NO 138
<211> LENGTH: 6
<212> TYPE: PRT
<213> ORGANISM: Homo sapiens

<400> SEQUENCE: 138

Gly Met Lys Lys Leu Ser
1               5

<210> SEQ ID NO 139
<211> LENGTH: 6
<212> TYPE: PRT
<213> ORGANISM: Homo sapiens

<400> SEQUENCE: 139

Lys Asp Gly Asp Phe Lys
1               5

<210> SEQ ID NO 140
<211> LENGTH: 6
<212> TYPE: PRT
<213> ORGANISM: Homo sapiens

<400> SEQUENCE: 140

His Leu Asp Gly Asn Lys
1               5

<210> SEQ ID NO 141
<211> LENGTH: 6
<212> TYPE: PRT
<213> ORGANISM: Homo sapiens

<400> SEQUENCE: 141

Cys Asp Val Met Tyr Gly
1               5

<210> SEQ ID NO 142
<211> LENGTH: 6
<212> TYPE: PRT
<213> ORGANISM: Homo sapiens

<400> SEQUENCE: 142

Asn Gly Phe Asp Gln Cys
1               5

<210> SEQ ID NO 143
<211> LENGTH: 6
<212> TYPE: PRT
<213> ORGANISM: Homo sapiens

<400> SEQUENCE: 143

Gln Asn Gly Asn Ile Lys
1               5

<210> SEQ ID NO 144
<211> LENGTH: 6
<212> TYPE: PRT
<213> ORGANISM: Homo sapiens

<400> SEQUENCE: 144

Ile Gly Gln Asp Tyr Lys
1               5

<210> SEQ ID NO 145
<211> LENGTH: 6
<212> TYPE: PRT
<213> ORGANISM: Homo sapiens

<400> SEQUENCE: 145

Gln Leu Thr His Asn Lys
1               5

<210> SEQ ID NO 146
<211> LENGTH: 6
<212> TYPE: PRT
<213> ORGANISM: Homo sapiens

<400> SEQUENCE: 146

Val Ser Ala Ala Phe Lys
1               5

<210> SEQ ID NO 147
<211> LENGTH: 6
<212> TYPE: PRT
<213> ORGANISM: Homo sapiens

<400> SEQUENCE: 147

Gly Leu Lys Ser Leu Glu
1               5

<210> SEQ ID NO 148
<211> LENGTH: 6
<212> TYPE: PRT
<213> ORGANISM: Homo sapiens

<400> SEQUENCE: 148

Glu Asp Ala Gly Ser Arg
1               5

<210> SEQ ID NO 149
<211> LENGTH: 6
<212> TYPE: PRT
<213> ORGANISM: Homo sapiens

<400> SEQUENCE: 149

Glu Phe Arg Glu Val Ser
1               5

<210> SEQ ID NO 150
<211> LENGTH: 6

```
<212> TYPE: PRT
<213> ORGANISM: Homo sapiens

<400> SEQUENCE: 150

Val Ala Gln Gln Asp Ser
1               5

<210> SEQ ID NO 151
<211> LENGTH: 6
<212> TYPE: PRT
<213> ORGANISM: Homo sapiens

<400> SEQUENCE: 151

Leu Glu Pro Glu Tyr Arg
1               5

<210> SEQ ID NO 152
<211> LENGTH: 6
<212> TYPE: PRT
<213> ORGANISM: Homo sapiens

<400> SEQUENCE: 152

Ser Ala Lys Glu Phe Arg
1               5

<210> SEQ ID NO 153
<211> LENGTH: 1466
<212> TYPE: PRT
<213> ORGANISM: Homo sapiens

<400> SEQUENCE: 153

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220
```

-continued

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
            245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
            275                 280                 285

Leu Pro Gly Glu Asn Gly Ala Pro Gly Pro Met Gly Pro Arg Gly Ala
            290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
                340                 345                 350

Val Gly Pro Ala Gly Ser Pro Gly Ser Asn Gly Ala Pro Gly Gln Arg
            355                 360                 365

Gly Glu Pro Gly Pro Gln Gly His Ala Gly Ala Gln Gly Pro Pro Gly
            370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
                420                 425                 430

Glu Pro Gly Lys Asn Gly Ala Lys Gly Glu Pro Gly Pro Arg Gly Glu
            435                 440                 445

Arg Gly Glu Ala Gly Ile Pro Gly Val Pro Gly Ala Lys Gly Glu Asp
450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
                500                 505                 510

Gly Pro Ala Gly Pro Arg Gly Ala Ala Gly Glu Pro Gly Arg Asp Gly
                515                 520                 525

Val Pro Gly Gly Pro Gly Met Arg Gly Met Pro Gly Ser Pro Gly Gly
            530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
                565                 570                 575

Val Met Gly Phe Pro Gly Pro Lys Gly Asn Asp Gly Ala Pro Gly Lys
                580                 585                 590

Asn Gly Glu Arg Gly Gly Pro Gly Gly Pro Gly Pro Gln Gly Pro Pro
            595                 600                 605

Gly Lys Asn Gly Glu Thr Gly Pro Gln Gly Pro Pro Gly Pro Thr Gly
            610                 615                 620

Pro Gly Gly Asp Lys Gly Asp Thr Gly Pro Pro Gly Pro Gln Gly Leu
625                 630                 635                 640

-continued

Gln Gly Leu Pro Gly Thr Gly Pro Pro Gly Glu Asn Gly Lys Pro
              645                 650                 655
Gly Glu Pro Gly Pro Lys Gly Asp Ala Gly Ala Pro Gly Ala Pro Gly
  660                 665                 670
Gly Lys Gly Asp Ala Gly Ala Pro Gly Glu Arg Gly Pro Pro Gly Leu
      675                 680                 685
Ala Gly Ala Pro Gly Leu Arg Gly Gly Ala Gly Pro Pro Gly Pro Glu
  690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
              725                 730                 735
Pro Gly Pro Lys Gly Asp Lys Gly Glu Pro Gly Gly Pro Gly Ala Asp
          740                 745                 750
Gly Val Pro Gly Lys Asp Gly Pro Arg Gly Pro Thr Gly Pro Ile Gly
      755                 760                 765
Pro Pro Gly Pro Ala Gly Gln Pro Gly Asp Lys Gly Glu Gly Gly Ala
  770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
              805                 810                 815
Gln Asn Gly Glu Pro Gly Gly Lys Gly Glu Arg Gly Ala Pro Gly Glu
          820                 825                 830
Lys Gly Glu Gly Gly Pro Pro Gly Val Ala Gly Pro Pro Gly Gly Ser
      835                 840                 845
Gly Pro Ala Gly Pro Gly Pro Gln Gly Val Lys Gly Glu Arg Gly
  850                 855                 860
Ser Pro Gly Gly Pro Gly Ala Ala Gly Phe Pro Gly Ala Arg Gly Leu
865                 870                 875                 880
Pro Gly Pro Pro Gly Ser Asn Gly Asn Pro Gly Pro Pro Gly Pro Ser
              885                 890                 895
Gly Ser Pro Gly Lys Asp Gly Pro Pro Gly Pro Ala Gly Asn Thr Gly
          900                 905                 910
Ala Pro Gly Ser Pro Gly Val Ser Gly Pro Lys Gly Asp Ala Gly Gln
      915                 920                 925
Pro Gly Glu Lys Gly Ser Pro Gly Ala Gln Gly Pro Pro Gly Ala Pro
  930                 935                 940
Gly Pro Leu Gly Ile Ala Gly Ile Thr Gly Ala Arg Gly Leu Ala Gly
945                 950                 955                 960
Pro Pro Gly Met Pro Gly Pro Arg Gly Ser Pro Gly Pro Gln Gly Val
              965                 970                 975
Lys Gly Glu Ser Gly Lys Pro Gly Ala Asn Gly Leu Ser Gly Glu Arg
          980                 985                 990
Gly Pro Pro Gly Pro Gln Gly Leu Pro Gly Leu Ala Gly Thr Ala Gly
      995                 1000                1005
Glu Pro Gly Arg Asp Gly Asn Pro Gly Ser Asp Gly Leu Pro Gly
      1010                1015                1020
Arg Asp Gly Ser Pro Gly Gly Lys Gly Asp Arg Gly Glu Asn Gly
      1025                1030                1035
Ser Pro Gly Ala Pro Gly Ala Pro Gly His Pro Gly Pro Pro Gly
      1040                1045                1050
Pro Val Gly Pro Ala Gly Lys Ser Gly Asp Arg Gly Glu Ser Gly

-continued

```
            1055                1060                1065

Pro Ala Gly Pro Ala Gly Ala Pro Gly Pro Ala Gly Ser Arg Gly
        1070                1075                1080

Ala Pro Gly Pro Gln Gly Pro Arg Gly Asp Lys Gly Glu Thr Gly
        1085                1090                1095

Glu Arg Gly Ala Ala Gly Ile Lys Gly His Arg Gly Phe Pro Gly
        1100                1105                1110

Asn Pro Gly Ala Pro Gly Ser Pro Gly Pro Ala Gly Gln Gln Gly
        1115                1120                1125

Ala Ile Gly Ser Pro Gly Pro Ala Gly Pro Arg Gly Pro Val Gly
        1130                1135                1140

Pro Ser Gly Pro Pro Gly Lys Asp Gly Thr Ser Gly His Pro Gly
        1145                1150                1155

Pro Ile Gly Pro Pro Gly Pro Arg Gly Asn Arg Gly Glu Arg Gly
        1160                1165                1170

Ser Glu Gly Ser Pro Gly His Pro Gly Gln Pro Gly Pro Pro Gly
        1175                1180                1185

Pro Pro Gly Ala Pro Gly Pro Cys Cys Gly Gly Val Gly Ala Ala
        1190                1195                1200

Ala Ile Ala Gly Ile Gly Gly Glu Lys Ala Gly Gly Phe Ala Pro
        1205                1210                1215

Tyr Tyr Gly Asp Glu Pro Met Asp Phe Lys Ile Asn Thr Asp Glu
        1220                1225                1230

Ile Met Thr Ser Leu Lys Ser Val Asn Gly Gln Ile Glu Ser Leu
        1235                1240                1245

Ile Ser Pro Asp Gly Ser Arg Lys Asn Pro Ala Arg Asn Cys Arg
        1250                1255                1260

Asp Leu Lys Phe Cys His Pro Glu Leu Lys Ser Gly Glu Tyr Trp
        1265                1270                1275

Val Asp Pro Asn Gln Gly Cys Lys Leu Asp Ala Ile Lys Val Phe
        1280                1285                1290

Cys Asn Met Glu Thr Gly Glu Thr Cys Ile Ser Ala Asn Pro Leu
        1295                1300                1305

Asn Val Pro Arg Lys His Trp Trp Thr Asp Ser Ala Glu Lys
        1310                1315                1320

Lys His Val Trp Phe Gly Glu Ser Met Asp Gly Gly Phe Gln Phe
        1325                1330                1335

Ser Tyr Gly Asn Pro Glu Leu Pro Glu Asp Val Leu Asp Val Gln
        1340                1345                1350

Leu Ala Phe Leu Arg Leu Leu Ser Ser Arg Ala Ser Gln Asn Ile
        1355                1360                1365

Thr Tyr His Cys Lys Asn Ser Ile Ala Tyr Met Asp Gln Ala Ser
        1370                1375                1380

Gly Asn Val Lys Lys Ala Leu Lys Leu Met Gly Ser Asn Glu Gly
        1385                1390                1395

Glu Phe Lys Ala Glu Gly Asn Ser Lys Phe Thr Tyr Thr Val Leu
        1400                1405                1410

Glu Asp Gly Cys Thr Lys His Thr Gly Glu Trp Ser Lys Thr Val
        1415                1420                1425

Phe Glu Tyr Arg Thr Arg Lys Ala Val Arg Leu Pro Ile Val Asp
        1430                1435                1440

Ile Ala Pro Tyr Asp Ile Gly Gly Pro Asp Gln Glu Phe Gly Val
        1445                1450                1455
```

Asp Val Gly Pro Val Cys Phe Leu
        1460                1465

<210> SEQ ID NO 154
<211> LENGTH: 20
<212> TYPE: PRT
<213> ORGANISM: Homo sapiens

<400> SEQUENCE: 154

Ala Gly Ile Pro Gly Ala Pro Gly Leu Met Gly Ala Arg Gly Pro Pro
1               5                   10                  15

Gly Pro Ala Gly
            20

<210> SEQ ID NO 155
<211> LENGTH: 19
<212> TYPE: PRT
<213> ORGANISM: Homo sapiens

<400> SEQUENCE: 155

Lys Gly Asp Pro Gly Pro Pro Gly Ile Pro Gly Arg Asn Gly Asp Pro
1               5                   10                  15

Gly Ile Pro

<210> SEQ ID NO 156
<211> LENGTH: 20
<212> TYPE: PRT
<213> ORGANISM: Homo sapiens

<400> SEQUENCE: 156

Gly Leu Ala Gly Pro Pro Gly Met Pro Gly Pro Arg Gly Ser Pro Gly
1               5                   10                  15

Pro Gln Gly Val
            20

<210> SEQ ID NO 157
<211> LENGTH: 21
<212> TYPE: PRT
<213> ORGANISM: Homo sapiens

<400> SEQUENCE: 157

Gly Glu Arg Gly Leu Pro Gly Pro Pro Gly Ile Lys Gly Pro Ala Gly
1               5                   10                  15

Ile Pro Gly Phe Pro
            20

<210> SEQ ID NO 158
<211> LENGTH: 22
<212> TYPE: PRT
<213> ORGANISM: Homo sapiens

<400> SEQUENCE: 158

Gly Ile Ala Gly Ile Thr Gly Ala Arg Gly Leu Ala Gly Pro Pro Gly
1               5                   10                  15

Met Pro Gly Pro Arg Gly
            20

<210> SEQ ID NO 159
<211> LENGTH: 23
<212> TYPE: PRT
<213> ORGANISM: Homo sapiens -continued

<400> SEQUENCE: 159

Gly Ile Lys Gly His Arg Gly Phe Pro Gly Asn Pro Gly Ala Pro Gly
1               5                   10                  15

Ser Pro Gly Pro Ala Gly Gln
            20

<210> SEQ ID NO 160
<211> LENGTH: 23
<212> TYPE: PRT
<213> ORGANISM: Homo sapiens

<400> SEQUENCE: 160

Ala Arg Gly Leu Ala Gly Pro Pro Gly Met Pro Gly Pro Arg Gly Ser
1               5                   10                  15

Pro Gly Pro Gln Gly Val Lys
            20

<210> SEQ ID NO 161
<211> LENGTH: 25
<212> TYPE: PRT
<213> ORGANISM: Homo sapiens

<400> SEQUENCE: 161

Ile Thr Gly Ala Arg Gly Leu Ala Gly Pro Pro Gly Met Pro Gly Pro
1               5                   10                  15

Arg Gly Ser Pro Gly Pro Gln Gly Val
            20                  25

<210> SEQ ID NO 162
<211> LENGTH: 26
<212> TYPE: PRT
<213> ORGANISM: Homo sapiens

<400> SEQUENCE: 162

Ile Thr Gly Ala Arg Gly Leu Ala Gly Pro Pro Gly Met Pro Gly Pro
1               5                   10                  15

Arg Gly Ser Pro Gly Pro Gln Gly Val Lys
            20                  25

<210> SEQ ID NO 163
<211> LENGTH: 26
<212> TYPE: PRT
<213> ORGANISM: Homo sapiens

<400> SEQUENCE: 163

Gly Ile Thr Gly Ala Arg Gly Leu Ala Gly Pro Pro Gly Met Pro Gly
1               5                   10                  15

Pro Arg Gly Ser Pro Gly Pro Gln Gly Val
            20                  25

<210> SEQ ID NO 164
<211> LENGTH: 26
<212> TYPE: PRT
<213> ORGANISM: Homo sapiens

<400> SEQUENCE: 164

Gly Val Lys Gly Glu Ser Gly Lys Pro Gly Ala Asn Gly Leu Ser Gly
1               5                   10                  15

Glu Arg Gly Pro Pro Gly Pro Gln Gly Leu
            20                  25

-continued

```
<210> SEQ ID NO 165
<211> LENGTH: 26
<212> TYPE: PRT
<213> ORGANISM: Homo sapiens

<400> SEQUENCE: 165

Gly Ser Arg Gly Ala Pro Gly Pro Gln Gly Pro Arg Gly Asp Lys Gly
1               5                   10                  15

Glu Thr Gly Glu Arg Gly Ala Ala Gly Ile
            20                  25

<210> SEQ ID NO 166
<211> LENGTH: 28
<212> TYPE: PRT
<213> ORGANISM: Homo sapiens

<400> SEQUENCE: 166

Pro Lys Gly Asp Ala Gly Gln Pro Gly Glu Lys Gly Ser Pro Gly Ala
1               5                   10                  15

Gln Gly Pro Pro Gly Ala Pro Gly Pro Leu Gly Ile
            20                  25

<210> SEQ ID NO 167
<211> LENGTH: 27
<212> TYPE: PRT
<213> ORGANISM: Homo sapiens

<400> SEQUENCE: 167

Gly Ile Thr Gly Ala Arg Gly Leu Ala Gly Pro Pro Gly Met Pro Gly
1               5                   10                  15

Pro Arg Gly Ser Pro Gly Pro Gln Gly Val Lys
            20                  25

<210> SEQ ID NO 168
<211> LENGTH: 32
<212> TYPE: PRT
<213> ORGANISM: Homo sapiens

<400> SEQUENCE: 168

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala Ala Gly Thr Pro Gly Leu
            20                  25                  30

<210> SEQ ID NO 169
<211> LENGTH: 35
<212> TYPE: PRT
<213> ORGANISM: Homo sapiens

<400> SEQUENCE: 169

Gly His Ala Gly Ala Gln Gly Pro Pro Gly Pro Pro Gly Ile Asn Gly
1               5                   10                  15

Ser Pro Gly Gly Lys Gly Glu Met Gly Pro Ala Gly Ile Pro Gly Ala
            20                  25                  30

Pro Gly Leu
        35

<210> SEQ ID NO 170
<211> LENGTH: 48
<212> TYPE: PRT
<213> ORGANISM: Homo sapiens

<400> SEQUENCE: 170
```

```
Ala Gly Lys Ser Gly Asp Arg Gly Glu Ser Gly Pro Ala Gly Pro Ala
1               5                   10                  15

Gly Ala Pro Gly Pro Ala Gly Ser Arg Gly Ala Pro Gly Pro Gln Gly
                20                  25                  30

Pro Arg Gly Asp Lys Gly Glu Thr Gly Glu Arg Gly Ala Ala Gly Ile
            35                  40                  45
```

<210> SEQ ID NO 171
<211> LENGTH: 50
<212> TYPE: PRT
<213> ORGANISM: Homo sapiens

<400> SEQUENCE: 171

```
Gly Leu Gln Gly Leu Pro Gly Thr Gly Pro Pro Gly Glu Asn Gly
1               5                   10                  15

Lys Pro Gly Glu Pro Gly Pro Lys Gly Asp Ala Gly Ala Pro Gly Ala
                20                  25                  30

Pro Gly Gly Lys Gly Asp Ala Gly Ala Pro Gly Glu Arg Gly Pro Pro
            35                  40                  45

Gly Leu
    50
```

<210> SEQ ID NO 172
<211> LENGTH: 21
<212> TYPE: PRT
<213> ORGANISM: Homo sapiens

<400> SEQUENCE: 172

```
Gly Glu Arg Gly Leu Pro Gly Pro Gly Ile Lys Gly Pro Ala Gly
1               5                   10                  15

Ile Pro Gly Phe Pro
            20
```

<210> SEQ ID NO 173
<211> LENGTH: 24
<212> TYPE: PRT
<213> ORGANISM: Homo sapiens

<400> SEQUENCE: 173

```
Ala Val Gly Gly Leu Ala Gly Tyr Pro Gly Pro Ala Gly Pro Pro Gly
1               5                   10                  15

Pro Pro Gly Pro Pro Gly Thr Ser
            20
```

<210> SEQ ID NO 174
<211> LENGTH: 24
<212> TYPE: PRT
<213> ORGANISM: Homo sapiens

<400> SEQUENCE: 174

```
Lys Asp Gly Thr Ser Gly His Pro Gly Pro Ile Gly Pro Pro Gly Pro
1               5                   10                  15

Arg Gly Asn Arg Gly Glu Arg Gly
            20
```

<210> SEQ ID NO 175
<211> LENGTH: 29
<212> TYPE: PRT
<213> ORGANISM: Homo sapiens

<400> SEQUENCE: 175

```
Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser
            20                  25
```

<210> SEQ ID NO 176
<211> LENGTH: 29
<212> TYPE: PRT
<213> ORGANISM: Homo sapiens

<400> SEQUENCE: 176

```
Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25
```

<210> SEQ ID NO 177
<211> LENGTH: 31
<212> TYPE: PRT
<213> ORGANISM: Homo sapiens

<400> SEQUENCE: 177

```
Ala Pro Gly Ala Pro Gly Gly Lys Gly Asp Ala Gly Ala Pro Gly Glu
1               5                   10                  15

Arg Gly Pro Pro Gly Leu Ala Gly Ala Pro Gly Leu Arg Gly Gly
            20                  25                  30
```

<210> SEQ ID NO 178
<211> LENGTH: 32
<212> TYPE: PRT
<213> ORGANISM: Homo sapiens

<400> SEQUENCE: 178

```
Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser Pro Gly Ser
            20                  25                  30
```

<210> SEQ ID NO 179
<211> LENGTH: 22
<212> TYPE: PRT
<213> ORGANISM: Homo sapiens

<400> SEQUENCE: 179

```
Ala Ile Gly Ser Pro Gly Pro Ala Gly Pro Arg Gly Pro Val Gly Pro
1               5                   10                  15

Ser Gly Pro Pro Gly Lys
            20
```

<210> SEQ ID NO 180
<211> LENGTH: 23
<212> TYPE: PRT
<213> ORGANISM: Homo sapiens

<400> SEQUENCE: 180

```
Gly Ala Ile Gly Ser Pro Gly Pro Ala Gly Pro Arg Gly Pro Val Gly
1               5                   10                  15

Pro Ser Gly Pro Pro Gly Lys
            20
```

<210> SEQ ID NO 181

```
<211> LENGTH: 15
<212> TYPE: PRT
<213> ORGANISM: Homo sapiens

<400> SEQUENCE: 181

Pro Ala Gly Gln Gln Gly Ala Ile Gly Ser Pro Gly Pro Ala Gly
1               5                   10                  15

<210> SEQ ID NO 182
<211> LENGTH: 20
<212> TYPE: PRT
<213> ORGANISM: Homo sapiens

<400> SEQUENCE: 182

Gly Gly Pro Pro Gly Val Ala Gly Pro Pro Gly Gly Ser Gly Pro Ala
1               5                   10                  15

Gly Pro Pro Gly
            20

<210> SEQ ID NO 183
<211> LENGTH: 19
<212> TYPE: PRT
<213> ORGANISM: Homo sapiens

<400> SEQUENCE: 183

Leu Ala Gly Pro Pro Gly Met Pro Gly Pro Arg Gly Ser Pro Gly Pro
1               5                   10                  15

Gln Gly Val

<210> SEQ ID NO 184
<211> LENGTH: 19
<212> TYPE: PRT
<213> ORGANISM: Homo sapiens

<400> SEQUENCE: 184

Gly Leu Ser Gly Glu Arg Gly Pro Pro Gly Pro Gln Gly Leu Pro Gly
1               5                   10                  15

Leu Ala Gly

<210> SEQ ID NO 185
<211> LENGTH: 21
<212> TYPE: PRT
<213> ORGANISM: Homo sapiens

<400> SEQUENCE: 185

Arg Gly Leu Ala Gly Pro Pro Gly Met Pro Gly Pro Arg Gly Ser Pro
1               5                   10                  15

Gly Pro Gln Gly Val
            20

<210> SEQ ID NO 186
<211> LENGTH: 21
<212> TYPE: PRT
<213> ORGANISM: Homo sapiens

<400> SEQUENCE: 186

Gly Leu Ala Gly Pro Pro Gly Met Pro Gly Pro Arg Gly Ser Pro Gly
1               5                   10                  15

Pro Gln Gly Val Lys
            20

<210> SEQ ID NO 187
```

-continued

```
<211> LENGTH: 22
<212> TYPE: PRT
<213> ORGANISM: Homo sapiens

<400> SEQUENCE: 187

Arg Gly Leu Ala Gly Pro Pro Gly Met Pro Gly Pro Arg Gly Ser Pro
1               5                   10                  15

Gly Pro Gln Gly Val Lys
            20

<210> SEQ ID NO 188
<211> LENGTH: 21
<212> TYPE: PRT
<213> ORGANISM: Homo sapiens

<400> SEQUENCE: 188

Gly Pro Gln Gly Pro Pro Gly Lys Asn Gly Glu Thr Gly Pro Gln Gly
1               5                   10                  15

Pro Pro Gly Pro Thr
            20

<210> SEQ ID NO 189
<211> LENGTH: 22
<212> TYPE: PRT
<213> ORGANISM: Homo sapiens

<400> SEQUENCE: 189

Gly Val Lys Gly Glu Arg Gly Ser Pro Gly Gly Pro Gly Ala Ala Gly
1               5                   10                  15

Phe Pro Gly Ala Arg Gly
            20

<210> SEQ ID NO 190
<211> LENGTH: 22
<212> TYPE: PRT
<213> ORGANISM: Homo sapiens

<400> SEQUENCE: 190

Ala Arg Gly Leu Ala Gly Pro Pro Gly Met Pro Gly Pro Arg Gly Ser
1               5                   10                  15

Pro Gly Pro Gln Gly Val
            20

<210> SEQ ID NO 191
<211> LENGTH: 23
<212> TYPE: PRT
<213> ORGANISM: Homo sapiens

<400> SEQUENCE: 191

Asn Gly Leu Ser Gly Glu Arg Gly Pro Pro Gly Pro Gln Gly Leu Pro
1               5                   10                  15

Gly Leu Ala Gly Thr Ala Gly
            20

<210> SEQ ID NO 192
<211> LENGTH: 24
<212> TYPE: PRT
<213> ORGANISM: Homo sapiens

<400> SEQUENCE: 192

Ala Val Gly Gly Leu Ala Gly Tyr Pro Gly Pro Ala Gly Pro Pro Gly
1               5                   10                  15
```

```
Pro Pro Gly Pro Pro Gly Thr Ser
            20

<210> SEQ ID NO 193
<211> LENGTH: 24
<212> TYPE: PRT
<213> ORGANISM: Homo sapiens

<400> SEQUENCE: 193

Gly Ser Pro Gly Gly Lys Gly Glu Met Gly Pro Ala Gly Ile Pro Gly
1               5                   10                  15

Ala Pro Gly Leu Met Gly Ala Arg
            20

<210> SEQ ID NO 194
<211> LENGTH: 24
<212> TYPE: PRT
<213> ORGANISM: Homo sapiens

<400> SEQUENCE: 194

Thr Gly Ala Arg Gly Leu Ala Gly Pro Pro Gly Met Pro Gly Pro Arg
1               5                   10                  15

Gly Ser Pro Gly Pro Gln Gly Val
            20

<210> SEQ ID NO 195
<211> LENGTH: 25
<212> TYPE: PRT
<213> ORGANISM: Homo sapiens

<400> SEQUENCE: 195

Val Lys Gly Glu Ser Gly Lys Pro Gly Ala Asn Gly Leu Ser Gly Glu
1               5                   10                  15

Arg Gly Pro Pro Gly Pro Gln Gly Leu
            20                  25

<210> SEQ ID NO 196
<211> LENGTH: 53
<212> TYPE: PRT
<213> ORGANISM: Homo sapiens

<400> SEQUENCE: 196

Gly Val Lys Gly Glu Arg Gly Ser Pro Gly Pro Gly Ala Ala Gly
1               5                   10                  15

Phe Pro Gly Ala Arg Gly Leu Pro Gly Pro Pro Gly Ser Asn Gly Asn
                20                  25                  30

Pro Gly Pro Pro Gly Pro Ser Gly Ser Pro Gly Lys Asp Gly Pro Pro
        35                  40                  45

Gly Pro Ala Gly Asn
        50

<210> SEQ ID NO 197
<211> LENGTH: 32
<212> TYPE: PRT
<213> ORGANISM: Homo sapiens

<400> SEQUENCE: 197

Gly Ser Pro Gly Ala Gln Gly Pro Gly Ala Pro Gly Pro Leu Gly
1               5                   10                  15

Ile Ala Gly Ile Thr Gly Ala Arg Gly Leu Ala Gly Pro Pro Gly Met
                20                  25                  30
```

```
<210> SEQ ID NO 198
<211> LENGTH: 32
<212> TYPE: PRT
<213> ORGANISM: Homo sapiens

<400> SEQUENCE: 198

Arg Gly Ala Pro Gly Glu Lys Gly Glu Gly Pro Pro Gly Val Ala
1               5                   10                  15

Gly Pro Pro Gly Gly Ser Gly Pro Ala Gly Pro Pro Gly Pro Gln Gly
            20                  25                  30

<210> SEQ ID NO 199
<211> LENGTH: 32
<212> TYPE: PRT
<213> ORGANISM: Homo sapiens

<400> SEQUENCE: 199

Arg Gly Ala Pro Gly Glu Lys Gly Glu Gly Pro Pro Gly Val Ala
1               5                   10                  15

Gly Pro Pro Gly Gly Ser Gly Pro Ala Gly Pro Pro Gly Pro Gln Gly
            20                  25                  30

<210> SEQ ID NO 200
<211> LENGTH: 29
<212> TYPE: PRT
<213> ORGANISM: Homo sapiens

<400> SEQUENCE: 200

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 201
<211> LENGTH: 14
<212> TYPE: PRT
<213> ORGANISM: Homo sapiens

<400> SEQUENCE: 201

Gly Ile Lys Gly Pro Ala Gly Ile Pro Gly Phe Pro Gly Met
1               5                   10

<210> SEQ ID NO 202
<211> LENGTH: 14
<212> TYPE: PRT
<213> ORGANISM: Homo sapiens

<400> SEQUENCE: 202

Gly Gln Pro Gly Val Met Gly Phe Pro Gly Pro Lys Gly Asn
1               5                   10

<210> SEQ ID NO 203
<211> LENGTH: 16
<212> TYPE: PRT
<213> ORGANISM: Homo sapiens

<400> SEQUENCE: 203

Gly Ile Lys Gly Pro Ala Gly Ile Pro Gly Phe Pro Gly Met Lys Gly
1               5                   10                  15

<210> SEQ ID NO 204
<211> LENGTH: 17
<212> TYPE: PRT
```

```
<213> ORGANISM: Homo sapiens

<400> SEQUENCE: 204

Gly Ile Lys Gly Pro Ala Gly Ile Pro Gly Phe Pro Gly Met Lys Gly
1               5                   10                  15

His

<210> SEQ ID NO 205
<211> LENGTH: 19
<212> TYPE: PRT
<213> ORGANISM: Homo sapiens

<400> SEQUENCE: 205

Ile Pro Gly Ala Pro Gly Leu Met Gly Ala Arg Gly Pro Pro Gly Pro
1               5                   10                  15

Ala Gly Ala

<210> SEQ ID NO 206
<211> LENGTH: 19
<212> TYPE: PRT
<213> ORGANISM: Homo sapiens

<400> SEQUENCE: 206

Gly Glu Arg Gly Leu Pro Gly Pro Gly Ile Lys Gly Pro Ala Gly
1               5                   10                  15

Ile Pro Gly

<210> SEQ ID NO 207
<211> LENGTH: 20
<212> TYPE: PRT
<213> ORGANISM: Homo sapiens

<400> SEQUENCE: 207

Gly Ile Pro Gly Ala Pro Gly Leu Met Gly Ala Arg Gly Pro Pro Gly
1               5                   10                  15

Pro Ala Gly Ala
            20

<210> SEQ ID NO 208
<211> LENGTH: 20
<212> TYPE: PRT
<213> ORGANISM: Homo sapiens

<400> SEQUENCE: 208

Gly Phe Arg Gly Pro Ala Gly Pro Asn Gly Ile Pro Gly Glu Lys Gly
1               5                   10                  15

Pro Ala Gly Glu
            20

<210> SEQ ID NO 209
<211> LENGTH: 20
<212> TYPE: PRT
<213> ORGANISM: Homo sapiens

<400> SEQUENCE: 209

Pro Gly Ile Pro Gly Gln Pro Gly Ser Pro Gly Ser Pro Gly Pro Pro
1               5                   10                  15

Gly Ile Cys Glu
            20

<210> SEQ ID NO 210
```

-continued

<211> LENGTH: 21
<212> TYPE: PRT
<213> ORGANISM: Homo sapiens

<400> SEQUENCE: 210

Gly Glu Arg Gly Leu Pro Gly Pro Gly Ile Lys Gly Pro Ala Gly
1               5                   10                  15

Ile Pro Gly Phe Pro
            20

<210> SEQ ID NO 211
<211> LENGTH: 23
<212> TYPE: PRT
<213> ORGANISM: Homo sapiens

<400> SEQUENCE: 211

Ala Val Gly Gly Leu Ala Gly Tyr Pro Gly Pro Ala Gly Pro Pro Gly
1               5                   10                  15

Pro Pro Gly Pro Pro Gly Thr
            20

<210> SEQ ID NO 212
<211> LENGTH: 23
<212> TYPE: PRT
<213> ORGANISM: Homo sapiens

<400> SEQUENCE: 212

Gly Val Lys Gly Glu Arg Gly Ser Pro Gly Gly Pro Gly Ala Ala Gly
1               5                   10                  15

Phe Pro Gly Ala Arg Gly Leu
            20

<210> SEQ ID NO 213
<211> LENGTH: 26
<212> TYPE: PRT
<213> ORGANISM: Homo sapiens

<400> SEQUENCE: 213

Gly Asp Ala Gly Ala Pro Gly Ala Pro Gly Gly Lys Gly Asp Ala Gly
1               5                   10                  15

Ala Pro Gly Glu Arg Gly Pro Pro Gly Leu
            20                  25

<210> SEQ ID NO 214
<211> LENGTH: 25
<212> TYPE: PRT
<213> ORGANISM: Homo sapiens

<400> SEQUENCE: 214

Gln Gly Pro Pro Gly Pro Thr Gly Pro Gly Gly Asp Lys Gly Asp Thr
1               5                   10                  15

Gly Pro Pro Gly Pro Gln Gly Leu Gln
            20                  25

<210> SEQ ID NO 215
<211> LENGTH: 25
<212> TYPE: PRT
<213> ORGANISM: Homo sapiens

<400> SEQUENCE: 215

Gly Ile Asn Gly Ser Pro Gly Gly Lys Gly Glu Met Gly Pro Ala Gly
1               5                   10                  15

-continued

Ile Pro Gly Ala Pro Gly Leu Met Gly
            20              25

<210> SEQ ID NO 216
<211> LENGTH: 26
<212> TYPE: PRT
<213> ORGANISM: Homo sapiens

<400> SEQUENCE: 216

Gln Gly Pro Pro Gly Glu Pro Gly Gln Ala Gly Pro Ser Gly Pro Pro
1               5                   10                  15

Gly Pro Pro Gly Ala Ile Gly Pro Ser Gly
            20              25

<210> SEQ ID NO 217
<211> LENGTH: 26
<212> TYPE: PRT
<213> ORGANISM: Homo sapiens

<400> SEQUENCE: 217

Pro Gly Pro Pro Gly Ile Asn Gly Ser Pro Gly Gly Lys Gly Glu Met
1               5                   10                  15

Gly Pro Ala Gly Ile Pro Gly Ala Pro Gly
            20              25

<210> SEQ ID NO 218
<211> LENGTH: 33
<212> TYPE: PRT
<213> ORGANISM: Homo sapiens

<400> SEQUENCE: 218

Arg Gly Leu Pro Gly Pro Pro Gly Ser Asn Gly Asn Pro Gly Pro Pro
1               5                   10                  15

Gly Pro Ser Gly Ser Pro Gly Lys Asp Gly Pro Pro Gly Pro Ala Gly
            20                  25                  30

Asn

<210> SEQ ID NO 219
<211> LENGTH: 32
<212> TYPE: PRT
<213> ORGANISM: Homo sapiens

<400> SEQUENCE: 219

Gly Lys Asn Gly Glu Thr Gly Pro Gln Gly Pro Pro Gly Pro Thr Gly
1               5                   10                  15

Pro Gly Gly Asp Lys Gly Asp Thr Gly Pro Pro Gly Pro Gln Gly Leu
            20                  25                  30

<210> SEQ ID NO 220
<211> LENGTH: 32
<212> TYPE: PRT
<213> ORGANISM: Homo sapiens

<400> SEQUENCE: 220

Gly Leu Pro Gly Ile Ala Gly Pro Arg Gly Ser Pro Gly Glu Arg Gly
1               5                   10                  15

Glu Thr Gly Pro Pro Gly Pro Ala Gly Phe Pro Gly Ala Pro Gly Gln
            20                  25                  30

<210> SEQ ID NO 221
<211> LENGTH: 35
<212> TYPE: PRT

<213> ORGANISM: Homo sapiens

<400> SEQUENCE: 221

Gly Ile Asn Gly Ser Pro Gly Gly Lys Gly Glu Met Gly Pro Ala Gly
1               5                   10                  15
Ile Pro Gly Ala Pro Gly Leu Met Gly Ala Arg Gly Pro Pro Gly Pro
            20                  25                  30
Ala Gly Ala
        35

<210> SEQ ID NO 222
<211> LENGTH: 36
<212> TYPE: PRT
<213> ORGANISM: Homo sapiens

<400> SEQUENCE: 222

Pro Gly Ile Asn Gly Ser Pro Gly Gly Lys Gly Glu Met Gly Pro Ala
1               5                   10                  15
Gly Ile Pro Gly Ala Pro Gly Leu Met Gly Ala Arg Gly Pro Pro Gly
            20                  25                  30
Pro Ala Gly Ala
        35

<210> SEQ ID NO 223
<211> LENGTH: 40
<212> TYPE: PRT
<213> ORGANISM: Homo sapiens

<400> SEQUENCE: 223

Pro Pro Gly Glu Asn Gly Lys Pro Gly Glu Pro Gly Pro Lys Gly Asp
1               5                   10                  15
Ala Gly Ala Pro Gly Ala Pro Gly Lys Gly Asp Ala Gly Ala Pro
            20                  25                  30
Gly Glu Arg Gly Pro Pro Gly Leu
        35                  40

<210> SEQ ID NO 224
<211> LENGTH: 38
<212> TYPE: PRT
<213> ORGANISM: Homo sapiens

<400> SEQUENCE: 224

Gly Leu Lys Gly Glu Asn Gly Leu Pro Gly Glu Asn Gly Ala Pro Gly
1               5                   10                  15
Pro Met Gly Pro Arg Gly Ala Pro Gly Glu Arg Gly Arg Pro Gly Leu
            20                  25                  30
Pro Gly Ala Ala Gly Ala
        35

<210> SEQ ID NO 225
<211> LENGTH: 41
<212> TYPE: PRT
<213> ORGANISM: Homo sapiens

<400> SEQUENCE: 225

Gly Asn Thr Gly Ala Pro Gly Ser Pro Gly Val Ser Gly Pro Lys Gly
1               5                   10                  15
Asp Ala Gly Gln Pro Gly Glu Lys Gly Ser Pro Gly Ala Gln Gly Pro
            20                  25                  30
Pro Gly Ala Pro Gly Pro Leu Gly Ile

```
                35                  40

<210> SEQ ID NO 226
<211> LENGTH: 41
<212> TYPE: PRT
<213> ORGANISM: Homo sapiens

<400> SEQUENCE: 226

Gly Leu Met Gly Ala Arg Gly Pro Gly Pro Ala Gly Ala Asn Gly
1               5                   10                  15

Ala Pro Gly Leu Arg Gly Gly Ala Gly Glu Pro Gly Lys Asn Gly Ala
            20                  25                  30

Lys Gly Glu Pro Gly Pro Arg Gly Glu
        35                  40

<210> SEQ ID NO 227
<211> LENGTH: 50
<212> TYPE: PRT
<213> ORGANISM: Homo sapiens

<400> SEQUENCE: 227

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala Ala Gly Thr Pro Gly Leu
            20                  25                  30

Gln Gly Met Pro Gly Glu Arg Gly Gly Leu Gly Ser Pro Gly Pro Lys
        35                  40                  45

Gly Asp
    50

<210> SEQ ID NO 228
<211> LENGTH: 26
<212> TYPE: PRT
<213> ORGANISM: Homo sapiens

<400> SEQUENCE: 228

Gly Gln Gln Gly Ala Ile Gly Ser Pro Gly Pro Ala Gly Pro Arg Gly
1               5                   10                  15

Pro Val Gly Pro Ser Gly Pro Pro Gly Lys
            20                  25

<210> SEQ ID NO 229
<211> LENGTH: 24
<212> TYPE: PRT
<213> ORGANISM: Homo sapiens

<400> SEQUENCE: 229

Lys Gly Asp Pro Gly Pro Pro Gly Ile Pro Gly Arg Asn Gly Asp Pro
1               5                   10                  15

Gly Ile Pro Gly Gln Pro Gly Ser
            20

<210> SEQ ID NO 230
<211> LENGTH: 26
<212> TYPE: PRT
<213> ORGANISM: Homo sapiens

<400> SEQUENCE: 230

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala
```

20                  25

<210> SEQ ID NO 231
<211> LENGTH: 32
<212> TYPE: PRT
<213> ORGANISM: Homo sapiens

<400> SEQUENCE: 231

Gly Lys Asn Gly Glu Thr Gly Pro Gln Gly Pro Pro Gly Pro Thr Gly
1               5                   10                  15

Pro Gly Gly Asp Lys Gly Asp Thr Gly Pro Pro Gly Pro Gln Gly Leu
                20                  25                  30

<210> SEQ ID NO 232
<211> LENGTH: 23
<212> TYPE: PRT
<213> ORGANISM: Homo sapiens

<400> SEQUENCE: 232

Gly Tyr Gln Gly Pro Pro Gly Glu Pro Gly Gln Ala Gly Pro Ser Gly
1               5                   10                  15

Pro Pro Gly Pro Pro Gly Ala
                20

<210> SEQ ID NO 233
<211> LENGTH: 20
<212> TYPE: PRT
<213> ORGANISM: Homo sapiens

<400> SEQUENCE: 233

Gly Val Ala Gly Pro Pro Gly Gly Ser Gly Pro Ala Gly Pro Pro Gly
1               5                   10                  15

Pro Gln Gly Val
                20

<210> SEQ ID NO 234
<211> LENGTH: 35
<212> TYPE: PRT
<213> ORGANISM: Homo sapiens

<400> SEQUENCE: 234

Gly Asp Lys Gly Glu Pro Gly Gly Pro Gly Ala Asp Gly Val Pro Gly
1               5                   10                  15

Lys Asp Gly Pro Arg Gly Pro Thr Gly Pro Ile Gly Pro Pro Gly Pro
                20                  25                  30

Ala Gly Gln
        35

<210> SEQ ID NO 235
<211> LENGTH: 17
<212> TYPE: PRT
<213> ORGANISM: Homo sapiens

<400> SEQUENCE: 235

Gln Gly His Ala Gly Ala Gln Gly Pro Pro Gly Pro Pro Gly Ile Asn
1               5                   10                  15

Gly

<210> SEQ ID NO 236
<211> LENGTH: 11
<212> TYPE: PRT
<213> ORGANISM: Homo sapiens

<400> SEQUENCE: 236

Ala Gly Glu Arg Gly Ala Pro Gly Pro Ala Gly
1               5                   10

<210> SEQ ID NO 237
<211> LENGTH: 11
<212> TYPE: PRT
<213> ORGANISM: Homo sapiens

<400> SEQUENCE: 237

Ala Gly Ile Pro Gly Phe Pro Gly Met Lys Gly
1               5                   10

<210> SEQ ID NO 238
<211> LENGTH: 12
<212> TYPE: PRT
<213> ORGANISM: Homo sapiens

<400> SEQUENCE: 238

Phe Pro Gly Met Lys Gly His Arg Gly Phe Asp Gly
1               5                   10

<210> SEQ ID NO 239
<211> LENGTH: 14
<212> TYPE: PRT
<213> ORGANISM: Homo sapiens

<400> SEQUENCE: 239

Gly Phe Pro Gly Ala Arg Gly Leu Pro Gly Pro Gly Ser
1               5                   10

<210> SEQ ID NO 240
<211> LENGTH: 15
<212> TYPE: PRT
<213> ORGANISM: Homo sapiens

<400> SEQUENCE: 240

Ala Gly Phe Pro Gly Ala Arg Gly Leu Pro Gly Pro Pro Gly Ser
1               5                   10                  15

<210> SEQ ID NO 241
<211> LENGTH: 15
<212> TYPE: PRT
<213> ORGANISM: Homo sapiens

<400> SEQUENCE: 241

Pro Pro Gly Pro Pro Gly Pro Pro Gly Thr Ser Gly His Pro Gly
1               5                   10                  15

<210> SEQ ID NO 242
<211> LENGTH: 13
<212> TYPE: PRT
<213> ORGANISM: Homo sapiens

<400> SEQUENCE: 242

Gly Phe Pro Gly Met Lys Gly His Arg Gly Phe Asp Gly
1               5                   10

<210> SEQ ID NO 243
<211> LENGTH: 17
<212> TYPE: PRT
<213> ORGANISM: Homo sapiens

<400> SEQUENCE: 243

```
Gln Pro Gly Asp Lys Gly Glu Gly Ala Pro Gly Leu Pro Gly Ile
1               5                   10                  15

Ala

<210> SEQ ID NO 244
<211> LENGTH: 17
<212> TYPE: PRT
<213> ORGANISM: Homo sapiens

<400> SEQUENCE: 244

Arg Gly Asp Lys Gly Glu Thr Gly Glu Arg Gly Ala Ala Gly Ile Lys
1               5                   10                  15

Gly

<210> SEQ ID NO 245
<211> LENGTH: 17
<212> TYPE: PRT
<213> ORGANISM: Homo sapiens

<400> SEQUENCE: 245

Asp Gly Arg Asn Gly Glu Lys Gly Glu Thr Gly Ala Pro Gly Leu Lys
1               5                   10                  15

Gly

<210> SEQ ID NO 246
<211> LENGTH: 20
<212> TYPE: PRT
<213> ORGANISM: Homo sapiens

<400> SEQUENCE: 246

Ala Gly Gln Pro Gly Asp Lys Gly Glu Gly Gly Ala Pro Gly Leu Pro
1               5                   10                  15

Gly Ile Ala Gly
            20

<210> SEQ ID NO 247
<211> LENGTH: 19
<212> TYPE: PRT
<213> ORGANISM: Homo sapiens

<400> SEQUENCE: 247

Gly Gly Pro Pro Gly Glu Asn Gly Lys Pro Gly Glu Pro Gly Pro Lys
1               5                   10                  15

Gly Asp Ala

<210> SEQ ID NO 248
<211> LENGTH: 17
<212> TYPE: PRT
<213> ORGANISM: Homo sapiens

<400> SEQUENCE: 248

Ala Gly Ile Pro Gly Phe Pro Gly Met Lys Gly His Arg Gly Phe Asp
1               5                   10                  15

Gly

<210> SEQ ID NO 249
<211> LENGTH: 20
<212> TYPE: PRT
<213> ORGANISM: Homo sapiens

<400> SEQUENCE: 249
```

```
Arg Gly Gly Ala Gly Glu Pro Gly Lys Asn Gly Ala Lys Gly Glu Pro
1               5                   10                  15

Gly Pro Arg Gly
            20

<210> SEQ ID NO 250
<211> LENGTH: 26
<212> TYPE: PRT
<213> ORGANISM: Homo sapiens

<400> SEQUENCE: 250

Lys Gly Glu Arg Gly Ser Pro Gly Gly Pro Gly Ala Ala Gly Phe Pro
1               5                   10                  15

Gly Ala Arg Gly Leu Pro Gly Pro Pro Gly
            20                  25

<210> SEQ ID NO 251
<211> LENGTH: 27
<212> TYPE: PRT
<213> ORGANISM: Homo sapiens

<400> SEQUENCE: 251

Ile Pro Gly Val Pro Gly Ala Lys Gly Glu Asp Gly Lys Asp Gly Ser
1               5                   10                  15

Pro Gly Glu Pro Gly Ala Asn Gly Leu Pro Gly
            20                  25

<210> SEQ ID NO 252
<211> LENGTH: 28
<212> TYPE: PRT
<213> ORGANISM: Homo sapiens

<400> SEQUENCE: 252

Gly Ala Ala Gly Phe Pro Gly Ala Arg Gly Leu Pro Gly Pro Pro Gly
1               5                   10                  15

Ser Asn Gly Asn Pro Gly Pro Pro Gly Pro Ser Gly
            20                  25

<210> SEQ ID NO 253
<211> LENGTH: 26
<212> TYPE: PRT
<213> ORGANISM: Homo sapiens

<400> SEQUENCE: 253

Arg Pro Gly Pro Pro Gly Pro Ser Gly Pro Arg Gly Gln Pro Gly Val
1               5                   10                  15

Met Gly Phe Pro Gly Pro Lys Gly Asn Asp
            20                  25

<210> SEQ ID NO 254
<211> LENGTH: 29
<212> TYPE: PRT
<213> ORGANISM: Homo sapiens

<400> SEQUENCE: 254

Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly
            20                  25

<210> SEQ ID NO 255
```

```
<211> LENGTH: 26
<212> TYPE: PRT
<213> ORGANISM: Homo sapiens

<400> SEQUENCE: 255

Ala Gly Lys Asp Gly Glu Ser Gly Arg Pro Gly Arg Pro Gly Glu Arg
1               5                   10                  15

Gly Leu Pro Gly Pro Pro Gly Ile Lys Gly
            20                  25

<210> SEQ ID NO 256
<211> LENGTH: 30
<212> TYPE: PRT
<213> ORGANISM: Homo sapiens

<400> SEQUENCE: 256

Ala Gly Ala Arg Gly Asn Asp Gly Ala Arg Gly Ser Asp Gly Gln Pro
1               5                   10                  15

Gly Pro Pro Gly Pro Pro Gly Thr Ala Gly Phe Pro Gly Ser
            20                  25                  30

<210> SEQ ID NO 257
<211> LENGTH: 31
<212> TYPE: PRT
<213> ORGANISM: Homo sapiens

<400> SEQUENCE: 257

Ser Pro Gly Val Ser Gly Pro Lys Gly Asp Ala Gly Gln Pro Gly Glu
1               5                   10                  15

Lys Gly Ser Pro Gly Ala Gln Gly Pro Pro Gly Ala Pro Gly Pro
            20                  25                  30

<210> SEQ ID NO 258
<211> LENGTH: 32
<212> TYPE: PRT
<213> ORGANISM: Homo sapiens

<400> SEQUENCE: 258

Arg Gly Ser Asp Gly Gln Pro Gly Pro Pro Gly Pro Pro Gly Thr Ala
1               5                   10                  15

Gly Phe Pro Gly Ser Pro Gly Ala Lys Gly Glu Val Gly Pro Ala Gly
            20                  25                  30

<210> SEQ ID NO 259
<211> LENGTH: 32
<212> TYPE: PRT
<213> ORGANISM: Homo sapiens

<400> SEQUENCE: 259

Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly Leu Met Gly
            20                  25                  30

<210> SEQ ID NO 260
<211> LENGTH: 33
<212> TYPE: PRT
<213> ORGANISM: Homo sapiens

<400> SEQUENCE: 260

Ala Gly Pro Pro Gly Pro Pro Gly Pro Pro Gly Thr Ser Gly His Pro
1               5                   10                  15
```

```
Gly Ser Pro Gly Ser Pro Gly Tyr Gln Gly Pro Pro Gly Glu Pro Gly
            20                  25                  30
Gln

<210> SEQ ID NO 261
<211> LENGTH: 33
<212> TYPE: PRT
<213> ORGANISM: Homo sapiens

<400> SEQUENCE: 261

Phe Pro Gly Ala Pro Gly Gln Asn Gly Glu Pro Gly Gly Lys Gly Glu
1               5                   10                  15

Arg Gly Ala Pro Gly Glu Lys Gly Glu Gly Gly Pro Pro Gly Val Ala
            20                  25                  30

Gly

<210> SEQ ID NO 262
<211> LENGTH: 33
<212> TYPE: PRT
<213> ORGANISM: Homo sapiens

<400> SEQUENCE: 262

Ala Gly Phe Pro Gly Ala Pro Gly Gln Asn Gly Glu Pro Gly Gly Lys
1               5                   10                  15

Gly Glu Arg Gly Ala Pro Gly Glu Lys Gly Glu Gly Gly Pro Pro Gly
            20                  25                  30

Val

<210> SEQ ID NO 263
<211> LENGTH: 41
<212> TYPE: PRT
<213> ORGANISM: Homo sapiens

<400> SEQUENCE: 263

Ala Gly Ala Arg Gly Asn Asp Gly Ala Arg Gly Ser Asp Gly Gln Pro
1               5                   10                  15

Gly Pro Pro Gly Pro Pro Gly Thr Ala Gly Phe Pro Gly Ser Pro Gly
            20                  25                  30

Ala Lys Gly Glu Val Gly Pro Ala Gly
        35                  40

<210> SEQ ID NO 264
<211> LENGTH: 53
<212> TYPE: PRT
<213> ORGANISM: Homo sapiens

<400> SEQUENCE: 264

Arg Gly Ala Ala Gly Glu Pro Gly Arg Asp Gly Val Pro Gly Gly Pro
1               5                   10                  15

Gly Met Arg Gly Met Pro Gly Ser Pro Gly Gly Pro Gly Ser Asp Gly
            20                  25                  30

Lys Pro Gly Pro Pro Gly Ser Gln Gly Glu Ser Gly Arg Pro Gly Pro
        35                  40                  45

Pro Gly Pro Ser Gly
        50

<210> SEQ ID NO 265
<211> LENGTH: 12
<212> TYPE: PRT
<213> ORGANISM: Homo sapiens
```

<400> SEQUENCE: 265

Gly Ile Ala Gly Ile Thr Gly Ala Arg Gly Leu Ala
1               5                   10

<210> SEQ ID NO 266
<211> LENGTH: 18
<212> TYPE: PRT
<213> ORGANISM: Homo sapiens

<400> SEQUENCE: 266

Ala Gly Pro Pro Gly Pro Pro Gly Ala Ala Gly Thr Pro Gly Leu Gln
1               5                   10                  15

Gly Met

<210> SEQ ID NO 267
<211> LENGTH: 18
<212> TYPE: PRT
<213> ORGANISM: Homo sapiens

<400> SEQUENCE: 267

Asn Gly Leu Ser Gly Glu Arg Gly Pro Pro Gly Pro Gln Gly Leu Pro
1               5                   10                  15

Gly Leu

<210> SEQ ID NO 268
<211> LENGTH: 20
<212> TYPE: PRT
<213> ORGANISM: Homo sapiens

<400> SEQUENCE: 268

Met Gly Ala Arg Gly Pro Pro Gly Pro Ala Gly Ala Asn Gly Ala Pro
1               5                   10                  15

Gly Leu Arg Gly
            20

<210> SEQ ID NO 269
<211> LENGTH: 20
<212> TYPE: PRT
<213> ORGANISM: Homo sapiens

<400> SEQUENCE: 269

Asn Gly Leu Ser Gly Glu Arg Gly Pro Pro Gly Pro Gln Gly Leu Pro
1               5                   10                  15

Gly Leu Ala Gly
            20

<210> SEQ ID NO 270
<211> LENGTH: 23
<212> TYPE: PRT
<213> ORGANISM: Homo sapiens

<400> SEQUENCE: 270

Gly Ile Ala Gly Ile Thr Gly Ala Arg Gly Leu Ala Gly Pro Pro Gly
1               5                   10                  15

Met Pro Gly Pro Arg Gly Ser
            20

<210> SEQ ID NO 271
<211> LENGTH: 29
<212> TYPE: PRT
<213> ORGANISM: Homo sapiens

```
<400> SEQUENCE: 271

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 272
<211> LENGTH: 32
<212> TYPE: PRT
<213> ORGANISM: Homo sapiens

<400> SEQUENCE: 272

Arg Gly Gly Ala Gly Pro Pro Gly Pro Glu Gly Gly Lys Gly Ala Ala
1               5                   10                  15

Gly Pro Pro Gly Pro Pro Gly Ala Ala Gly Thr Pro Gly Leu Gln Gly
            20                  25                  30

<210> SEQ ID NO 273
<211> LENGTH: 30
<212> TYPE: PRT
<213> ORGANISM: Homo sapiens

<400> SEQUENCE: 273

Ser Gly Pro Lys Gly Asp Ala Gly Gln Pro Gly Glu Lys Gly Ser Pro
1               5                   10                  15

Gly Ala Gln Gly Pro Pro Gly Ala Pro Gly Pro Leu Gly Ile
            20                  25                  30

<210> SEQ ID NO 274
<211> LENGTH: 31
<212> TYPE: PRT
<213> ORGANISM: Homo sapiens

<400> SEQUENCE: 274

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val Lys Gly
            20                  25                  30

<210> SEQ ID NO 275
<211> LENGTH: 37
<212> TYPE: PRT
<213> ORGANISM: Homo sapiens

<400> SEQUENCE: 275

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser Pro Gly Ser
            20                  25                  30

Pro Gly Tyr Gln Gly
        35

<210> SEQ ID NO 276
<211> LENGTH: 40
<212> TYPE: PRT
<213> ORGANISM: Homo sapiens

<400> SEQUENCE: 276

Glu Pro Gly Pro Gln Gly His Ala Gly Ala Gln Gly Pro Pro Gly Pro
1               5                   10                  15
```

```
Pro Gly Ile Asn Gly Ser Pro Gly Lys Gly Glu Met Gly Pro Ala
            20                  25                  30
Gly Ile Pro Gly Ala Pro Gly Leu
        35                  40
```

<210> SEQ ID NO 277
<211> LENGTH: 12
<212> TYPE: PRT
<213> ORGANISM: Homo sapiens

<400> SEQUENCE: 277

```
Ile Pro Gly Phe Pro Gly Met Lys Gly His Arg Gly
1               5                   10
```

<210> SEQ ID NO 278
<211> LENGTH: 17
<212> TYPE: PRT
<213> ORGANISM: Homo sapiens

<400> SEQUENCE: 278

```
Arg Gly Ser Pro Gly Gly Pro Gly Ala Ala Gly Phe Pro Gly Ala Arg
1               5                   10                  15
Gly
```

<210> SEQ ID NO 279
<211> LENGTH: 17
<212> TYPE: PRT
<213> ORGANISM: Homo sapiens

<400> SEQUENCE: 279

```
Lys Gly Pro Ala Gly Ile Pro Gly Phe Pro Gly Met Lys Gly His Arg
1               5                   10                  15
Gly
```

<210> SEQ ID NO 280
<211> LENGTH: 20
<212> TYPE: PRT
<213> ORGANISM: Homo sapiens

<400> SEQUENCE: 280

```
Arg Gly Leu Ala Gly Pro Pro Gly Met Pro Gly Pro Arg Gly Ser Pro
1               5                   10                  15
Gly Pro Gln Gly
            20
```

<210> SEQ ID NO 281
<211> LENGTH: 20
<212> TYPE: PRT
<213> ORGANISM: Homo sapiens

<400> SEQUENCE: 281

```
Ala Gly Ile Thr Gly Ala Arg Gly Leu Ala Gly Pro Pro Gly Met Pro
1               5                   10                  15
Gly Pro Arg Gly
            20
```

<210> SEQ ID NO 282
<211> LENGTH: 23
<212> TYPE: PRT
<213> ORGANISM: Homo sapiens

<400> SEQUENCE: 282

Leu Gly Ile Ala Gly Ile Thr Gly Ala Arg Gly Leu Ala Gly Pro Pro
1               5                   10                  15

Gly Met Pro Gly Pro Arg Gly
            20

<210> SEQ ID NO 283
<211> LENGTH: 23
<212> TYPE: PRT
<213> ORGANISM: Homo sapiens

<400> SEQUENCE: 283

Thr Gly Ala Arg Gly Leu Ala Gly Pro Pro Gly Met Pro Gly Pro Arg
1               5                   10                  15

Gly Ser Pro Gly Pro Gln Gly
            20

<210> SEQ ID NO 284
<211> LENGTH: 24
<212> TYPE: PRT
<213> ORGANISM: Homo sapiens

<400> SEQUENCE: 284

Gln Gly Pro Pro Gly Pro Gly Ile Asn Gly Ser Pro Gly Gly Lys
1               5                   10                  15

Gly Glu Met Gly Pro Ala Gly Ile
            20

<210> SEQ ID NO 285
<211> LENGTH: 24
<212> TYPE: PRT
<213> ORGANISM: Homo sapiens

<400> SEQUENCE: 285

Leu Pro Gly Pro Pro Gly Ile Lys Gly Pro Ala Gly Ile Pro Gly Phe
1               5                   10                  15

Pro Gly Met Lys Gly His Arg Gly
            20

<210> SEQ ID NO 286
<211> LENGTH: 26
<212> TYPE: PRT
<213> ORGANISM: Homo sapiens

<400> SEQUENCE: 286

Ala Gly Ile Thr Gly Ala Arg Gly Leu Ala Gly Pro Pro Gly Met Pro
1               5                   10                  15

Gly Pro Arg Gly Ser Pro Gly Pro Gln Gly
            20                  25

<210> SEQ ID NO 287
<211> LENGTH: 26
<212> TYPE: PRT
<213> ORGANISM: Homo sapiens

<400> SEQUENCE: 287

Thr Gly Ala Arg Gly Leu Ala Gly Pro Pro Gly Met Pro Gly Pro Arg
1               5                   10                  15

Gly Ser Pro Gly Pro Gln Gly Val Lys Gly
            20                  25

<210> SEQ ID NO 288
<211> LENGTH: 26

```
<212> TYPE: PRT
<213> ORGANISM: Homo sapiens

<400> SEQUENCE: 288

Arg Gly Leu Pro Gly Pro Pro Gly Ile Lys Gly Pro Ala Gly Ile Pro
1               5                   10                  15
Gly Phe Pro Gly Met Lys Gly His Arg Gly
            20                  25

<210> SEQ ID NO 289
<211> LENGTH: 29
<212> TYPE: PRT
<213> ORGANISM: Homo sapiens

<400> SEQUENCE: 289

Gly Arg Pro Gly Leu Pro Gly Ala Ala Gly Ala Arg Gly Asn Asp Gly
1               5                   10                  15
Ala Arg Gly Ser Asp Gly Gln Pro Gly Pro Pro Gly Pro
            20                  25

<210> SEQ ID NO 290
<211> LENGTH: 29
<212> TYPE: PRT
<213> ORGANISM: Homo sapiens

<400> SEQUENCE: 290

Asn Gly Ala Pro Gly Pro Met Gly Pro Arg Gly Ala Pro Gly Glu Arg
1               5                   10                  15
Gly Arg Pro Gly Leu Pro Gly Ala Ala Gly Ala Arg Gly
            20                  25

<210> SEQ ID NO 291
<211> LENGTH: 29
<212> TYPE: PRT
<213> ORGANISM: Homo sapiens

<400> SEQUENCE: 291

Ala Gly Ser Arg Gly Ala Pro Gly Pro Gln Gly Pro Arg Gly Asp Lys
1               5                   10                  15
Gly Glu Thr Gly Glu Arg Gly Ala Ala Gly Ile Lys Gly
            20                  25

<210> SEQ ID NO 292
<211> LENGTH: 32
<212> TYPE: PRT
<213> ORGANISM: Homo sapiens

<400> SEQUENCE: 292

Arg Gly Leu Ala Gly Pro Pro Gly Met Pro Gly Pro Arg Gly Ser Pro
1               5                   10                  15
Gly Pro Gln Gly Val Lys Gly Glu Ser Gly Lys Pro Gly Ala Asn Gly
            20                  25                  30

<210> SEQ ID NO 293
<211> LENGTH: 34
<212> TYPE: PRT
<213> ORGANISM: Homo sapiens

<400> SEQUENCE: 293

Arg Gly Leu Ala Gly Pro Pro Gly Met Pro Gly Pro Arg Gly Ser Pro
1               5                   10                  15
Gly Pro Gln Gly Val Lys Gly Glu Ser Gly Lys Pro Gly Ala Asn Gly
```

Leu Ser

<210> SEQ ID NO 294
<211> LENGTH: 37
<212> TYPE: PRT
<213> ORGANISM: Homo sapiens

<400> SEQUENCE: 294

Pro Gly Pro Pro Gly Ser Asn Gly Asn Pro Gly Pro Pro Gly Pro Ser
1               5                   10                  15

Gly Ser Pro Gly Lys Asp Gly Pro Gly Pro Ala Gly Asn Thr Gly
            20                  25                  30

Ala Pro Gly Ser Pro
        35

<210> SEQ ID NO 295
<211> LENGTH: 35
<212> TYPE: PRT
<213> ORGANISM: Homo sapiens

<400> SEQUENCE: 295

Thr Gly Ala Arg Gly Leu Ala Gly Pro Pro Gly Met Pro Gly Pro Arg
1               5                   10                  15

Gly Ser Pro Gly Pro Gln Gly Val Lys Gly Glu Ser Gly Lys Pro Gly
            20                  25                  30

Ala Asn Gly
        35

<210> SEQ ID NO 296
<211> LENGTH: 38
<212> TYPE: PRT
<213> ORGANISM: Homo sapiens

<400> SEQUENCE: 296

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly
        35

<210> SEQ ID NO 297
<211> LENGTH: 40
<212> TYPE: PRT
<213> ORGANISM: Homo sapiens

<400> SEQUENCE: 297

Gly Gly Pro Pro Gly Val Ala Gly Pro Pro Gly Gly Ser Gly Pro Ala
1               5                   10                  15

Gly Pro Pro Gly Pro Gln Gly Val Lys Gly Glu Arg Gly Ser Pro Gly
            20                  25                  30

Gly Pro Gly Ala Ala Gly Phe Pro
        35                  40

<210> SEQ ID NO 298
<211> LENGTH: 48
<212> TYPE: PRT
<213> ORGANISM: Homo sapiens

<400> SEQUENCE: 298

```
Lys Ser Gly Asp Arg Gly Glu Ser Gly Pro Ala Gly Pro Ala Gly Ala
1               5                   10                  15

Pro Gly Pro Ala Gly Ser Arg Gly Ala Pro Gly Pro Gln Gly Pro Arg
                20                  25                  30

Gly Asp Lys Gly Glu Thr Gly Glu Arg Gly Ala Ala Gly Ile Lys Gly
            35                  40                  45
```

<210> SEQ ID NO 299
<211> LENGTH: 12
<212> TYPE: PRT
<213> ORGANISM: Homo sapiens

<400> SEQUENCE: 299

```
Ile Pro Gly Phe Pro Gly Met Lys Gly His Arg Gly
1               5                   10
```

<210> SEQ ID NO 300
<211> LENGTH: 14
<212> TYPE: PRT
<213> ORGANISM: Homo sapiens

<400> SEQUENCE: 300

```
Arg Gly Leu Ala Gly Pro Pro Gly Met Pro Gly Pro Arg Gly
1               5                   10
```

<210> SEQ ID NO 301
<211> LENGTH: 16
<212> TYPE: PRT
<213> ORGANISM: Homo sapiens

<400> SEQUENCE: 301

```
Gly Pro Gln Gly Leu Gln Gly Leu Pro Gly Thr Gly Gly Pro Pro Gly
1               5                   10                  15
```

<210> SEQ ID NO 302
<211> LENGTH: 17
<212> TYPE: PRT
<213> ORGANISM: Homo sapiens

<400> SEQUENCE: 302

```
Lys Gly Pro Ala Gly Ile Pro Gly Phe Pro Gly Met Lys Gly His Arg
1               5                   10                  15

Gly
```

<210> SEQ ID NO 303
<211> LENGTH: 21
<212> TYPE: PRT
<213> ORGANISM: Homo sapiens

<400> SEQUENCE: 303

```
Arg Gly Leu Ala Gly Pro Pro Gly Met Pro Gly Pro Arg Gly Ser Pro
1               5                   10                  15

Gly Pro Gln Gly Val
                20
```

<210> SEQ ID NO 304
<211> LENGTH: 23
<212> TYPE: PRT
<213> ORGANISM: Homo sapiens

<400> SEQUENCE: 304

```
Gly Gly Pro Pro Gly Glu Asn Gly Lys Pro Gly Glu Pro Gly Pro Lys
```

```
1               5                   10                  15
Gly Asp Ala Gly Ala Pro Gly
            20

<210> SEQ ID NO 305
<211> LENGTH: 24
<212> TYPE: PRT
<213> ORGANISM: Homo sapiens

<400> SEQUENCE: 305

Ala Pro Gly Phe Arg Gly Pro Ala Gly Pro Asn Gly Ile Pro Gly Glu
1               5                   10                  15

Lys Gly Pro Ala Gly Glu Arg Gly
            20

<210> SEQ ID NO 306
<211> LENGTH: 27
<212> TYPE: PRT
<213> ORGANISM: Homo sapiens

<400> SEQUENCE: 306

Glu Lys Gly Ser Pro Gly Ala Gln Gly Pro Pro Gly Ala Pro Gly Pro
1               5                   10                  15

Leu Gly Ile Ala Gly Ile Thr Gly Ala Arg Gly
            20                  25

<210> SEQ ID NO 307
<211> LENGTH: 27
<212> TYPE: PRT
<213> ORGANISM: Homo sapiens

<400> SEQUENCE: 307

Glu Lys Gly Ser Pro Gly Ala Gln Gly Pro Pro Gly Ala Pro Gly Pro
1               5                   10                  15

Leu Gly Ile Ala Gly Ile Thr Gly Ala Arg Gly
            20                  25

<210> SEQ ID NO 308
<211> LENGTH: 26
<212> TYPE: PRT
<213> ORGANISM: Homo sapiens

<400> SEQUENCE: 308

Arg Gly Ala Pro Gly Phe Arg Gly Pro Ala Gly Pro Asn Gly Ile Pro
1               5                   10                  15

Gly Glu Lys Gly Pro Ala Gly Glu Arg Gly
            20                  25

<210> SEQ ID NO 309
<211> LENGTH: 26
<212> TYPE: PRT
<213> ORGANISM: Homo sapiens

<400> SEQUENCE: 309

Arg Gly Leu Pro Gly Pro Pro Gly Ile Lys Gly Pro Ala Gly Ile Pro
1               5                   10                  15

Gly Phe Pro Gly Met Lys Gly His Arg Gly
            20                  25

<210> SEQ ID NO 310
<211> LENGTH: 29
<212> TYPE: PRT
```

-continued

<213> ORGANISM: Homo sapiens

<400> SEQUENCE: 310

```
Arg Gly Pro Val Gly Pro Ser Gly Pro Pro Gly Lys Asp Gly Thr Ser
1               5                   10                  15
Gly His Pro Gly Pro Ile Gly Pro Pro Gly Pro Arg Gly
            20                  25
```

<210> SEQ ID NO 311
<211> LENGTH: 27
<212> TYPE: PRT
<213> ORGANISM: Homo sapiens

<400> SEQUENCE: 311

```
Ala Pro Gly Pro Gln Gly Pro Arg Gly Asp Lys Gly Glu Thr Gly Glu
1               5                   10                  15
Arg Gly Ala Ala Gly Ile Lys Gly His Arg Gly
            20                  25
```

<210> SEQ ID NO 312
<211> LENGTH: 29
<212> TYPE: PRT
<213> ORGANISM: Homo sapiens

<400> SEQUENCE: 312

```
Arg Gly Ala Pro Gly Pro Gln Gly Pro Arg Gly Asp Lys Gly Glu Thr
1               5                   10                  15
Gly Glu Arg Gly Ala Ala Gly Ile Lys Gly His Arg Gly
            20                  25
```

<210> SEQ ID NO 313
<211> LENGTH: 32
<212> TYPE: PRT
<213> ORGANISM: Homo sapiens

<400> SEQUENCE: 313

```
Arg Gly Phe Pro Gly Asn Pro Gly Ala Pro Gly Ser Pro Gly Pro Ala
1               5                   10                  15
Gly Gln Gln Gly Ala Ile Gly Ser Pro Gly Pro Ala Gly Pro Arg Gly
            20                  25                  30
```

<210> SEQ ID NO 314
<211> LENGTH: 29
<212> TYPE: PRT
<213> ORGANISM: Homo sapiens

<400> SEQUENCE: 314

```
Leu Pro Gly Pro Pro Gly Ile Lys Gly Pro Ala Gly Ile Pro Gly Phe
1               5                   10                  15
Pro Gly Met Lys Gly His Arg Gly Phe Asp Gly Arg Asn
            20                  25
```

<210> SEQ ID NO 315
<211> LENGTH: 33
<212> TYPE: PRT
<213> ORGANISM: Homo sapiens

<400> SEQUENCE: 315

```
Asp Ala Gly Gln Pro Gly Glu Lys Gly Ser Pro Gly Ala Gln Gly Pro
1               5                   10                  15
Pro Gly Ala Pro Gly Pro Leu Gly Ile Ala Gly Ile Thr Gly Ala Arg
            20                  25                  30
```

Gly

<210> SEQ ID NO 316
<211> LENGTH: 35
<212> TYPE: PRT
<213> ORGANISM: Homo sapiens

<400> SEQUENCE: 316

Arg Gly Pro Thr Gly Pro Ile Gly Pro Pro Gly Pro Ala Gly Gln Pro
1               5                   10                  15

Gly Asp Lys Gly Glu Gly Gly Ala Pro Gly Leu Pro Gly Ile Ala Gly
            20                  25                  30

Pro Arg Gly
        35

<210> SEQ ID NO 317
<211> LENGTH: 35
<212> TYPE: PRT
<213> ORGANISM: Homo sapiens

<400> SEQUENCE: 317

Lys Gly Asp Ala Gly Gln Pro Gly Glu Lys Gly Ser Pro Gly Ala Gln
1               5                   10                  15

Gly Pro Pro Gly Ala Pro Gly Pro Leu Gly Ile Ala Gly Ile Thr Gly
            20                  25                  30

Ala Arg Gly
        35

<210> SEQ ID NO 318
<211> LENGTH: 33
<212> TYPE: PRT
<213> ORGANISM: Homo sapiens

<400> SEQUENCE: 318

Arg Asn Gly Glu Lys Gly Glu Thr Gly Ala Pro Gly Leu Lys Gly Glu
1               5                   10                  15

Asn Gly Leu Pro Gly Glu Asn Gly Ala Pro Gly Pro Met Gly Pro Arg
            20                  25                  30

Gly

<210> SEQ ID NO 319
<211> LENGTH: 35
<212> TYPE: PRT
<213> ORGANISM: Homo sapiens

<400> SEQUENCE: 319

Ala Pro Gly Phe Arg Gly Pro Ala Gly Pro Asn Gly Ile Pro Gly Glu
1               5                   10                  15

Lys Gly Pro Ala Gly Glu Arg Gly Ala Pro Gly Pro Ala Gly Pro Arg
            20                  25                  30

Gly Ala Ala
        35

<210> SEQ ID NO 320
<211> LENGTH: 35
<212> TYPE: PRT
<213> ORGANISM: Homo sapiens

<400> SEQUENCE: 320

Arg Gly Ala Pro Gly Phe Arg Gly Pro Ala Gly Pro Asn Gly Ile Pro

```
                1               5                   10                  15
Gly Glu Lys Gly Pro Ala Gly Glu Arg Gly Ala Pro Gly Pro Ala Gly
                    20                  25                  30

Pro Arg Gly
        35

<210> SEQ ID NO 321
<211> LENGTH: 35
<212> TYPE: PRT
<213> ORGANISM: Homo sapiens

<400> SEQUENCE: 321

Arg Gly Ser Pro Gly Glu Arg Gly Glu Thr Gly Pro Pro Gly Pro Ala
1               5                   10                  15

Gly Phe Pro Gly Ala Pro Gly Gln Asn Gly Glu Pro Gly Gly Lys Gly
                    20                  25                  30

Glu Arg Gly
        35

<210> SEQ ID NO 322
<211> LENGTH: 38
<212> TYPE: PRT
<213> ORGANISM: Homo sapiens

<400> SEQUENCE: 322

Gly His Ala Gly Ala Gln Gly Pro Pro Gly Pro Pro Gly Ile Asn Gly
1               5                   10                  15

Ser Pro Gly Gly Lys Gly Glu Met Gly Pro Ala Gly Ile Pro Gly Ala
                    20                  25                  30

Pro Gly Leu Met Gly Ala
        35

<210> SEQ ID NO 323
<211> LENGTH: 38
<212> TYPE: PRT
<213> ORGANISM: Homo sapiens

<400> SEQUENCE: 323

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
                    20                  25                  30

Leu Ser Gly Glu Arg Gly
        35

<210> SEQ ID NO 324
<211> LENGTH: 13
<212> TYPE: PRT
<213> ORGANISM: Homo sapiens

<400> SEQUENCE: 324

Leu Gly Ile Ala Gly Ile Thr Gly Ala Arg Gly Leu Ala
1               5                   10

<210> SEQ ID NO 325
<211> LENGTH: 12
<212> TYPE: PRT
<213> ORGANISM: Homo sapiens

<400> SEQUENCE: 325

Ile Pro Gly Phe Pro Gly Met Lys Gly His Arg Gly
```

<210> SEQ ID NO 326
<211> LENGTH: 14
<212> TYPE: PRT
<213> ORGANISM: Homo sapiens

<400> SEQUENCE: 326

Arg Gly Leu Ala Gly Pro Pro Gly Met Pro Gly Pro Arg Gly
1               5                   10

<210> SEQ ID NO 327
<211> LENGTH: 20
<212> TYPE: PRT
<213> ORGANISM: Homo sapiens

<400> SEQUENCE: 327

Gln Gly Pro Pro Gly Ala Pro Gly Pro Leu Gly Ile Ala Gly Ile Thr
1               5                   10                  15

Gly Ala Arg Gly
            20

<210> SEQ ID NO 328
<211> LENGTH: 20
<212> TYPE: PRT
<213> ORGANISM: Homo sapiens

<400> SEQUENCE: 328

Ala Gly Ile Thr Gly Ala Arg Gly Leu Ala Gly Pro Pro Gly Met Pro
1               5                   10                  15

Gly Pro Arg Gly
            20

<210> SEQ ID NO 329
<211> LENGTH: 23
<212> TYPE: PRT
<213> ORGANISM: Homo sapiens

<400> SEQUENCE: 329

Ala Gly Ile Pro Gly Ala Pro Gly Leu Met Gly Ala Arg Gly Pro Pro
1               5                   10                  15

Gly Pro Ala Gly Ala Asn Gly
            20

<210> SEQ ID NO 330
<211> LENGTH: 24
<212> TYPE: PRT
<213> ORGANISM: Homo sapiens

<400> SEQUENCE: 330

Arg Gly Leu Ala Gly Pro Pro Gly Met Pro Gly Pro Arg Gly Ser Pro
1               5                   10                  15

Gly Pro Gln Gly Val Lys Gly Glu
            20

<210> SEQ ID NO 331
<211> LENGTH: 26
<212> TYPE: PRT
<213> ORGANISM: Homo sapiens

<400> SEQUENCE: 331

Lys Gly Ser Pro Gly Ala Gln Gly Pro Pro Gly Ala Pro Gly Pro Leu
1               5                   10                  15

Gly Ile Ala Gly Ile Thr Gly Ala Arg Gly
              20                  25

<210> SEQ ID NO 332
<211> LENGTH: 24
<212> TYPE: PRT
<213> ORGANISM: Homo sapiens

<400> SEQUENCE: 332

Leu Pro Gly Pro Pro Gly Ile Lys Gly Pro Ala Gly Ile Pro Gly Phe
1               5                   10                  15

Pro Gly Met Lys Gly His Arg Gly
              20

<210> SEQ ID NO 333
<211> LENGTH: 24
<212> TYPE: PRT
<213> ORGANISM: Homo sapiens

<400> SEQUENCE: 333

Lys Asp Gly Thr Ser Gly His Pro Gly Pro Ile Gly Pro Pro Gly Pro
1               5                   10                  15

Arg Gly Asn Arg Gly Glu Arg Gly
              20

<210> SEQ ID NO 334
<211> LENGTH: 26
<212> TYPE: PRT
<213> ORGANISM: Homo sapiens

<400> SEQUENCE: 334

Ala Gly Ile Thr Gly Ala Arg Gly Leu Ala Gly Pro Pro Gly Met Pro
1               5                   10                  15

Gly Pro Arg Gly Ser Pro Gly Pro Gln Gly
              20                  25

<210> SEQ ID NO 335
<211> LENGTH: 27
<212> TYPE: PRT
<213> ORGANISM: Homo sapiens

<400> SEQUENCE: 335

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys
              20                  25

<210> SEQ ID NO 336
<211> LENGTH: 32
<212> TYPE: PRT
<213> ORGANISM: Homo sapiens

<400> SEQUENCE: 336

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
              20                  25                  30

<210> SEQ ID NO 337
<211> LENGTH: 34
<212> TYPE: PRT
<213> ORGANISM: Homo sapiens

<400> SEQUENCE: 337

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

Leu Ser

<210> SEQ ID NO 338
<211> LENGTH: 37
<212> TYPE: PRT
<213> ORGANISM: Homo sapiens

<400> SEQUENCE: 338

Pro Gly Pro Pro Gly Ser Asn Gly Asn Pro Gly Pro Pro Gly Pro Ser
1               5                   10                  15

Gly Ser Pro Gly Lys Asp Gly Pro Gly Pro Ala Gly Asn Thr Gly
            20                  25                  30

Ala Pro Gly Ser Pro
            35

<210> SEQ ID NO 339
<211> LENGTH: 38
<212> TYPE: PRT
<213> ORGANISM: Homo sapiens

<400> SEQUENCE: 339

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly
            35

<210> SEQ ID NO 340
<211> LENGTH: 44
<212> TYPE: PRT
<213> ORGANISM: Homo sapiens

<400> SEQUENCE: 340

Lys Ser Gly Asp Arg Gly Glu Ser Gly Pro Ala Gly Pro Ala Gly Ala
1               5                   10                  15

Pro Gly Pro Ala Gly Ser Arg Gly Ala Pro Gly Pro Gln Pro Arg
            20                  25                  30

Gly Asp Lys Gly Glu Thr Gly Glu Arg Gly Ala Ala
            35                  40

<210> SEQ ID NO 341
<211> LENGTH: 53
<212> TYPE: PRT
<213> ORGANISM: Homo sapiens

<400> SEQUENCE: 341

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly Ser Pro Gly Gly Pro Gly Ala Ala Gly Phe
            35                  40                  45

Pro Gly Ala Arg Gly
    50

<210> SEQ ID NO 342
<211> LENGTH: 6
<212> TYPE: PRT
<213> ORGANISM: Homo sapiens

<400> SEQUENCE: 342

Ala Ile Gly Pro Ser Gly
1               5

<210> SEQ ID NO 343
<211> LENGTH: 6
<212> TYPE: PRT
<213> ORGANISM: Homo sapiens

<400> SEQUENCE: 343

Gly Ile Pro Gly Ala Pro
1               5

<210> SEQ ID NO 344
<211> LENGTH: 6
<212> TYPE: PRT
<213> ORGANISM: Homo sapiens

<400> SEQUENCE: 344

Ile Lys Gly His Arg Gly
1               5

<210> SEQ ID NO 345
<211> LENGTH: 6
<212> TYPE: PRT
<213> ORGANISM: Homo sapiens

<400> SEQUENCE: 345

Val Lys Gly Glu Ser Gly
1               5

<210> SEQ ID NO 346
<211> LENGTH: 6
<212> TYPE: PRT
<213> ORGANISM: Homo sapiens

<400> SEQUENCE: 346

His Ala Gly Ala Gln Gly
1               5

<210> SEQ ID NO 347
<211> LENGTH: 6
<212> TYPE: PRT
<213> ORGANISM: Homo sapiens

<400> SEQUENCE: 347

Asp Gly Thr Ser Gly His
1               5

<210> SEQ ID NO 348
<211> LENGTH: 6
<212> TYPE: PRT
<213> ORGANISM: Homo sapiens

<400> SEQUENCE: 348

Ile Gly Ser Pro Gly Pro
1               5

<210> SEQ ID NO 349
<211> LENGTH: 6
<212> TYPE: PRT
<213> ORGANISM: Homo sapiens

<400> SEQUENCE: 349

Leu Ser Gly Glu Arg Gly
1               5

<210> SEQ ID NO 350
<211> LENGTH: 6
<212> TYPE: PRT
<213> ORGANISM: Homo sapiens

<400> SEQUENCE: 350

Val Lys Gly Glu Arg Gly
1               5

<210> SEQ ID NO 351
<211> LENGTH: 6
<212> TYPE: PRT
<213> ORGANISM: Homo sapiens

<400> SEQUENCE: 351

Gly Ala Arg Gly Leu Ala
1               5

<210> SEQ ID NO 352
<211> LENGTH: 6
<212> TYPE: PRT
<213> ORGANISM: Homo sapiens

<400> SEQUENCE: 352

Gly Ala Pro Gly Glu Lys
1               5

<210> SEQ ID NO 353
<211> LENGTH: 6
<212> TYPE: PRT
<213> ORGANISM: Homo sapiens

<400> SEQUENCE: 353

Ile Lys Gly Pro Ala Gly
1               5

<210> SEQ ID NO 354
<211> LENGTH: 6
<212> TYPE: PRT
<213> ORGANISM: Homo sapiens

<400> SEQUENCE: 354

Gly Ile Pro Gly Gln Pro
1               5

<210> SEQ ID NO 355
<211> LENGTH: 6
<212> TYPE: PRT
<213> ORGANISM: Homo sapiens

<400> SEQUENCE: 355

Gly Pro Pro Gly Pro Thr
1               5

```
<210> SEQ ID NO 356
<211> LENGTH: 6
<212> TYPE: PRT
<213> ORGANISM: Homo sapiens

<400> SEQUENCE: 356

Lys Asn Gly Glu Thr Gly
1               5

<210> SEQ ID NO 357
<211> LENGTH: 6
<212> TYPE: PRT
<213> ORGANISM: Homo sapiens

<400> SEQUENCE: 357

Leu Lys Gly Glu Asn Gly
1               5

<210> SEQ ID NO 358
<211> LENGTH: 6
<212> TYPE: PRT
<213> ORGANISM: Homo sapiens

<400> SEQUENCE: 358

Gly Asp Pro Gly Pro Pro
1               5

<210> SEQ ID NO 359
<211> LENGTH: 6
<212> TYPE: PRT
<213> ORGANISM: Homo sapiens

<400> SEQUENCE: 359

Gly Asp Pro Gly Pro Pro
1               5

<210> SEQ ID NO 360
<211> LENGTH: 6
<212> TYPE: PRT
<213> ORGANISM: Homo sapiens

<400> SEQUENCE: 360

Phe Pro Gly Ala Arg Gly
1               5

<210> SEQ ID NO 361
<211> LENGTH: 6
<212> TYPE: PRT
<213> ORGANISM: Homo sapiens

<400> SEQUENCE: 361

Gly Asp Lys Gly Glu Thr
1               5

<210> SEQ ID NO 362
<211> LENGTH: 6
<212> TYPE: PRT
<213> ORGANISM: Homo sapiens

<400> SEQUENCE: 362

Gly Gly Ala Gly Glu Pro
1               5

<210> SEQ ID NO 363
```

```
<400> SEQUENCE: 363

000

<210> SEQ ID NO 364
<211> LENGTH: 6
<212> TYPE: PRT
<213> ORGANISM: Homo sapiens

<400> SEQUENCE: 364

Gly Pro Pro Gly Pro Pro
1               5

<210> SEQ ID NO 365
<211> LENGTH: 6
<212> TYPE: PRT
<213> ORGANISM: Homo sapiens

<400> SEQUENCE: 365

Gly Ala Ala Gly Glu Pro
1               5

<210> SEQ ID NO 366
<211> LENGTH: 6
<212> TYPE: PRT
<213> ORGANISM: Homo sapiens

<400> SEQUENCE: 366

Gly Leu Ser Gly Glu Arg
1               5

<210> SEQ ID NO 367
<211> LENGTH: 6
<212> TYPE: PRT
<213> ORGANISM: Homo sapiens

<400> SEQUENCE: 367

Ile Ala Gly Ile Thr Gly
1               5

<210> SEQ ID NO 368
<211> LENGTH: 6
<212> TYPE: PRT
<213> ORGANISM: Homo sapiens

<400> SEQUENCE: 368

Pro Gly Phe Pro Gly Met
1               5

<210> SEQ ID NO 369
<211> LENGTH: 6
<212> TYPE: PRT
<213> ORGANISM: Homo sapiens

<400> SEQUENCE: 369

Gly Ile Ala Gly Ile Thr
1               5

<210> SEQ ID NO 370
<211> LENGTH: 6
<212> TYPE: PRT
<213> ORGANISM: Homo sapiens

<400> SEQUENCE: 370

Gly Ala Arg Gly Leu Ala
```

```
1               5

<210> SEQ ID NO 371
<211> LENGTH: 6
<212> TYPE: PRT
<213> ORGANISM: Homo sapiens

<400> SEQUENCE: 371

Gly Leu Ala Gly Pro Pro
1               5

<210> SEQ ID NO 372
<211> LENGTH: 6
<212> TYPE: PRT
<213> ORGANISM: Homo sapiens

<400> SEQUENCE: 372

Gly Pro Pro Gly Val Ala
1               5

<210> SEQ ID NO 373
<211> LENGTH: 6
<212> TYPE: PRT
<213> ORGANISM: Homo sapiens

<400> SEQUENCE: 373

Gly Pro Ala Gly Ile Pro
1               5

<210> SEQ ID NO 374
<211> LENGTH: 6
<212> TYPE: PRT
<213> ORGANISM: Homo sapiens

<400> SEQUENCE: 374

Pro Gly Pro Pro Gly Ile
1               5

<210> SEQ ID NO 375
<211> LENGTH: 6
<212> TYPE: PRT
<213> ORGANISM: Homo sapiens

<400> SEQUENCE: 375

Gly Ala Pro Gly Pro Gln
1               5

<210> SEQ ID NO 376
<211> LENGTH: 6
<212> TYPE: PRT
<213> ORGANISM: Homo sapiens

<400> SEQUENCE: 376

Gly Asp Ala Gly Gln Pro
1               5

<210> SEQ ID NO 377
<211> LENGTH: 6
<212> TYPE: PRT
<213> ORGANISM: Homo sapiens

<400> SEQUENCE: 377

His Ala Gly Ala Gln Gly
1               5
```

```
<210> SEQ ID NO 378
<211> LENGTH: 6
<212> TYPE: PRT
<213> ORGANISM: Homo sapiens

<400> SEQUENCE: 378

Gly Pro Pro Gly Ala Pro
1               5

<210> SEQ ID NO 379
<211> LENGTH: 6
<212> TYPE: PRT
<213> ORGANISM: Homo sapiens

<400> SEQUENCE: 379

Gly Leu Ala Gly Pro Pro
1               5

<210> SEQ ID NO 380
<211> LENGTH: 6
<212> TYPE: PRT
<213> ORGANISM: Homo sapiens

<400> SEQUENCE: 380

Ala Ile Gly Pro Ser Gly
1               5

<210> SEQ ID NO 381
<211> LENGTH: 6
<212> TYPE: PRT
<213> ORGANISM: Homo sapiens

<400> SEQUENCE: 381

Gly Pro Pro Gly Pro Ala
1               5

<210> SEQ ID NO 382
<211> LENGTH: 6
<212> TYPE: PRT
<213> ORGANISM: Homo sapiens

<400> SEQUENCE: 382

Ser Pro Gly Pro Ala Gly
1               5

<210> SEQ ID NO 383
<211> LENGTH: 6
<212> TYPE: PRT
<213> ORGANISM: Homo sapiens

<400> SEQUENCE: 383

Ala Ala Gly Thr Pro Gly
1               5

<210> SEQ ID NO 384
<211> LENGTH: 6
<212> TYPE: PRT
<213> ORGANISM: Homo sapiens

<400> SEQUENCE: 384

Thr Ser Gly His Pro Gly
1               5

<210> SEQ ID NO 385
```

```
<210> SEQ ID NO 385
<211> LENGTH: 6
<212> TYPE: PRT
<213> ORGANISM: Homo sapiens

<400> SEQUENCE: 385

Pro Ser Gly Pro Pro Gly
1               5

<210> SEQ ID NO 386
<211> LENGTH: 6
<212> TYPE: PRT
<213> ORGANISM: Homo sapiens

<400> SEQUENCE: 386

Pro Gly Leu Met Gly Ala
1               5

<210> SEQ ID NO 387
<211> LENGTH: 6
<212> TYPE: PRT
<213> ORGANISM: Homo sapiens

<400> SEQUENCE: 387

Ser Pro Gly Pro Gln Gly
1               5

<210> SEQ ID NO 388
<211> LENGTH: 6
<212> TYPE: PRT
<213> ORGANISM: Homo sapiens

<400> SEQUENCE: 388

Pro Pro Gly Pro Pro Gly
1               5

<210> SEQ ID NO 389
<211> LENGTH: 6
<212> TYPE: PRT
<213> ORGANISM: Homo sapiens

<400> SEQUENCE: 389

Gly Ala Ile Gly Pro Ser
1               5

<210> SEQ ID NO 390
<211> LENGTH: 6
<212> TYPE: PRT
<213> ORGANISM: Homo sapiens

<400> SEQUENCE: 390

Pro Pro Gly Pro Ala Gly
1               5

<210> SEQ ID NO 391
<211> LENGTH: 6
<212> TYPE: PRT
<213> ORGANISM: Homo sapiens

<400> SEQUENCE: 391

Ser Pro Gly Pro Lys Gly
1               5

<210> SEQ ID NO 392
<211> LENGTH: 6
<212> TYPE: PRT
```

<213> ORGANISM: Homo sapiens

<400> SEQUENCE: 392

Pro Pro Gly Pro Ala Gly
1               5

<210> SEQ ID NO 393
<211> LENGTH: 6
<212> TYPE: PRT
<213> ORGANISM: Homo sapiens

<400> SEQUENCE: 393

Leu Pro Gly Pro Pro Gly
1               5

<210> SEQ ID NO 394
<211> LENGTH: 6
<212> TYPE: PRT
<213> ORGANISM: Homo sapiens

<400> SEQUENCE: 394

Gly Ala Pro Gly Leu Lys
1               5

<210> SEQ ID NO 395
<211> LENGTH: 6
<212> TYPE: PRT
<213> ORGANISM: Homo sapiens

<400> SEQUENCE: 395

Gly Leu Pro Gly Pro Pro
1               5

<210> SEQ ID NO 396
<211> LENGTH: 6
<212> TYPE: PRT
<213> ORGANISM: Homo sapiens

<400> SEQUENCE: 396

Gly Pro Pro Gly Ile Lys
1               5

<210> SEQ ID NO 397
<211> LENGTH: 6
<212> TYPE: PRT
<213> ORGANISM: Homo sapiens

<400> SEQUENCE: 397

Gly Pro Pro Gly Val Ala
1               5

<210> SEQ ID NO 398
<211> LENGTH: 6
<212> TYPE: PRT
<213> ORGANISM: Homo sapiens

<400> SEQUENCE: 398

Thr Pro Gly Leu Gln Gly
1               5

<210> SEQ ID NO 399
<211> LENGTH: 6
<212> TYPE: PRT
<213> ORGANISM: Homo sapiens

```
<400> SEQUENCE: 399

Gly Thr Pro Gly Leu Gln
1               5

<210> SEQ ID NO 400
<211> LENGTH: 6
<212> TYPE: PRT
<213> ORGANISM: Homo sapiens

<400> SEQUENCE: 400

Gly Phe Pro Gly Ala Arg
1               5

<210> SEQ ID NO 401
<211> LENGTH: 6
<212> TYPE: PRT
<213> ORGANISM: Homo sapiens

<400> SEQUENCE: 401

Gln Pro Gly Pro Pro Gly
1               5

<210> SEQ ID NO 402
<211> LENGTH: 6
<212> TYPE: PRT
<213> ORGANISM: Homo sapiens

<400> SEQUENCE: 402

Thr Gly Ala Pro Gly Ser
1               5

<210> SEQ ID NO 403
<211> LENGTH: 6
<212> TYPE: PRT
<213> ORGANISM: Homo sapiens

<400> SEQUENCE: 403

Ser Pro Gly Pro Gln Gly
1               5

<210> SEQ ID NO 404
<211> LENGTH: 6
<212> TYPE: PRT
<213> ORGANISM: Homo sapiens

<400> SEQUENCE: 404

Gly Pro Ala Gly Pro Arg
1               5

<210> SEQ ID NO 405
<211> LENGTH: 6
<212> TYPE: PRT
<213> ORGANISM: Homo sapiens

<400> SEQUENCE: 405

Ala Pro Gly Leu Met Gly
1               5

<210> SEQ ID NO 406
<211> LENGTH: 6
<212> TYPE: PRT
<213> ORGANISM: Homo sapiens

<400> SEQUENCE: 406
```

Gly Asn Arg Gly Glu Arg
1               5

<210> SEQ ID NO 407
<211> LENGTH: 6
<212> TYPE: PRT
<213> ORGANISM: Homo sapiens

<400> SEQUENCE: 407

Thr Gly Ala Pro Gly Ser
1               5

<210> SEQ ID NO 408
<211> LENGTH: 6
<212> TYPE: PRT
<213> ORGANISM: Homo sapiens

<400> SEQUENCE: 408

Gly Asp Pro Gly Pro Pro
1               5

<210> SEQ ID NO 409
<211> LENGTH: 6
<212> TYPE: PRT
<213> ORGANISM: Homo sapiens

<400> SEQUENCE: 409

Arg Gly Leu Ala Gly Pro
1               5

<210> SEQ ID NO 410
<211> LENGTH: 6
<212> TYPE: PRT
<213> ORGANISM: Homo sapiens

<400> SEQUENCE: 410

Ser Arg Gly Ala Pro Gly
1               5

<210> SEQ ID NO 411
<211> LENGTH: 6
<212> TYPE: PRT
<213> ORGANISM: Homo sapiens

<400> SEQUENCE: 411

Gly Lys Ser Gly Asp Arg
1               5

<210> SEQ ID NO 412
<211> LENGTH: 6
<212> TYPE: PRT
<213> ORGANISM: Homo sapiens

<400> SEQUENCE: 412

Val Gly Gly Leu Ala Gly
1               5

<210> SEQ ID NO 413
<211> LENGTH: 6
<212> TYPE: PRT
<213> ORGANISM: Homo sapiens

<400> SEQUENCE: 413

Ala Ile Gly Ser Pro Gly
1               5

<210> SEQ ID NO 414
<211> LENGTH: 6
<212> TYPE: PRT
<213> ORGANISM: Homo sapiens

<400> SEQUENCE: 414

Gly Leu Ala Gly Pro Pro
1               5

<210> SEQ ID NO 415
<211> LENGTH: 6
<212> TYPE: PRT
<213> ORGANISM: Homo sapiens

<400> SEQUENCE: 415

Arg Gly Leu Ala Gly Pro
1               5

<210> SEQ ID NO 416
<211> LENGTH: 6
<212> TYPE: PRT
<213> ORGANISM: Homo sapiens

<400> SEQUENCE: 416

Lys Gly Glu Ser Gly Lys
1               5

<210> SEQ ID NO 417
<211> LENGTH: 6
<212> TYPE: PRT
<213> ORGANISM: Homo sapiens

<400> SEQUENCE: 417

Ile Ala Gly Ile Thr Gly
1               5

<210> SEQ ID NO 418
<211> LENGTH: 6
<212> TYPE: PRT
<213> ORGANISM: Homo sapiens

<400> SEQUENCE: 418

Pro Gly Ala Pro Gly Leu
1               5

<210> SEQ ID NO 419
<211> LENGTH: 6
<212> TYPE: PRT
<213> ORGANISM: Homo sapiens

<400> SEQUENCE: 419

Glu Arg Gly Leu Pro Gly
1               5

<210> SEQ ID NO 420
<211> LENGTH: 6
<212> TYPE: PRT
<213> ORGANISM: Homo sapiens

<400> SEQUENCE: 420

Ile Asn Gly Ser Pro Gly
1               5

```
<210> SEQ ID NO 421
<211> LENGTH: 6
<212> TYPE: PRT
<213> ORGANISM: Homo sapiens

<400> SEQUENCE: 421

Leu Pro Gly Ile Ala Gly
1               5

<210> SEQ ID NO 422
<211> LENGTH: 6
<212> TYPE: PRT
<213> ORGANISM: Homo sapiens

<400> SEQUENCE: 422

Asn Thr Gly Ala Pro Gly
1               5

<210> SEQ ID NO 423
<211> LENGTH: 6
<212> TYPE: PRT
<213> ORGANISM: Homo sapiens

<400> SEQUENCE: 423

Leu Arg Gly Gly Ala Gly
1               5

<210> SEQ ID NO 424
<211> LENGTH: 6
<212> TYPE: PRT
<213> ORGANISM: Homo sapiens

<400> SEQUENCE: 424

Gly His Ala Gly Ala Gln
1               5

<210> SEQ ID NO 425
<211> LENGTH: 6
<212> TYPE: PRT
<213> ORGANISM: Homo sapiens

<400> SEQUENCE: 425

Gly Phe Pro Gly Ala Arg
1               5

<210> SEQ ID NO 426
<211> LENGTH: 6
<212> TYPE: PRT
<213> ORGANISM: Homo sapiens

<400> SEQUENCE: 426

Gly Arg Asn Gly Glu Lys
1               5

<210> SEQ ID NO 427
<211> LENGTH: 6
<212> TYPE: PRT
<213> ORGANISM: Homo sapiens

<400> SEQUENCE: 427

Gly Glu Arg Gly Ser Pro
1               5

<210> SEQ ID NO 428
<211> LENGTH: 6
```

```
<212> TYPE: PRT
<213> ORGANISM: Homo sapiens

<400> SEQUENCE: 428

Gly Lys Asp Gly Glu Ser
1               5

<210> SEQ ID NO 429
<211> LENGTH: 6
<212> TYPE: PRT
<213> ORGANISM: Homo sapiens

<400> SEQUENCE: 429

Ile Ala Gly Ile Thr Gly
1               5

<210> SEQ ID NO 430
<211> LENGTH: 6
<212> TYPE: PRT
<213> ORGANISM: Homo sapiens

<400> SEQUENCE: 430

Gly Pro Lys Gly Asp Ala
1               5

<210> SEQ ID NO 431
<211> LENGTH: 6
<212> TYPE: PRT
<213> ORGANISM: Homo sapiens

<400> SEQUENCE: 431

Gly Ser Pro Gly Gly Pro
1               5

<210> SEQ ID NO 432
<211> LENGTH: 6
<212> TYPE: PRT
<213> ORGANISM: Homo sapiens

<400> SEQUENCE: 432

Gly Leu Pro Gly Pro Pro
1               5

<210> SEQ ID NO 433
<211> LENGTH: 6
<212> TYPE: PRT
<213> ORGANISM: Homo sapiens

<400> SEQUENCE: 433

Ser Gly Asp Arg Gly Glu
1               5

<210> SEQ ID NO 434
<211> LENGTH: 6
<212> TYPE: PRT
<213> ORGANISM: Homo sapiens

<400> SEQUENCE: 434

Gly Leu Ala Gly Pro Pro
1               5

<210> SEQ ID NO 435
<211> LENGTH: 6
<212> TYPE: PRT
<213> ORGANISM: Homo sapiens
```

<400> SEQUENCE: 435

Gly Ala Pro Gly Phe Arg
1               5

<210> SEQ ID NO 436
<211> LENGTH: 6
<212> TYPE: PRT
<213> ORGANISM: Homo sapiens

<400> SEQUENCE: 436

Gly Phe Pro Gly Asn Pro
1               5

<210> SEQ ID NO 437
<211> LENGTH: 6
<212> TYPE: PRT
<213> ORGANISM: Homo sapiens

<400> SEQUENCE: 437

Asn Gly Glu Lys Gly Glu
1               5

<210> SEQ ID NO 438
<211> LENGTH: 6
<212> TYPE: PRT
<213> ORGANISM: Homo sapiens

<400> SEQUENCE: 438

Gly Leu Ala Gly Pro Pro
1               5

<210> SEQ ID NO 439
<211> LENGTH: 6
<212> TYPE: PRT
<213> ORGANISM: Homo sapiens

<400> SEQUENCE: 439

Gly Ile Thr Gly Ala Arg
1               5

<210> SEQ ID NO 440
<211> LENGTH: 6
<212> TYPE: PRT
<213> ORGANISM: Homo sapiens

<400> SEQUENCE: 440

Asp Gly Thr Ser Gly His
1               5

<210> SEQ ID NO 441
<211> LENGTH: 6
<212> TYPE: PRT
<213> ORGANISM: Homo sapiens

<400> SEQUENCE: 441

Gly Pro Pro Gly Ser Asn
1               5

<210> SEQ ID NO 442
<211> LENGTH: 6
<212> TYPE: PRT
<213> ORGANISM: Homo sapiens

<400> SEQUENCE: 442

Asn Gly Asp Pro Gly Ile
1               5

<210> SEQ ID NO 443
<211> LENGTH: 6
<212> TYPE: PRT
<213> ORGANISM: Homo sapiens

<400> SEQUENCE: 443

Pro Gly Pro Gln Gly Val
1               5

<210> SEQ ID NO 444
<211> LENGTH: 6
<212> TYPE: PRT
<213> ORGANISM: Homo sapiens

<400> SEQUENCE: 444

Ile Pro Gly Ala Pro Gly
1               5

<210> SEQ ID NO 445
<211> LENGTH: 6
<212> TYPE: PRT
<213> ORGANISM: Homo sapiens

<400> SEQUENCE: 445

Ser Pro Gly Pro Gln Gly
1               5

<210> SEQ ID NO 446
<211> LENGTH: 6
<212> TYPE: PRT
<213> ORGANISM: Homo sapiens

<400> SEQUENCE: 446

Gly Ser Pro Gly Pro Ala
1               5

<210> SEQ ID NO 447
<211> LENGTH: 6
<212> TYPE: PRT
<213> ORGANISM: Homo sapiens

<400> SEQUENCE: 447

Gln Gly Pro Pro Gly Pro
1               5

<210> SEQ ID NO 448
<211> LENGTH: 6
<212> TYPE: PRT
<213> ORGANISM: Homo sapiens

<400> SEQUENCE: 448

Ile Pro Gly Phe Pro Gly
1               5

<210> SEQ ID NO 449
<211> LENGTH: 6
<212> TYPE: PRT
<213> ORGANISM: Homo sapiens

<400> SEQUENCE: 449

Gly Pro Ala Gly Ile Pro

```
1               5

<210> SEQ ID NO 450
<211> LENGTH: 6
<212> TYPE: PRT
<213> ORGANISM: Homo sapiens

<400> SEQUENCE: 450

Phe Pro Gly Ala Arg Gly
1               5

<210> SEQ ID NO 451
<211> LENGTH: 6
<212> TYPE: PRT
<213> ORGANISM: Homo sapiens

<400> SEQUENCE: 451

Gly Ile Pro Gly Ala Pro
1               5

<210> SEQ ID NO 452
<211> LENGTH: 6
<212> TYPE: PRT
<213> ORGANISM: Homo sapiens

<400> SEQUENCE: 452

Glu Arg Gly Pro Pro Gly
1               5

<210> SEQ ID NO 453
<211> LENGTH: 6
<212> TYPE: PRT
<213> ORGANISM: Homo sapiens

<400> SEQUENCE: 453

Pro Ser Gly Pro Pro Gly
1               5

<210> SEQ ID NO 454
<211> LENGTH: 6
<212> TYPE: PRT
<213> ORGANISM: Homo sapiens

<400> SEQUENCE: 454

Gly Pro Pro Gly Ile Asn
1               5

<210> SEQ ID NO 455
<211> LENGTH: 6
<212> TYPE: PRT
<213> ORGANISM: Homo sapiens

<400> SEQUENCE: 455

Gly Thr Ser Gly His Pro
1               5

<210> SEQ ID NO 456
<211> LENGTH: 6
<212> TYPE: PRT
<213> ORGANISM: Homo sapiens

<400> SEQUENCE: 456

Gly Leu Pro Gly Ile Ala
1               5
```

<210> SEQ ID NO 457
<211> LENGTH: 6
<212> TYPE: PRT
<213> ORGANISM: Homo sapiens

<400> SEQUENCE: 457

Gly Ala Asn Gly Leu Pro
1               5

<210> SEQ ID NO 458
<211> LENGTH: 6
<212> TYPE: PRT
<213> ORGANISM: Homo sapiens

<400> SEQUENCE: 458

Thr Ala Gly Phe Pro Gly
1               5

<210> SEQ ID NO 459
<211> LENGTH: 6
<212> TYPE: PRT
<213> ORGANISM: Homo sapiens

<400> SEQUENCE: 459

Glu Gly Gly Pro Pro Gly
1               5

<210> SEQ ID NO 460
<211> LENGTH: 6
<212> TYPE: PRT
<213> ORGANISM: Homo sapiens

<400> SEQUENCE: 460

Pro Gln Gly Leu Pro Gly
1               5

<210> SEQ ID NO 461
<211> LENGTH: 6
<212> TYPE: PRT
<213> ORGANISM: Homo sapiens

<400> SEQUENCE: 461

Ala Pro Gly Pro Leu Gly
1               5

<210> SEQ ID NO 462
<211> LENGTH: 6
<212> TYPE: PRT
<213> ORGANISM: Homo sapiens

<400> SEQUENCE: 462

Gly Ser Pro Gly Pro Gln
1               5

<210> SEQ ID NO 463
<211> LENGTH: 6
<212> TYPE: PRT
<213> ORGANISM: Homo sapiens

<400> SEQUENCE: 463

Gly Ala Ala Gly Ala Arg
1               5

<210> SEQ ID NO 464

```
<211> LENGTH: 6
<212> TYPE: PRT
<213> ORGANISM: Homo sapiens

<400> SEQUENCE: 464

Gly Val Lys Gly Glu Arg
1               5

<210> SEQ ID NO 465
<211> LENGTH: 6
<212> TYPE: PRT
<213> ORGANISM: Homo sapiens

<400> SEQUENCE: 465

Gly Asp Ala Gly Ala Pro
1               5

<210> SEQ ID NO 466
<211> LENGTH: 6
<212> TYPE: PRT
<213> ORGANISM: Homo sapiens

<400> SEQUENCE: 466

Arg Gly Phe Asp Gly Arg
1               5

<210> SEQ ID NO 467
<211> LENGTH: 6
<212> TYPE: PRT
<213> ORGANISM: Homo sapiens

<400> SEQUENCE: 467

Gly Leu Ser Gly Glu Arg
1               5

<210> SEQ ID NO 468
<211> LENGTH: 6
<212> TYPE: PRT
<213> ORGANISM: Homo sapiens

<400> SEQUENCE: 468

Gly Ser Pro Gly Pro Gln
1               5

<210> SEQ ID NO 469
<211> LENGTH: 6
<212> TYPE: PRT
<213> ORGANISM: Homo sapiens

<400> SEQUENCE: 469

Gly Val Lys Gly Glu Arg
1               5

<210> SEQ ID NO 470
<211> LENGTH: 6
<212> TYPE: PRT
<213> ORGANISM: Homo sapiens

<400> SEQUENCE: 470

Leu Ala Gly Pro Pro Gly
1               5

<210> SEQ ID NO 471
<211> LENGTH: 6
<212> TYPE: PRT
```

<213> ORGANISM: Homo sapiens

<400> SEQUENCE: 471

Thr Gly Ala Arg Gly Leu
1               5

<210> SEQ ID NO 472
<211> LENGTH: 6
<212> TYPE: PRT
<213> ORGANISM: Homo sapiens

<400> SEQUENCE: 472

Lys Gly Asp Ala Gly Gln
1               5

<210> SEQ ID NO 473
<211> LENGTH: 6
<212> TYPE: PRT
<213> ORGANISM: Homo sapiens

<400> SEQUENCE: 473

Leu Gln Gly Leu Pro Gly
1               5

<210> SEQ ID NO 474
<211> LENGTH: 6
<212> TYPE: PRT
<213> ORGANISM: Homo sapiens

<400> SEQUENCE: 474

Ile Ala Gly Ile Thr Gly
1               5

<210> SEQ ID NO 475
<211> LENGTH: 6
<212> TYPE: PRT
<213> ORGANISM: Homo sapiens

<400> SEQUENCE: 475

Ala Gly Gln Gln Gly Ala
1               5

<210> SEQ ID NO 476
<211> LENGTH: 6
<212> TYPE: PRT
<213> ORGANISM: Homo sapiens

<400> SEQUENCE: 476

Leu Ala Gly Pro Pro Gly
1               5

<210> SEQ ID NO 477
<211> LENGTH: 6
<212> TYPE: PRT
<213> ORGANISM: Homo sapiens

<400> SEQUENCE: 477

Gly Leu Ser Gly Glu Arg
1               5

<210> SEQ ID NO 478
<211> LENGTH: 6
<212> TYPE: PRT
<213> ORGANISM: Homo sapiens

```
<400> SEQUENCE: 478

Val Lys Gly Glu Arg Gly
1               5

<210> SEQ ID NO 479
<211> LENGTH: 6
<212> TYPE: PRT
<213> ORGANISM: Homo sapiens

<400> SEQUENCE: 479

Ile Lys Gly Pro Ala Gly
1               5

<210> SEQ ID NO 480
<211> LENGTH: 6
<212> TYPE: PRT
<213> ORGANISM: Homo sapiens

<400> SEQUENCE: 480

Glu Arg Gly Leu Pro Gly
1               5

<210> SEQ ID NO 481
<211> LENGTH: 6
<212> TYPE: PRT
<213> ORGANISM: Homo sapiens

<400> SEQUENCE: 481

Val Gly Gly Leu Ala Gly
1               5

<210> SEQ ID NO 482
<211> LENGTH: 6
<212> TYPE: PRT
<213> ORGANISM: Homo sapiens

<400> SEQUENCE: 482

Gly Pro Pro Gly Glu Pro
1               5

<210> SEQ ID NO 483
<211> LENGTH: 6
<212> TYPE: PRT
<213> ORGANISM: Homo sapiens

<400> SEQUENCE: 483

Ile Asn Gly Ser Pro Gly
1               5

<210> SEQ ID NO 484
<211> LENGTH: 6
<212> TYPE: PRT
<213> ORGANISM: Homo sapiens

<400> SEQUENCE: 484

Leu Met Gly Ala Arg Gly
1               5

<210> SEQ ID NO 485
<211> LENGTH: 6
<212> TYPE: PRT
<213> ORGANISM: Homo sapiens

<400> SEQUENCE: 485
```

```
Lys Asn Gly Glu Thr Gly
1               5

<210> SEQ ID NO 486
<211> LENGTH: 6
<212> TYPE: PRT
<213> ORGANISM: Homo sapiens

<400> SEQUENCE: 486

Gly Glu Arg Gly Ala Pro
1               5

<210> SEQ ID NO 487
<211> LENGTH: 6
<212> TYPE: PRT
<213> ORGANISM: Homo sapiens

<400> SEQUENCE: 487

Pro Gly Pro Pro Gly Pro
1               5

<210> SEQ ID NO 488
<211> LENGTH: 6
<212> TYPE: PRT
<213> ORGANISM: Homo sapiens

<400> SEQUENCE: 488

Gly Gln Pro Gly Asp Lys
1               5

<210> SEQ ID NO 489
<211> LENGTH: 6
<212> TYPE: PRT
<213> ORGANISM: Homo sapiens

<400> SEQUENCE: 489

Pro Gly Val Pro Gly Ala
1               5

<210> SEQ ID NO 490
<211> LENGTH: 6
<212> TYPE: PRT
<213> ORGANISM: Homo sapiens

<400> SEQUENCE: 490

Gly Ala Arg Gly Asn Asp
1               5

<210> SEQ ID NO 491
<211> LENGTH: 6
<212> TYPE: PRT
<213> ORGANISM: Homo sapiens

<400> SEQUENCE: 491

Pro Gly Ala Pro Gly Gln
1               5

<210> SEQ ID NO 492
<211> LENGTH: 6
<212> TYPE: PRT
<213> ORGANISM: Homo sapiens

<400> SEQUENCE: 492

Gly Pro Pro Gly Pro Pro
1               5
```

<210> SEQ ID NO 493
<211> LENGTH: 6
<212> TYPE: PRT
<213> ORGANISM: Homo sapiens

<400> SEQUENCE: 493

Ile Ala Gly Ile Thr Gly
1               5

<210> SEQ ID NO 494
<211> LENGTH: 6
<212> TYPE: PRT
<213> ORGANISM: Homo sapiens

<400> SEQUENCE: 494

Gly Pro Ala Gly Ile Pro
1               5

<210> SEQ ID NO 495
<211> LENGTH: 6
<212> TYPE: PRT
<213> ORGANISM: Homo sapiens

<400> SEQUENCE: 495

Gly Pro Pro Gly Pro Pro
1               5

<210> SEQ ID NO 496
<211> LENGTH: 6
<212> TYPE: PRT
<213> ORGANISM: Homo sapiens

<400> SEQUENCE: 496

Arg Pro Gly Leu Pro Gly
1               5

<210> SEQ ID NO 497
<211> LENGTH: 6
<212> TYPE: PRT
<213> ORGANISM: Homo sapiens

<400> SEQUENCE: 497

Gly Pro Pro Gly Ser Asn
1               5

<210> SEQ ID NO 498
<211> LENGTH: 6
<212> TYPE: PRT
<213> ORGANISM: Homo sapiens

<400> SEQUENCE: 498

Pro Gly Phe Pro Gly Met
1               5

<210> SEQ ID NO 499
<211> LENGTH: 6
<212> TYPE: PRT
<213> ORGANISM: Homo sapiens

<400> SEQUENCE: 499

Gly Pro Pro Gly Glu Asn
1               5

```
<210> SEQ ID NO 500
<211> LENGTH: 6
<212> TYPE: PRT
<213> ORGANISM: Homo sapiens

<400> SEQUENCE: 500

Gly Leu Pro Gly Pro Pro
1               5

<210> SEQ ID NO 501
<211> LENGTH: 6
<212> TYPE: PRT
<213> ORGANISM: Homo sapiens

<400> SEQUENCE: 501

Pro Gly Pro Pro Gly Ile
1               5

<210> SEQ ID NO 502
<211> LENGTH: 6
<212> TYPE: PRT
<213> ORGANISM: Homo sapiens

<400> SEQUENCE: 502

Pro Gly Phe Arg Gly Pro
1               5

<210> SEQ ID NO 503
<211> LENGTH: 6
<212> TYPE: PRT
<213> ORGANISM: Homo sapiens

<400> SEQUENCE: 503

Gly Ile Ala Gly Ile Thr
1               5

<210> SEQ ID NO 504
<211> LENGTH: 6
<212> TYPE: PRT
<213> ORGANISM: Homo sapiens

<400> SEQUENCE: 504

Gly Ile Pro Gly Ala Pro
1               5

<210> SEQ ID NO 505
<211> LENGTH: 6
<212> TYPE: PRT
<213> ORGANISM: Homo sapiens

<400> SEQUENCE: 505

Gly Ile Thr Gly Ala Arg
1               5

<210> SEQ ID NO 506
<211> LENGTH: 6
<212> TYPE: PRT
<213> ORGANISM: Homo sapiens

<400> SEQUENCE: 506

Gly Ala Pro Gly Glu Lys
1               5

<210> SEQ ID NO 507
<211> LENGTH: 6
```

```
<212> TYPE: PRT
<213> ORGANISM: Homo sapiens

<400> SEQUENCE: 507

Ser Pro Gly Pro Gln Gly
1               5

<210> SEQ ID NO 508
<211> LENGTH: 6
<212> TYPE: PRT
<213> ORGANISM: Homo sapiens

<400> SEQUENCE: 508

Pro Pro Gly Pro Gln Gly
1               5

<210> SEQ ID NO 509
<211> LENGTH: 6
<212> TYPE: PRT
<213> ORGANISM: Homo sapiens

<400> SEQUENCE: 509

Glu Arg Gly Pro Pro Gly
1               5

<210> SEQ ID NO 510
<211> LENGTH: 6
<212> TYPE: PRT
<213> ORGANISM: Homo sapiens

<400> SEQUENCE: 510

Ala Pro Gly Leu Arg Gly
1               5

<210> SEQ ID NO 511
<211> LENGTH: 6
<212> TYPE: PRT
<213> ORGANISM: Homo sapiens

<400> SEQUENCE: 511

Gly Pro Ala Gly Pro Pro
1               5

<210> SEQ ID NO 512
<211> LENGTH: 6
<212> TYPE: PRT
<213> ORGANISM: Homo sapiens

<400> SEQUENCE: 512

Ser Pro Gly Pro Gln Gly
1               5

<210> SEQ ID NO 513
<211> LENGTH: 6
<212> TYPE: PRT
<213> ORGANISM: Homo sapiens

<400> SEQUENCE: 513

Leu Ala Gly Pro Pro Gly
1               5

<210> SEQ ID NO 514
<211> LENGTH: 6
<212> TYPE: PRT
<213> ORGANISM: Homo sapiens
```

<400> SEQUENCE: 514

Phe Pro Gly Pro Lys Gly
1               5

<210> SEQ ID NO 515
<211> LENGTH: 6
<212> TYPE: PRT
<213> ORGANISM: Homo sapiens

<400> SEQUENCE: 515

Pro Pro Gly Pro Ala Gly
1               5

<210> SEQ ID NO 516
<211> LENGTH: 6
<212> TYPE: PRT
<213> ORGANISM: Homo sapiens

<400> SEQUENCE: 516

Leu Pro Gly Ala Ala Gly
1               5

<210> SEQ ID NO 517
<211> LENGTH: 6
<212> TYPE: PRT
<213> ORGANISM: Homo sapiens

<400> SEQUENCE: 517

Ile Pro Gly Gln Pro Gly
1               5

<210> SEQ ID NO 518
<211> LENGTH: 6
<212> TYPE: PRT
<213> ORGANISM: Homo sapiens

<400> SEQUENCE: 518

Gly Ala Pro Gly Pro Ala
1               5

<210> SEQ ID NO 519
<211> LENGTH: 6
<212> TYPE: PRT
<213> ORGANISM: Homo sapiens

<400> SEQUENCE: 519

Gly His Arg Gly Phe Asp
1               5

<210> SEQ ID NO 520
<211> LENGTH: 6
<212> TYPE: PRT
<213> ORGANISM: Homo sapiens

<400> SEQUENCE: 520

Pro Gly Pro Lys Gly Asp
1               5

<210> SEQ ID NO 521
<211> LENGTH: 6
<212> TYPE: PRT
<213> ORGANISM: Homo sapiens

<400> SEQUENCE: 521

```
Gly Pro Pro Gly Pro Ser
1               5

<210> SEQ ID NO 522
<211> LENGTH: 6
<212> TYPE: PRT
<213> ORGANISM: Homo sapiens

<400> SEQUENCE: 522

Pro Pro Gly Ala Pro Gly
1               5

<210> SEQ ID NO 523
<211> LENGTH: 6
<212> TYPE: PRT
<213> ORGANISM: Homo sapiens

<400> SEQUENCE: 523

Gly Glu Val Gly Pro Ala
1               5

<210> SEQ ID NO 524
<211> LENGTH: 6
<212> TYPE: PRT
<213> ORGANISM: Homo sapiens

<400> SEQUENCE: 524

Gly Ala Pro Gly Leu Arg
1               5

<210> SEQ ID NO 525
<211> LENGTH: 6
<212> TYPE: PRT
<213> ORGANISM: Homo sapiens

<400> SEQUENCE: 525

Gly Pro Gln Gly Val Lys
1               5

<210> SEQ ID NO 526
<211> LENGTH: 6
<212> TYPE: PRT
<213> ORGANISM: Homo sapiens

<400> SEQUENCE: 526

Gly Met Pro Gly Pro Arg
1               5

<210> SEQ ID NO 527
<211> LENGTH: 6
<212> TYPE: PRT
<213> ORGANISM: Homo sapiens

<400> SEQUENCE: 527

Gly Ala Ala Gly Ile Lys
1               5

<210> SEQ ID NO 528
<211> LENGTH: 6
<212> TYPE: PRT
<213> ORGANISM: Homo sapiens

<400> SEQUENCE: 528

Pro Gly Ala Ala Gly Phe
```

```
1               5

<210> SEQ ID NO 529
<211> LENGTH: 6
<212> TYPE: PRT
<213> ORGANISM: Homo sapiens

<400> SEQUENCE: 529

Gly Pro Ala Gly Glu Arg
1               5

<210> SEQ ID NO 530
<211> LENGTH: 6
<212> TYPE: PRT
<213> ORGANISM: Homo sapiens

<400> SEQUENCE: 530

Gly Ile Ala Gly Pro Arg
1               5

<210> SEQ ID NO 531
<211> LENGTH: 6
<212> TYPE: PRT
<213> ORGANISM: Homo sapiens

<400> SEQUENCE: 531

Thr Gly Ala Arg Gly Leu
1               5

<210> SEQ ID NO 532
<211> LENGTH: 6
<212> TYPE: PRT
<213> ORGANISM: Homo sapiens

<400> SEQUENCE: 532

Val Lys Gly Glu Ser Gly
1               5

<210> SEQ ID NO 533
<211> LENGTH: 6
<212> TYPE: PRT
<213> ORGANISM: Homo sapiens

<400> SEQUENCE: 533

Thr Gly Glu Arg Gly Ala
1               5

<210> SEQ ID NO 534
<211> LENGTH: 6
<212> TYPE: PRT
<213> ORGANISM: Homo sapiens

<400> SEQUENCE: 534

Glu Arg Gly Leu Pro Gly
1               5

<210> SEQ ID NO 535
<211> LENGTH: 6
<212> TYPE: PRT
<213> ORGANISM: Homo sapiens

<400> SEQUENCE: 535

Ile Thr Gly Ala Arg Gly
1               5
```

<210> SEQ ID NO 536
<211> LENGTH: 6
<212> TYPE: PRT
<213> ORGANISM: Homo sapiens

<400> SEQUENCE: 536

Glu Arg Gly Leu Pro Gly
1               5

<210> SEQ ID NO 537
<211> LENGTH: 6
<212> TYPE: PRT
<213> ORGANISM: Homo sapiens

<400> SEQUENCE: 537

Pro Gly Ala Pro Gly Gly
1               5

<210> SEQ ID NO 538
<211> LENGTH: 6
<212> TYPE: PRT
<213> ORGANISM: Homo sapiens

<400> SEQUENCE: 538

Gly Pro Pro Gly Val Ala
1               5

<210> SEQ ID NO 539
<211> LENGTH: 6
<212> TYPE: PRT
<213> ORGANISM: Homo sapiens

<400> SEQUENCE: 539

Gly Leu Ala Gly Pro Pro
1               5

<210> SEQ ID NO 540
<211> LENGTH: 6
<212> TYPE: PRT
<213> ORGANISM: Homo sapiens

<400> SEQUENCE: 540

Val Gly Gly Leu Ala Gly
1               5

<210> SEQ ID NO 541
<211> LENGTH: 6
<212> TYPE: PRT
<213> ORGANISM: Homo sapiens

<400> SEQUENCE: 541

Ser Pro Gly Ala Gln Gly
1               5

<210> SEQ ID NO 542
<211> LENGTH: 6
<212> TYPE: PRT
<213> ORGANISM: Homo sapiens

<400> SEQUENCE: 542

Gln Pro Gly Val Met Gly
1               5

<210> SEQ ID NO 543

```
<211> LENGTH: 6
<212> TYPE: PRT
<213> ORGANISM: Homo sapiens

<400> SEQUENCE: 543

Ile Pro Gly Ala Pro Gly
1               5

<210> SEQ ID NO 544
<211> LENGTH: 6
<212> TYPE: PRT
<213> ORGANISM: Homo sapiens

<400> SEQUENCE: 544

Val Lys Gly Glu Arg Gly
1               5

<210> SEQ ID NO 545
<211> LENGTH: 6
<212> TYPE: PRT
<213> ORGANISM: Homo sapiens

<400> SEQUENCE: 545

Gly Pro Pro Gly Ile Asn
1               5

<210> SEQ ID NO 546
<211> LENGTH: 6
<212> TYPE: PRT
<213> ORGANISM: Homo sapiens

<400> SEQUENCE: 546

Gly Ile Asn Gly Ser Pro
1               5

<210> SEQ ID NO 547
<211> LENGTH: 6
<212> TYPE: PRT
<213> ORGANISM: Homo sapiens

<400> SEQUENCE: 547

Leu Arg Gly Gly Ala Gly
1               5

<210> SEQ ID NO 548
<211> LENGTH: 6
<212> TYPE: PRT
<213> ORGANISM: Homo sapiens

<400> SEQUENCE: 548

Tyr Gln Gly Pro Pro Gly
1               5

<210> SEQ ID NO 549
<211> LENGTH: 6
<212> TYPE: PRT
<213> ORGANISM: Homo sapiens

<400> SEQUENCE: 549

Gly Ile Pro Gly Phe Pro
1               5

<210> SEQ ID NO 550
<211> LENGTH: 6
<212> TYPE: PRT
```

<213> ORGANISM: Homo sapiens

<400> SEQUENCE: 550

Phe Pro Gly Met Lys Gly
1               5

<210> SEQ ID NO 551
<211> LENGTH: 6
<212> TYPE: PRT
<213> ORGANISM: Homo sapiens

<400> SEQUENCE: 551

Gly Pro Pro Gly Glu Asn
1               5

<210> SEQ ID NO 552
<211> LENGTH: 6
<212> TYPE: PRT
<213> ORGANISM: Homo sapiens

<400> SEQUENCE: 552

Ala Ala Gly Phe Pro Gly
1               5

<210> SEQ ID NO 553
<211> LENGTH: 6
<212> TYPE: PRT
<213> ORGANISM: Homo sapiens

<400> SEQUENCE: 553

Pro Gly Val Ser Gly Pro
1               5

<210> SEQ ID NO 554
<211> LENGTH: 6
<212> TYPE: PRT
<213> ORGANISM: Homo sapiens

<400> SEQUENCE: 554

Gly Phe Pro Gly Ala Pro
1               5

<210> SEQ ID NO 555
<211> LENGTH: 6
<212> TYPE: PRT
<213> ORGANISM: Homo sapiens

<400> SEQUENCE: 555

Gly Leu Ser Gly Glu Arg
1               5

<210> SEQ ID NO 556
<211> LENGTH: 6
<212> TYPE: PRT
<213> ORGANISM: Homo sapiens

<400> SEQUENCE: 556

Gly Gly Ala Gly Pro Pro
1               5

<210> SEQ ID NO 557
<211> LENGTH: 6
<212> TYPE: PRT
<213> ORGANISM: Homo sapiens

```
<400> SEQUENCE: 557

Val Gly Gly Leu Ala Gly
1               5

<210> SEQ ID NO 558
<211> LENGTH: 6
<212> TYPE: PRT
<213> ORGANISM: Homo sapiens

<400> SEQUENCE: 558

Gly Leu Ala Gly Pro Pro
1               5

<210> SEQ ID NO 559
<211> LENGTH: 6
<212> TYPE: PRT
<213> ORGANISM: Homo sapiens

<400> SEQUENCE: 559

Pro Gly Pro Pro Gly Ile
1               5

<210> SEQ ID NO 560
<211> LENGTH: 6
<212> TYPE: PRT
<213> ORGANISM: Homo sapiens

<400> SEQUENCE: 560

Gly Ala Pro Gly Pro Met
1               5

<210> SEQ ID NO 561
<211> LENGTH: 6
<212> TYPE: PRT
<213> ORGANISM: Homo sapiens

<400> SEQUENCE: 561

Gly Ala Arg Gly Leu Ala
1               5

<210> SEQ ID NO 562
<211> LENGTH: 6
<212> TYPE: PRT
<213> ORGANISM: Homo sapiens

<400> SEQUENCE: 562

Gly Leu Ala Gly Pro Pro
1               5

<210> SEQ ID NO 563
<211> LENGTH: 6
<212> TYPE: PRT
<213> ORGANISM: Homo sapiens

<400> SEQUENCE: 563

Pro Gly Phe Arg Gly Pro
1               5

<210> SEQ ID NO 564
<211> LENGTH: 6
<212> TYPE: PRT
<213> ORGANISM: Homo sapiens

<400> SEQUENCE: 564
```

Gly Pro Val Gly Pro Ser
1               5

<210> SEQ ID NO 565
<211> LENGTH: 6
<212> TYPE: PRT
<213> ORGANISM: Homo sapiens

<400> SEQUENCE: 565

Ala Gly Gln Pro Gly Glu
1               5

<210> SEQ ID NO 566
<211> LENGTH: 6
<212> TYPE: PRT
<213> ORGANISM: Homo sapiens

<400> SEQUENCE: 566

Gly Ala Pro Gly Phe Arg
1               5

<210> SEQ ID NO 567
<211> LENGTH: 6
<212> TYPE: PRT
<213> ORGANISM: Homo sapiens

<400> SEQUENCE: 567

Pro Gly Phe Pro Gly Met
1               5

<210> SEQ ID NO 568
<211> LENGTH: 6
<212> TYPE: PRT
<213> ORGANISM: Homo sapiens

<400> SEQUENCE: 568

Gly Leu Ala Gly Pro Pro
1               5

<210> SEQ ID NO 569
<211> LENGTH: 6
<212> TYPE: PRT
<213> ORGANISM: Homo sapiens

<400> SEQUENCE: 569

Ser Gly Asp Arg Gly Glu
1               5

<210> SEQ ID NO 570
<211> LENGTH: 6
<212> TYPE: PRT
<213> ORGANISM: Homo sapiens

<400> SEQUENCE: 570

Ala Gly Ile Pro Gly Phe
1               5

<210> SEQ ID NO 571
<211> LENGTH: 6
<212> TYPE: PRT
<213> ORGANISM: Homo sapiens

<400> SEQUENCE: 571

Glu Arg Gly Ala Ala Gly
1               5

```
<210> SEQ ID NO 572
<211> LENGTH: 6
<212> TYPE: PRT
<213> ORGANISM: Homo sapiens

<400> SEQUENCE: 572

Pro Gly Pro Pro Gly Thr
1               5

<210> SEQ ID NO 573
<211> LENGTH: 6
<212> TYPE: PRT
<213> ORGANISM: Homo sapiens

<400> SEQUENCE: 573

His Pro Gly Ser Pro Gly
1               5

<210> SEQ ID NO 574
<211> LENGTH: 6
<212> TYPE: PRT
<213> ORGANISM: Homo sapiens

<400> SEQUENCE: 574

Ser Pro Gly Pro Gln Gly
1               5

<210> SEQ ID NO 575
<211> LENGTH: 6
<212> TYPE: PRT
<213> ORGANISM: Homo sapiens

<400> SEQUENCE: 575

Gly Leu Ala Gly Thr Ala
1               5

<210> SEQ ID NO 576
<211> LENGTH: 6
<212> TYPE: PRT
<213> ORGANISM: Homo sapiens

<400> SEQUENCE: 576

Gly Pro Pro Gly Pro Gln
1               5

<210> SEQ ID NO 577
<211> LENGTH: 6
<212> TYPE: PRT
<213> ORGANISM: Homo sapiens

<400> SEQUENCE: 577

Gly Phe Pro Gly Met Lys
1               5

<210> SEQ ID NO 578
<211> LENGTH: 6
<212> TYPE: PRT
<213> ORGANISM: Homo sapiens

<400> SEQUENCE: 578

Glu Lys Gly Pro Ala Gly
1               5
```

```
<210> SEQ ID NO 579
<211> LENGTH: 6
<212> TYPE: PRT
<213> ORGANISM: Homo sapiens

<400> SEQUENCE: 579

Pro Gly Pro Gln Gly Leu
1               5

<210> SEQ ID NO 580
<211> LENGTH: 6
<212> TYPE: PRT
<213> ORGANISM: Homo sapiens

<400> SEQUENCE: 580

Phe Pro Gly Ala Pro Gly
1               5

<210> SEQ ID NO 581
<211> LENGTH: 6
<212> TYPE: PRT
<213> ORGANISM: Homo sapiens

<400> SEQUENCE: 581

Ala Pro Gly Pro Leu Gly
1               5

<210> SEQ ID NO 582
<211> LENGTH: 6
<212> TYPE: PRT
<213> ORGANISM: Homo sapiens

<400> SEQUENCE: 582

Gly Phe Pro Gly Met Lys
1               5

<210> SEQ ID NO 583
<211> LENGTH: 6
<212> TYPE: PRT
<213> ORGANISM: Homo sapiens

<400> SEQUENCE: 583

Pro Gly Leu Pro Gly Ile
1               5

<210> SEQ ID NO 584
<211> LENGTH: 6
<212> TYPE: PRT
<213> ORGANISM: Homo sapiens

<400> SEQUENCE: 584

Gly His Arg Gly Phe Asp
1               5

<210> SEQ ID NO 585
<211> LENGTH: 6
<212> TYPE: PRT
<213> ORGANISM: Homo sapiens

<400> SEQUENCE: 585

Pro Gly Pro Lys Gly Asn
1               5

<210> SEQ ID NO 586
<211> LENGTH: 6
```

```
<212> TYPE: PRT
<213> ORGANISM: Homo sapiens

<400> SEQUENCE: 586

Gly Glu Val Gly Pro Ala
1               5

<210> SEQ ID NO 587
<211> LENGTH: 6
<212> TYPE: PRT
<213> ORGANISM: Homo sapiens

<400> SEQUENCE: 587

Gly Pro Pro Gly Pro Ser
1               5

<210> SEQ ID NO 588
<211> LENGTH: 6
<212> TYPE: PRT
<213> ORGANISM: Homo sapiens

<400> SEQUENCE: 588

Gly Leu Pro Gly Leu Ala
1               5

<210> SEQ ID NO 589
<211> LENGTH: 6
<212> TYPE: PRT
<213> ORGANISM: Homo sapiens

<400> SEQUENCE: 589

Gly Ser Pro Gly Tyr Gln
1               5

<210> SEQ ID NO 590
<211> LENGTH: 6
<212> TYPE: PRT
<213> ORGANISM: Homo sapiens

<400> SEQUENCE: 590

Glu Met Gly Pro Ala Gly
1               5

<210> SEQ ID NO 591
<211> LENGTH: 6
<212> TYPE: PRT
<213> ORGANISM: Homo sapiens

<400> SEQUENCE: 591

Gly Lys Pro Gly Ala Asn
1               5

<210> SEQ ID NO 592
<211> LENGTH: 6
<212> TYPE: PRT
<213> ORGANISM: Homo sapiens

<400> SEQUENCE: 592

Gly Met Pro Gly Pro Arg
1               5

<210> SEQ ID NO 593
<211> LENGTH: 6
<212> TYPE: PRT
<213> ORGANISM: Homo sapiens
```

<400> SEQUENCE: 593

Gly Ile Thr Gly Ala Arg
1               5

<210> SEQ ID NO 594
<211> LENGTH: 6
<212> TYPE: PRT
<213> ORGANISM: Homo sapiens

<400> SEQUENCE: 594

Ala Gly Pro Arg Gly Ala
1               5

<210> SEQ ID NO 595
<211> LENGTH: 6
<212> TYPE: PRT
<213> ORGANISM: Homo sapiens

<400> SEQUENCE: 595

Gly Pro Ala Gly Ala Asn
1               5

<210> SEQ ID NO 596
<211> LENGTH: 6
<212> TYPE: PRT
<213> ORGANISM: Homo sapiens

<400> SEQUENCE: 596

Gly Lys Pro Gly Ala Asn
1               5

<210> SEQ ID NO 597
<211> LENGTH: 6
<212> TYPE: PRT
<213> ORGANISM: Homo sapiens

<400> SEQUENCE: 597

Gly Phe Pro Gly Ala Arg
1               5

<210> SEQ ID NO 598
<211> LENGTH: 6
<212> TYPE: PRT
<213> ORGANISM: Homo sapiens

<400> SEQUENCE: 598

Ile Ala Gly Ile Thr Gly
1               5

<210> SEQ ID NO 599
<211> LENGTH: 6
<212> TYPE: PRT
<213> ORGANISM: Homo sapiens

<400> SEQUENCE: 599

Ile Thr Gly Ala Arg Gly
1               5

<210> SEQ ID NO 600
<211> LENGTH: 6
<212> TYPE: PRT
<213> ORGANISM: Homo sapiens

<400> SEQUENCE: 600

Leu Arg Gly Gly Ala Gly
1               5

<210> SEQ ID NO 601
<211> LENGTH: 6
<212> TYPE: PRT
<213> ORGANISM: Homo sapiens

<400> SEQUENCE: 601

Val Gly Gly Leu Ala Gly
1               5

<210> SEQ ID NO 602
<211> LENGTH: 6
<212> TYPE: PRT
<213> ORGANISM: Homo sapiens

<400> SEQUENCE: 602

Ala Gly Pro Pro Gly Met
1               5

<210> SEQ ID NO 603
<211> LENGTH: 6
<212> TYPE: PRT
<213> ORGANISM: Homo sapiens

<400> SEQUENCE: 603

Pro Gln Gly Pro Pro Gly
1               5

<210> SEQ ID NO 604
<211> LENGTH: 6
<212> TYPE: PRT
<213> ORGANISM: Homo sapiens

<400> SEQUENCE: 604

Ser Pro Gly Gly Lys Gly
1               5

<210> SEQ ID NO 605
<211> LENGTH: 6
<212> TYPE: PRT
<213> ORGANISM: Homo sapiens

<400> SEQUENCE: 605

Gly Ala Pro Gly Glu Lys
1               5

<210> SEQ ID NO 606
<211> LENGTH: 6
<212> TYPE: PRT
<213> ORGANISM: Homo sapiens

<400> SEQUENCE: 606

Ile Lys Gly Pro Ala Gly
1               5

<210> SEQ ID NO 607
<211> LENGTH: 6
<212> TYPE: PRT
<213> ORGANISM: Homo sapiens

<400> SEQUENCE: 607

Phe Arg Gly Pro Ala Gly

```
<210> SEQ ID NO 608
<211> LENGTH: 6
<212> TYPE: PRT
<213> ORGANISM: Homo sapiens

<400> SEQUENCE: 608

Asp Ala Gly Ala Pro Gly
1               5

<210> SEQ ID NO 609
<211> LENGTH: 6
<212> TYPE: PRT
<213> ORGANISM: Homo sapiens

<400> SEQUENCE: 609

Gly Leu Pro Gly Pro Pro
1               5

<210> SEQ ID NO 610
<211> LENGTH: 6
<212> TYPE: PRT
<213> ORGANISM: Homo sapiens

<400> SEQUENCE: 610

Pro Gly Glu Asn Gly Lys
1               5

<210> SEQ ID NO 611
<211> LENGTH: 6
<212> TYPE: PRT
<213> ORGANISM: Homo sapiens

<400> SEQUENCE: 611

Gln Gln Gly Ala Ile Gly
1               5

<210> SEQ ID NO 612
<211> LENGTH: 6
<212> TYPE: PRT
<213> ORGANISM: Homo sapiens

<400> SEQUENCE: 612

Val Ala Gly Pro Pro Gly
1               5

<210> SEQ ID NO 613
<211> LENGTH: 6
<212> TYPE: PRT
<213> ORGANISM: Homo sapiens

<400> SEQUENCE: 613

Pro Gly Met Lys Gly His
1               5

<210> SEQ ID NO 614
<211> LENGTH: 6
<212> TYPE: PRT
<213> ORGANISM: Homo sapiens

<400> SEQUENCE: 614

Pro Gly Asp Lys Gly Glu
1               5
```

<210> SEQ ID NO 615
<211> LENGTH: 6
<212> TYPE: PRT
<213> ORGANISM: Homo sapiens

<400> SEQUENCE: 615

Gly Ser Asp Gly Gln Pro
1               5

<210> SEQ ID NO 616
<211> LENGTH: 6
<212> TYPE: PRT
<213> ORGANISM: Homo sapiens

<400> SEQUENCE: 616

Gly Ala Arg Gly Asn Asp
1               5

<210> SEQ ID NO 617
<211> LENGTH: 6
<212> TYPE: PRT
<213> ORGANISM: Homo sapiens

<400> SEQUENCE: 617

Gly Ala Arg Gly Pro Pro
1               5

<210> SEQ ID NO 618
<211> LENGTH: 6
<212> TYPE: PRT
<213> ORGANISM: Homo sapiens

<400> SEQUENCE: 618

Gly Pro Lys Gly Asp Ala
1               5

<210> SEQ ID NO 619
<211> LENGTH: 6
<212> TYPE: PRT
<213> ORGANISM: Homo sapiens

<400> SEQUENCE: 619

Pro Gly Pro Gln Gly His
1               5

<210> SEQ ID NO 620
<211> LENGTH: 6
<212> TYPE: PRT
<213> ORGANISM: Homo sapiens

<400> SEQUENCE: 620

Gly Ile Thr Gly Ala Arg
1               5

<210> SEQ ID NO 621
<211> LENGTH: 6
<212> TYPE: PRT
<213> ORGANISM: Homo sapiens

<400> SEQUENCE: 621

Gly Ser Arg Gly Ala Pro
1               5

<210> SEQ ID NO 622

```
<211> LENGTH: 6
<212> TYPE: PRT
<213> ORGANISM: Homo sapiens

<400> SEQUENCE: 622

Gly Ala Pro Gly Glu Lys
1               5

<210> SEQ ID NO 623
<211> LENGTH: 6
<212> TYPE: PRT
<213> ORGANISM: Homo sapiens

<400> SEQUENCE: 623

Pro Gln Gly Leu Gln Gly
1               5

<210> SEQ ID NO 624
<211> LENGTH: 6
<212> TYPE: PRT
<213> ORGANISM: Homo sapiens

<400> SEQUENCE: 624

Lys Gly Ser Pro Gly Ala
1               5

<210> SEQ ID NO 625
<211> LENGTH: 6
<212> TYPE: PRT
<213> ORGANISM: Homo sapiens

<400> SEQUENCE: 625

Pro Gly Pro Gln Gly Pro
1               5

<210> SEQ ID NO 626
<211> LENGTH: 6
<212> TYPE: PRT
<213> ORGANISM: Homo sapiens

<400> SEQUENCE: 626

Gly Pro Thr Gly Pro Ile
1               5

<210> SEQ ID NO 627
<211> LENGTH: 6
<212> TYPE: PRT
<213> ORGANISM: Homo sapiens

<400> SEQUENCE: 627

Gly Ser Pro Gly Glu Arg
1               5

<210> SEQ ID NO 628
<211> LENGTH: 6
<212> TYPE: PRT
<213> ORGANISM: Homo sapiens

<400> SEQUENCE: 628

Gly Ser Pro Gly Ala Gln
1               5

<210> SEQ ID NO 629
<211> LENGTH: 6
<212> TYPE: PRT
```

```
<213> ORGANISM: Homo sapiens

<400> SEQUENCE: 629

Gly Leu Ala Gly Pro Pro
1               5

<210> SEQ ID NO 630
<211> LENGTH: 6
<212> TYPE: PRT
<213> ORGANISM: Homo sapiens

<400> SEQUENCE: 630

Gly Ala Pro Gly Glu Lys
1               5

<210> SEQ ID NO 631
<211> LENGTH: 6
<212> TYPE: PRT
<213> ORGANISM: Homo sapiens

<400> SEQUENCE: 631

Gly Met Pro Gly Pro Arg
1               5

<210> SEQ ID NO 632
<211> LENGTH: 6
<212> TYPE: PRT
<213> ORGANISM: Homo sapiens

<400> SEQUENCE: 632

Pro Gly Pro Leu Gly Ile
1               5

<210> SEQ ID NO 633
<211> LENGTH: 6
<212> TYPE: PRT
<213> ORGANISM: Homo sapiens

<400> SEQUENCE: 633

Gly Asn Arg Gly Glu Arg
1               5

<210> SEQ ID NO 634
<211> LENGTH: 6
<212> TYPE: PRT
<213> ORGANISM: Homo sapiens

<400> SEQUENCE: 634

Pro Ser Gly Pro Pro Gly
1               5

<210> SEQ ID NO 635
<211> LENGTH: 6
<212> TYPE: PRT
<213> ORGANISM: Homo sapiens

<400> SEQUENCE: 635

Gly Leu Pro Gly Leu Ala
1               5

<210> SEQ ID NO 636
<211> LENGTH: 6
<212> TYPE: PRT
<213> ORGANISM: Homo sapiens
```

```
<400> SEQUENCE: 636

Pro Gly Pro Pro Gly Thr
1               5

<210> SEQ ID NO 637
<211> LENGTH: 6
<212> TYPE: PRT
<213> ORGANISM: Homo sapiens

<400> SEQUENCE: 637

Gly Pro Pro Gly Pro Gln
1               5

<210> SEQ ID NO 638
<211> LENGTH: 6
<212> TYPE: PRT
<213> ORGANISM: Homo sapiens

<400> SEQUENCE: 638

Phe Pro Gly Met Lys Gly
1               5

<210> SEQ ID NO 639
<211> LENGTH: 6
<212> TYPE: PRT
<213> ORGANISM: Homo sapiens

<400> SEQUENCE: 639

Gly Pro Pro Gly Ile Cys
1               5

<210> SEQ ID NO 640
<211> LENGTH: 6
<212> TYPE: PRT
<213> ORGANISM: Homo sapiens

<400> SEQUENCE: 640

Gly Pro Pro Gly Ile Cys
1               5

<210> SEQ ID NO 641
<211> LENGTH: 6
<212> TYPE: PRT
<213> ORGANISM: Homo sapiens

<400> SEQUENCE: 641

Gly Ala Pro Gly Leu Met
1               5

<210> SEQ ID NO 642
<211> LENGTH: 6
<212> TYPE: PRT
<213> ORGANISM: Homo sapiens

<400> SEQUENCE: 642

Glu Pro Gly Pro Arg Gly
1               5

<210> SEQ ID NO 643
<211> LENGTH: 6
<212> TYPE: PRT
<213> ORGANISM: Homo sapiens

<400> SEQUENCE: 643
```

Gly His Arg Gly Phe Asp
1               5

<210> SEQ ID NO 644
<211> LENGTH: 6
<212> TYPE: PRT
<213> ORGANISM: Homo sapiens

<400> SEQUENCE: 644

Gly Ala Ala Gly Ile Lys
1               5

<210> SEQ ID NO 645
<211> LENGTH: 6
<212> TYPE: PRT
<213> ORGANISM: Homo sapiens

<400> SEQUENCE: 645

Gly Glu Pro Gly Pro Arg
1               5

<210> SEQ ID NO 646
<211> LENGTH: 6
<212> TYPE: PRT
<213> ORGANISM: Homo sapiens

<400> SEQUENCE: 646

Gly Ile Pro Gly Ala Pro
1               5

<210> SEQ ID NO 647
<211> LENGTH: 6
<212> TYPE: PRT
<213> ORGANISM: Homo sapiens

<400> SEQUENCE: 647

Gly Ala Pro Gly Leu Met
1               5

<210> SEQ ID NO 648
<211> LENGTH: 6
<212> TYPE: PRT
<213> ORGANISM: Homo sapiens

<400> SEQUENCE: 648

Thr Gly Ala Arg Gly Leu
1               5

<210> SEQ ID NO 649
<211> LENGTH: 6
<212> TYPE: PRT
<213> ORGANISM: Homo sapiens

<400> SEQUENCE: 649

Met Pro Gly Pro Arg Gly
1               5

<210> SEQ ID NO 650
<211> LENGTH: 6
<212> TYPE: PRT
<213> ORGANISM: Homo sapiens

<400> SEQUENCE: 650

Gly Met Lys Gly His Arg
1               5

<210> SEQ ID NO 651
<211> LENGTH: 6
<212> TYPE: PRT
<213> ORGANISM: Homo sapiens

<400> SEQUENCE: 651

Gly Pro Gln Gly Val Lys
1               5

<210> SEQ ID NO 652
<211> LENGTH: 6
<212> TYPE: PRT
<213> ORGANISM: Homo sapiens

<400> SEQUENCE: 652

Pro Gly Ala Asn Gly Leu
1               5

<210> SEQ ID NO 653
<211> LENGTH: 6
<212> TYPE: PRT
<213> ORGANISM: Homo sapiens

<400> SEQUENCE: 653

Gly Thr Gly Gly Pro Pro
1               5

<210> SEQ ID NO 654
<211> LENGTH: 6
<212> TYPE: PRT
<213> ORGANISM: Homo sapiens

<400> SEQUENCE: 654

Gly Pro Pro Gly Pro Arg
1               5

<210> SEQ ID NO 655
<211> LENGTH: 6
<212> TYPE: PRT
<213> ORGANISM: Homo sapiens

<400> SEQUENCE: 655

Gly Gly Lys Gly Glu Arg
1               5

<210> SEQ ID NO 656
<211> LENGTH: 6
<212> TYPE: PRT
<213> ORGANISM: Homo sapiens

<400> SEQUENCE: 656

Pro Gln Gly Val Lys Gly
1               5

<210> SEQ ID NO 657
<211> LENGTH: 6
<212> TYPE: PRT
<213> ORGANISM: Homo sapiens

<400> SEQUENCE: 657

Pro Gly Ala Asn Gly Leu
1               5

```
<210> SEQ ID NO 658
<211> LENGTH: 161
<212> TYPE: PRT
<213> ORGANISM: Homo sapiens

<400> SEQUENCE: 658

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
                20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
    50                  55                  60

Arg Gly Thr Val Phe Ser Arg Met Pro Pro Arg Asp Lys Thr Met Arg
65                  70                  75                  80

Phe Phe Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
                100                 105                 110

His Ile Cys Thr Ser Trp Glu Ser Ala Ser Gly Ile Val Glu Phe Trp
            115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Gln Asp Ser Phe
145                 150                 155                 160

Gly

<210> SEQ ID NO 659
<211> LENGTH: 317
<212> TYPE: PRT
<213> ORGANISM: Homo sapiens

<400> SEQUENCE: 659

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175
```

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 660
<211> LENGTH: 17
<212> TYPE: PRT
<213> ORGANISM: Homo sapiens

<400> SEQUENCE: 660

Ala Lys Val Glu Gln Ala Val Glu Thr Glu Pro Glu Pro Glu Leu Arg
1               5                   10                  15

Gln

<210> SEQ ID NO 661
<211> LENGTH: 17
<212> TYPE: PRT
<213> ORGANISM: Homo sapiens

<400> SEQUENCE: 661

Ala Lys Val Glu Gln Ala Val Glu Thr Glu Pro Glu Pro Glu Leu Arg
1               5                   10                  15

Gln

<210> SEQ ID NO 662
<211> LENGTH: 16
<212> TYPE: PRT
<213> ORGANISM: Homo sapiens

<400> SEQUENCE: 662

Val Ala Glu Val Arg Ala Lys Leu Glu Glu Gln Ala Gln Gln Ile Arg
1               5                   10                  15

<210> SEQ ID NO 663
<211> LENGTH: 17
<212> TYPE: PRT
<213> ORGANISM: Homo sapiens

<400> SEQUENCE: 663

Ala Lys Val Glu Gln Ala Val Glu Thr Glu Pro Glu Pro Glu Leu Arg
1               5                   10                  15

Gln

```
<210> SEQ ID NO 664
<211> LENGTH: 13
<212> TYPE: PRT
<213> ORGANISM: Homo sapiens

<400> SEQUENCE: 664

Ala Met Leu Gly Gln Ser Thr Glu Glu Leu Arg Val Arg
1               5                   10

<210> SEQ ID NO 665
<211> LENGTH: 14
<212> TYPE: PRT
<213> ORGANISM: Homo sapiens

<400> SEQUENCE: 665

Glu Gln Ala Val Glu Thr Glu Pro Glu Pro Glu Leu Arg Gln
1               5                   10

<210> SEQ ID NO 666
<211> LENGTH: 14
<212> TYPE: PRT
<213> ORGANISM: Homo sapiens

<400> SEQUENCE: 666

Arg Gln Gln Thr Glu Trp Gln Ser Gly Gln Arg Trp Glu Leu
1               5                   10

<210> SEQ ID NO 667
<211> LENGTH: 18
<212> TYPE: PRT
<213> ORGANISM: Homo sapiens

<400> SEQUENCE: 667

Leu Ala Val Tyr Gln Ala Gly Ala Arg Glu Gly Ala Glu Arg Gly Leu
1               5                   10                  15

Ser Ala

<210> SEQ ID NO 668
<211> LENGTH: 13
<212> TYPE: PRT
<213> ORGANISM: Homo sapiens

<400> SEQUENCE: 668

Arg Ala Lys Leu Glu Glu Gln Ala Gln Gln Ile Arg Leu
1               5                   10

<210> SEQ ID NO 669
<211> LENGTH: 14
<212> TYPE: PRT
<213> ORGANISM: Homo sapiens

<400> SEQUENCE: 669

Ala Lys Leu Glu Glu Gln Ala Gln Gln Ile Arg Leu Gln Ala
1               5                   10

<210> SEQ ID NO 670
<211> LENGTH: 17
<212> TYPE: PRT
<213> ORGANISM: Homo sapiens

<400> SEQUENCE: 670

Ala Lys Val Glu Gln Ala Val Glu Thr Glu Pro Glu Pro Glu Leu Arg
1               5                   10                  15

Gln
```

<210> SEQ ID NO 671
<211> LENGTH: 16
<212> TYPE: PRT
<213> ORGANISM: Homo sapiens

<400> SEQUENCE: 671

Lys Val Glu Gln Ala Val Glu Thr Glu Pro Glu Pro Glu Leu Arg Gln
1               5                   10                  15

<210> SEQ ID NO 672
<211> LENGTH: 14
<212> TYPE: PRT
<213> ORGANISM: Homo sapiens

<400> SEQUENCE: 672

Glu Gln Ala Val Glu Thr Glu Pro Glu Pro Glu Leu Arg Gln
1               5                   10

<210> SEQ ID NO 673
<211> LENGTH: 16
<212> TYPE: PRT
<213> ORGANISM: Homo sapiens

<400> SEQUENCE: 673

Asp Glu Val Lys Glu Gln Val Ala Glu Val Arg Ala Lys Leu Glu Glu
1               5                   10                  15

<210> SEQ ID NO 674
<211> LENGTH: 16
<212> TYPE: PRT
<213> ORGANISM: Homo sapiens

<400> SEQUENCE: 674

Lys Glu Ser Asp Thr Ser Tyr Val Ser Leu Lys Ala Pro Leu Thr Lys
1               5                   10                  15

<210> SEQ ID NO 675
<211> LENGTH: 16
<212> TYPE: PRT
<213> ORGANISM: Homo sapiens

<400> SEQUENCE: 675

Gly Gly Asn Phe Glu Gly Ser Gln Ser Leu Val Gly Asp Ile Gly Asn
1               5                   10                  15

<210> SEQ ID NO 676
<211> LENGTH: 16
<212> TYPE: PRT
<213> ORGANISM: Homo sapiens

<400> SEQUENCE: 676

Ala Leu Lys Tyr Glu Val Gln Gly Glu Val Phe Thr Lys Pro Gln Leu
1               5                   10                  15

<210> SEQ ID NO 677
<211> LENGTH: 14
<212> TYPE: PRT
<213> ORGANISM: Homo sapiens

<400> SEQUENCE: 677

Gly Ile Val Glu Phe Trp Val Asp Gly Lys Pro Arg Val Arg
1               5                   10

```
<210> SEQ ID NO 678
<211> LENGTH: 10
<212> TYPE: PRT
<213> ORGANISM: Homo sapiens

<400> SEQUENCE: 678

Arg Lys Ala Phe Val Phe Pro Lys Glu Ser
1               5                   10

<210> SEQ ID NO 679
<211> LENGTH: 16
<212> TYPE: PRT
<213> ORGANISM: Homo sapiens

<400> SEQUENCE: 679

Lys Tyr Glu Val Gln Gly Glu Val Phe Thr Lys Pro Gln Leu Trp Pro
1               5                   10                  15

<210> SEQ ID NO 680
<211> LENGTH: 13
<212> TYPE: PRT
<213> ORGANISM: Homo sapiens

<400> SEQUENCE: 680

Asp Ser Phe Gly Gly Asn Phe Glu Gly Ser Gln Ser Leu
1               5                   10

<210> SEQ ID NO 681
<211> LENGTH: 12
<212> TYPE: PRT
<213> ORGANISM: Homo sapiens

<400> SEQUENCE: 681

Asp Phe Val Leu Ser Pro Asp Glu Ile Asn Thr Ile
1               5                   10

<210> SEQ ID NO 682
<211> LENGTH: 13
<212> TYPE: PRT
<213> ORGANISM: Homo sapiens

<400> SEQUENCE: 682

Ser Leu Lys Lys Gly Tyr Thr Val Gly Ala Glu Ala Ser
1               5                   10

<210> SEQ ID NO 683
<211> LENGTH: 12
<212> TYPE: PRT
<213> ORGANISM: Homo sapiens

<400> SEQUENCE: 683

Ala Phe Gly Gln Thr Asp Met Ser Arg Lys Ala Phe
1               5                   10

<210> SEQ ID NO 684
<211> LENGTH: 14
<212> TYPE: PRT
<213> ORGANISM: Homo sapiens

<400> SEQUENCE: 684

Ser Leu Lys Lys Gly Tyr Thr Val Gly Ala Glu Ala Ser Ile
1               5                   10

<210> SEQ ID NO 685
<211> LENGTH: 11
```

<212> TYPE: PRT
<213> ORGANISM: Homo sapiens

<400> SEQUENCE: 685

Gly Glu Val Phe Thr Lys Pro Gln Leu Trp Pro
1               5                   10

<210> SEQ ID NO 686
<211> LENGTH: 15
<212> TYPE: PRT
<213> ORGANISM: Homo sapiens

<400> SEQUENCE: 686

Ser Ile Ile Leu Gly Gln Glu Gln Asp Ser Phe Gly Gly Asn Phe
1               5                   10                  15

<210> SEQ ID NO 687
<211> LENGTH: 14
<212> TYPE: PRT
<213> ORGANISM: Homo sapiens

<400> SEQUENCE: 687

Lys Tyr Glu Val Gln Gly Glu Val Phe Thr Lys Pro Gln Leu
1               5                   10

<210> SEQ ID NO 688
<211> LENGTH: 6
<212> TYPE: PRT
<213> ORGANISM: Homo sapiens

<400> SEQUENCE: 688

Lys Val Glu Gln Ala Val
1               5

<210> SEQ ID NO 689
<211> LENGTH: 6
<212> TYPE: PRT
<213> ORGANISM: Homo sapiens

<400> SEQUENCE: 689

Ala Glu Val Arg Ala Lys
1               5

<210> SEQ ID NO 690
<211> LENGTH: 6
<212> TYPE: PRT
<213> ORGANISM: Homo sapiens

<400> SEQUENCE: 690

Met Leu Gly Gln Ser Thr
1               5

<210> SEQ ID NO 691
<211> LENGTH: 6
<212> TYPE: PRT
<213> ORGANISM: Homo sapiens

<400> SEQUENCE: 691

Gln Ala Val Glu Thr Glu
1               5

<210> SEQ ID NO 692
<211> LENGTH: 6
<212> TYPE: PRT
<213> ORGANISM: Homo sapiens

<400> SEQUENCE: 692

Gln Gln Thr Glu Trp Gln
1               5

<210> SEQ ID NO 693
<211> LENGTH: 6
<212> TYPE: PRT
<213> ORGANISM: Homo sapiens

<400> SEQUENCE: 693

Ala Val Tyr Gln Ala Gly
1               5

<210> SEQ ID NO 694
<211> LENGTH: 6
<212> TYPE: PRT
<213> ORGANISM: Homo sapiens

<400> SEQUENCE: 694

Ala Lys Leu Glu Glu Gln
1               5

<210> SEQ ID NO 695
<211> LENGTH: 6
<212> TYPE: PRT
<213> ORGANISM: Homo sapiens

<400> SEQUENCE: 695

Lys Leu Glu Glu Gln Ala
1               5

<210> SEQ ID NO 696
<211> LENGTH: 6
<212> TYPE: PRT
<213> ORGANISM: Homo sapiens

<400> SEQUENCE: 696

Val Glu Gln Ala Val Glu
1               5

<210> SEQ ID NO 697
<211> LENGTH: 6
<212> TYPE: PRT
<213> ORGANISM: Homo sapiens

<400> SEQUENCE: 697

Gln Ala Val Glu Thr Glu
1               5

<210> SEQ ID NO 698
<211> LENGTH: 6
<212> TYPE: PRT
<213> ORGANISM: Homo sapiens

<400> SEQUENCE: 698

Glu Val Lys Glu Gln Val
1               5

<210> SEQ ID NO 699
<211> LENGTH: 6
<212> TYPE: PRT
<213> ORGANISM: Homo sapiens

<400> SEQUENCE: 699

```
Ala Phe Val Phe Pro Lys
1               5

<210> SEQ ID NO 700
<211> LENGTH: 6
<212> TYPE: PRT
<213> ORGANISM: Homo sapiens

<400> SEQUENCE: 700

Tyr Glu Val Gln Gly Glu
1               5

<210> SEQ ID NO 701
<211> LENGTH: 6
<212> TYPE: PRT
<213> ORGANISM: Homo sapiens

<400> SEQUENCE: 701

Lys Ala Phe Val Phe Pro
1               5

<210> SEQ ID NO 702
<211> LENGTH: 6
<212> TYPE: PRT
<213> ORGANISM: Homo sapiens

<400> SEQUENCE: 702

Ser Phe Gly Gly Asn Phe
1               5

<210> SEQ ID NO 703
<211> LENGTH: 6
<212> TYPE: PRT
<213> ORGANISM: Homo sapiens

<400> SEQUENCE: 703

Phe Val Leu Ser Pro Asp
1               5

<210> SEQ ID NO 704
<211> LENGTH: 6
<212> TYPE: PRT
<213> ORGANISM: Homo sapiens

<400> SEQUENCE: 704

Leu Lys Lys Gly Tyr Thr
1               5

<210> SEQ ID NO 705
<211> LENGTH: 6
<212> TYPE: PRT
<213> ORGANISM: Homo sapiens

<400> SEQUENCE: 705

Phe Gly Gln Thr Asp Met
1               5

<210> SEQ ID NO 706
<211> LENGTH: 6
<212> TYPE: PRT
<213> ORGANISM: Homo sapiens

<400> SEQUENCE: 706

Leu Lys Lys Gly Tyr Thr
```

```
1               5

<210> SEQ ID NO 707
<211> LENGTH: 6
<212> TYPE: PRT
<213> ORGANISM: Homo sapiens

<400> SEQUENCE: 707

Ile Ile Leu Gly Gln Glu
1               5

<210> SEQ ID NO 708
<211> LENGTH: 6
<212> TYPE: PRT
<213> ORGANISM: Homo sapiens

<400> SEQUENCE: 708

Tyr Glu Val Gln Gly Glu
1               5

<210> SEQ ID NO 709
<211> LENGTH: 6
<212> TYPE: PRT
<213> ORGANISM: Homo sapiens

<400> SEQUENCE: 709

Leu Lys Tyr Glu Val Gln
1               5

<210> SEQ ID NO 710
<211> LENGTH: 6
<212> TYPE: PRT
<213> ORGANISM: Homo sapiens

<400> SEQUENCE: 710

Ile Val Glu Phe Trp Val
1               5

<210> SEQ ID NO 711
<211> LENGTH: 6
<212> TYPE: PRT
<213> ORGANISM: Homo sapiens

<400> SEQUENCE: 711

Glu Ser Asp Thr Ser Tyr
1               5

<210> SEQ ID NO 712
<211> LENGTH: 6
<212> TYPE: PRT
<213> ORGANISM: Homo sapiens

<400> SEQUENCE: 712

Gly Asn Phe Glu Gly Ser
1               5

<210> SEQ ID NO 713
<211> LENGTH: 6
<212> TYPE: PRT
<213> ORGANISM: Homo sapiens

<400> SEQUENCE: 713

Thr Glu Pro Glu Pro Glu
1               5
```

<210> SEQ ID NO 714
<211> LENGTH: 6
<212> TYPE: PRT
<213> ORGANISM: Homo sapiens

<400> SEQUENCE: 714

Thr Glu Pro Glu Pro Glu
1               5

<210> SEQ ID NO 715
<211> LENGTH: 6
<212> TYPE: PRT
<213> ORGANISM: Homo sapiens

<400> SEQUENCE: 715

Glu Gln Ala Gln Gln Ile
1               5

<210> SEQ ID NO 716
<211> LENGTH: 6
<212> TYPE: PRT
<213> ORGANISM: Homo sapiens

<400> SEQUENCE: 716

Thr Glu Glu Leu Arg Val
1               5

<210> SEQ ID NO 717
<211> LENGTH: 6
<212> TYPE: PRT
<213> ORGANISM: Homo sapiens

<400> SEQUENCE: 717

Pro Glu Pro Glu Leu Arg
1               5

<210> SEQ ID NO 718
<211> LENGTH: 6
<212> TYPE: PRT
<213> ORGANISM: Homo sapiens

<400> SEQUENCE: 718

Ser Gly Gln Arg Trp Glu
1               5

<210> SEQ ID NO 719
<211> LENGTH: 6
<212> TYPE: PRT
<213> ORGANISM: Homo sapiens

<400> SEQUENCE: 719

Glu Gly Ala Glu Arg Gly
1               5

<210> SEQ ID NO 720
<211> LENGTH: 6
<212> TYPE: PRT
<213> ORGANISM: Homo sapiens

<400> SEQUENCE: 720

Gln Ala Gln Gln Ile Arg
1               5

<210> SEQ ID NO 721

```
<211> LENGTH: 6
<212> TYPE: PRT
<213> ORGANISM: Homo sapiens

<400> SEQUENCE: 721

Gln Gln Ile Arg Leu Gln
1               5

<210> SEQ ID NO 722
<211> LENGTH: 6
<212> TYPE: PRT
<213> ORGANISM: Homo sapiens

<400> SEQUENCE: 722

Glu Pro Glu Pro Glu Leu
1               5

<210> SEQ ID NO 723
<211> LENGTH: 6
<212> TYPE: PRT
<213> ORGANISM: Homo sapiens

<400> SEQUENCE: 723

Pro Glu Pro Glu Leu Arg
1               5

<210> SEQ ID NO 724
<211> LENGTH: 6
<212> TYPE: PRT
<213> ORGANISM: Homo sapiens

<400> SEQUENCE: 724

Glu Val Arg Ala Lys Leu
1               5

<210> SEQ ID NO 725
<211> LENGTH: 7
<212> TYPE: PRT
<213> ORGANISM: Homo sapiens

<400> SEQUENCE: 725

Lys Ala Phe Val Phe Pro Lys
1               5

<210> SEQ ID NO 726
<211> LENGTH: 6
<212> TYPE: PRT
<213> ORGANISM: Homo sapiens

<400> SEQUENCE: 726

Ala Phe Val Phe Pro Lys
1               5

<210> SEQ ID NO 727
<211> LENGTH: 6
<212> TYPE: PRT
<213> ORGANISM: Homo sapiens

<400> SEQUENCE: 727

Lys Pro Gln Leu Trp Pro
1               5

<210> SEQ ID NO 728
<211> LENGTH: 6
<212> TYPE: PRT
```

<213> ORGANISM: Homo sapiens

<400> SEQUENCE: 728

Phe Val Phe Pro Lys Glu
1               5

<210> SEQ ID NO 729
<211> LENGTH: 6
<212> TYPE: PRT
<213> ORGANISM: Homo sapiens

<400> SEQUENCE: 729

Pro Asp Glu Ile Asn Thr
1               5

<210> SEQ ID NO 730
<211> LENGTH: 6
<212> TYPE: PRT
<213> ORGANISM: Homo sapiens

<400> SEQUENCE: 730

Asp Met Ser Arg Lys Ala
1               5

<210> SEQ ID NO 731
<211> LENGTH: 6
<212> TYPE: PRT
<213> ORGANISM: Homo sapiens

<400> SEQUENCE: 731

Val Gly Ala Glu Ala Ser
1               5

<210> SEQ ID NO 732
<211> LENGTH: 6
<212> TYPE: PRT
<213> ORGANISM: Homo sapiens

<400> SEQUENCE: 732

Lys Pro Gln Leu Trp Pro
1               5

<210> SEQ ID NO 733
<211> LENGTH: 6
<212> TYPE: PRT
<213> ORGANISM: Homo sapiens

<400> SEQUENCE: 733

Asp Ser Phe Gly Gly Asn
1               5

<210> SEQ ID NO 734
<211> LENGTH: 6
<212> TYPE: PRT
<213> ORGANISM: Homo sapiens

<400> SEQUENCE: 734

Val Phe Thr Lys Pro Gln
1               5

<210> SEQ ID NO 735
<211> LENGTH: 757
<212> TYPE: PRT
<213> ORGANISM: Homo sapiens

```
<400> SEQUENCE: 735

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Val Phe Tyr Pro Gly Ala Gly Leu
        35                  40                  45

Gly Ala Leu Gly Gly Ala Leu Gly Pro Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Val
                85                  90                  95

Ala Asp Ala Ala Ala Tyr Lys Ala Ala Lys Ala Gly Ala Gly Leu
        100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Lys Ala Ala Lys Tyr Gly
            370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415
```

Val Ala Gly Val Pro Ser Val Gly Val Pro Val Gly Val
            420             425             430

Pro Gly Val Gly Ile Ser Pro Glu Ala Gln Ala Ala Ala Ala Lys
            435             440             445

Ala Ala Lys Tyr Gly Val Gly Thr Pro Ala Ala Ala Ala Lys Ala
450             455             460

Ala Ala Lys Ala Ala Gln Phe Gly Leu Val Pro Gly Val Gly Val Ala
465             470             475             480

Pro Gly Val Gly Val Ala Pro Gly Val Gly Val Ala Pro Gly Val Gly
            485             490             495

Leu Ala Pro Gly Val Gly Val Ala Pro Gly Val Gly Val Ala Pro Gly
            500             505             510

Val Gly Val Ala Pro Gly Ile Gly Pro Gly Gly Val Ala Ala Ala
            515             520             525

Lys Ser Ala Ala Lys Val Ala Ala Lys Ala Gln Leu Arg Ala Ala
530             535             540

Gly Leu Gly Ala Gly Ile Pro Gly Leu Gly Val Gly Val Gly Val Pro
545             550             555             560

Gly Leu Gly Val Gly Ala Gly Val Pro Gly Leu Gly Val Gly Ala Gly
            565             570             575

Val Pro Gly Phe Gly Ala Gly Ala Asp Glu Gly Val Arg Arg Ser Leu
            580             585             590

Ser Pro Glu Leu Arg Glu Gly Asp Pro Ser Ser Ser Gln His Leu Pro
            595             600             605

Ser Thr Pro Ser Ser Pro Arg Val Pro Gly Ala Leu Ala Ala Ala Lys
            610             615             620

Ala Ala Lys Tyr Gly Ala Ala Val Pro Gly Val Leu Gly Gly Leu Gly
625             630             635             640

Ala Leu Gly Gly Val Gly Ile Pro Gly Gly Val Val Gly Ala Gly Pro
            645             650             655

Ala Ala Ala Ala Ala Ala Ala Lys Ala Ala Lys Ala Ala Gln Phe
            660             665             670

Gly Leu Val Gly Ala Ala Gly Leu Gly Gly Leu Gly Val Gly Gly Leu
            675             680             685

Gly Val Pro Gly Val Gly Gly Leu Gly Gly Ile Pro Pro Ala Ala Ala
            690             695             700

Ala Lys Ala Ala Lys Tyr Gly Ala Ala Gly Leu Gly Gly Val Leu Gly
705             710             715             720

Gly Ala Gly Gln Phe Pro Leu Gly Gly Val Ala Ala Arg Pro Gly Phe
            725             730             735

Gly Leu Ser Pro Ile Phe Pro Gly Gly Ala Cys Leu Gly Lys Ala Cys
            740             745             750

Gly Arg Lys Arg Lys
            755

<210> SEQ ID NO 736
<211> LENGTH: 20
<212> TYPE: PRT
<213> ORGANISM: Homo sapiens

<400> SEQUENCE: 736

Ala Arg Pro Gly Val Gly Val Gly Gly Ile Pro Thr Tyr Gly Val Gly
1               5                   10                  15

Ala Gly Gly Phe

-continued

```
                20

<210> SEQ ID NO 737
<211> LENGTH: 17
<212> TYPE: PRT
<213> ORGANISM: Homo sapiens

<400> SEQUENCE: 737

Gly Leu Pro Tyr Thr Thr Gly Lys Leu Pro Tyr Gly Tyr Gly Pro Gly
1               5                   10                  15

Gly

<210> SEQ ID NO 738
<211> LENGTH: 25
<212> TYPE: PRT
<213> ORGANISM: Homo sapiens

<400> SEQUENCE: 738

Gly Val Ala Pro Gly Val Gly Val Ala Pro Gly Val Gly Val Ala Pro
1               5                   10                  15

Gly Ile Gly Pro Gly Gly Val Ala Ala
            20                  25

<210> SEQ ID NO 739
<211> LENGTH: 23
<212> TYPE: PRT
<213> ORGANISM: Homo sapiens

<400> SEQUENCE: 739

Gly Gly Ala Gly Val Pro Gly Val Pro Gly Ala Ile Pro Gly Ile Gly
1               5                   10                  15

Gly Ile Ala Gly Val Gly Thr
            20

<210> SEQ ID NO 740
<211> LENGTH: 23
<212> TYPE: PRT
<213> ORGANISM: Homo sapiens

<400> SEQUENCE: 740

Gly Gly Ala Gly Val Pro Gly Val Pro Gly Ala Ile Pro Gly Ile Gly
1               5                   10                  15

Gly Ile Ala Gly Val Gly Thr
            20

<210> SEQ ID NO 741
<211> LENGTH: 16
<212> TYPE: PRT
<213> ORGANISM: Homo sapiens

<400> SEQUENCE: 741

Gly Val Gly Ile Ser Pro Glu Ala Gln Ala Ala Ala Ala Ala Lys Ala
1               5                   10                  15

<210> SEQ ID NO 742
<211> LENGTH: 16
<212> TYPE: PRT
<213> ORGANISM: Homo sapiens

<400> SEQUENCE: 742

Gly Val Gly Ile Ser Pro Glu Ala Gln Ala Ala Ala Ala Ala Lys Ala
1               5                   10                  15
```

```
<210> SEQ ID NO 743
<211> LENGTH: 6
<212> TYPE: PRT
<213> ORGANISM: Homo sapiens

<400> SEQUENCE: 743

Arg Pro Gly Val Gly Val
1               5

<210> SEQ ID NO 744
<211> LENGTH: 6
<212> TYPE: PRT
<213> ORGANISM: Homo sapiens

<400> SEQUENCE: 744

Leu Pro Tyr Thr Thr Gly
1               5

<210> SEQ ID NO 745
<211> LENGTH: 6
<212> TYPE: PRT
<213> ORGANISM: Homo sapiens

<400> SEQUENCE: 745

Val Ala Pro Gly Val Gly
1               5

<210> SEQ ID NO 746
<211> LENGTH: 6
<212> TYPE: PRT
<213> ORGANISM: Homo sapiens

<400> SEQUENCE: 746

Gly Ala Gly Val Pro Gly
1               5

<210> SEQ ID NO 747
<211> LENGTH: 6
<212> TYPE: PRT
<213> ORGANISM: Homo sapiens

<400> SEQUENCE: 747

Val Gly Ile Ser Pro Glu
1               5

<210> SEQ ID NO 748
<211> LENGTH: 6
<212> TYPE: PRT
<213> ORGANISM: Homo sapiens

<400> SEQUENCE: 748

Arg Pro Gly Val Gly Val
1               5

<210> SEQ ID NO 749
<211> LENGTH: 6
<212> TYPE: PRT
<213> ORGANISM: Homo sapiens

<400> SEQUENCE: 749

Leu Pro Tyr Thr Thr Gly
1               5

<210> SEQ ID NO 750
```

```
<211> LENGTH: 6
<212> TYPE: PRT
<213> ORGANISM: Homo sapiens

<400> SEQUENCE: 750

Gly Val Gly Ala Gly Gly
1               5

<210> SEQ ID NO 751
<211> LENGTH: 6
<212> TYPE: PRT
<213> ORGANISM: Homo sapiens

<400> SEQUENCE: 751

Tyr Gly Tyr Gly Pro Gly
1               5

<210> SEQ ID NO 752
<211> LENGTH: 6
<212> TYPE: PRT
<213> ORGANISM: Homo sapiens

<400> SEQUENCE: 752

Gly Pro Gly Gly Val Ala
1               5

<210> SEQ ID NO 753
<211> LENGTH: 6
<212> TYPE: PRT
<213> ORGANISM: Homo sapiens

<400> SEQUENCE: 753

Gly Ile Ala Gly Val Gly
1               5

<210> SEQ ID NO 754
<211> LENGTH: 13
<212> TYPE: PRT
<213> ORGANISM: Homo sapiens

<400> SEQUENCE: 754

Lys Asn Gly Glu Thr Gly Pro Gln Gly Pro Gly Gly Cys
1               5                   10

<210> SEQ ID NO 755
<211> LENGTH: 13
<212> TYPE: PRT
<213> ORGANISM: Homo sapiens

<400> SEQUENCE: 755

Lys Asn Gly Glu Thr Gly Pro Gln Gly Pro Pro Gly Lys
1               5                   10

<210> SEQ ID NO 756
<211> LENGTH: 13
<212> TYPE: PRT
<213> ORGANISM: Homo sapiens

<400> SEQUENCE: 756

Lys Asp Gly Glu Thr Gly Ala Ala Gly Pro Pro Gly Lys
1               5                   10

<210> SEQ ID NO 757
<211> LENGTH: 13
<212> TYPE: PRT
```

<213> ORGANISM: Homo sapiens

<400> SEQUENCE: 757

Lys Asp Gly Glu Ala Gly Ala Gln Gly Pro Pro Gly Lys
1               5                   10

<210> SEQ ID NO 758
<211> LENGTH: 14
<212> TYPE: PRT
<213> ORGANISM: Homo sapiens

<400> SEQUENCE: 758

Pro Gly Lys Asn Gly Glu Thr Pro Gly Pro Gln Gly Pro Lys
1               5                   10

<210> SEQ ID NO 759
<211> LENGTH: 13
<212> TYPE: PRT
<213> ORGANISM: Homo sapiens

<400> SEQUENCE: 759

Ile Ala Gly Ile Thr Gly Ala Arg Gly Leu Gly Gly Cys
1               5                   10

<210> SEQ ID NO 760
<211> LENGTH: 13
<212> TYPE: PRT
<213> ORGANISM: Homo sapiens

<400> SEQUENCE: 760

Ile Ala Gly Ile Thr Gly Ala Arg Gly Leu Ala Gly Lys
1               5                   10

<210> SEQ ID NO 761
<211> LENGTH: 13
<212> TYPE: PRT
<213> ORGANISM: Homo sapiens

<400> SEQUENCE: 761

Ile Ala Gly Leu Thr Gly Ala Arg Gly Leu Ala Gly Lys
1               5                   10

<210> SEQ ID NO 762
<211> LENGTH: 15
<212> TYPE: PRT
<213> ORGANISM: Homo sapiens

<400> SEQUENCE: 762

Leu Gly Ile Ala Gly Ile Thr Gly Ala Arg Gly Leu Ala Gly Lys
1               5                   10                  15

<210> SEQ ID NO 763
<211> LENGTH: 6
<212> TYPE: PRT
<213> ORGANISM: Homo sapiens

<400> SEQUENCE: 763

Lys Asp Gly Thr Ser Gly
1               5

<210> SEQ ID NO 764
<211> LENGTH: 13
<212> TYPE: PRT
<213> ORGANISM: Homo sapiens

```
<400> SEQUENCE: 764

Lys Asp Gly Thr Ser Gly His Pro Gly Pro Gly Gly Cys
1               5                   10

<210> SEQ ID NO 765
<211> LENGTH: 13
<212> TYPE: PRT
<213> ORGANISM: Homo sapiens

<400> SEQUENCE: 765

Lys Asp Gly Thr Ser Gly His Pro Gly Pro Ile Gly Lys
1               5                   10

<210> SEQ ID NO 766
<211> LENGTH: 13
<212> TYPE: PRT
<213> ORGANISM: Homo sapiens

<400> SEQUENCE: 766

Lys Asp Gly Ser Ser Gly His Pro Gly Pro Ile Gly Lys
1               5                   10

<210> SEQ ID NO 767
<211> LENGTH: 13
<212> TYPE: PRT
<213> ORGANISM: Homo sapiens

<400> SEQUENCE: 767

Pro Gly Lys Asp Gly Thr Ser Gly His Pro Gly Pro Lys
1               5                   10

<210> SEQ ID NO 768
<211> LENGTH: 13
<212> TYPE: PRT
<213> ORGANISM: Homo sapiens

<400> SEQUENCE: 768

Cys Gly Gly Gly Pro Pro Gly Ala Pro Gly Pro Leu Gly
1               5                   10

<210> SEQ ID NO 769
<211> LENGTH: 12
<212> TYPE: PRT
<213> ORGANISM: Homo sapiens

<400> SEQUENCE: 769

Ala Gln Gly Pro Pro Gly Ala Pro Gly Pro Leu Gly
1               5                   10

<210> SEQ ID NO 770
<211> LENGTH: 12
<212> TYPE: PRT
<213> ORGANISM: Homo sapiens

<400> SEQUENCE: 770

Ala Gln Gly Pro Pro Gly Ser Pro Gly Pro Leu Gly
1               5                   10

<210> SEQ ID NO 771
<211> LENGTH: 12
<212> TYPE: PRT
<213> ORGANISM: Homo sapiens

<400> SEQUENCE: 771
```

-continued

Asp Asp Gly Pro Ser Gly Ala Glu Gly Pro Pro Gly
1               5                   10

<210> SEQ ID NO 772
<211> LENGTH: 12
<212> TYPE: PRT
<213> ORGANISM: Homo sapiens

<400> SEQUENCE: 772

Gly Pro Pro Gly Ala Pro Gly Pro Leu Gly Ile Ala
1               5                   10

<210> SEQ ID NO 773
<211> LENGTH: 13
<212> TYPE: PRT
<213> ORGANISM: Homo sapiens

<400> SEQUENCE: 773

Asn Thr Gly Ala Pro Gly Ser Pro Gly Val Cys Gly Gly
1               5                   10

<210> SEQ ID NO 774
<211> LENGTH: 13
<212> TYPE: PRT
<213> ORGANISM: Homo sapiens

<400> SEQUENCE: 774

Asn Thr Gly Ala Pro Gly Ser Pro Gly Val Ser Gly Lys
1               5                   10

<210> SEQ ID NO 775
<211> LENGTH: 13
<212> TYPE: PRT
<213> ORGANISM: Homo sapiens

<400> SEQUENCE: 775

Asn Ser Gly Ser Pro Gly Asn Pro Gly Val Ala Gly Lys
1               5                   10

<210> SEQ ID NO 776
<211> LENGTH: 12
<212> TYPE: PRT
<213> ORGANISM: Homo sapiens

<400> SEQUENCE: 776

Ala Gly Asn Thr Gly Ala Pro Gly Ser Pro Gly Val
1               5                   10

<210> SEQ ID NO 777
<211> LENGTH: 13
<212> TYPE: PRT
<213> ORGANISM: Homo sapiens

<400> SEQUENCE: 777

Ala Ile Gly Pro Ser Gly Pro Ala Gly Lys Gly Gly Cys
1               5                   10

<210> SEQ ID NO 778
<211> LENGTH: 13
<212> TYPE: PRT
<213> ORGANISM: Homo sapiens

<400> SEQUENCE: 778

Ala Ile Gly Pro Ser Gly Pro Ala Gly Lys Asp Gly Lys
1               5                   10

<210> SEQ ID NO 779
<211> LENGTH: 13
<212> TYPE: PRT
<213> ORGANISM: Homo sapiens

<400> SEQUENCE: 779

Ala Ile Gly Pro Ala Gly Pro Ala Gly Lys Asp Gly Lys
1               5                   10

<210> SEQ ID NO 780
<211> LENGTH: 13
<212> TYPE: PRT
<213> ORGANISM: Homo sapiens

<400> SEQUENCE: 780

Pro Gly Ala Ile Gly Pro Ser Gly Pro Ala Gly Lys Asp
1               5                   10

<210> SEQ ID NO 781
<211> LENGTH: 6
<212> TYPE: PRT
<213> ORGANISM: Homo sapiens

<400> SEQUENCE: 781

Ala Gly Gly Phe Ala Pro
1               5

<210> SEQ ID NO 782
<211> LENGTH: 11
<212> TYPE: PRT
<213> ORGANISM: Homo sapiens

<400> SEQUENCE: 782

Cys Gly Gly Glu Lys Ala Gly Gly Phe Ala Pro
1               5                   10

<210> SEQ ID NO 783
<211> LENGTH: 10
<212> TYPE: PRT
<213> ORGANISM: Homo sapiens

<400> SEQUENCE: 783

Cys Gly Glu Lys Ala Gly Gly Phe Ala Pro
1               5                   10

<210> SEQ ID NO 784
<211> LENGTH: 10
<212> TYPE: PRT
<213> ORGANISM: Homo sapiens

<400> SEQUENCE: 784

Cys Gly Glu Lys Ser Gly Gly Phe Ser Pro
1               5                   10

<210> SEQ ID NO 785
<211> LENGTH: 12
<212> TYPE: PRT
<213> ORGANISM: Homo sapiens

<400> SEQUENCE: 785

Gly Gly Glu Lys Ala Gly Gly Phe Ala Pro Tyr Tyr
1               5                   10

<210> SEQ ID NO 786
<211> LENGTH: 6
<212> TYPE: PRT
<213> ORGANISM: Homo sapiens

<400> SEQUENCE: 786

Gln Asn Gly Asn Ile Lys
1               5

<210> SEQ ID NO 787
<211> LENGTH: 13
<212> TYPE: PRT
<213> ORGANISM: Homo sapiens

<400> SEQUENCE: 787

Ile Val Ile Glu Leu Gly Thr Asn Pro Leu Gly Gly Cys
1               5                   10

<210> SEQ ID NO 788
<211> LENGTH: 13
<212> TYPE: PRT
<213> ORGANISM: Homo sapiens

<400> SEQUENCE: 788

Ile Val Ile Glu Leu Gly Thr Asn Pro Leu Lys Ser Lys
1               5                   10

<210> SEQ ID NO 789
<211> LENGTH: 13
<212> TYPE: PRT
<213> ORGANISM: Homo sapiens

<400> SEQUENCE: 789

Leu Val Ile Glu Leu Gly Gly Asn Pro Leu Lys Asn Lys
1               5                   10

<210> SEQ ID NO 790
<211> LENGTH: 13
<212> TYPE: PRT
<213> ORGANISM: Homo sapiens

<400> SEQUENCE: 790

Ile Val Val Glu Leu Gly Gly Asn Pro Leu Thr Asn Lys
1               5                   10

<210> SEQ ID NO 791
<211> LENGTH: 14
<212> TYPE: PRT
<213> ORGANISM: Homo sapiens

<400> SEQUENCE: 791

Gln Met Ile Val Ile Glu Leu Gly Thr Asn Pro Leu Lys Lys
1               5                   10

<210> SEQ ID NO 792
<211> LENGTH: 13
<212> TYPE: PRT
<213> ORGANISM: Homo sapiens

<400> SEQUENCE: 792

Asn Val Leu Val Ile Glu Leu Gly Gly Asn Pro Leu Lys
1               5                   10

<210> SEQ ID NO 793
<211> LENGTH: 13

```
<212> TYPE: PRT
<213> ORGANISM: Homo sapiens

<400> SEQUENCE: 793

Cys Gly Gly Leu Asp Leu Gln Asn Asn Asp Ile Ser Glu
1               5                   10

<210> SEQ ID NO 794
<211> LENGTH: 12
<212> TYPE: PRT
<213> ORGANISM: Homo sapiens

<400> SEQUENCE: 794

Thr Leu Leu Asp Leu Gln Asn Asn Asp Ile Ser Glu
1               5                   10

<210> SEQ ID NO 795
<211> LENGTH: 12
<212> TYPE: PRT
<213> ORGANISM: Homo sapiens

<400> SEQUENCE: 795

Leu Asp Leu Gln Asn Asn Asp Ile Ser Glu Leu Arg
1               5                   10

<210> SEQ ID NO 796
<211> LENGTH: 16
<212> TYPE: PRT
<213> ORGANISM: Homo sapiens

<400> SEQUENCE: 796

Gln Asn Gly Asn Ile Lys Ile Gly Gln Asp Gly Gly Cys Lys Leu His
1               5                   10                  15

<210> SEQ ID NO 797
<211> LENGTH: 12
<212> TYPE: PRT
<213> ORGANISM: Homo sapiens

<400> SEQUENCE: 797

Gln Asn Gly Asn Ile Lys Ile Gly Gln Asp Tyr Lys
1               5                   10

<210> SEQ ID NO 798
<211> LENGTH: 12
<212> TYPE: PRT
<213> ORGANISM: Homo sapiens

<400> SEQUENCE: 798

Gln Asp Gly Asn Ile Lys Ile Gly Gln Asp Tyr Lys
1               5                   10

<210> SEQ ID NO 799
<211> LENGTH: 13
<212> TYPE: PRT
<213> ORGANISM: Homo sapiens

<400> SEQUENCE: 799

Val Ala Gln Asn Gly Asn Ile Lys Ile Gly Gln Asp Lys
1               5                   10

<210> SEQ ID NO 800
<211> LENGTH: 13
<212> TYPE: PRT
<213> ORGANISM: Homo sapiens
```

```
<400> SEQUENCE: 800

Val Ala Gln Asp Gly Asn Ile Lys Ile Gly Gln Asp Lys
1               5                   10

<210> SEQ ID NO 801
<211> LENGTH: 13
<212> TYPE: PRT
<213> ORGANISM: ARTIFICIAL
<220> FEATURE:
<223> OTHER INFORMATION: Human sequence with synthetic extension

<400> SEQUENCE: 801

Lys Asn Gly Glu Thr Gly Pro Gln Gly Pro Gly Gly Cys
1               5                   10

<210> SEQ ID NO 802
<211> LENGTH: 13
<212> TYPE: PRT
<213> ORGANISM: artificial
<220> FEATURE:
<223> OTHER INFORMATION: Human sequence with synthetic extension

<400> SEQUENCE: 802

Lys Asn Gly Glu Thr Gly Pro Gln Gly Pro Pro Gly Lys
1               5                   10

<210> SEQ ID NO 803
<211> LENGTH: 13
<212> TYPE: PRT
<213> ORGANISM: artificial
<220> FEATURE:
<223> OTHER INFORMATION: Deselection peptide

<400> SEQUENCE: 803

Lys Asp Gly Glu Thr Gly Ala Ala Gly Pro Pro Gly Lys
1               5                   10

<210> SEQ ID NO 804
<211> LENGTH: 13
<212> TYPE: PRT
<213> ORGANISM: artificial
<220> FEATURE:
<223> OTHER INFORMATION: Deselection peptide

<400> SEQUENCE: 804

Lys Asp Gly Glu Ala Gly Ala Gln Gly Pro Pro Gly Lys
1               5                   10

<210> SEQ ID NO 805
<211> LENGTH: 14
<212> TYPE: PRT
<213> ORGANISM: Artificial
<220> FEATURE:
<223> OTHER INFORMATION: Deselection sequence

<400> SEQUENCE: 805

Pro Gly Lys Asn Gly Glu Thr Pro Gly Pro Gln Gly Pro Lys
1               5                   10

<210> SEQ ID NO 806
<211> LENGTH: 13
<212> TYPE: PRT
<213> ORGANISM: Artificial
<220> FEATURE:
<223> OTHER INFORMATION: Human with synthetic extension
```

<400> SEQUENCE: 806

Ile Ala Gly Ile Thr Gly Ala Arg Gly Leu Gly Gly Cys
1               5                   10

<210> SEQ ID NO 807
<211> LENGTH: 13
<212> TYPE: PRT
<213> ORGANISM: Artificial
<220> FEATURE:
<223> OTHER INFORMATION: Human with synthetic extension

<400> SEQUENCE: 807

Ile Ala Gly Ile Thr Gly Ala Arg Gly Leu Ala Gly Lys
1               5                   10

<210> SEQ ID NO 808
<211> LENGTH: 13
<212> TYPE: PRT
<213> ORGANISM: Artificial
<220> FEATURE:
<223> OTHER INFORMATION: Human with synthetic extension

<400> SEQUENCE: 808

Ile Ala Gly Leu Thr Gly Ala Arg Gly Leu Ala Gly Lys
1               5                   10

<210> SEQ ID NO 809
<211> LENGTH: 15
<212> TYPE: PRT
<213> ORGANISM: Artificial
<220> FEATURE:
<223> OTHER INFORMATION: Deselection peptide

<400> SEQUENCE: 809

Leu Gly Ile Ala Gly Ile Thr Gly Ala Arg Gly Leu Ala Gly Lys
1               5                   10                  15

<210> SEQ ID NO 810
<211> LENGTH: 13
<212> TYPE: PRT
<213> ORGANISM: Artificial
<220> FEATURE:
<223> OTHER INFORMATION: Human with synthetic extension

<400> SEQUENCE: 810

Lys Asp Gly Thr Ser Gly His Pro Gly Pro Gly Gly Cys
1               5                   10

<210> SEQ ID NO 811
<211> LENGTH: 13
<212> TYPE: PRT
<213> ORGANISM: Artificial
<220> FEATURE:
<223> OTHER INFORMATION: Human with synthetic extension

<400> SEQUENCE: 811

Lys Asp Gly Thr Ser Gly His Pro Gly Pro Ile Gly Lys
1               5                   10

<210> SEQ ID NO 812
<211> LENGTH: 13
<212> TYPE: PRT
<213> ORGANISM: Artificial
<220> FEATURE:
<223> OTHER INFORMATION: Human with synthetic extension

<400> SEQUENCE: 812

```
Lys Asp Gly Ser Ser Gly His Pro Gly Pro Ile Gly Lys
1               5                   10
```

<210> SEQ ID NO 813
<211> LENGTH: 13
<212> TYPE: PRT
<213> ORGANISM: Artificial
<220> FEATURE:
<223> OTHER INFORMATION: Deselection peptide

<400> SEQUENCE: 813

```
Lys Asp Gly Ser Ser Gly His Pro Gly Pro Ile Gly Lys
1               5                   10
```

<210> SEQ ID NO 814
<211> LENGTH: 13
<212> TYPE: PRT
<213> ORGANISM: Artificial
<220> FEATURE:
<223> OTHER INFORMATION: Human with synthetic extension

<400> SEQUENCE: 814

```
Cys Gly Gly Gly Pro Pro Gly Ala Pro Gly Pro Leu Gly
1               5                   10
```

<210> SEQ ID NO 815
<211> LENGTH: 12
<212> TYPE: PRT
<213> ORGANISM: Artificial
<220> FEATURE:
<223> OTHER INFORMATION: Human with synthetic extension

<400> SEQUENCE: 815

```
Ala Gln Gly Pro Pro Gly Ala Pro Gly Pro Leu Gly
1               5                   10
```

<210> SEQ ID NO 816
<211> LENGTH: 12
<212> TYPE: PRT
<213> ORGANISM: Artificial
<220> FEATURE:
<223> OTHER INFORMATION: Human with synthetic extension

<400> SEQUENCE: 816

```
Ala Gln Gly Pro Pro Gly Ser Pro Gly Pro Leu Gly
1               5                   10
```

<210> SEQ ID NO 817
<211> LENGTH: 12
<212> TYPE: PRT
<213> ORGANISM: Artificial
<220> FEATURE:
<223> OTHER INFORMATION: Deselection peptide

<400> SEQUENCE: 817

```
Asp Asp Gly Pro Ser Gly Ala Glu Gly Pro Pro Gly
1               5                   10
```

<210> SEQ ID NO 818
<211> LENGTH: 12
<212> TYPE: PRT
<213> ORGANISM: Artificial
<220> FEATURE:
<223> OTHER INFORMATION: Deselection peptide

<400> SEQUENCE: 818

```
Gly Pro Pro Gly Ala Pro Gly Pro Leu Gly Ile Ala
1               5                   10

<210> SEQ ID NO 819
<211> LENGTH: 13
<212> TYPE: PRT
<213> ORGANISM: Artificial
<220> FEATURE:
<223> OTHER INFORMATION: Human with synthetic extension

<400> SEQUENCE: 819

Asn Thr Gly Ala Pro Gly Ser Pro Gly Val Cys Gly Gly
1               5                   10

<210> SEQ ID NO 820
<211> LENGTH: 13
<212> TYPE: PRT
<213> ORGANISM: Artificial
<220> FEATURE:
<223> OTHER INFORMATION: Human with synthetic extension

<400> SEQUENCE: 820

Asn Thr Gly Ala Pro Gly Ser Pro Gly Val Ser Gly Lys
1               5                   10

<210> SEQ ID NO 821
<211> LENGTH: 13
<212> TYPE: PRT
<213> ORGANISM: Artificial
<220> FEATURE:
<223> OTHER INFORMATION: Human with synthetic extension

<400> SEQUENCE: 821

Asn Ser Gly Ser Pro Gly Asn Pro Gly Val Ala Gly Lys
1               5                   10

<210> SEQ ID NO 822
<211> LENGTH: 12
<212> TYPE: PRT
<213> ORGANISM: Artificial
<220> FEATURE:
<223> OTHER INFORMATION: Deselection peptide

<400> SEQUENCE: 822

Ala Gly Asn Thr Gly Ala Pro Gly Ser Pro Gly Val
1               5                   10

<210> SEQ ID NO 823
<211> LENGTH: 13
<212> TYPE: PRT
<213> ORGANISM: Artificial
<220> FEATURE:
<223> OTHER INFORMATION: Human with synthetic extension

<400> SEQUENCE: 823

Ala Ile Gly Pro Ser Gly Pro Ala Gly Lys Gly Gly Cys
1               5                   10

<210> SEQ ID NO 824
<211> LENGTH: 13
<212> TYPE: PRT
<213> ORGANISM: Artificial
<220> FEATURE:
<223> OTHER INFORMATION: Human with synthetic extension

<400> SEQUENCE: 824

Ala Ile Gly Pro Ser Gly Pro Ala Gly Lys Asp Gly Lys
```

```
1               5                  10
```

<210> SEQ ID NO 825
<211> LENGTH: 13
<212> TYPE: PRT
<213> ORGANISM: Artificial
<220> FEATURE:
<223> OTHER INFORMATION: Human with synthetic extension

<400> SEQUENCE: 825

```
Ala Ile Gly Pro Ala Gly Pro Ala Gly Lys Asp Gly Lys
1               5                   10
```

<210> SEQ ID NO 826
<211> LENGTH: 13
<212> TYPE: PRT
<213> ORGANISM: Artificial
<220> FEATURE:
<223> OTHER INFORMATION: Deselection peptide

<400> SEQUENCE: 826

```
Pro Gly Ala Ile Gly Pro Ser Gly Pro Ala Gly Lys Asp
1               5                   10
```

<210> SEQ ID NO 827
<211> LENGTH: 11
<212> TYPE: PRT
<213> ORGANISM: Artificial
<220> FEATURE:
<223> OTHER INFORMATION: Human with synthetic extension

<400> SEQUENCE: 827

```
Cys Gly Gly Glu Lys Ala Gly Gly Phe Ala Pro
1               5                   10
```

<210> SEQ ID NO 828
<211> LENGTH: 10
<212> TYPE: PRT
<213> ORGANISM: Artificial
<220> FEATURE:
<223> OTHER INFORMATION: Human with synthetic extension

<400> SEQUENCE: 828

```
Cys Gly Glu Lys Ala Gly Gly Phe Ala Pro
1               5                   10
```

<210> SEQ ID NO 829
<211> LENGTH: 10
<212> TYPE: PRT
<213> ORGANISM: Artificial
<220> FEATURE:
<223> OTHER INFORMATION: Human with synthetic extension

<400> SEQUENCE: 829

```
Cys Gly Glu Lys Ser Gly Gly Phe Ser Pro
1               5                   10
```

<210> SEQ ID NO 830
<211> LENGTH: 12
<212> TYPE: PRT
<213> ORGANISM: Artificial
<220> FEATURE:
<223> OTHER INFORMATION: Deselection peptide

<400> SEQUENCE: 830

```
Gly Gly Glu Lys Ala Gly Gly Phe Ala Pro Tyr Tyr
1               5                   10
```

<210> SEQ ID NO 831
<211> LENGTH: 13
<212> TYPE: PRT
<213> ORGANISM: Artificial
<220> FEATURE:
<223> OTHER INFORMATION: Human with synthetic extension

<400> SEQUENCE: 831

Ile Val Ile Glu Leu Gly Thr Asn Pro Leu Gly Gly Cys
1               5                   10

<210> SEQ ID NO 832
<211> LENGTH: 13
<212> TYPE: PRT
<213> ORGANISM: Artificial
<220> FEATURE:
<223> OTHER INFORMATION: Human with synthetic extension

<400> SEQUENCE: 832

Ile Val Ile Glu Leu Gly Thr Asn Pro Leu Lys Ser Lys
1               5                   10

<210> SEQ ID NO 833
<211> LENGTH: 13
<212> TYPE: PRT
<213> ORGANISM: Artificial
<220> FEATURE:
<223> OTHER INFORMATION: Human with synthetic extension

<400> SEQUENCE: 833

Leu Val Ile Glu Leu Gly Gly Asn Pro Leu Lys Asn Lys
1               5                   10

<210> SEQ ID NO 834
<211> LENGTH: 13
<212> TYPE: PRT
<213> ORGANISM: Artificial
<220> FEATURE:
<223> OTHER INFORMATION: Human with synthetic extension

<400> SEQUENCE: 834

Ile Val Val Glu Leu Gly Gly Asn Pro Leu Thr Asn Lys
1               5                   10

<210> SEQ ID NO 835
<211> LENGTH: 14
<212> TYPE: PRT
<213> ORGANISM: Artificial
<220> FEATURE:
<223> OTHER INFORMATION: Deselection peptide

<400> SEQUENCE: 835

Gln Met Ile Val Ile Glu Leu Gly Thr Asn Pro Leu Lys Lys
1               5                   10

<210> SEQ ID NO 836
<211> LENGTH: 13
<212> TYPE: PRT
<213> ORGANISM: Artificial
<220> FEATURE:
<223> OTHER INFORMATION: Deselection peptide

<400> SEQUENCE: 836

Asn Val Leu Val Ile Glu Leu Gly Gly Asn Pro Leu Lys
1               5                   10

<210> SEQ ID NO 837
<211> LENGTH: 13
<212> TYPE: PRT
<213> ORGANISM: Artificial
<220> FEATURE:
<223> OTHER INFORMATION: Human with synthetic extension

<400> SEQUENCE: 837

Cys Gly Gly Leu Asp Leu Gln Asn Asn Asp Ile Ser Glu
1               5                   10

<210> SEQ ID NO 838
<211> LENGTH: 12
<212> TYPE: PRT
<213> ORGANISM: Artificial
<220> FEATURE:
<223> OTHER INFORMATION: Human with synthetic extension

<400> SEQUENCE: 838

Thr Leu Leu Asp Leu Gln Asn Asn Asp Ile Ser Glu
1               5                   10

<210> SEQ ID NO 839
<211> LENGTH: 12
<212> TYPE: PRT
<213> ORGANISM: Artificial
<220> FEATURE:
<223> OTHER INFORMATION: Deselection peptide

<400> SEQUENCE: 839

Leu Asp Leu Gln Asn Asn Asp Ile Ser Glu Leu Arg
1               5                   10

<210> SEQ ID NO 840
<211> LENGTH: 13
<212> TYPE: PRT
<213> ORGANISM: Artificial
<220> FEATURE:
<223> OTHER INFORMATION: Human with synthetic extension

<400> SEQUENCE: 840

Gln Asn Gly Asn Ile Lys Ile Gly Gln Asp Gly Gly Cys
1               5                   10

<210> SEQ ID NO 841
<211> LENGTH: 12
<212> TYPE: PRT
<213> ORGANISM: Artificial
<220> FEATURE:
<223> OTHER INFORMATION: Human with synthetic extension

<400> SEQUENCE: 841

Gln Asn Gly Asn Ile Lys Ile Gly Gln Asp Tyr Lys
1               5                   10

<210> SEQ ID NO 842
<211> LENGTH: 12
<212> TYPE: PRT
<213> ORGANISM: Artificial
<220> FEATURE:
<223> OTHER INFORMATION: Human with synthetic extension

<400> SEQUENCE: 842

Gln Asp Gly Asn Ile Lys Ile Gly Gln Asp Tyr Lys
1               5                   10

```
<210> SEQ ID NO 843
<211> LENGTH: 13
<212> TYPE: PRT
<213> ORGANISM: Artificial
<220> FEATURE:
<223> OTHER INFORMATION: Deselection peptide

<400> SEQUENCE: 843

Val Ala Gln Asn Gly Asn Ile Lys Ile Gly Gln Asp Lys
1               5                   10

<210> SEQ ID NO 844
<211> LENGTH: 13
<212> TYPE: PRT
<213> ORGANISM: Artificial
<220> FEATURE:
<223> OTHER INFORMATION: Deselection peptide

<400> SEQUENCE: 844

Val Ala Gln Asn Gly Asn Ile Lys Ile Gly Gln Asp Lys
1               5                   10
```